US005846757A

United States Patent [19]
Harpold et al.

[11] Patent Number: 5,846,757
[45] Date of Patent: *Dec. 8, 1998

[54] HUMAN CALCIUM CHANNEL $\alpha_1$, $\alpha_2$, AND $\beta$ SUBUNITS AND ASSAYS USING THEM

[75] Inventors: Michael M. Harpold, El Cajon; Steven B. Ellis, San Diego; Mark E. Williams, Carlsbad, all of Calif.; Daniel H. Feldman, Gainesville, Fla.; Ann F. McCue, La Mesa, Calif.; Robert Brenner, Austin, Tex.

[73] Assignee: Sibia Neurosciences, Inc., La Jolla, Calif.

[ * ] Notice: The term of this patent shall not extend beyond the expiration date of Pat. No. 5,429,921.

[21] Appl. No.: 193,078

[22] PCT Filed: Aug. 14, 1992

[86] PCT No.: PCT/US92/06903

§ 371 Date: Feb. 7, 1994

§ 102(e) Date: Feb. 7, 1994

[87] PCT Pub. No.: WO93/04083

PCT Pub. Date: Mar. 4, 1993

Related U.S. Application Data

[63] Continuation-in-part of Ser. No. 868,354, Apr. 10, 1992, abandoned, and Ser. No. 745,206, Aug. 15, 1991, Pat. No. 5,429,921, said Ser. No. 868,354, is a continuation-in-part of Ser. No. 745,206, Aug. 15, 1991, Pat. No. 5,429,921, which is a continuation-in-part of Ser. No. 620,250, Nov. 30, 1990, which is a continuation-in-part of Ser. No. 176,899, Apr. 4, 1988, abandoned, said Ser. No. 868,354, and Ser. No. 745,206, each is a continuation-in-part of Ser. No.482,384, Feb. 20, 1990, and Ser. No. 603,751, Apr. 4, 1989, abandoned.

[51] Int. Cl.[6] .............................. C12A 1/02; C07K 14/705
[52] U.S. Cl. ...................... 435/29; 435/325; 435/254.11; 435/69.1; 435/7.21; 435/6; 530/350; 530/395; 514/2; 514/8
[58] Field of Search ................... 536/23.5; 435/240.2, 435/254.11, 320.1, 69.1, 6, 7.21, 29, 325; 530/350, 395; 514/2, 8

[56] References Cited

U.S. PATENT DOCUMENTS

| | | | |
|---|---|---|---|
| 4,675,285 | 6/1987 | Clark et al. | 435/6 |
| 4,788,135 | 11/1988 | Davis et al. | 435/6 |
| 4,912,202 | 3/1990 | Campbell et al. | 530/388.22 |
| 4,954,436 | 9/1990 | Froehner et al. | 424/1.49 |
| 5,024,939 | 6/1991 | Gorman | 435/69.1 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,386,025 | 1/1995 | Jay et al. | 536/23.5 |
| 5,407,820 | 4/1995 | Ellis et al. | 435/325 |
| 5,424,218 | 6/1995 | Miljanich et al. | 436/503 |

FOREIGN PATENT DOCUMENTS

| | | |
|---|---|---|
| 2085502 | 8/1993 | Canada . |
| 0507170 | 3/1992 | European Pat. Off. . |
| 0556651 | 4/1993 | European Pat. Off. . |
| 8907608 | 8/1989 | WIPO . |
| 8909834 | 10/1989 | WIPO . |
| 9113077 | 9/1991 | WIPO . |
| 9202639 | 2/1992 | WIPO . |
| 9308469 | 4/1993 | WIPO . |
| 9402511 | 2/1994 | WIPO . |
| 9504144 | 2/1995 | WIPO . |

OTHER PUBLICATIONS

Brust et al., "Human Neuronal Voltage–Dependent Calcium Channels: Studies on Subunit Structure and Role in Channel Assembly", *Neuropharmacology* 32(11):1089–1102 (1993).

Williams, et al., "Structure and Functional Characterization of Neuronal $\alpha_{1E}$ Calcium Channel Subtypes," *J. Biol. Chem.* 269(35):22347–22357 (1994).

Soong et al., "Structure and Functional Expression of a Member of the Low Voltage–Activated Calcium Channel Family", *Science* 260:1133–1136 (1993).

Powers, et al., "Assignment of the human gene for the $\alpha_1$ subunit of the cardiac DHP–sensitive $Ca^{2+}$channel (CCHL1A1) to Chromosome 12p12–pter," *Genomics*, 10: 835–839 (1991).

Kim, et al., "IgG from patients with Lambert–Eaton syndrome blocks voltage–dependent calcium channels," *Science*, 239: 405–408 (1988).

Claudio, et al., "Genetic reconstitution of functional acetylcholine receptor channels in mouse fibroblasts," *Science*, 238: 1688–1694 (1987).

Tanabe, et al., "Primary structure of the receptor for calcium channel blockers from skeletal muscle," *Nature*, 328: 313–318 (1987).

Nakayama, et al., "Purification of a putative $Ca^{2+}$channel protein from rabbit skeletal muscle," *J.Biol.Chem.*, 262: 6572–6576 (1987).

Vaghy, et al., "Identification of a novel 1,4–dihydropyridine– and phenylalkylamine–binding polypeptide in calcium channel preparations," *J.Biol.Chem.*, 262(29): 14337–14342 (1987).

Leung, et al., "Structural characterization of the 1,4–dihydropyridine receptor of the voltage–dependent $Ca^{2+}$channel from rabbit skeletal muscle," *J.Biol.Chem.*, 262(17): 7943–7946 (1987).

Sharp, et al., "Identification and characterization of the dihydropyridine–binding subunit of the skeletal muscle dihydropyridine receptor," *J.Biol.Chem.*, 62(25): 12309–12315 (1987).

(List continued on next page.)

*Primary Examiner*—David L. Fitzgerald
*Attorney, Agent, or Firm*—Stephanie L. Seidman; Brown, Martin, Haller & McClain

[57] ABSTRACT

Isolated DNA encoding each of human calcium channel $\alpha_1$-, $\alpha_2$-, $\beta$- and $\gamma$-subunits, including subunits that arise as splice variants of primary transcripts, is provided. Cells and vectors containing the DNA and methods for identifying compounds that modulate the activity of human calcium channels are also provided.

42 Claims, No Drawings

OTHER PUBLICATIONS

Takahashi, et al., "Subunit structure of dihydropyridine–sensitive calcium channels from skeletal muscle," *Proc.Natl.Acad.Sci.* (*USA*), 84: 5478–5482 (1987).

Morton et al., "Monoclonal antibody identifies a 200–kDA subunit of the dihydropyridine–sensitive calcium channel," *J.Biol.Chem.*, 262(25): 11904–11907 (1987).

Barhanin, et al., "The calcium channel antagonists receptor from rabbit skeletal muscle: reconstitution after purification and subunit characterization," *Eur.J.Biochem.*, 164: 525–531 (1987).

Sieber, et al., "The 165–kDa peptide of the purified skeletal muscle dihydropyridine receptor contains the known regulatory sites of the calcium channel," *Eur.J.Biochem.*, 167: 117–122 (1987).

Lang, et al., "The effect of myasthenic syndrome antibody on presynaptic calcium channels in the mouse," *J.Physiol.*, 390: 257–270 (1987).

Curran and Morgan, "Barium modules c–fos expression and post–translational modification," *Proc.Natl.Acad.Sci.*, 83: 3521–8524 (1986).

Fisch, et al., "c–fos sequences necessary for basal expression and induction by epidermal growth factor, 12–O–tetradecanoyl phorbol—13–acetate, and the calcium inophore," *Mol.Cell.Biol.*, 7(10): 3490–3502 (1987).

Noda, et al., "Existence of distinct sodium channel messenger RNAs in rat brain," *Nature*, 320: 188–192 (1986).

Noda, et al., "Expression of functional sodium channels from cloned cDNA," *Nature*, 322: 826–828 (1986).

Mierendorf, et al., "Gene isolation by screening kgtll libraries with antibodies," *Methods in Enz.*, 152: 458–469 (1986).

Gustin, et al., "Ion channels in yeast," *Science*, 233: 1195–1197 (1986).

Striessnig, et al., "Photoaffinity labelling of the phenylalkylamine receptor of the skeletal muscle transverse–tubule calcium channel," *FEBS Letters*, 212(2):247–253 (1987).

Froehner, "New insights into the molecular structure of the dihydropyridine–sensitive calcium channel," *TINS*, 11(3): 90–92 (1988).

Catterall, et al., "Molecular properties of dihydropyridine–sensitive calcium channels in skeletal muscle," *J.Biol.Chem.*, 263(8): 3535–3538 (1988).

Curtis, et al., "Purification fo the calcium antagonist receptor of the voltage–sensitive calcium channel from skeletal muscle transverse tubules," *Biochemistry*, 23(10): 2113–2118 (1984).

Borsotto, et al., "The 1,4–dihydropyridine receptor associated with the skeletal muscle voltage–dependent $Ca^{2+}$ channel," *J.Biol.Chem.*, 260(26): 14255–14263 (1985).

Cooper, et al., "Purification and characterization of the dihydropyridine–sensitive voltage–dependent calcium channel from cardiac tissue," *J.Biol.Chem.*, 262(2): 509–512 (1987).

Wood, "Gene cloning based on long oligonucleotide probes," *Methods in Enzymology*, 152: 443–447 (1987).

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry*, 25: 3492–3495 (1986).

Mishina, et al., "Location of functional regions of acetylcholine receptor α–subunit by site–directed mutagenesis," *Nature*, 313: 364–369 (1985).

Hamill, et al., "Improved patch–clamp techniques for high–resolution current recording from cells and cell–free membrane patches," *Pfluger Archiv.European Journal of Physiology*, 391: 85–100 (1981).

Hess, et al., "Different modes of Ca channel gating behavior favored by dihydropyridine Ca agonist and antagonists," *Nature*, 311: 538–544 (1984).

Leung, et al., "Biochemical and ultrastructural characterization of the 1,4–dihydropyridine receptor from rabbit skeletal muscle," *J. of Biol.Chem.*, 263(2): 994–1001 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol.Chem,.* 262(17): 8333–8339 (1987).

Miller, "Multiple calcium channels and neuronal function," *Science*, 235: 46–52 (1987).

Kozak, "An analysis of 5'–noncoding sequences from 699 vertebrate messenger RNAs," *Nucleic Acids Research*, 15(20): 8125–8148 (1987).

von Heijne, "Signal sequences: the limits of variation," *Jour. of Mol.Biol.*, 184: 99–105 (1985).

Hubbard, et al., "Synthesis and processing of asparagine–linked oligosaccharides[1,2]," *Ann.Rev.Biochem.*, 50: 555–583 (1981).

Feramisco, et al., "Optimal spatial requirements for the location of basic residues in peptide substrates for the cyclic AMP–dependent protein kinase," *Journal of Biological Chemistry*, 255(9): 4240–4245 (1980).

Takahashi, et al., "Identification of an α subunit of dihydropyridine–sensitive brain calcium channels," *Science*, 236: 88–91 (1987).

Hofmann, et al., "Regulation of the L–type calcium channel," *TINS*, 8: 393–398 (1987).

Curtis, et al., "Reconstitution of the voltage–sensitive calcium channel purified from skeletal muscle transverse tubules," *Biochemistry*, 25:3077–3083 (1986).

Smith, et al., "Calcium channel activity in a purified dihydropyridine–receptor preparation of skeletal muscle," *Biochemistry*, 26: 7182–7188 (1987).

Meshi, et al., "Nucleotide sequence of the 30K protein cistron of cowpea strain of tobacco mosaic virus," *Nucleic Acids Research*, 10(19): 6111–6117 (1982).

Nikaido, et al., "Molecular cloning of cDNA encoding human interleukin—2 receptor," *Nature*, 311: 631–636 (1984).

Roberts, et al., "Paraneoplastic myasthenic syndrome IgG inhibits $^{45}Ca^{2+}$ flux in a human small cell carcinoma line," *Nature*, 317: 737–739 (1985).

Starr, et al., "Primary structure of a calcium channel that is highly expressed in rat cerebellum," *Proc.Natl.Acad.Sci. USA*, 88: 5621–5625 (1991).

Snutch, et al., "Distinct calcium channels are generated by alternative splicing and are differentially expressed in the mammalian CNS," *Neuron*, 7: 45–57 (1991).

Hui, et al., "Molecular cloning of multiple sybtypes of a novel rat brain isoform of the $a_1$ subunit of the voltage–dependent calcium channel," *Neuron*, 7: 35–44 (1991).

Bean et al., "Classes of calcium channels in vertebrate cells," *Annu.Rev. Physiol.*, 51: 367–384 (1989).

Swandulla, et al., "Do calcium channel classifications account for neuronal calcium channel diversity?" *TINS*, 14(2): 46–51 (1991).

Ruth, et al., "Primary structure of the α subunit of the DHP–sensitive calcium channel from skeletal muscle," *Science*, 245: 1115–1118 (1989).

Mikami, et al., "Primary structure and functional expression of the cardiac dihydropyridine–sensitive calcium channel," *Nature*, 340: 230–233 (1989).

Biel, et al., "Primary structure and functional expression of a high voltage activiated calcium channel from rabbit lung," *FEBS Letters*, 269(2): 409–412 (1990).

Mori, et al., "Primary structure and functional expression from complementary DNA of a brain calcium channel," *Nature*, 350: 398–402 (1991).

Snutch, et al., "Rat brain expresses a heterogeneous family of calcium channels," *Proc.Natl.Acad.Sci. USA*, 87: 3391–3395 (1990).

Perez–Reyes, et al., "Molecular diversity of L–type calcium channels," *J. of Biol.Chem.*, 265(33): 20430–20436 (1990).

Perez–Reyes, et al., "Induction of calcium currents by the expression of the $\alpha_1$–subunit of the dihydropyridine receptor from skeletal muscle," *Nature*, 340: 233–236 (1989).

Koch, et al., "Characterization of cDNA clones encoding two putative isoforms of the $\alpha_1$–subunit of the dihydropyridine–sensitive voltage–dependent calcium channel isolated from rat brain and rat aorta," *FEBS Letters*, 250(2): 386–388 (1989).

Slish, et al.,"Evidence for the existence of a cardiac specific isoform of the $\alpha_1$–subunit of the voltage dependent calcium channel," *FEBS Letters*, 250(2): 509–514 (1989).

Varadi, et al., "Development regulation of expression of the $\alpha_1$ and $\alpha_2$ subunits mRNAs of the voltage–dependent calcium channel in a differentiating myogenic cell line," *FEBS Letters*, 250(2)CE: 515–518 (1989).

Ruth, et al., "Primary structure of the $\alpha$–subunit of the DHP–sensitive calcium channel from skeletal muscle," *Science*, 245: 1115–1118 (1989).

Jongh, et al., "Subunits of purified calcium channels: a 212–kDa form of $\alpha_1$ and partial amino acid sequence of a phosphorylation site of an independent $\beta$–subunit," *Proc.Natl.Acad.Sci. USA*, 86:8585–8589 (1989).

Hamilton, et al., "Subunit composition of the purified dihydropyridine binding protein from skeletal muscle," *Biochemistry*, 28: 7820–7828 (1989).

Nunoki, et al., "Activation of purified calcium channels by stoichiometric protein phosphorylation," *Proc.Natl.Acad.Sci. USA*, 86: 6816–6820 (1989).

Ichida, et al., "Photoaffinity labeling with dihydropyridine derivatives of crude membranes from rat skeletal, cardiac, ileal, and uterine muscles and whole brain," *J.Biochem.*, 105:767–774 (1989).

Sharp and Campbell, "Characterization of the 1,4–dihydropyridine receptor using subunit–specific polyclonal antibodies," *J.Biol.Chem.*, 264(5): 2816–2825 (1989).

Campbell, et al., "The biochemistry and molecular biology of the dihydropyridine–sensitive calcium channel," *TINS*, 11(10): 4425–430 (1988).

Pelzer, et al., "Properties and regulation of calcium channels in muscle cells," *Rev. Physiol.Biochem.Pharmacol.*, 114: 107–207 (1990).

Kim, et al., "Studies on the structural requirements for the activity of the skeletal muscle dihydropyridine receptor/slow $Ca^{2+}$channel," *J.Biol.Chem.*, 11858–11863 (1990).

Lotan, et al., "Specific block of calcium channel expression by a fragment of dihydropyridine receptor cDNA," *Science*, 243: 666–669 (1989).

Rampe, et al., "[$^3$H]Pn200–110 binding in a fibrobblast cell line transformed with the $\alpha_1$ subunit of the skeletal muscle L–type $Ca^{2+}$channel," *Biochem. and Biophys.Research Communications*, 169(3): 825–831 (1990).

Adams, et al., "Intramembrane charge movement restored in dysgenic skeletal muscle by injection of dihydropyridine receptor cDNAs," *Nature*, 346: 569–572 (1990).

Tanabe, et al., "Cardiac–type excitation–contraction coupling in dysgenic skeletal muscle injected with cardiac dihydropyridine receptor cDNA," *Nature*, 344: 451–453 (1990).

Tanabe, et al., "Regions of the skeletal muscle dihydropyridine receptor critical for excitation–contraction coupling," *Nature*, 346: 567–569 (1991).

Regulla, et al., "Identification of the site of interaction of the dihydropyridine channel blockers nitrendipine and azidopine with the calcium–channel $\alpha_1$ subunit," *EMBO Journal*, 10(1): 45–49 (1991).

Williams, et al., "Structure and functional expression of $\alpha_1$, $\alpha_2$ and $\beta$ subunits of a novel human neuronal calcium channel subtype," *Neuron*, 8:71–84 (1992).

Olivera, et al., "Conotoxins," *J. of Biol.Chem.*, 266(33): 22067–22070 (1991).

Seino, et al., "Cloning of $\alpha_1$ subunit of a voltage–dependent calcium channel expressed in pancreatic $\beta$ cells," *Proc.Natl.Acad.Sci. USA*, 89: 584–588 (1992).

Perez–Reyes, et al.,"Cloning and expression of a cardiac/brain $\beta$ subunit of the L–type calcium channel," *J. of Biol.Chem.*, 267(3): 1792–1797 (1992).

Miller, R., "Voltage–sensitive $Ca^{2+}$ channels," *J. of Biol.Chem.*, 267(3): 1403–1406 (1992).

Artalejo, et al., "w–Conotoxin GVIA blocks a $Ca^{2+}$ current in bovine chromaffin cells that is not of the 'classic' N type," *Neuron*, 8: 85–95 (1992).

Kasai, H., "Tonic inhibition and rebound facilitation of a neuronal calcium channel by a GTP–binding protein," *Proc.Natl.Acad.Sci. USA*, 88: 8855–8859 (1991).

Sher, et al., "Voltage–operated calcium channels in small cell lung carcinoma cell lines: pharmacological, functional, and immunological properties," *Cancer Research*, 5: 3892–3896 (1990).

Sher, et al., "w–Conotoxin binding and effects on calcium channel function in human neuroblastoma and rat pheochromocytoma cell lines," *FEBS Letters*, 235: (1,2): 178–182 (1988).

Koch, et al., "cDNA cloning of a dihydropyridine–sensitive calcium channel from rat aorta," *J. of Biol.Chem.*, 265(29): 17786–17791 (1990).

Cohen, et al., "Distribution of $Ca^{2+}$ channels on frog motor nerve terminals revealed by fluorescent w–conotoxin," *J. of Neuroscience*, 11(4): 1032–1039 (1991).

Bosse, et al., "The cDNA and deduced amino acid sequence of the $\gamma$ subunit of the L–type calcium channel from rabbit skeletal muscle," *FEBS*, 267(1): 153–156 (1990).

Burns, et al., "Calcium channel activity of purified human synexin and structure of the human synexin gene," *Proc.Natl.Acad.Sci.*, 86: 3798–3802 (1989).

Campbell, et al., "32,000–Dalton subunit of the 1,4–dihydropyridine receptor," *Ann.N.Y.Acad.Sci.*, 560: 251–257 (1989).

Dascal, N., "The use of Xenopus oocytes for the study of ion channels," *CRC Critical Rev.Biochem.*, 22(4): 317–387 (1987).

DeJongh, et al., "Subunits of purified calcium channels," *J.Biol.Chem.*, 265(25): 14738–14741 (1990) (best available copy submitted).

Jay, et al., "Primary Structure of the $\gamma$ subunit of the DHP–sensitive calcium channel from skeletal muscle," *Science*, 248: 490–492 (1990).

Jay, et al., "Structural characterization of the dihydropyridine–sensitive calcium channel $\alpha_2$–subunit and the associated δ peptides," *J.Biol.Chem.*, 266(5): 3287–3293 (1991).

Leung, et al., "Monoclonal antibody characterization of the 1,4–dihydropyridine receptor of rabbit skeletal muscle," *Ann.N.Y.Acad.Sci.*, 522: 43–46 (1988).

Vaghy, et al., "Mechanism of action of calcium channel modulator drugs," *Ann.N.Y.Acad.Sci.*, 522: 176–186 (1988).

Ahlijanian, et al., "Subunit structure and localization of dihydropyridine–sensitive calcium channels in mammalian brain, spinal cord, and retina," *Neuron*, 4:819–832 (1990).

Blount, et al., "Assembly intermediates of the mouse muscle nicotinic Acetylcholine receptor in stably transfected fibroblasts," *J.Cell.Biol.*, 111: 2601 (1990).

Carbone, et al., "Ca currents in human neuroblastoma IMR32 cells: kinetics, permeability and pharmacology," *Pfluegers Arch*, 416:170–179 (1990) (best available copy submitted).

Dascal, et al., "Expression of modulation of voltage–gated calcium channels after RNA injection in Xexopus oocytes," *Science*, 231: 1147–1150 (1986).

Hess, et al., "Calcium channels in vertebrate cells," *Ann.Rev.Neurosci.*, 13: 337–356 (1990).

Stanley, et al., "Characterization of a calcium current in a vertebrate cholinergic presynaptic nerve terminal," *J.Neurosci.*, 11: 985 (1991).

Wei, et al., "Heterologous regulation of the cardiac $Ca^{2+}$ channel $\alpha_1$ subunit by skeletal muscle β and γ subunits," *J.Biol.Chem.*, 266: 21943–21947 (1991).

Ahlijanian, et al., "Phosphorylation of an α1–like subunit of an w–conotoxin–sensitive brain calcium channel by cAMP–dependent protein kinase and protein kinase C," *J.Biol.Chem.*, 266: 20192 (1991).

Claudio, T., "Stable expression of transfected Torpedo acetylcholine receptor α subunits in mouse fibroblast L cells," *Proc.Natl.Acad.Sci.*, 84: 5967–5971 (1987).

Hullin, et al., "Calcium channel β subunit heterogeneity: functional expression of cloned cDNA from heat, aorta and brain," *EMBO J.*, 11: 885 (1992).

Kim, et al., "Rat brain expresses and alternatively spliced form of the dihydropyridine–sensitive L–type calcium channel α2 subunit," *Proc.Natl.Acad.Sci.*, 89:3251 (1992).

Pragnell, et al., "Cloning and tissue–specific expression of the brain calcium channel β–subunit," *FEBS Letters*, 291: 253 (1991).

Sakamoto, et al., "A monoclonal antibody to the β subunit of the skeletal muscle dihydropyridine receptor immunoprecipitates the brain w–conotoxin GVIA receptor," *J.Biol.Chem.*, 266: 18914 (1991).

Seager, et al., "Molecular properties of dehydropyrine–sensitive calcium channels," *Ann.N.Y.Acad.Sci.*, 552: 162–175 (1988).

Tsien, et al., "Molecular diversity of voltage–dependent $Ca^{2+}$ channels," *Trends in Pharmacol.Sci.*, 12: 349 (1991).

Takahashi and Catterall, "Dihydropyridine–sensitive calcium channels in cardiac and skeletal muscle membranes: studies with antibodies against the α–subunits," *Biochemistry*, 26(17): 1518–1526 (1987).

Cruz et al., "Characterization of ω–Conotoxin Target. Evidence for Tissue–Specific Heterogeneity ion Calcium Channel Types", *Biochem. J.* 26:820 (1987).

Ellis et al. (1988) "Sequence and Expression of mRNAs Encoding the $\alpha_1$ and $\beta_2$ Subunits of a DHP–Sensitive Calcium Channel", *Science* 241: 1661–1664.

Breitbart et al. "Alternatvie Splicing: A Ubiquitous Mechanism for the Generation of Multiple Protein Isoforms From Single Genes" *Ann.Rev.Biochem.* 56:467–495(1984).

Williams et al., "Structure and Functional Expression of an ω–Conotoxin–Sensitive Human N–Type Calcium Channel", *Science* 257:389–395 (1992).

Rosenfield et al., "Cloning and Characterization of a Lambert–Eaton Myasthenic Syndrome Antigen", *Annals of Neurology* 33: 113–120 (1993).

Powers et al., "Skeletal Muscle and Brain Isoforms of a β–Subunit of Human Voltage–dependent Calcium Channels Are Encoded by a Single Gene", *J. Biol. Chem.* 267:22967–22972 (1992).

Wah et al. ,"Structure and Functional Expression of a Member of the Low–Voltage–Activated Calcium channel Family", *Science* 260:1133–1136.

Horne et al., "Molecular diversity of $Ca^{2+}$ channel $\alpha_1$ subunits from the marine ray *Discopyge ommata*", *Proc.Natl.Acad.Sci.* 90:3787–3791 (1993).

Yu et al., "Molecular characterization and nephron distribution of a family of transcripts encoding the pore–forming subunit of $Ca^{2+}$ channels in the kidney", *Proc.Natl.Acad.Sci.* 89:10494–10498 (1992).

Dubel et al., "Molecular cloning of the α–1 subunit of an ω–conotoxin–sensitive calcium channel", *Proc.Natl.Acad..Sci.* 89:5058–5062 (1992).

Soldatov, "Molecular diversity of L–type $Ca^{2+}$ channel transcripts in human fibroblasts", *Proc.Natl.Acad.Sci.* 89:4628–4632 (1992).

Leveque et al., "The synaptic vesicle protein synaptotagmim associates with calcium channels and is a putative Lambert–Eaton myasthenic syndrome antigen", *Proc.Natl.Acad..Sci.* 89:3625–3629 (1992).

Niidome et al., "Molecular cloning and characterization of a novel calcium channel from rabbit brain", *FEBS LTTRS* 308:7–13 (1992).

Elinor et al., "Functional expression of a rapidly inactivating neuronal calcium channel", *Nature* 363:455–458 (1993).

Spedding et al., 'Calcium Antgonists': A Class of Drugs with a Bright Future. Part II. Determination of Basic Pharmacological Properties, *Life Sciences* 35:575–587 (1984).

HUMAN CALCIUM CHANNEL $\alpha_1$, $\alpha_2$, AND $\beta$ SUBUNITS AND ASSAYS USING THEM This application is the national stage (35 U.S.C. §371) of International Application PCT/US92/6903, filed Aug. 14, 1992, which is a continuation-in-part of U.S. Ser. No. 07/868,354, filed Apr. 10, 1992, now abandoned, and is also a continuation-in-part of U.S. Ser. No. 07/745,206, filed Aug. 15, 1991, now U.S. Pat. No. 5,429,921.

U.S. Ser. No. 07/868,354 is a continuation-in-part of U.S. Ser. No. 07/745,206, which is a continuation-in-part of U.S. Ser. No. 07/620,250, filed Nov. 30, 1990, which is a continuation-in-part of U.S. Ser. No. 07/176,899, filed Apr. 4, 1988, now abandoned. U.S. Ser. No. 07/868,354 and 07/745,206 are also a continuation-in-part of U.S. Ser. No. 07/482,384, filed Feb. 20, 1990, and are also a continuation-in-part of 07/603,751, filed Apr. 4, 1989, now abandoned.

TECHNICAL FIELD

The present invention relates to molecular biology and pharmacology. More particularly, the invention relates to calcium channel compositions and methods of making and using the same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. "Opening" of a voltage-dependent channel to allow an influx of $Ca^{2+}$ ions into the cells requires a depolarization to a certain level of the potential difference between the inside of the cell bearing the channel and the extracellular medium bathing the cell. The rate of influx of $Ca^{2+}$ into the cell depends on this potential difference. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Multiple types of calcium channels have been identified in mammalian cells from various tissues, including skeletal muscle, cardiac muscle, lung, smooth muscle and brain, [see, e.g., Bean, B. P.(1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists.

Calcium channels are multisubunit proteins. For example, rabbit skeletal muscle calcium channel contains two large subunits, designated $\alpha_1$ and $\alpha_2$, which have molecular weights between about 130 and about 200 kilodaltons ("kD"), and one to three different smaller subunits of less than about 60 kD in molecular weight. At least one of the larger subunits and possibly some of the smaller subunits are glycosylated. Some of the subunits are capable of being phosphorylated. The $\alpha_1$ subunit has a molecular weight of about 150 to about 170 kD when analyzed by sodium dodecylsulfate (SDS)-polyacrylamide gel electrophoresis (PAGE) after isolation from mammalian muscle tissue and has specific binding sites for various 1,4-dihydropyridines (DHPs) and phenylalkylamines. Under non-reducing conditions (in the presence of N-ethylmaleimide), the $\alpha_2$ subunit migrates in SDS-PAGE as a band corresponding to a molecular weight-of about 160–190 kD. Upon reduction, a large fragment and smaller fragments are released. The $\beta$ subunit of the rabbit skeletal muscle calcium channel is a phosphorylated protein that has a molecular weight of 52–65 kD as determined by SDS-PAGE analysis. This subunit is insensitive to reducing conditions. The $\gamma$ subunit of the calcium channel, which is not observed in all purified preparations, appears to be a glycoprotein with an apparent molecular weight of 30–33 kD, as determined by SDS-PAGE analysis.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, difficulties in obtaining tissues of interest, and the modifications of the native protein that can occur during the isolation procedure, it is extremely difficult to obtain large amounts of highly purified, completely intact calcium channel protein.

Characterization of a particular type of calcium channel by analysis of whole cells is severely restricted by the presence of mixed populations of different types of calcium channels in the majority of cells. Single-channel recording methods that are used to examine individual calcium channels do not reveal any information regarding the molecular structure or biochemical composition of the channel. Furthermore, in performing this type of analysis, the channel is isolated from other cellular constituents that might be important for natural functions and pharmacological interactions.

Characterization of the gene or genes encoding calcium channels provides another means of characterization of different types of calcium channels. The amino acid sequence determined from a complete nucleotide sequence of the coding region of a gene encoding a calcium channel protein represents the primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

The cDNA and corresponding amino acid sequences of the $\alpha_1$, $\alpha_2$, $\beta$ and $\gamma$ subunits of the rabbit skeletal muscle calcium channel [see, Tanabe et al. (1987) *Nature* 328:313–318; International Application No. WO 89/09834, which is U.S. application Ser. No. 07/603,751, now abandoned, which is a continuation-in-part of U.S. application Ser. No. 07/176,899 also now abandoned; Ruth et al. (1989) *Science* 245:1115–1118; and U.S. patent application Ser. No. 482,384, filed Feb. 20, 1990] have been determined. The cDNA and corresponding amino acid sequences of $\alpha_1$ subunits of rabbit cardiac muscle [Mikami, A. et al. (1989) *Nature* 340:230–233] and lung (Biel, M. (1990) *FEBS Letters* 269:409–412) calcium channels have been determined.

In addition, a cDNA clone encoding a rabbit brain calcium channel (designated the BI channel) has been isolated [Mori, Y. et al. (1991) *Nature* 350:398–402]. Partial cDNA clones encoding portions of several different subtypes, referred to as rat brain class A, B, C and D, of the calcium channel $\alpha_1$ subunit have been isolated from rat brain cDNA libraries

[Snutch, T. et al. (1990) *Proc. Natl. Acad. Sci. USA* 87:3391–3395]. More recently full-length rat brain class, A [Starr, T. et al. (1991) *Proc. Natl. Acad. Sci. USA* 88:5621–5625] and class C [Snutch, T. et al. (1991) *Neuron* 7:45–57] cDNA clones have been isolated. Although the amino acid sequence encoded by the rat brain class C DNA is approximately 95% identical to that encoded by the rabbit cardiac muscle calcium channel $\alpha_1$ subunit-encoding DNA, the amino acid sequence encoded by the rat brain class A DNA shares only 33% sequence identity with the amino acid sequence encoded by the rabbit skeletal or cardiac muscle $\alpha_1$ subunit-encoding DNA. A cDNA clone encoding another rat brain calcium channel $\alpha_1$ subunit has also been obtained [Hui, A. et al. (1991) *Neuron* 7:35–44). The amino acid sequence encoded by this clone is ~70% homologous to the proteins encoded by the rabbit skeletal and cardiac muscle calcium channel DNA. A cDNA clone closely related to the rat brain class C $\alpha_1$ subunit-encoding cDNA and sequences of partial cDNA clones closely related to other partial cDNA clones encoding-apparently different calcium channel $\alpha_1$ subunits have also been isolated [see Snutch, T. et al. (1991) *Neuron* 1:45–57; Perez-Reyes, E. et al. (1990) *J. Biol. Chem.* 265:20430; and Hui, A. et al. (1991) *Neuron* 7:35–44]. DNA clones encoding other calcium channels have also been identified and isolated.

Expression of cDNA encoding calcium channel subunits has been achieved with several of the different rabbit or rat $\alpha_1$ subunit cDNA clones discussed above. Voltage-dependent calcium currents have been detected in murine L cells transfected with DNA encoding the rabbit skeletal muscle calcium channel $\alpha_1$ subunit [Perez-Reyes et al. (1989) *Nature* 340:233–236 (1989)]. These currents were enhanced in the presence of the calcium channel agonist Bay K 8644. Bay K 8644-sensitive $Ba^{2+}$ currents have been detected in oöcytes injected with in vitro transcripts of the rabbit cardiac muscle calcium channel $\alpha_1$ subunit cDNA [Mikami, A. et al. (1989) *Nature* 340:230–233]. These currents were substantially reduced in the presence of the calcium channel antagonist nifedipine. Barium currents of an oöcyte co-injected with RNA encoding the rabbit cardiac muscle calcium channel $\alpha_1$ subunit and the RNA encoding the rabbit skeletal muscle calcium channel $\alpha_2$ subunit were more than 2-fold larger than those of oöcytes injected with transcripts of the rabbit cardiac calcium channel $\alpha_1$ subunit-encoding cDNA. Similar results were obtained when oöcytes were co-injected with RNA encoding the rabbit lung calcium channel $\alpha_1$ subunit and the rabbit skeletal muscle calcium channel $\alpha_2$ subunit. The barium current was greater than that detected in oöcytes injected only with RNA encoding the rabbit lung calcium channel $\alpha_1$ subunit [Biel, M. et al. (1990) *FEBS Letters* 269:409–412]. Inward barium currents have been detected in oöcytes injected with in vitro RNA transcripts encoding the rabbit brain BI channel [Mori et al. (1991) *Nature* 350:398–402]. These currents were increased by two orders of magnitude when In vitro transcripts of the rabbit skeletal muscle calcium channel $\alpha_2$, $\beta$, or $\alpha_2$, $\beta$ and $\gamma$ subunits were co-injected with transcripts of the BI-encoding cDNA. Barium currents in oöcytes co-injected with transcripts encoding the BI channel and the rabbit skeletal muscle calcium channel $\alpha_2$ and $\beta$ were unaffected by the calcium channel antagonists nifedipine or ω-CgTx and inhibited by Bay K 8644 and crude venom from *Agelenopsis aperta*.

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated, in these recombinant cells to the actual current generated by calcium channels containing as one component the respective $\alpha_1$ subunits in vivo is unclear. In order to completely and accurately characterize and evaluate different calcium channel types, however, it is essential to examine the functional properties of recombinant channels containing all of the subunits as found in vivo. Although there has been limited success in expressing DNA encoding rabbit and rat calcium channel subunits, far less has been achieved with respect to human calcium channels. Little is known about human calcium channel structure and function and gene expression. An understanding of the structure and function of human calcium channels would permit identification of substances that, in some manner, modulate the activity of calcium channels and that have potential for use in treating such disorders.

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as CNS and cardiovascular diseases. Calcium channels, thus, are also implicated in numerous disorders. A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the call membrane.

An understanding of the pharmacology of compounds that interact with calcium channels in other organ systems, such as the CNS, may aid in the rational design of compounds that specifically interact with subtypes of human calcium channels to have desired therapeutic effects, such as in the treatment of neurodegenerative and cardiovascular disorders. Such understanding and the ability to rationally design therapeutically effective compounds, however, have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding specific calcium channel subunits and to provide eukaryotic cells bearing recombinant tissue-specific or subtype- specific calcium channels. It is also an object to provide assays for identification of potentially therapeutic compounds that act as calcium channel antagonists and agonists.

SUMMARY OF THE INVENTION

Eukaryotic cells containing heterologous DNA encoding one or more calcium channel subunits, particularly human calcium channel subunits, or containing RNA transcripts of DNA clones encoding one or more of the subunits are provided. In preferred embodiments, the cells contain DNA or RNA encoding a human $\alpha_1$ subunit, preferably, at least an $\alpha_{1D}$ or $\alpha_{1B}$ subunit. In more preferred embodiments, the cells contain DNA or RNA encoding additional heterologous subunits, including at least one β, $α_2$ or γ subunits are included. In such embodiments, eukaryotic cells stably or transiently transfected with any combination of one, two, three or four of the subunit-encoding cDNA clones,,such as $α_1$, $α_1+β$, $α_1+β+α_2$, are provided. In more preferred embodiments, the subunits encoded by the heterologous DNA are human subunits.

In preferred embodiments, the cells express such heterologous calcium channel subunits and include one or more of the subunits in membrane spanning heterologous calcium channels. In more preferred embodiments, the eukaryotic cells express functional, heterologous calcium channels that are capable of gating the passage of calcium channel selective ions and/or binding compounds that, at physiological concentrations, modulate the activity of the heterologous calcium channel. In certain embodiments, the heterologous calcium channels include at least one heterologous calcium channel subunit. In most preferred embodiments, the calcium channels that are expressed on the surface of the eukaryotic cells are composed substantially or entirely of subunits encoded by the heterologous DNA or RNA. In preferred embodiments, the heterologous calcium channels of such cells are distinguishable from any endogenous calcium channels of the host cell.

In certain embodiments the recombinant eukaryotic cells that contain the heterologous DNA encoding the calcium channel subunits are produced by transfection with DNA encoding one or more of the subunits or are injected with RNA transcripts of cDNA encoding one or more of the calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous calcium channels may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

The recombinant eukaryotic cells that express membrane spanning heterologous calcium channels may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions.

Assays using the eukaryotic cells for identifying compounds that modulate calcium channel activity are provided.

Isolated and purified DNA fragments that encode human calcium channel subunits are provided. DNA encoding a, subunits of a human calcium channel, and RNA, encoding such subunits, made upon transcription of such DNA are provided. In particular, DNA fragments encoding $α_1$ subunits of voltage-dependent human calcium channels (VDCCs) type A, type B (also referred to as VDCC IV), type C (also referred to as VDCC II) and type D (also referred to as VDCC III) are provided.

In particular, DNA encoding an $α_{1D}$ subunit that includes the amino acids substantially as set forth as residues 10-2161 of sequence ID No. 1 is provided. DNA encoding an $α_{1D}$ subunit includes substantially the amino acids set forth as amino acids 1–34 in sequence ID No. 2 in place of amino acids 373–406 of SEQ ID No. 1 is also provided. DNA encoding an $α_{1C}$ subunit that includes the amino acids substantially as set forth in sequence ID No. 3 or sequence ID No. 6 and DNA encoding an $α_{1B}$ subunit that includes an amino acid sequence substantially as set forth in sequence ID No. 7 or in sequence. ID No. 8 is also provided. A phage lysate of an E. coli host containing DNA encoding $α_{1A}$ have been deposited in the American Type culture Collection, 12301 Parklawn Drive, Rockville, Md. 20852 U.S.A. under Accession No. in accord with the Budapest Treaty. The DNA in such phage includes a DNA fragment having the sequence set forth in SEQ ID No. 21. This fragment hybridizes to DNA encoding $α_{1A}$ but not to DNA encoding $α_{1B}$.

DNA encoding $α_2$ subunits of a human calcium channel, and RNA encoding such subunits, made upon transcription of such a DNA are provided. DNA encoding splice variants of the $α_2$ subunit, including tissue specific splice variants, are also provided. In particular, DNA encoding the $α_{2a}$–$α_{2c}$ subunit subtypes is provided. In particularly preferred embodiments, the DNA encoding the $α_2$ subunit is produced by alternative processing of a primary transcript that includes DNA encoding the amino acids set forth in SEQ ID 11 and the DNA of SEQ ID No. 13 inserted between nucleotides 1624 and 1625 of SEQ ID No. 11. The aqueous of those splice variants which are designated $α_{2b}$, $α_{2a}$, and $α_{2c}$–$α_{2e}$ are set forth in SEQ. ID Nos. 11 and 22–25, respectively Isolated and purified DNA fragments encoding human calcium channel β subunits, including DNA encoding $β_1$ subunit splice variants and the $β_3$ subunit is provided. In particular, DNA encoding the $β_1$ and $β_3$ subunits, including the $β_1$ subunit splice variants $β_{1-1}$–$β_{1-5}$, is provided. RNA, encoding β subunits, made upon transcription of the DNA is also provided. Escherichia. coli (E. coli) containing plasmids containing DNA encoding $β_3$ have been deposited in accord with the Budapest Treaty under Accession No. 69048 at the American Type Culture Collection. A partial sequence of the deposited clone is set forth in SEQ ID No. 19 (sequence from the 5' end) and SEQ ID No. 20 (sequence from the 3' end).

DNA encoding β subunits that are produced by alternative processing of a primary transcript encoding a β subunit, including a transcript that includes DNA encoding the amino acids set forth in SEQ ID No. 9 or including a primary transcript that encodes $β_3$ as deposited under ATCC Accession No. 69048, but lacking and including alternative exons are provided or may be constructed from the DNA provided herein. For example, DNA encoding a β subunit that is produced by alternative processing of a primary transcript that includes DNA encoding the amino acids set forth in SEQ ID No. 9, but including the DNA set forth in SEQ ID No. 12 inserted in place of nucleotides 615–781 of SEQ ID No. 9 is also provided. DNA encoding β subunits that are encoded by transcripts that have the sequence set forth in SEQ ID No. 9 including the DNA set forth in SEQ ID No. 12 inserted in place of nucleotides 615–781 of SEQ ID No. 9, but that lack one or more of the following sequences of nucleotides: nucleotides 14–34 of SEQ ID No. 12, nucleotides 13–34 of SEQ ID No. 12, nucleotides 35–55 of SEQ ID No 12, nucleotides 56–190 of SEQ ID No. 12 and nucleotides 191–271 of SEQ ID No. 12 are also provided.

DNA encoding γ subunits of human calcium channels is also provided. RNA, encoding γ subunits, made upon transcription of the DNA is also provided. In particular, DNA containing the sequence of nucleotides set forth in SEQ ID No. 14 is provided.

Full-length DNA clones and corresponding RNA transcripts, encoding the $\alpha_1$, including $\alpha_{1D}$, $\alpha_{1B}$, $\beta_2$ and $\beta$ subunits, including $\beta_{1-1}$–$\beta_{1-5}$, of human calcium channels are provided. The sequences of DNA encoded the $\beta_1$ splice variants $\beta_{1-1}$, $\beta_{1-2}$, $\beta_{1-3}$, $\beta_{1-4}$ and $\beta_{1-5}$ are set forth in SEQ ID Nos. 26, 9, 10, 27 and 28. Also provided are DNA clones encoding substantial portions of the $\alpha_{1A}$, $\alpha_{1C}$, $\beta_3$ and $\gamma$ subunits of voltage-dependent human calcium channels for the preparation of full-length DNA clones encoding the full-length $\alpha_{1A}$, $\alpha_{1C}$, $\beta_3$ and $\gamma$ subunits.

Nucleic acid probes containing at least about 14 contiguous nucleotides of $\alpha_{1D}\alpha_{1C}$, $\alpha_{1B}$, $\alpha_{1A}$, $\alpha_2$, $\beta$, including $\beta_1$ splice variants and $\beta_3$ and $\gamma$ subunit-encoding DNA are provided. Methods using the probes for the isolation and cloning of calcium channel subunit-encoding cDNA, including splice variants within tissues and inter-tissue variants are also provided.

Purified human calcium channel subunits and purified human calcium channels are provided. The subunits and channels can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. E. coli fusion proteins including a fragment of a human calcium channel subunit may also be used as immunogen. Such fusion proteins may contain a bacterial protein or portion thereof, such as the E. coli TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample.

A diagnostic method for determining the presence of Lambert Eaton Syndrome (LES) in a human based on immunological reactivity of LES immunoglobulin G (IgG) with a human calcium channel subunit or a eukaryotic cell which expresses a recombinant human calcium channel or a subunit thereof is also provided. In particular, an immunoassay method for diagnosing Lambert-Eaton Syndrome in a person by combining serum or an IgG fraction from the person (test serum) with calcium channel proteins, including the $\alpha$ and $\beta$ subunits, and ascertaining whether antibodies in the test serum react with one or more of the subunits, or a recombinant cell which expresses one or more of the subunits to a greater extent than antibodies in control serum, obtained from a person or group of persons known to be free of the Syndrome, is provided. Any immunoassay procedure known in the art for detecting antibodies against a given antigen in serum can be employed in the method.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to he rein are incorporated by reference herein.

Reference to each of the calcium channel subunits includes, the subunits that are specifically disclosed herein and human calcium channel subunits encoded by DNA that can be isolated by using the DNA disclosed as probes and screening an appropriate human cDNA or genomic library under at least low stringency. Such DNA also includes DNA that encodes proteins that have about 40% homology to any of the subunits proteins described herein or DNA that hybridizes under conditions of at least low stringency to the DNA provided herein and the protein encoded by such DNA exhibits additional identifying characteristics, such as function or molecular weight.

It is understood that subunits that are encoded by transcripts that represent splice variants of the disclosed subunits or other such subunits may exhibit less than 40% overall homology to any single subunit, but will include regions of such homology to one or more such subunits. It is also understood that 40% homology refers to proteins that share approximately 40% of their amino acids in common or that share somewhat less, but include conservative amino acid substitutions, whereby the activity of the protein is not substantially altered.

As used herein, the $\alpha_1$ subunits types, encoded by different genes, are designated as type $\alpha_{1A}$, $\alpha_{1B}$, $\alpha_{1C}$, and $\alpha_{1D}$. These types may also be also referred to as VDCC IV for $\alpha_{1B}$, VDCC II for $\alpha_{1C}$ and VDCC III for $\alpha_{1D}$. Subunit subtypes, which are splice variants, are referred to, for example as $\alpha_{1B-1}$, $\alpha_{1B-2}$, $\alpha_{1C-1}$ etc.

Thus, as used herein, DNA encoding the $\alpha_1$ subunit refers to DNA that hybridizes to the DNA provided herein under conditions of at least low stringency or encodes a subunit that has roughly about 40% homology to protein encoded by DNA disclosed herein that encodes an $\alpha_1$ subunit of a human calcium. An $\alpha_1$ subunit may be identified by its ability to form a calcium channel. Typically, $\alpha_1$ subunits have molecular weights greater than at least about 120 kD. The activity of a calcium channel may be assessed in vitro by methods known to those of skill in the art, including the electrophysiological and other methods described herein. Typically, $\alpha_1$ subunits include regions to which one or more modulators of calcium channel activity, such as a 1,4 DHP or $\omega$-CgTx, interact directly of indirectly. Types of $\alpha_1$ subunits may be distinguished by any method known to those of skill in the art, including on the basis of binding specificity. For example, it has been found herein that $\alpha_{1B}$ subunits participate in the formation of N-type channels, $\alpha_{1D}$ subunits participate in the formation of L-type channels, and $\alpha_{1A}$ subunits appear to participate in the formation of channels that exhibit characteristics typical of P-type channels. Thus, for example, the activity of channels that contain the $\alpha_{1B}$ subunit are insensitive to 1,4 DHPs; whereas the activity of channels that contain the $\alpha_{1D}$ subunit are modulated or altered by a 1,4 DHP. Types and subtypes of $\alpha_1$ subunits may be characterized on the basis of the effects of such modulators on the subunit or a channel containing the subunit as well as differences in currents and current kinetics produced by calcium channels containing the subunit.

As used herein, an $\alpha_2$ subunit is encoded by DNA that hybridizes to the DNA provided herein under conditions of low stringency or encodes a protein that has about 40% homology with that disclosed herein. Such DNA encodes a protein that typically has a molecular weight greater than about 120 kD, but does not form a calcium channel in the absence of an $\alpha_1$ subunit, and may alter the activity of a calcium channel that contains an $\alpha_1$ subunit. Subtypes of the $\alpha_2$ subunit that arise as splice variants are designated by lower case letter, such as $\alpha_{2a}$, ... $\alpha_{2e}$. In addition, the $\alpha_2$ subunit and the large fragment produced under reducing conditions appear to be glycosylated with at least N-linked sugars and do not specifically bind to the 1,4-DHPs and phenylalkylamines that specifically bind to the $\alpha_1$ subunit. The smaller fragment, the C-terminal fragment, is referred to as the $\delta$ subunit and includes amino acids from about 946 (SEQ ID No. 11) through about the C-terminus. This fragment may dissociate from the remaining portion of $\alpha_2$ when the $\alpha_2$ subunit is exposed to reducing conditions.

As used herein, a $\beta$ subunit is encoded by DNA that hybridizes to the DNA provided herein under conditions of low stringency or encodes a protein that has about 40% homology with that disclosed herein and is a protein that typically has a molecular weight lower than the a subunits and on the order of about 50–80 kD, does not form a detectable calcium channel in the absence of an $\alpha_1$ subunit, but may alter the activity of a calcium channel that contains an a, subunit or that contains an $\alpha_1$ and $\alpha_2$ subunit.

Types of the $\beta$ subunit that are encoded by different genes are designated with subscripts, such as $\beta_1$ and $\beta_3$. Subtypes of $\beta$ suits that arise as splice variants of a particular type are designated with a numerical subscript referring to the subtype and to the variant. Such subtypes include, but are not limited to the $\beta_1$ splice variants, including $\beta_{1-1}$–$\beta_{1-5}$.

As used herein, a $\gamma$ subunit is a subunit encoded by DNA disclosed herein as encoding the $\gamma$ subunit and may be isolated and identified using the DNA disclosed herein as a probe by hybridization or other such method known to those of skill in the art, whereby full-length clones encoding a $\gamma$ subunit may be isolated or constructed. A $\gamma$ subunit will be encoded by DNA that hybridizes to the DNA provided herein under conditions of low stringency or exhibits sufficient sequence homology to encode a protein that has about 40% homology with the $\gamma$ subunit described herein.

Thus, one of skill in the art, in light of the disclosure herein, can identify DNA encoding $\alpha_1$, $\alpha_2$, $\beta$, $\gamma$ and calcium channel subunits, including types encoded by different genes and subtypes that represent splice variants. For example, DNA probes based on the DNA disclosed herein may be used to screen an appropriate library, including a genomic or cDNA library, and obtain DNA in one or more clones that includes an open reading fragment that encodes an entire protein. Subsequent to screening an appropriate library with the DNA disclosed herein, the isolated DNA can be examined for the presence of an open reading frame from which the sequence of the encoded protein may be deduced. Determination of the molecular weight and comparison with the sequences herein should reveal the identity of the subunit as an $\alpha_1$, $\alpha_2$ etc. subunit. Functional assays may, if necessary, be used to determine whether the subunit is an $\alpha_1$, $\alpha_2$ subunit or $\beta$ subunit.

For example, DNA encoding $\alpha_{1A}$ may be isolated by screening an appropriate library with DNA, encoding all or a portion of the human $\alpha_{1A}$ subunit, isolated from the phage deposited under ATCC Accession No. 75293, including screening with an oligonucleotide having the sequence set forth in SEQ ID No. 21. Similarly, DNA encoding $\beta_3$ may be isolated by screening a human cDNA library with DNA probes prepared from the plasmid $\beta$1.42 deposited under ATCC Accession No. 69048 or probes having sequences prepared according to the sequences set forth in SEQ ID Nos. 19 and 20. Any method known to those of skill in the art for isolation and identification of DNA and preparation of full-length genomic or cDNA clones, including methods exemplified herein, may be used.

The subunit encoded by isolated DNA may be identified by comparison with the DNA and amino acid sequences of the whereas subunits provided herein. Splice variants share extensive regions of homology, but include non-homologous regions, whereas subunits encoded by different genes share a uniform distribution of non-homologous sequences.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have regions of identical amino acids and regions of different amino acid sequences are referred to herein as "splice variants".

As used herein, a "calcium channel selective ion" is an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel selective ion.

As used herein, a compound that modulates calcium channel activity is one that affects the ability of the calcium channel to pass calcium channel selective ions or affects other detectable calcium channel features, such as current kinetics. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding the calcium channel subunit, may contain DNA encoding the same or different calcium channel subunits. The heterologous DNA need not be expressed and may be introduced in a manner such that it is integrated into the host dell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al.

(1982) *Molecular Cloning: A Laboratory Manual,* Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cells that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel selective ions, including, but not limited to, $Ca^{2+}$ or $Ba^{2+}$, in response to a stimulus and/or bind ligands with affinity for the channel. Preferably such calcium channel activity is distinguishable, such as electrophysiological, pharmacological and other means known to those of skill in the art, from any endogenous calcium channel activity that in the host cell.

As used herein, a peptide having an amino acid sequence substantially as set forth in a particular SEQ ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel selective ion is a concentration of the calcium channel selective ion necessary and sufficient to provide an inward current when the channels open.

As used herein, activity of a calcium channel refers to the movement of a calcium selective ion through a calcium channel. Such activity may be measured by any method known to those of skill in the art, including, but not limited to, measurement of the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally requires comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of test cell to the test compound compared to the response (or lack of response) of the receptor-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

Assays

Assays for identifying compounds that modulate calcium channel activity

In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit subtype- or tissue-specific calcium channel antagonist and agonist activities.

These assays should accurately predict the relative therapeutic efficacy of a compound for the treatment of certain disorders in humans. In addition, since subtype- and tissue-specific calcium channel subunits are provided, cells with tissue- specific or subtype-specific recombinant calcium channels may be prepared and used in assays for identification of human calcium channel tissue- or subtype-specific drugs.

The assays involve contacting the cell membrane of a recombinant eukaryotic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell which has a calcium channel containing an $\alpha_1$ subunit of a human calcium channel in combination with a $\beta$-subunit of a human calcium channel and/or an $\alpha_2$ subunit of a human calcium channel. Recombinant cells expressing heterologous calcium channels containing each of the $\alpha_1$, $\beta$ and $\alpha_2$ human subunits, and, optionally, a $\gamma$ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel selective ion and comparing the measured calcium channel activity to the calcium channel activity of the same cell or a substantially identical control cell in a solution not containing the test compound. The cell is maintained in a solution having a concentration of calcium channel selective ions sufficient to provide an inward current when the channels open. Especially preferred for use, is a recombinant cell expressing calcium channels that include each of the $\alpha_1$, $\beta$ and $\alpha_2$ human subunits, and, optionally, a $\gamma$ subunit of a human calcium channel. Methods for practicing such assays are known to those of skill in the art. For example, for similar methods applied with *Xenopus laevis* oöcytes and acetylcholine receptors, see, Mishina et al. [(1985) *Nature* 313:364] and, with such oöcytes and sodium channels [see, Noda et al. (1986) *Nature* 322:826–828]; For similar studies which have been carried out with the acetylcholine receptor, see, e.g., Claudio et al. [(1987) *Science* 238:1688–1694].

The assays thus use cells, provided herein, that express heterologous functional calcium channels and measure functionally, such as electrophysiologically, the ability of a test compound to potentiate, antagonize or otherwise modulate the magnitude and duration of the flow of calcium channel selective ions, such as $Ca^{++}$ or $Ba^{++}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner.

Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel selective on, such as $Ca^{2+}$ and $Ba^+$. The details of such transcriptional based assays are described in commonly owned PCT International Patent Application No. PCT/US91/5625, filed Aug, 7, 1991, which claims priority to copending commonly owned U.S. application Ser. No. 07/563,751, filed Aug. 7, 1990, the contents of which applications are herein incorporated by reference thereto.

Assays for diagnosis of LFS

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, Sciences 239:405–408 (1988)]. A diagnostic assay for Lambert Eaton Syndrome (LES) is provided herein. The diagnostic assay for LES relies on the immunological reactivity of LES IgG with the human calcium channels or particular subunits alone or in combination or expressed on the surface of recombinant cells. For example, such an assay may be based on immunoprecipitation of LES IgG by the human calcium channel subunits and cells that express such subunits provided herein.

Identification and isolation of DNA encoding human calcium channel subunits

Methods for identifying and isolating DNA encoding $\alpha_1$, $\alpha_2$, $\beta$ and $\gamma$ subunits of human calcium channels are provided.

Identification and isolation of such DNA may be accomplished by hybridizing, under appropriate conditions, at least low stringency whereby DNA that encodes the desired subunit is isolated, restriction enzyme-digested human DNA with a labeled probe having at least 14 nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. Full-length clones may be identified by the presence of a complete open reading frame and the identity of the encoded protein verified by sequence comparison with the subunits provided herein and by functional assays to assess calcium channel forming ability or other function. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences the DNA. Such sequence differences may indicate that the transcripts from which the cDNA was produced result from alternative splicing of a primary transcript, if the non-homologous and homologous regions are clustered, or from a different gene if the non-homologous regions are distributed throughout the cloned DNA.

Any suitable method for isolating genes using the DNA provided herein may be used. For example, oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled, including, but not limited to, radioactively or enzymatically labeled, RNA or single-stranded DNA of at least 14 substantially contiguous bases, preferably at least 30 contiguous bases of a nucleic acid which encodes at least a portion of a human calcium channel subunit, the sequence of which nucleic acid corresponds to a segment of a nucleic acid sequence disclosed herein by reference to a SEQ ID No. are provided. Such nucleic acid segments may be used as probes in the methods provided herein for cloning DNA encoding calcium channel subunits. See, generally, Sambrook et al. (1989) *Molecular Cloning: A Laboratory Manual*, 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization an yield DNA containing multiple exons, separated by introns, that correspond to different splice variants of transcripts encoding human calcium channel subunits.

DNA encoding types and subtypes of each of the $\alpha_1$, $\alpha_2$, $\beta$ and $\gamma$ subunit of voltage-dependent human calcium channels have been cloned herein by screening human cDNA libraries prepared from isolated poly A+ mRNA from cell lines or tissue of human origin having such calcium channels. Among the sources of such cells or tissue for obtaining ERA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

With respect to each of the respective subunits of a human calcium channel ($\alpha_1$, $\alpha_2$, $\beta$ or $\gamma$), once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start), and translation termination (stop) codons. For expression of the cloned DNA, the 5' noncoding region and other transcriptional and translational control regions of such a clone may be replaced with an efficient ribosome binding site and other regulatory regions as known in the art. Examples II–VI, below, describe in detail the cloning of each of the various subunits of a human calcium channel as well as subtypes and splice variants, including tissue-specific variants thereof. In the instances in which partial sequences of a subunit are disclosed, it is well within the skill of the art, in view of the teaching herein, to obtain the corresponding full-length nucleotide sequence encoding the subunit, subtype or splice variant thereof.

Identification and isolation of DNA encoding $\alpha_1$ subunits

A number of voltage-dependent calcium channel $\alpha_1$ subunit genes, which are expressed in the human CNS, have been identified and have been designated as $\alpha_{1A}$, $\alpha_{1B}$ (or VDCC IV), $\alpha_{1C}$ (or VDCC II) and $\alpha_{1D}$ (or VDCC III). DNA, isolated from a human neuronal cDNA library, that encodes each of the subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunits types A B, C, and D of voltage-dependent calcium channels, and subtypes thereof, differ with respect to sensitivity to known classes of calcium channel agonists and antagonists, such as DHPs, phenylalkylamines, omega conotoxin ($\omega$-CgTx) and pyrazonoylguanidines. They also appear to differ in the holding potential and ion the kinetics of currents produced upon depolarization of cell membranes containing calcium channels that include different types of $\alpha_1$ subunits.

DNA that encodes an $\alpha_1$-subunit that binds to at least one compound selected from among dihydropyridines, phenylalkylamines, $\omega$-CgTx, components of funnel web spider toxin, and pyrazonoylguanidines is provided. For example, the $\alpha_{1B}$ subunit provided herein appears to specifically interact with $\omega$-CgTx in N-type channels, and the $\alpha_{1D}$ subunit provided herein specifically interacts with DHPs in L-type channels.

Identification and isolation of DNA encoding the $\alpha_{1D}$ human calcium channel subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IXR32, to obtain clone $\alpha$1.36. This clone was used as a probe to screen additional IMR32 cell cDNA libraries to obtain overlapping clones, which were then employed for screening until a sufficient series of clones to span the length of the nucleotide sequence encoding the human. $\alpha_{1D}$ subunit were obtained. Full-length clones encoding $\alpha_{1D}$ were constructed by ligating portions of partial $\alpha_{1D}$ clones as described in Example II. SEQ ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in SEQ ID No. 1).

SEQ ID No. 2 provides the sequence of an alternative exon encoding the IS6 transmembrane domain [see Tanabe, T., et al. (1987) *Nature* 328:313–318 for a description of transmembrane domain terminology) of the $\alpha_{1D}$ subunit.

SEQ ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The $\alpha_{1D}$ subunit of the calcium channel contains four putative internal repeated sequence regions. Four internally repeated regions represent 24 putative transmembrane segments, and the amino- and carboxyl-termini extend intracellularly.

The $\alpha_{1D}$ subunit has been shown to madiate DHP-sensitive, high-voltage-activated, long-lasting calcium channel activity. This calcium channel activity was detected when oocytes were co-injected with. RNA transcripts encoding an $\alpha_{1D}$ and $\beta_1$ or $\alpha_{1D}$, $\alpha_2$ and $\beta_1$ subunits. This activity was distinguished from $Ba^{2+}$ currents detected when oocytes were injected with RNA transcripts encoding the $\beta_1$ $\pm\alpha_2$ subunits. These currents pharmacologically and biophysically resembled $Ca^{2+}$ currents reported for uninjected oocytes.

Identification and isolation DNA encoding the $\alpha_{1A}$ human calcium channel subunit Biological material containing DNA encoding the $\alpha_{1A}$ subunit had been deposited in the American Type Culture Collection, 12301 Parklawn Drive, Rockville, Md. 20852 U.S.A. under the terms of the Budapest treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The $\alpha_1$, subunit is encoded by an approximately 3 kb insert in λgt10 phage designated α1.254 in E. coli host strain NM514. A phage lysate of this material has been deposited as at the American Type Culture Collection under ATCC Accession No. 75293, as described above. DNA encoding $\alpha_{1A}$ may also be identified by screening with a probe prepared from DNA that has SEQ ID No. 21:

5' CTCAGTACCATCTCTGATACCAGCCCCA 3'.

Identification and isolation of DNA encoding the $\alpha_{1B}$ human calcium channel subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. PCR amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. SEQ ID Nos. 7 and 8 show the nucleotide sequences of DNA clones encoding the $\alpha_{1B}$ subunit as well as the deduced amino acid sequences. The $\alpha_{1B}$ subunit encoded by SEQ ID No. 7 is referred to as the $\alpha_{1B-1}$ subunit to distinguish it from another $\alpha_{1B}$ subunit $\alpha_{1b-2}$, encoded by the nucleotide sequence shown as SEQ ID No. 8, which is derived from alternative splicing of the $\alpha_{1B}$ subunit transcript.

PCR amplification of IMR32 cell mRNA using oligonucleotide primers designed according to nucleotide sequences within the $\alpha_{1B-1}$-encoding DNA has identified variants of the $\alpha_{1B}$ transcript that appear to be splice variants because they contain divergent coding sequences.

Identification and isolation of DNA encoding the $\alpha_{1C}$ human calcium channel subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. SEQ ID No. 3 sets forth DNA encoding an $\alpha_{1C}$ subunit. The DNA sequences set forth in SEQ ID No. 4 and No. 5 encode two possible amino terminal ends of the $\alpha_{1C}$ protein. SEQ ID No. 6 encodes an alternative exon for the IV S3 transmembrane domain.

The isolation and identification of DNA clones encoding portions of the $\alpha_{1C}$ subunit is described in detail in Example II.

DNA encoding other $\alpha_1$ subunits, including $\alpha_{1A}$, has also been isolated. Additional such subunits may also be, isolated and identified using the DNA provided herein as described for the $\alpha_{1B}$, $\alpha_{1C}$ and $\alpha_{1D}$ subunits or using other methods known to those of skill in the art.

Identification and isolation DNA encoding β human calcium channel subunits DNA encoding $\beta_1$ To isolate DNA encoding the $\beta_1$ subunit, a human hippocampus cDNA library was screened by hybridization to a DNA fragment encoding a rabbit skeletal muscle calcium channel β subunit. A hybridizing clone was selected and was in turn used to isolate overlapping clones until the overlapping clones encompassing DNA encoding the entire the human calcium channel β subunit were isolated and sequenced.

Five alternatively spliced forms of the human calcium channel $\beta_1$ subunit have been identified and DNA encoding a number of forms have been isolated. These forms are designated $\beta_{1-1}$, expressed in skeletal muscle, $\beta_{1-2}$, expressed in the CNS, $\beta_{1-3}$, also expressed in the in the CNS, $\beta_{1-4}$, expressed in aorta tissue and HEK 293 cells, and $\beta_{1-5}$, expressed in HEK 293 cells. A full-length DNA clone encoding the β1-2 subunit has been constructed. The subunits $\beta_{1-1}$, $\beta_{1-2}$, $\beta_{1-4}$ and $\beta_{1-5}$ have been identified by PCR analysis as alternatively spliced forms of the β subunit.

The alternatively spliced variants were identified by comparison of amino acid sequences encoded by the human neuronal and rabbit skeletal muscle calcium channel β subunit-encoding DNA. This comparison revealed a 45-amino acid deletion in the human β subunit compared to the rabbit β subunit. Using DNA from the region as a probe for DNA cloning, as well as PCR analysis and DNA sequencing of this area of sequence divergence, alternatively spliced forms of the human calcium channel β subunit transcript were identified. For example, the sequence of DNA encoding one splice variant $\beta_{12}$ is set forth in SEQ ID No. 9. SEQ ID No. 10 sets forth the sequence of the $\beta_{1-3}$ subunit (nt 1-1851, including 3' untranslated sequence nt 1795–1851), which is another splice variant of the β subunit primary transcript. $\beta_{1-2}$ and $\beta_{1-3}$ are human neuronal β subunits. DNA distinctive for a portion of a β subunit ($\beta_{1-4}$) of a human aortic calcium channel and also human embryonic kidney (HEK) cells is set forth in SEQ ID No. 12 (nt 1–13 and 191–271). The sequence of DNA encoding a portion of a human calcium channel β subunit expressed in skeletal muscle ($\beta_{1-1}$) is shown in SEQ ID No. 12 (nt 1-13 and 35-271).

DNA encoding $\beta_3$

DNA encoding the $\beta_3$ subunit and any splice variants thereof may be isolated by screening a library, as described above for the $\beta_1$ subunit, using DNA probes prepared according to SEQ ID Nos. 19 and 20 or using all or a portion of the deposited 3 clone plasmid β1.42 (ATCC Accession No. 69048).

The E. coli host containing plasmid β1.42 that includes DNA encoding the $\beta_3$ subunit has been deposited as ATCC Accession No. 69048 in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The $\beta_3$ encoding plasmid is designated $\beta$1.42. The plasmid contains a 2.5 kb EcoRI fragment encoding $\beta_3$ inserted into vector pGem7zF(+) and has been deposited in *E. coli* host strain DN5α. A partial DNA sequence of the 5' and 3' ends of $\beta_3$ are set forth in SEQ ID Nos. 19 and 20, respectively.

Identification and isolation DNA encoding the $\alpha_2$ human calcium channel subunit DNA encoding a human neuronal calcium channel $\alpha_2$ subunit was isolated in a manner substantially similar to that used for isolating DNA encoding an $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having, a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520, which is a continuation-in-parts of U.S. Ser. No. 176,899, filed Apr. 4, 1988, which applications have been incorporated herein by reference.

Example IV describes the isolation of DNA clones encoding $\alpha_2$ subunits of a human calcium channel from a human DNA library using genomic DNA and cDNA clones, identified by hybridization to the genomic DNA, as probes.

SEQ ID No. 11 shows the sequence of DNA encoding an 2 subunit. As described in Example V, PCR analysis of RNA from human skeletal muscle, brain tissue and aorta using oligonucleotide primers specific for a region of the human neuronal $\alpha_2$ subunit cDNA that diverges from the rabbit skeletal muscle calcium channel β2 subunit cDNA identified splice variants of the human calcium channel $\alpha_2$ subunit transcript.

Identification and isolation of DNA encoding γ human calcium channel subunits

DNA encoding a human neuronal calcium channel γ subunit has been isolated as described in detail in Example VI. SEQ ID No. 14 shows the nucleotide sequence at the 3'-end of this DNA which includes a reading frame encoding a sequence of 43 amino acid residues.

Preparation of recombinant eukaryotic cells containing DNA encoding heterologous calcium channel subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one, or more distinct genes or with linear DNA, and selection of transfected cells are also well known in the art [see, e.g., Sambrook et al. (1989) *Molecular Cloning: A Laboratory Manual, Second Edition,* Cold Spring Harbor Laboratory Press].

Cloned full-length DNA encoding any of the subunits of a human calcium channel may be introduced into a plasmid vector for expression in a eukaryotic cell. Such DNA may be genomic DNA or cDNA. Host cells may be transfected with one or a combination of said plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* [see, e.g., Cregg et al. (1987) *Bio/Technology* 5:479], mammalian expression systems for expression of the DNA encoding the human calcium channel subunits provided herein are preferred.

The heterologous DNA may be introduced by maintaining method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV or pCDNA1, and MMTV promoter-based vectors. DNA encoding the human calcium channel subunits has been inserted in the vector pCDNA1 at a position immediately following the CMV promoter.

Stably or transiently transfected mammalian cells may be prepared by methods known in the art by transfecting cells with an expression vector having a selectable marker gene such as the gene for thymidine kinase, dihydrofolate reductase, neomycin resistance or the like, and, for transient transfection, growing the transfected cells under conditions selective for cells expressing the marker gene. Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to cells of mammalian origin, such as CCS cells, mouse L cells, CHO cells, human embryonic kidney cells, African green morkey cells and other such cells known to those of skill in the art, amphibian cells, such as *Xenopus laevis* oöcytes, or those of yeast such as *Saccharomyces cerevisiae* or *Pichia pastoris*. Preferred cells for expressing injected RNA transcripts include *Xenopus laevis* oöcytes. Cells that are preferred for transfection of DNA are those that can be readily and efficiently transfected. Such cells are known to those of skill in the art or may be empirically identified. Preferred cells include DG44 cells and HEK 293 cells, particularly HEK 293 cells that have been adapted for growth in suspension and that can be frozen in liquid nitrogen and then thawed and regrown. Such HEK 293 cells are described, for example in U.S. Pat. No. 5,024,939 to Gorman [see, also Stillman et al. (1985) *Mol. Cell.Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or calcium channels containing the subunits.

Substantially pure subunits of a human calcium channel $\alpha_1$ subunits of a human calcium channel, $\alpha_2$ subunits of a human calcium channel, $\beta$ subunits of a human calcium channel and $\gamma$ subunits of a human calcium channel are provided. Substantially pure isolated calcium channels that contain at least one of the human calcium channel subunits are also provided. Substantially pure calcium channels that contain a mixture of one or more subunits encoded by the host cell and one or more subunits encoded by heterologous DNA or RNA that has been introduced into the cell are also provided. Substantially pure subtype- or tissue-type specific calcium channels are also provided.

In other embodiments, eukaryotic cells that contain heterologous DNA encoding at least one of an $\alpha_1$ subunit of a human calcium channel, an $\alpha_2$ subunit of a human calcium channel, a $\beta$ subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude not exhibited in the untransfected cell.

Preferred among such cells is a recombinant eukaryotic cell with a functional heterologous calcium channel. The recombinant cell can be produced by introduction of and expression of heterologous DNA or RNA transcripts encoding an $\alpha_1$ subunit of a human calcium channel, more preferably also expressing, a heterologous DNA encoding a $\beta$ subunit of a human calcium channel and/or heterologous DNA encoding an $\beta_2$ subunit of a human calcium channel. Especially preferred is the expression in such a recombinant cell of each of the $\alpha_1$, $\beta$ and $\alpha_1$ subunits encoded by such heterologous DNA or RNA transcripts, and optionally expression of heterologous DNA or an RNA transcript encoding a $\gamma$ subunit of a human calcium channel.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $\alpha_1$ subunit of a human calcium channel. More preferably, the composition that is introduced contains an RNA transcript which encodes an $\alpha_1$ subunit of a human calcium channel and also contains (1) an RNA transcript which encodes a $\beta$ subunit of a human calcium channel and/or (2) an RNA transcript which encodes an $\alpha_2$ subunit of a human calcium channel. Especially preferred is the introduction of RNA encoding an $\alpha_1$, a $\beta$ and an $\alpha_2$ human calcium channel subunit, and, optionally, a $\gamma$ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oöcytes are particularly preferred for expression of in vitro transcripts of the human calcium channel subunit cDNA clones provided herein.

The functional calcium channels may preferably include at least an $\alpha_1$ subunit and a $\beta$ subunit of a human calcium channel. Eukaryotic cells expressing these two subunits and also cells expressing additional subunits, have been prepared by transfection of DNA and by injection of RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a $\beta$ subunit have been shown to exhibit increased calcium selective ion flow across the cellular membrane in response to depolarization, indicating that the $\alpha_2$ subunit may potentiate calcium channel function.

Eukaryotic cells which express heterologous calcium channels containing at least a human $\alpha_1$ subunit, a human $\beta$ subunit and a human $\beta_2$ subunit are preferred. Eukaryotic cells transformed with a composition containing cDNA or an RNA transcript that encodes an $\alpha_1$ subunit alone or in combination with a $\beta$ and/or an $\alpha_2$ subunit may be used to produce cells that express functional calcium channels. Since recombinant cells expressing human calcium channels containing all of the of the human subunits encoded by the heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, pharmacological and electrophysiological means, including the use of differential holding potential, to increase the S/N ratio of the measured heterologous calcium channel activity.

Among the uses for eukaryotic cells which recombinantly express one or more subunits are assays for determining whether a test compound has calcium channel agonist or antagonist activity. Desirably, a host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays.

With respect to ligand binding assays, the host cells preferably should not produce endogenous calcium channels which detectably interact with compounds having, at physiological concentrations (generally nanomolar or picomolar concentrations), affinity for calcium channels that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically alter the activity of a calcium channel. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

Stably or transiently transfected cells or injected cells which express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium through a human calcium channel can be accomplished by (a) maintaining a eukaryotic cell which is transfected or injected to express a heterologous functional calcium channel capable of regulating the flow of calcium-channel selective ions into the cell in a medium containing calcium channel selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

Functional recombinant or heterologous calcium channels may be identified by any method known to those of skill in the art. For example, electrophysiological procedures for measuring the currently across an ion-selective membrane of a cell, which are well known, may be used. The amount and duration of the flow of calcium selective ions through heterologous calcium channels of a recombinant cell containing DNA encoding one or more of the subunits provided herein has been measured using electrophysiological recordings using a two electrode and the whole-cell patch clamp techniques. In order to improve the sensitivity of the assays, known methods can be used to eliminate or reduce non-calcium currents and calcium currents resulting from endogenous calcium channels, when measuring calcium currents through recombinant channels. For example, the DHP Bay K 8644 specifically enhances L-type calcium channel function by increasing the duration of the open state of the channels [see, e.g., Hess, J. B., et al. (1984) Nature 311:538–544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

EXAMPLES

The following examples are included for illustrative purposes only and are not intended to limit the scope of the invention.

EXAMPLE I

PREPARATION OF LIBRARIES USED FOR ISOLATION OF DNA ENCODING HUMAN NEURONAL VOLTAGE-DEPENDENT CALCIUM CHANNEL SUBUNITS

A. RNA Isolation

1. IMR32 cells

IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [(1988) *Nucleic Acids Research* 16:1487–1497]. Poly(A$^+$) RNA was selected according to standard procedures [see, e.g., Sambrook et al. (1989) is *Molecular Cloning, A Laboratory Manual*, Cold Spring Harbor Laboratory Press; pg. 7.26–7.29].

2. Human thalamus tissue

Human thalamus tissue. (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7M CsCl, 0.1M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25M NaCl and two volumes of 95% ethanol.

The precipitate was collected by centrifugation and resuspended in 4 ml PK buffer (0.05M TRIS, pH 8.4, 0.14M NaCl, 0.01M EDTA, 1% SDS). Proteinase K was added to the sample to a final concentration of 200 µg/ml. The sample was incubated at 22° C. for 1 h, followed by extraction with an equal volumes of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly A$^+$ RNA (3C μg) was isolated from the total RNA according to standard methods as stated in Example I.A.1.

B. Library construction

Double-stranded cDNA was synthesized according to standard methods [see, e.g., Sambrook et al. (1989) IN: *Molecular Cloning, A Laboratory Manual,* Cold Spring Harbor Laboratory Press, Chapter 8]. Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA library #1

Single-stranded cDNA was synthesized using IMR32 poly(A$^+$) RNA (Example I.A.1.) as a template and was primed using oligo (dT)$_{12-18}$ (Collaborative Research Inc., Bedford, Mass.). The single-stranded cDNA was converted to double-stranded cDNA and the yield was approximately 2μg. Ecol adapters:

5'-AATTCGGTACGTACACTCGAGc-3'-22-mer (SEQ ID No.15)

3'- GCCATGCATGTGAGCTCG-5'-18-mer (SEQ ID No.16)

also containing SnaBI and XhoI restriction sites were then added to the double-stranded cDNA according to the following procedure.

a. Phosphorylation of 18-mer

The 18-mer was phosphorylated using standard methods [see, e.g., Sambrook et al. (1989) IN: *Molecular Cloning, A Laboratory Manual,* Cold Spring Harbor Laboratory Press, Chapter 8] by combining in a 10 μl total volume the 18 mer (225 pmoles) with [$^{32}$P]γ-ATP (7000 Ci/mmole; 1.0 μl) and kinase (2 U) and incubating at 37° C. for 15 minutes. After incubation, 1 μL 10 mM ATP and an additional 2 U of kinase were added and incubated at 37° C. for 15 minutes. Kinase was then inactivated by boiling for 10 minutes.

b. Hybridization of 22-mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slow cool to room temperature.

The adapters were thus present at a concentration of 15 pmoles/μl, and were ready for cDNA-adapter ligation.

c. Ligation of adapters to cDNA

After the EcoRI, SnaBI, XhoI adapters were ligated to the double-stranded cDNA using a standard protocol [see, e.g., Sambrook, et al. (1989) *IN: Molecular Cloning, A Laboratory Manual,* Cold Spring Harbor Laboratory Press, Chapter 8], the ligase was inactivated by heating the mixture to 72° C. for 15 minutes. The following reagents were added to the cDNA ligation reaction and heated at 37° C. for 30 minutes: cDNA ligation reaction (20 μl), water (24 μl) lox kinase buffer (3 μl), 10 mM ATP (1 μl) and kinase (2 μl of 2 μl). The reaction was stopped by the addition of 2 μl 0.5M EDTA, followed by one phenol/chloroform extraction and one chloroform extraction.

A. Size selection and Packaging of cDNA

The double-stranded cDNA with the EcoRI, SnaBI, XhoI adapters ligated was purified away from the free or unligated adapters using a 5 ml Sepharose CL-4B column. (Sigma, St. Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λgt11 in a 5 μl reaction volume at a 2- to 4- fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA library #2

This library was prepared as described (Example I.B.1.) with the exception that 3 to 9 kb cDNA fragments were ligated into the λgt11 phage vector rather than the 1 to 3 kb fragments.

3. IMR32 cDNA library #3

IMR32 cell poly(A$^+$) RNA (Example I.A.1.) was used as a template to synthesize single-stranded cDNA. The primers for the first strand cDNA synthesis were random primers (hexadeoxy-nucleotides [pd(N)$_6$] Cat #5020-1, Clontech, Palo Alto, Calif.). The double-stranded cDNA was synthesized (Example 1.B.1.), EcoRI, SnaBI, XhoI adapters were added to the cDNA (Example I.B.1.), the unligated adapters were removed (Example I.B.1.), and the double-stranded cDNA with the ligated adapters was fractionated on an agarose gel (Example I.B.1.). The cDNA fraction greater than 1.8 kb was eluted from the agarose (Example I.B.1.), ligated into λgt11, packaged, and plated into a bacterial lawn of Y1088 (Example I.B.1.).

4. IMR32 cDNA library #4

IMR32 cell poly(A+) RNA (Example I.A.1.) was used as a template to synthesize single-stranded cDNA. The primers for the first strand cDNA synthesis were oligonucleotides: 89–365a specific for the $α_{1D}$ (VDCC III) type $α_1$-subunit (see Example II.A.) coding sequence (the complementary sequence of nt 292, to 2956, SEQ ID No. 1), 89–495 specific for the $α_{1C}$ (VDCC II) type $α_1$-subunit (see Example II.B.) coding sequence (the complementary sequence of nt 852 to 873, SEQ ID No. 3), and 90-12 specific for the $α_{1C}$-subunit coding sequence (the complementary sequence of nt 24.96 to 2520, SEQ ID No. 3). The cDNA library was then constructed as described (Example I.B.3), except that the cDNA size-fraction greater than 1.5 kb was eluted from the agarose rather than the greater than 1.8 kb fraction.

5. IMR32 cDNA library #5

The cDNA library was constructed as described (Example I.B.3.) with the exception that the size-fraction greater than 1.2 kb was eluted from the agarose rather than the greater than 1.8 kb fraction.

6. Human thalamus cDNA library #6

Human thalamus poly (A$^+$) RNA (Example I.A.2.) was used as a template to synthesize single-stranded cDNA.

Oligo (dT) was used to prime the first strand synthesis (Example I.B.1.). The double-stranded cDNA was synthesized (Example I.B.1.) and EcoRI, KpnI, NcoI adapters of the following sequence:

5'CCATGGTACCTTCGTTGACG 3'=20 mer (SEQ ID NO. 17)

3'GGTACCATGGAAGCAACTGCTTAA 5'=24 mer (SEQ ID No. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 µl) were collected and 1 µl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and washing Conditions

Hybridization of radiolabelled nucleic acids to immobilized DNA for the purpose of screening cDNA libraries, DNA Southern transfers, or northern transfers was routinely performed in standard hybridization conditions (5 x SSPE, 5x Denhardt's, 50% deionized formamide, 200 µg/ml sonicated herring sperm DNA (Cat 0223646, Boehringer Mannheim Biochemicals, Indianapolis, Ind.)]. The recipes for SSPE and Denhardt's and the preparation of deionized formamide are described, for example, in Sambrook et al. (1989) *Molecular Cloning, A Laboratory Manual,* Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1 x SSPE, 0.1% SDS, 65° C.

2) medium stringency: 0.2 x SSPE, 0.1% SDS, 50° C.

3) low stringency: 1.0 x SSPE, 0.1% SDS, 50° C.

It is understood that equivalent stringencies may be achieved using alternative buffers, salts and temperatures.

EXAMPLE II

ISOLATION OF DNA ENCODING THE HUMAN NEURONAL CALCIUM CHANNEL $\alpha_1$ SUBUNIT A. Isolation of DNA encoding the $\alpha_{ID}$ subunit 1. Reference list of partial $\alpha_{ID}$ cDNA clones Numerous $\alpha_{ID}$-specific cDNA clones were isolated in order to characterize the complete $\alpha_{ID}$ coding sequence plus portions of the 5' and 3' untranslated sequences. SEQ ID No. 1 shows the complete $\alpha_{1D}$ DNA coding sequence, plus 510 nucleotides of $\alpha_{ID}$ 5' untranslated sequence ending in the quanidine nucleotide adjacent to the adenine nucleotide of the proposed initiation of translation as well as 642 nucleotides of 3' untranslated sequence. Also shown in SEQ ID No. 1 is the deduced amino acid sequence, A list of partial cDNA clones used to characterize the $\alpha_{ID}$ sequence and the nucleotide position of each clone relative to the full-length $\alpha_{ID}$ cDNA sequence, which is set forth in SEQ ID No. 1, is shown below. The isolation and characterization of these clones are described below (Example II.A.2.).

| IMR32 | 1.144 | nt. 1 to 510 of 5' untranslated sequence, nt. 511 to 2431, | SEQ ID No. 1 SEQ ID No. 1 |
|---|---|---|---|
| IMR32* | 1.136 | nt. 1627 to 2988, nt. 1 to 104 of additional exon, | SEQ ID No. 1 SEQ ID No. 2 |
| IMR32@ | 1.80 | nt. 2083 to 6468, | SEQ ID No. 1 |
| IMR32# | 1.36 | nt. 2857 to 4281, | SEQ ID No. 1 |
| IMR32 | 1.163 | nt. 5200 to 7635, | SEQ ID No. 1 |

*5' of nt 1627, IMR32 1.136 encodes an intron and an additional exon described in Example II.A.2.d.
@IMR32 1.80 contains two deletions, nt 2984 to 3131 and nt 5303 to 5349 (SEQ ID No. 1). The 148 nt deletion (nt. 2984 to 3131) was corrected by performing a polymerase chain reaction described in Example II.A.3.b.
IMR32 1.36 contains a 132 nt deletion (nt. 3081 to 3212).

2. Isolation and characterization of individual clones listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel $\alpha_1$ cDNA for the sequence of the rabbit skeletal muscle calcium channel $\alpha_1$ subunit cDNA, see, Tanabe et al. (1987). *Nature* 328:313–318]:

| Fragment | Nuoleotides |
|---|---|
| KpnI—EcoRI | –78 to 1006 |
| EcoRI—XhoI | 1006 to 2653 |
| ApaI—ApaI | 3093 to 4182 |
| BglII—SacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the 2×10⁶ screened was identified. IMR32 1.36 was plaque purified by standard methods (J. Sambrook et al. (1989) *Molecular Cloning, A Laboratory Manual,* Cold Spring Harbor Laboratory Press, Chapter 8) subcloned into pGEM3 (Promega, Madison, Wis.) and characterized by DNA sequencing.

b. IMR32 1.80

Approximately 1×10⁶ recombinants of the IMR32 cDNA library 12 (Example I.B.2.) were screened in duplicate At a density of approximately 100,000 plaques per 150 mm plate using the IMR32 1.36 cDNA fragment (Example II.A.1) as a probe. Standard hybridization conditions were used (Example I.C), and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

C. IXR32 1.144

Approximately 1×10⁵ recombinants of the IMR32 cDNA library #3 (Example I.B.3) were screened with the EcoRI-PvuII fragment (nt 2083 to 2518, SEQ ID No. 1) of IMR32 1.80. The hybridization was performed using standard hybridization conditions (Example I.C.) and the filters were washed under high stringency (Example I.C.). Three positive plaques were identified one of which was IMR32 1.144. IM32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, SEQ ID No: 1). PCR analysis, and DNA sequencing of cloned PCR products encoding these seven ATG codons confirmed that this sequence is present in the $\alpha_{1D}$ transcript expressed in dbcAMP-induced IMR32 cells.

d. IMR32 1.136

Approximately $1 \times 10^6$ recombinants of the IMR32 cDNA library #4 (Example I.B.4) were screened with the EcoRI-PvuII fragment (nt 2083 to 2518, SEQ ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, pSP72 (Promega, Madison, Wis.), and characterized by DNA sequencing. This characterization revealed that IMR32 1.136 encodes an incompletely spliced $\alpha_{1D}$, transcript. The clone contains nucleotides 1627 to 2988 of SEQ ID No. 1 preceded by an approximate 640 bp intron. This intron is then preceded by a 104 nt ekon (SEQ ID No. 2), which is an alternative exon encoding the IS6 transmembrane domain [see, e.g., Tanabe et al. (1987) Nature 328:313–318 for a description of the IS1 to IVS6 transmembrane terminology] of the $\alpha_{1D}$ subunit and can replace nt 1627 to 1730, SEQ ID No. 1, to produce a completely spliced $\alpha_{1D}$ transcript.

e. IMR32 1.163

Approximately $1 \times 10^6$ recombinants of the IMR32 cDNA library #3 (Example I.B.3.) were screened with the NcoI-XhoI fragment of IMR32 1.80 (Example II.A.1.) containing nt 5811 to 6468 (SEQ ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, pSP72 (Promega, Madison, Wis.), and characterized by DNA sequencing. This characterization revealed that IMR32 1.163 contains the $\alpha_{1D}$ termination codon, nt 6994 to 6996 (SEQ ID No. 1).

3. Construction of a full-length $\alpha_{1D}$ cDNA [pVDCCIII (A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (SEQ ID No. 1), with the exception of a 148 bp deletion, nt 2984 to 3131 (SEQ ID No. 1). Portions of these partial cDNA clones were ligated to generate a full-length $\alpha_{1D}$ cDNA in a eukaryotic expression vector. The resulting vector was called pVDCCIII(A). The construction of PVDCOIII(A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII(A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatoan, Clifton, N.J.) and elution from the filter paper using 1.0M. NaCl, 10 mM TRIS, pH 8.0, 1 mM EDTA. The ligations typically were performed in a 10 μl reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2.c.) was digested with XhoI and EcoRI and the fragment containing the vector (pGEM7Z), $\alpha_{1D}$ nt 1 to 510 (SEQ ID No. 1), and $\alpha_{1D}$ nt 511 to 1732 (SEQ ID No. 1) was isolated by gel electrophoresis. The EcoRI-ApaI fragment of IMR32 1.136 (Example II.A.2.d.) nucleotides 1732 to 2667 (SEQ ID No. 1) was isolated, and the ApaI-HindIII fragment of IMR32 1.80 (Example II.A.2.b.), nucleotides 2667 to 4492 (SEQ ID No. 1) was isolated. The three DNA clones were ligated to form pVDCCIII/5' containing nt 1 to 510 (5' untranslated sequence; SEQ ID No. 1) and nt 511 to 4492 (SEQ ID No. 1).

b. pVDCCIII/5'.3

Comparison of the IMR32 1.36 and IMR32 1.80 DNA sequences revealed that these two cDNA clones differ through the AID coding sequence, nucleotides 2984 to 3212. PCR analysis of IMR32 1.80 and dbcAMP-induced,(1.0 mM, 10 days) IMR32 cytoplasmic RNA (isolated according to Ausubel, F. M. et al. (Eds) (1988) Current Protocols in Molecular Biology, John Wiley and Sons, New York) revealed that IMR32 1.80 had a 148 nt deletion, nt 2984 to 3131 (SEQ ID No. 1), and that IMR32 1.36 had a 132 nt deletion, nt 3081 to 3212. To perform the PCR analysis, amplification was primed with $\alpha_{1D}$-specific oligonucleotides 112 (nt 2548 to 2572, SEQ ID No. 1) and 311 (the complementary sequence of nt 3928 to 3957, SEQ ID No. 1). These products were then reamplified using $\alpha_{1D}$-specific oligonucleotides 310 (nt 2583 to 2600 SEQ ID No. 1) and 312 (the complementary sequence of nt 3883 to 3909). This reamplified product, which contains AccI and BglII restriction sites, was digested with AccI and BglII and the AccI-BglII fragment, nt 2764 to 3890 (SEQ ID No. 1) was cloned into AccI-BglII digested pVDCCIII/5' to replace the AccI-BglII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5α cells transformed with this plasmid due to fusion with the lacz gene. This plasmid was then digested with HindIII and BglII and the HindIII—BglII fragment (the HindIII site comes from the vector and the BglII site is at nt 6220, SEQ ID No. 1) was eliminated, thus deleting nt 5200 to 6220 (SEQ ID No. 1) of the IMR32 1.163 clone and removing this sequence from the remainder of the plasmid which contained the 3' BglII—XhoI fragment, nt 6220 to 7635 (SEQ ID No. 1). pVDCCIII/3'.1 was then made by splicing together the HindIII-PvuII fragment from IMR32 1.80 (nucleotides 4492–5294, SEQ ID No. 1), the PvuII—BgII fragment of IMR32 1.163 (nucleotides 5294 to 6220, SEQ TD No. 1) and the HindIII-BglII-digested pBluescript plasmid containing the 3' BglII/Xho3 IMR32 1.163 fragment (nt 6220 to 7635, SEQ ID No. 1).

d. pVDCCIII(A): the full-length $\alpha_{1D}$ construct

To construct pVDCCIII(A), the DraI-HindIII fragment (5' untranslated sequence nt 327 to 510, SEQ ID No. 1 and, coding sequence nt 511 to 4492, SEQ ID, No. 1) of pVDCCIII/5'.3 (Example II.A.3.b.) was isolated; the HindIII-XhoI fragment of pVDCCIII/3'.1 (containing nt 4492 to 7635, SEQ ID No. 1, plus the XhoI site of the adapter) (Example II.A.3.c.) was isolated; and the plasmid vector, pcDNA1, was digested with EcoRV and XhoI and isolated on an agarose gel. The three DNA fragments were ligated and MC1061-P3 (Invitrogen, San Diego, Calif.) was transformed. Isolated clones were analyzed by restriction mapping and DNA sequencing and pVDCCIII(A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, SEQ ID No. 1). This 5' portion plus nt 532 to 537, encoding two lysine residues, were deleted from pVDCCIII(A) and replaced with an efficient ribosomal binding site (5'-ACCACC-3') to form pVDCCIII.RBS (A). Expression experiments in which transcripts of this construct where injected into *Xenopus laevis* oöcytes did not result in an enhancement in the recombinant voltage-dependent calcium channel expression level relative to the level of expression in oöcytes injected with transcripts of pVDCCIII(A).

B. Isolation of DNA encoding the $\alpha_{1C}$ subunit

1. Reference List of Partial $\alpha_{1C}$ cDNA clones

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. SEQ ID No. 3 sets forth the characterized $\alpha_{1C}$ coding sequence nt 1 to 5904) and deduced amino acid sequence. SEQ ID No. 4 and No. 5 encode two possible amino terminal ends of the $\alpha_{1C}$ protein. SEQ ID No. 6 encodes an alternative exon for the IV S3 transmembrane domain. Shown below is a list of clones used to characterize the $\alpha_{1C}$ sequence and the nucleotide position of each clone relative to the characterized $\alpha_{1C}$ sequence (SEQ ID No. 3). The isolation and characterization of these cDNA clones are described below (Example II.B.2).

| IMR32 | 1.66 | nt 1 to 916, SEQ ID No. 3 |
| | | nt 1 to 132, SEQ ID No. 4 |
| IMR32 | 1.157 | nt 1 to 873, SEQ ID No. 3 |
| | | nt 1 to 89, SEQ ID No. 5 |
| IMR32 | 1.67 | nt 50 to 1717, SEQ ID No. 3 |
| *IMR32 | 1.86 | nt 1366 to 2583, SEQ ID No. 3 |
| (*) 1.16G | | nt 758 to 867, SEQ ID No. 3 |
| IMR32 | 1.37 | nt 2804 to 5904, SEQ ID No. 3 |
| CNS | 1.30 | nt 2199 to 3903, SEQ ID No. 3 |
| | | nt 1 to 84 of alternative exon, SEQ ID No. 6 |
| IMR32 | 1.38 | nt 2448 to 4702, SEQ ID No. 3 |
| | | nt 1 to 84 of alternative exon, SEQ ID No. 6 |

*IMR32 1.86 has a 73 nt deletion compared to the rabbit cardiac muscle calcium channel $\alpha_1$ subunit cDNA sequence.
(*) 1.16G is an $\alpha_{1C}$ genomic clone.

2. Isolation and characterization of clones described in Example 11.8.1.

a. CNS 1.30

Approximately $1\times10^6$ recombinants of the human thalamus cDNA library No. 6 (Example I.B.6.) were screened with fragments of the rabbit skeletal muscle calcium channel $\alpha_1$ cDNA described in. Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes $\alpha_{1C}$-specific sequence nt 2199 to 3903 (SEQ ID No. 3) followed by nt 1 to 84 of one of two identified alternative $\alpha_{1C}$ exons (SEQ ID No. 6). 3' of SEQ ID No. 6, CNS 1.30 contains an intron and, thus, CNS 1.30 encodes a partially spliced $\alpha_{1C}$ transcript.

b. 1.16G

Approximately $1\times10^6$ recombinants of a λEMBL3-based human genomic DNA library (Cat # HL1006d Clontech Corp., Palo Alto, Calif.) were screened using a rabbit skeletal muscle cDNA fragment (nt −78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$-specific sequence as described in Example II.B.1.

c. IMR32 1.66 and IMR32 1.67

Approximately $1\times10^6$ recombinants of IR32 cDNA library #5 (Example I.B.S.) were screened with a 151 bp KpnI-SacI fragment of 1.16G (Example II.B.2.b.) encoding tic sequence (nt 758 to 867, SEQ ID No. 3). The hybridization was performed using standard hybridization conditions (Example I.C.). The filters were then washed in 0.5 x SSPE at 65° C. Of the positive plaques, IMR32 1.66 and IMR32 1.67 were identified. The hybridizing plaques, were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32, 1.66 encodes a partially spliced $\alpha_{1C}$ transcript marked by a GT splice donor dinucleotide beginning at the nucleotide 3' of nt 916 (SEQ ID No. 3). The intron sequence within 1.66 is 101 nt long. IMR32 1.66 encodes the $\alpha_{1C}$ initiation of translation, nt 1 to 3 (SEQ ID No. 3) and 132 nt of 5' untranslated sequence (SEQ ID No. 4) precede the start codon in IMR32 1.66.

d. IMR32 1.37 and IMR32 1.38

Approximately $2\times10^6$ recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (SEQ ID No. 3) and IMR32 1.38 appears to be anomalously spliced to contain both exons juxtaposed, nt 3904 to 3987 (SEQ ID No. 3) followed by nt 1 to 84 (SEQ ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 contains nt 1 to 84 (SEQ ID No. 6) preceded by the identical sequence contained in IMR32 1.37 for nt 2199 to 3903 (SEQ ID No. 3). As described in Example II.B.2.a., an intron follows nt 1 to 84 (SEQ ID No. 6). Two alternative exons have been spliced adjacent to nt 3903 (SEQ ID No. 3) represented by CNS 1.30 and IMR32 1.37.

e. IMR32 1.86

IMR32 cDNA library #1 (Example I.B.1.) was screened in duplicate using oligonucleotide probes 90-9 (nt 1462 to 1491, SEQ ID No. 3) and 90-12 (nt 2496 to 2520, SEQ ID No. 3). These oligonucleotide probes were chosen in order to isolate a clone that encodes the $\alpha_{1C}$ subunit between the 3' end of IMR32 1.67 (nt 1717, SEQ ID No. 3) and the 5' end of CNS 1.30 (nt 2199, SEQ ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) *Nature* 340:230], nt 2191 to 2263. These missing nucleotides correspond to nt 2176-2248 of SEQ ID No. 3. Because the 5'-end of CNS 1.30 overlaps the 3'-end of IMR32 1.86, some of these missing nucleotides, i.e., nt 2205-2248 of SEQ ID No. 3, are accounted for by CNS 1.30. The remaining missing nucleotides of the 73 nucleotide deletion in IMR32 1.86 (i.e., nt 2176-220. SEQ ID No. 3) were determined by PCR analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and PCR analysis of IMR32 cell RNA) can be inserted into IMR32 1.86 by standard methods, e.g., replacement of a restriction fragment or site-directed mutagenesis.

f. IMR32 1.1S7

One million recombinants of IMR32 cDNA library #4 (Example I.B.4.) were screened with an XhoI-EcoRI fragment of IMR32 1.67 encoding $\alpha_{1C}$ nt 50 to 774 (SEQ ID No. 3). The hybridization was performed using standard hybridization conditions (Example I.C.). The filters were washed under high stringency (Example I.C.). One of the positive plaques identified was IMR32 1.157. This plaque was purified, the insert was restriction mapped and subcloned to a standard plasmid vector pGEM7Z (Promega, Madison, Wis.). The DNA was characterized by sequencing. IMR32 1.157 appears to encodes an alternative 5' portion of the $\alpha_{1C}$ sequence beginning with nt 1 to 89 (SEQ ID No. 5) and followed by nt 1 to 873 (SEQ ID No. 3). Analysis of the 1.66 and 1.157 5' sequence is described below (Example II.B.3.).

3. Characterization of the $\alpha_{1C}$ initiation of translation site

Portions of the sequences of IMR32 1.157 (nt 57 to 89, SEQ ID No. 5; nt 1 to 67, SEQ ID No. 3), IMR32 1.66 (nt 100 to 132, SEQ ID No. 4; nt 1 to 67, SEQ ID No. 3), were compared to he rabbit lung CaCB-receptor cDNA sequence, nt −33 to 67 [Biel et al. (1990) FEBS Lett. 269:409]. The human sequences are possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (SEQ ID No. 4). The start codon identified in the CaCB receptor cDNA sequence is the same start codon used to describe the $\alpha_{1C}$ coding sequence, nt 1 to 3 (SEQ ID No. 3). The functional significance of the IMR32 1.157 sequence, nt 1 to 89 (SEQ ID No. 5), is not clear. Chimeras containing sequence between 1.157 and the $\alpha_{1C}$ coding sequence can be constructed and functional differences can be tested.

C. Isolation of partial cDNA clones encoding the $\alpha_{1B}$ subunit and construction of a full-length clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of PCR analysis of IMR32 cell RNA to determine the accuracy of the cDNA sequences.

PCR analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding mRNA in IMR32 cells. This second mRNA product is the result of differential splicing of the $\alpha_{1B}$ subunit transcript to include another exon that is not present in the mRNA corresponding to the other 3' $\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B-1}$ (SEQ ID No. 7), whereas the subunit encoded by a DNA sequence corresponding to the form lacking the additional exon is referred to as $\alpha_{1B-2}$ (SEQ ID No. 8). The sequence of $\alpha_{1B-1}$ diverges from that of $\alpha_{1B-2}$ beginning at nt 6633 (SEQ ID No. 7). Following the sequence of the additional exon in $\alpha_{1B-1}$ (nt 6633-6819; SEQ ID No. 7), the $\alpha_{1B-1}$ and $\alpha_{1B-2}$ sequences are identical (i.e., nt 6820-7362 in SEQ ID No. 7 and nt 6633-7175 in SEQ ID No. 8). SEQ ID No. 7 and No. 8 set forth 143 nt of 5' untranslated sequence (nt 1-143) as well as 202 nt of 3' untranslated sequence (nt 7161-7362, SEQ ID No. 7) of the DNA encoding $\alpha_{1B-1}$ and 321 nt of 3' untranslated sequence (nt 6855-7175, SEQ ID No. 8) of the DNA encoding $\alpha_{1B-2}$.

PCR analysis of the IS6 region of the $\alpha_{1B}$ transcript revealed what appear to be additional splice variants based on multiple fragment sizes seen on an ethidium bromide-stained agarose gel containing the products of the PCR reaction.

A full-length $\alpha_{1B-1}$ cDNA clone designated pcDNA-$\alpha_{1B-1}$ was prepared in an eight-step process as follows.

STEP 1: The SacI restriction site of pGEM3 (Promega, Madison, Wis.) was destroyed by digestion at the SacI site, producing blunt ends by treatment with T4 DNA polymerase, and religation. The new vector was designated pGEMΔSac.

STEP 2: Fragment 1 (HindIII/KpnI; nt 2337 to 4303 of SEQ ID No. 7) was ligated into HindIII/KpnI digested pGEM3ΔSac to produce pα1.177HK.

STEP 3: Fragment 1 has a 2 nucleotide deletion (nt 3852 and 3853 of SEQ ID No. 7). The deletion was repaired by inserting a PCR fragment (fragment 2) of IMR32 RNA into pα1.177HK. Thus, fragment 2 (NarI/KpnI; nt 3828 to 4303 of SEQ ID No. 7) was inserted into NarI/XpnI digested pα1.177HK replacing the NarI/KpnI portion of fragment 1 and producing pα1.177HK/PCR.

STEP 4: Fragment 3 (XpnI/KpnI; nt,4303 to 5663 of SEQ ID No. 7) was ligated into KpnI digested pα1.177HK/PCR to produce pα1B5'K.

STEP 5: Fragment 4 (EcoRI/HindIII; EcoRI adaptor plus nt 1 to 2337 of SEQ ID No. 7) and fragment 5 (HindIII/XhoI fragment of pα1B5'K; nt 2337 to 5446 of SEQ ID No. 7) were ligated together into EcoRI/XhoI digested pcDNA1 (Invitrogen, San Diego, Calif.) to produce pα1B5'.

STEP 6: Fragment 6 (EcoRI/EcoRI; EcoRI adapters on both ends plus nt 5749 to 7362 of SEQ ID No. 7) was ligated into EcoRI digested pBluescript II KS (Stratagene, La Jolla, Calif.) with the 5' end of the fragment proximal to the KpnI site in the polylinker to produce pα1.230.

STEP 7: Fragment 7 (XpnI/XhoI; nt 4303 to 5446 of SEQ ID No. 7), and fragment 8 (XhoI/CspI, nt 5446 to 6259 of SEQ ID No. 7) were ligated into XpnI/CspI digested pα1.230 (removes nt 5749 to 6259 of SEQ ID No. 7 that was encoded in pα1.230 and maintains nt 6259 to 7362 of SEQ ID No. 7) to produce pα1B3'.

STEP 8: Fragment 9 (SphI/XhoI; nt 4993 to 5446 of SEQ ID No. 7) and fragment 10 (XhoI/XbaI of pα1B3'; nt 5446 to 7319 of SEQ ID No. 7) were ligated into SphI/XbaI digested pα1B5' (removes nt 4993 to 5446 of SEQ ID No. 7 that were encoded in pα1B5' and maintains nt 1 to 4850 of SEQ ID No. 7) to produce pcDNAα$_{1B-1}$.

The resulting construct, pcDNAα$_{1B-1}$, contains, in pcDNA1, a full-length coding region encoding α$_{1B-1}$ (nt 144-7362, SEQ ID No. 7), plus 5' untranslated sequence (nt 1-143, SEQ ID No. 7) and 3' untranslated sequence (nt 7161-7319, SEQ ID No. 7) under the transcriptional control of the CMV promoter.

EXAMPLE III

ISOLATION OF cDNA CLONES ENCODING THE HUMAN NEURONAL CALCIUM CHANNEL β$_1$ subunit A. Isolation of partial cDNA clones encoding the β subunit and construction of a full-length clone encoding the β$_1$ subunit A human hippocampus cDNA library was screened with the rabbit skeletal muscle calcium channel β$_1$ subunit cDNA fragment (nt 441 to 1379) [for isolation and sequence of the rabbit skeletal muscle calcium channel β$_1$ subunit cDNA, see U.S. patent application Ser. No. 482,384 or Ruth et al. (1989) Science 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel β$_1$ subunit cDNA sequence.

Portions of the partial β$_1$ subunit cDNA clones were ligated to generate a full-length clone encoding the entire β$_1$ subunit. SEQ ID No. 9 shows the β$_1$ subunit coding sequence (nt 1-1434) as well as a portion of the 3' untranslated sequence (nt 1435-1546). The deduced amino acid sequence is also provided in SEQ ID No. 9. In order to perform expression experiments, full-length β$_1$ subunit cDNA clones were constructed as follows.

Step 1: DNA fragment 1 (~800 bp of 5' untranslated sequence plus nt 1-277 of SEQ ID No. 9) was ligated to DNA fragment 2 (nt 277-1546 of SEQ ID No. 9 plus 448 bp of intron sequence) and cloned into pGEM7Z. The resulting plasmid, pβ1-1.18, contained a full-length β$_1$ subunit clone that included a 448-bp intron.

Step 2: To replace the 5' untranslated sequence of pβ1-1.18 with a ribosome binding site, a double-stranded adapter was synthesized that contains an EcoRI site, sequence encoding a ribosome binding site (5'-ACCACC-3') and nt 1-25 of SEQ ID No. 9. The adapter was ligated to SmaI-digested pβ1-1.18, and the products of the ligation reaction were digested with EcoRI.

Step 3: The EcoRI fragment from step 2 containing the EcoRI adapter, efficient ribosome binding site and nt 1-1546 of SEQ ID No. 9 plus intron sequence was cloned into a plasmid vector and designated pβ1-1.18RBS. The EcoRI fragment of pβ1-1.18RBS was subcloned into EcoRI-digested pcDNA1 with the initiation codon proximal to CMV promoter to form pHBCaCHβ$_{1a}$RBS(A).

Step 4: To generate a full-length clone encoding the β$_1$ subunit lacking intron sequence, DNA fragment 3 (nt 69-1146 of, SEQ ID No. 9 plus 448 bp of intron sequence followed by nt 1147-1546 of SEQ ID No. 9), was subjected to site-directed mutagenesis to delete the intron sequence, thereby yielding pα1(-). The EcoRI-XhoI fragment of pβ1-1.18RBS (containing of the ribosome binding site and nt 1-277 of SEQ ID No. 9) was ligated to the XhoI-EcoRI fragment of pβ1(-) (containing of nt 277-1546 of SEQ ID No. 9) and cloned into pcDNA1 with the initiation of translation proximal to the CMV promoter. The resulting Expression plasmid was designated pHBCaCHβ$_{1b}$RBS(A).

B. Splice variant β$_{1-3}$

DNA sequence analysis of the DNA clones encoding the β$_1$ subunit indicated that in the CNS at least two alternatively spliced forms of the same human β$_1$ subunit primary transcript are expressed. One form is represented by the sequence shown in SEQ ID No. 9 and is referred to as β$_{1-2}$. The sequences of β1-2 and the alternative form, β$_{1-3}$, diverge at nt 1334 (SEQ ID No. 9). The complete β$_{1-3}$ sequence (nt 1-1851), including 3' untranslated sequence (nt 1795-1851), is set forth in SEQ ID No. 10.

EXAMPLE IV

ISOLATION OF cDNA CLONES ENCODING THE HUMAN NEURONAL CALCIUM CHANNEL α$_2$-subunit A. Isolation of cDNA clones The complete human neuronal α$_2$ coding sequence (nt 35-3307) plus a portion of the 5' untranslated sequence (nt 1 to 34) as well as a portion of the 3' untranslated sequence (nt 3308-3600) is set forth in SEQ ID No. 11.

To isolate DNA encoding the human neuronal α$_2$ subunit, human α2 genomic clones first were isolated by probing human genomic Southern blots using a rabbit skeletal muscle calcium channel α$_2$ subunit cDNA fragment [nt 43 to 272, Ellis et al. (1988) *Science* 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a λgt11 library containing human genomic EcoRl fragments ranging from 2.2 kb to 4.3 kb. The library was screened as described above using the rabbit α$_2$ probe, hybridizing clones were isolated and characterized by DNA sequencing.

HGCaCHα2.20 contained the 3.5 kb fragment and HGCaCHα2.9 contained the 3.0 kb fragment.

Restriction mapping and DNA sequencing revealed that HGCaCHα2.20 contains an 82 bp exon (nt 130 to 211 of the human $\alpha_2$ coding sequence, SEQ ID No. 11) on a 650 bp PstI-XbaI restriction fragment and that HGCaCα2.9 contains 105 bp of an exon (nt 212 to 316 of the coding sequence, SEQ ID No. 11) on a 750 bp XbaI-BglII restriction fragment. These restriction fragments were used to screen the human basal ganglia cDNA library (Example II.C.2.a.). HBCaCHα2.1 was isolated (nt 29 to 1163, SEQ ID No. 11) and used to screen a human brain stem cDNA library (ATCC Accession No. 37432) obtained from the American Type Culture Collection, 12301 Parklawn Drive, Rockville, Md. 20852. Two clones were isolated, HBCaCHα2.5 (nt 1 to 1162, SEQ ID No. 11) and HBCaCHβ2.8 (nt 714 to 1562, SEQ ID No. 11, followed by 1600 nt of intervening sequence). A 2400 bp fragment of HBCaCHα2.8 (beginning at nt 759 of SEQ ID No. 11 and ending at a SmaI site in the intron) was used to rescreen the brain stem library and to isolate HBCaCHα2.11 (nt 879 to 3600, SEQ ID No. 11). Clones HBCaCHα2.5 and HBCaCHα2.11 overlap to encode an entire human brain $\alpha_2$ protein.

B. Construction of pHBCaCHα2

To construct pHBCaCHα2A containing DNA encoding a full-length human calcium channel $\alpha_2$ subunit, an (EcoRI)-PvUII fragment of HBCaCHα2.5 (nt 1 to 1061, SEQ ID No. 11, EcoRI adapter, PvuII partial digest) and a PvuII-PstI fragment of HBCaCHα2.11 (nt 1061 to 2424 SEQ ID No. 11; PvuII partial digest) were ligated into EcoRI-PstI-digested pIBI24 (Stratagene, La Jolla, Calif.). Subsequently, an (EcoRI)-PstI fragment (nt 1 to 2424 SEQ ID No. 11) was isolated and ligated to a PstI-(EcoRI) fragment (nt 2424 to 3600 SEQ ID No. 11) of HBCaCHα2.11 in EcoRI-digested pIBI24 to produce DNA, HBCaCHα2, encoding a full-length human brain $\alpha_2$ subunit. The 3600 bp EcoRI insert of HBCaCHα2 (nt 1 to 3600, SEQ ID No. 11) was subcloned into pcDNA1 (pHBaCHα2A) with the methionine initiating codon proximal to the CMV promoter. The 3600 bp EcoRI insert of HBCaCHα2 was also subcloned into pSV2dHFR [Subramani et al. (1981). *Mol. Cell. Biol.* 1:854–8643 which contains the SV40 early promoter, mouse dihydrofolate reductase (dhfr) gene, SV40 polyadenylation and splice sites and sequences required for maintenance of the vector in bacteria.

EXAMPLE V

DIFFERENTIAL PROCESSING OF THE HUMAN $\beta_1$ TRANSCRIPT AND THE HUMAN $\alpha_1$ TRANSCRIPT A. Differential processing of the $\beta_1$ transcript PCR analysis of the human $\beta_1$ transcript present in skeletal muscle, aorta, hippocampus and basal ganglia, and HEK 293 cells revealed differential processing of the region corresponding to nt 615-781 of SEQ ID No. 9 in each of the tissues. Four different sequences that result in five different processed $\beta_1$ transcripts through this region were identified. The $\beta_1$ transcripts from the different tissues contained different combinations of the four sequences, except for one of the $\beta_1$ transcripts expressed in HEK 293 cells ($\beta_{1-5}$) which lacked all four sequences.

None of the $\beta_1$ transcripts contained each of the four sequences; however, for ease of reference, all four sequences are set forth end-to-end as a single long sequence in SEQ ID No. 12. The four sequences that are differentially processed are sequence 1 (nt 14-34 in SEQ ID No. 12), sequence 2 (nt 35-55 in SEQ ID No. 12), sequence 3 (nt 56-190 in SEQ ID No. 12) and sequence 4 (nt 191-271 in SEQ ID No. 12). The forms of the $\beta_1$ transcript that have been identified include: (1) a form that lacks sequence 1 called $\beta_{1-1}$ (expressed in skeletal muscle), (2) a form that lacks sequences 2 and 3 called β1-2 (expressed in CNS), (3) a form that lacks sequences 1, 2 and 3 called $\beta_{1-4}$ (expressed in aorta and HEK cells) and (4) a form that lacks sequences 1–4 called $\beta_{1-5}$ (expressed in HEK cells). Additionally, the $\beta_{1-4}$ and $\beta_{1-5}$ forms contain the guanine nucleotide (nt 13 in SEQ ID No. 12) which is absent in the $\beta_{1-1}$ and $\beta_{1-2}$ forms. The sequences of DNA encoded the $\beta_1$ splice variants $\beta_{1-1}$, $\beta_{1-2}$, $\beta_{1-3}$, $\beta_{1-4}$ and $\beta_{1-5}$ are set forth in SEQ ID Nos. 26, 9, 10, 27 and 28, respectively B. Differential processing of transcripts encoding the $\alpha_2$ subunit.

The complete human neuronal $\alpha_2$ coding sequence (nt 35-3307) plus a portion of the 5' untranslated sequence (nt 1 to 34) as well as a portion of the 3' untranslated sequence (nt 3308-3600) is set forth as SEQ ID No. 11.

PCR analysis of the human $\alpha_2$ transcript present in skeletal muscle, aorta, and CNS revealed differential processing of the region corresponding to nt 1595-1942 of SEQ ID No. 11 in each of the tissues.

The analysis indicated that the primary transcript of the genomic DNA that includes the nucleotides corresponding to nt. 1595-1942 also includes an additional sequence (SEQ ID No. 13: 5'CCTATTGGTGTAGGTATACCAACAAT-TAATTT AAGAAAAAGGAGACCCAATATCCAG 3') inserted between nt. 1624 and 1625 of SEQ ID No. 11. Five alternatively spliced variant transcripts that differ in the presence or absence of one to three different portions of the region of the primary transcript that includes the region of nt. 1595-1942 of SEQ ID No. 11 plus SEQ ID No. 13 inserted between nt. 1624 and 1625 have been identified. The five $\alpha_2$-encocding transcripts from the different tissues include different combinations of the three sequences, except for one of the $\alpha_2$ transcripts expressed in aorta which lacks all three sequences. None of the $\alpha_2$ transcripts contained each of the three sequences. The sequences of the three regions that are differentially processed are sequence 1 (SEQ ID No. 13), sequence 2 ( 5' AACCCCAAATCTCAG 3,', which is nt. 1625-1639 of SEQ ID No. 11), and sequence 3 ( 5'CAAAAAAGGGCAAAATGAAGG 3', which is nt 1908-1928. of SEQ ID No. 11). The five α2 forms identified are (1) a form that lacks sequence 3 called $\alpha_{2a}$ (expressed in skeletal muscle), (2) a form that lacks sequence 1 called $\alpha_{2b}$, (expressed in CNS), (3) a form that lacks sequences 1 and 2 called $\alpha_{2c}$ expressed in aorta), (4) a form that lacks sequences 1, 2 and 3 called $\alpha_2$ (expressed in aorta) and (5) a form that lacks sequences 1 and 3 called $\beta_{2c}$ (expressed in aorta) The sequences of these splice variants, which are designated $\alpha_{2b}$, $\alpha_{2a}$, and $\alpha_{2c}$–$\alpha_{2c}$ are set forth in SEQ. ID Nos. 11 and 22–25, respectively.

EXAMPLE VI

ISOLATION OF DNA ENCODING A CALCIUM CHANNEL γ SUBUNIT FROM A HUMAN BRAIN cDNA LIBRARY

A isolation of DNA encoding the γ subunit

Approximately 1×10$^6$ recombinants from a λgt11-based human hippocampus cDNA library (Clontech catalog #HL1088b, Palo Alto, Calif.) were screened by hybridization to a 484 bp sequence of the rabbit skeletal muscle calcium channel γ subunit cDNA (nucleotides 621–626 of the coding sequence plus 438 nucleotides of 3'-untranslated sequence) contained in vector γJ10 (Jay, S. et al. (1990). *Science* 248:490–4923. Hybridization was performed using moderate stringency conditions (20% deionized formamide, 5x Denhardt's, 6 x SSPE, 0.2% SDS, 20 μg/ml herring sperm DNA, 42° C.) and the filters were washed under low stringency (see Example I.C.). A plaque that hybridized to this probe was purified and insert DNA was subcloned into pGEM7Z. This cDNA insert was designated γ1.4.

B. Characterization of γ1.4

γ1.4 was confirmed by DNA hybridization and characterized by DNA sequencing. The 1500 bp SstI fragment of γ1.4 hybridized to the rabbit skeletal muscle calcium channel γ subunit cDNA γJ10 on a Southern blot. SEQ analysis of this fragment revealed that it contains of approximately 500 nt of human DNA sequence and ~1000 nt of λgt11 sequence (included due to apparent destruction of one of the EcoRI cloning sites in λgt11). The human DNA sequence contains of 129 nt of coding sequence followed immediately by a translational STOP codon and 3' untranslated sequence (SEQ ID No. 14).

To isolate the remaining 5' sequence of the human γ subunit cDNA, human CNS cDNA libraries and/or preparations of mRNA from human CNS tissues can first be assayed by RCR methods using oligonucleotide primers based on the γ cDNA-specific sequence of γ1.4. Additional human neuronal γ subunit-encoding DNA can isolated from cDNA libraries that, based on the results of the PCR assay, contain γ-specific amplifiable cDNA. Alternatively, cDNA libraries can be constructed from mRNA preparations that, based on the results of pCR assays, contain γ-specific amplifiable transcripts. Such libraries are constructed by standard methods using oligo dT to prime first-strand cDNA synthesis from poly A+RNA (see Example I.B.). Alternatively, first-strand cDNA can be specified by priming first-strand cDNA synthesis with a γ cDNA-specific oligonucleotide based on the human DNA sequence in γ1.4. A cDNA library can then be constructed based on this first-strand synthesis and screened with the γ-specific portion of γ1.4.

EXAMPLE VII

RECOMBINANT EXPRESSION OF HUMAN NEURONAL CALCIUM CHANNEL SUBUNIT-ENCODING cDNA AND RNA TRANSCRIPTS IN MAMMALIAN CELLS

A. Recombinant Expression of the Human Neuronal Calcium Channel $\alpha_2$ subunit cDNA in DG44 Cells 1. Stable transfection of DG44cells DG44 cells [dhfr⁻ Chinese hamster ovary cells; see, e.g., Urlaub, G. et al. (1986) *Som. Cell Molec. Genet.* 12:555–566] obtained from Lawrence Chasin at Columbia University were stably transfected by $CaPO_4$ precipitation methods [Wigler et al. (1979) *Proc. Natl. Acad. Sci. USA* 76:1373–13763 with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ subunit cDNA expression in transfected DG44 cells

Total RNA was extracted according to the method of Birnboim [(1988) *Nuc. Acids Res.* 16:1487–1497] from four of the DG44 cell lines that had been stably transtected with pSV2dhfr containing the human neuronal calcium channel $\alpha_2$ subunit cDNA. RNA (~15 μg per lane) was separated on a 1% agarose formaldehyde gel, transferred to nitrocellulose and hybridized to the random-primed human neuronal calcium channel $\alpha_2$ cDNA (hybridization: 50% formamide, 5 x PESPE, 5 x Denhardt's, 42° C.; wash :0.2 x SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter [Gorman, C. and Howard, B. (1983) *Nucleic Acids Res.* 11:1631]. This cell line, $44\alpha_{2-9}$, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire 2 subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 μl of a solution containing 50 mM HEPES, 1 mM EDTA, 1 mM PMSP. An equal volume of 2x loading dye [Laemmli, U.K. (1970). *Nature* 227:690] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{123}$I]-protein A. The blot was exposed to X-ray film at –70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in $44\alpha_2$-9 cells that had been grown in the presence of 10 mM sodium butyrate than in $44\alpha_2$-9 cells that were grown in the absence of sodium butyrate. These data correlate well with those obtained in northern analyses of total RNA from $44\alpha_2$-9 and untransfected DG44 cells. Cell line $44\alpha_2$-9 also produced a 110 kD immunoreactive protein that may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA encoding human neuronal calcium channel $\alpha_1$, $\alpha_2$ and $\beta_1$ subunits in NK cells Human embryonic kidney cells (HEK 293 cells) were transiently and stably transfected with human neuronal DNA encoding calcium channel subunits. Individual transfectants were analyzed electrophysiologically for the presence of voltage-activated, barium, currents and functional recombinant voltage-dependent calcium channels were.

1. Transfection of REX 293 cells

Separate expression vectors containing DNA encoding human neuronal calcium channel $\alpha_{1D}$, $\alpha_2$ and $\beta_1$ subunits, plasmids pVDCCIII(A), pHBCaCHα-A, and pHBCaCHβ$_{1a}$RBS(A), respectively, were constructed as described in Examples II.A.3, IV.B. and III.B.3., respectively. These three vectors were used to transiently co-transfect HEK 293 cells. For stable transfection of HEK 293 cells, vector pHBCaCHβ$_{1b}$RBS(A) (Example III.B.3.) was used in place of pHBCaCHβ$_{1b}$RBS(A) to introduce the DNA encoding the $\beta_1$ subunit into the cells along with pVDCCIII(A) and pHBCaCHα$_2$A.

a. Transient transfection

Expression vectors pVDCCIII(A), pHBCaCHα$_2$A and pHBCaCHβ$_{1a}$RBS(A) were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta_1$ subunit cDNA expression plasmid and plasmid pCMVβgal (Clontech Laboratories, Palo Alto, Calif.). Plasmid pCMVβgal contains the lacZ gene (encoding E. coli β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII(A) and pCMVβgal. In both transfections, $2-4\times10^6$ HEK 293 cells in a 10-cm tissue culture plate were transiently co-transfected with 5 μg of each of the plasmids included in the experiment according to standard CaPO$_4$ precipitation transfection procedures (Wigler et al. (1979) Proc. Natl. Acad. Sci. USA 76:1373–1376). The transfectants were analyzed for β-galactosidase expression by direct staining of the product of a reaction involving β-galactosidase and the X-gal substrate [Jones, J. R. (1986) EMBO 5:3133–3142] and by measurement of β-galactosidase activity [Miller, J. H. (1972) Experiments in Molecular Genetics, pp. 352–355, Cold Spring Harbor Press]. To evaluate subunit cDNA expression in these transfectants,. the cells were analyzed for subunit transcript production (northern analysis), subunit protein production (immunoblot analysis of cell lysates) and functional calcium channel expression (electrophysiological analysis).

b. Stable transfection

HEK 293 cells were transfected using the calcium phosphate transfection procedure (Current Protocols In Molecular Biology, Vol. 1, Wiley Inter-Science, Supplement 14, Unit 9.1.1–9.1.9 (1990)]. Ten-cm plates, each containing ore-to-two million HEK 293 cells, were transfected with 1 ml of DNA/calcium phosphate precipitate containing 5 μg pVDCCIII(A), 5 μg pHBCaCHα2A, 5 μg pHBCaCHβ$_{1b}$RBS(A), 5 μg pCMVBgal and 1 μg pSV2neo (as a selectable marker). After 10–20 days of growth in media containing 500 μg G418, colonies had formed and were isolated using cloning cylinders.

2. Analysis of HEX 293 cells transiently transfected with DNA encoding human neuronal calcium channel subunits a. Analysis of β-galactosidase expression Transient transfectants were assayed for β-galactosidase expression by β-galactosidase activity assays (Miller, J. H., (1972) Experiments in Molecular Genetics, pp. 352–355, Cold Spring Harbor Press) of cell lysates (prepared as described in Example VII.A.2) and staining of fixed cells (Jones, J. R. (1986) EMBO 5:3133–3142). The results of these assays indicated that approximately 30% of the HEK 293 cells had been transfected.

b. Northern analysis

PolyA+ RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta_1$ subunits and the lacZ gene or the $\alpha_1$ subunit and the lacz gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit encoding cDNA, human neuronal calcium channel $\alpha_2$ subunit-encoding cDNA or human neuronal calcium channel $\beta_1$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta_1$ subunits and the lacz gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this stranscript. RNA of the size expected for the transcript of the lacZ gene was detected in cells transfected with the $\alpha_1$, $\alpha_2$ and β1, subunit-encoding cDNA and the lacZ gene and in cells transfected with the $\alpha_1$ subunit cDNA and the lacz gene by hybridization to the lacz gene sequence.

RNA from cells transfected with the $\alpha_1$, $\alpha_2$ and $\beta_1$ subunit-encoding cDNA and the lacz gene was also hybridized with the $\alpha_2$ and $\beta_1$ subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta_1$ subunit-encoding cDNA and the lacZ gene hybridized to the $\beta_1$ subunit cDNA probe. Multiple β-subunit transcripts of varying sizes were produced since the β subunit cDNA expression vector contains two potential polyA$^+$ addition sites.

c. Electrophysiological analysis

Individual transiently transfected HEK 293 cells were assayed for the presence of voltage-dependent barium currents using the whole-cell variant of the patch clamp technique (Hamill et al. (1981). Pflugers Arch. 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM MgCl$_2$ and was buffered at pH 7.3 with 10 mM HEPES (pH adjusted with sodium or tetraethylammonium hydroxide). Patch pipettes were filled with a solution containing 135 mM CsCl, 1 mM MgCl$_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data, were analyzed with pclamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath, solution before they were applied.

Twenty-one negative control HEK 293 cells (transiently transfected with the lacZ gene expression vector pCMVβgal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\alpha_2$ and $\beta_1$ subunit-encoding cDNA and the lacZ gene, individual transfectants were assayed for voltage dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (~160 pA) was recorded when the membrane was depolarized to 0 mV in the presence of 1 μM Bay K 8644. A comparison of the I–V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta_1$ subunit-encoding cDNA and the lacZ gene, indicating that the recombinant calcium channels responsible for the voltage-activated barium currents recorded in this transfected appear to be DHP-sensitive.

The second of the two transfected cells that displayed inward barium currents expressed a −50 pA current when the membrane was depolarized from −9.0 mV. This current was nearly completely blocked by 200 μM cadmium, an established calcium channel blocker.

Ten cells that were transiently transfected with the DNA encoding the $\alpha_1$ subunit and the lacz gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of REK 293 cells stably transfected with DNA encoding human neuronal calcium channel subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) Rev. *Physiol. Biochem. Pharmacol.* 114:107–207], cAMP (Na salt, 250 μM) was added to the pipet solution and forskolin (10 μM) was added to the bath solution in some of the recordings. Qualitatively similar results were obtained whether these compounds were present or not.

Barium currents were recorded from stably transfected cells in the absence and presence of Bay K 8644 (1 μM). When the cell was depolarized to −10 mV from a holding potential of −90 mV in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, are negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-based vectors and pcDNA1-based vectors for expression of DNA encoding human neuronal calcium channel subunits 1. Preparation of constructs To determine if the levels of recombinant expression of human calcium channel subunit-encoding DNA in host cells could be enhanced by using pCMV-based instead of pcDNA1-based expression vectors, additional expression vectors were constructed. The full-length $\alpha_{1D}$ cDNA from pVDCCIII(A) (see Example II.A.3.d), the full-length $\alpha_2$ cDNA, contained on a 3600 bp EcoRI fragment from HBCaCH$\alpha_2$ (see Example IV.B) and a full-length $\beta_1$ subunit cDNA from pHDCaCHβ$_{1b}$RBS(A) (see Example III.B.3) were separately subcloned into plasmid pCMVβgal. Plasmid pCMVβgal was digested with NotI to remove the lacz gene. The remaining vector portion of the plasmid, referred to as pCMV, was blunt-ended at the NotI sites. The full-length $\alpha_2$-encoding DNA and $\beta_1$-encoding DNA, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence of restriction enzyme recognition sites:

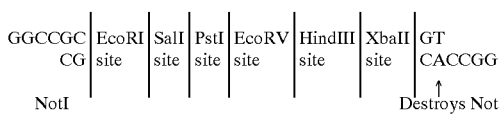

The $\alpha_{1D}$-encoding DNA, isolated as a BamHI/XhoI fragment from pVDCCIII(A), was then ligated to XbaII/SalI-digested pCMV to place it between the CMV promoter and SV40 polyadanylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 cells

HEK 293 cells were transiently co-transfected with the $\alpha_{1D}$, $\alpha_2$ and $\beta_1$ subunit-encoding DNA in pCMV or with the $\alpha_{1D}$, $\alpha_2$ and $\beta$ subunit-encoding DNA in pcDNA1 (vectors pVDCCIII(A), pHBCaCH$\alpha_2$A and pHBCaCH$\beta_{1b}$RBS (A), respectively), as described in Example VII.B.1.a. Plasmid pCMV$\beta$gal was included in each transfection to as a measure of transfection efficiency. The results of $\beta$-galactosidase assays of the transfectants (see Example VII.B.2.), indicated that HEX 293 cells were transfected equally efficiently with pCMV- and pcDNA1-based plasmids.

3. Northern analysis

Total and polyA$^+$ RNA were isolated from the transiently transfected cells as described in Examples VII.A.2 and VII.B.2.b. Northern blots of the RNA were hybridized with the following radiolabeled probes: $\alpha_{1D}$ cDNA, human neuronal calcium channel $\alpha_2$ subunit cDNA and DNA encoding the human neuronal calcium channel $\beta_1$ subunit. Messenger RNA of sizes expected for $\alpha_{1D}$, $\alpha_2$ and $\beta_1$ subunit transcripts were detected in all transfectants. A greater amount of the $\alpha_{1D}$ transcript was present in cells that were co-transfected with pCMV-based plasmids then in cells that were co-transfected with pcDNA1-based plasmids. Equivalent amounts of $\alpha_2$ and $\beta_1$ subunit transcripts were detected in all transfectants.

D. Expression in *Xenopus laevis* oöcytes of RNA encoding human neuronal calcium channel subunits Various combinations of the transcripts of DNA encoding the human neuronal $\alpha_{1D}$, $\alpha_2$ and $\beta_1$ subunits prepared in vitro were injected into *Xenopus laevis* oöcytes. Those injected with combinations that included a D exhibited voltage-activated barium currents.

1. Preparation of transcripts

Transcripts encoding the human neuronal calcium channel $\alpha_{1D}$, $\alpha_2$ and $\beta_1$ subunits were synthesized according to the instructions of the mCAP mRNA CAPPING KIT (Strategene, La Jolla, Calif. catalog #200350). Plasmids PVDCC III.RBS(A), containing of pcDNA1 and the $\alpha_{1D}$ cDNA that begins with a ribosome binding site and the eighth ATG codon of the coding sequence (see Example III.A.3.d), plasmid pHBCaCH$\alpha_1$A containing of pcDNA1 and an $\alpha$2 subunit cDNA (see Example IV), and plasmid pHBCaCHP$\alpha_1$RBS(A) containing pcDNA1 and the $\beta_1$ DNA lacking intron sequence and containing a ribosome binding site (see Example III), were linearized by restriction digestion. The $\alpha_{1D}$ cDNA- and $a_2$ subunit-encoding plasmids were digested with XhoI, and the $\beta_1$ subunit-encoding plasmid was digested with EcoRV. The DNA insert was transcribed with T7 RNA polymerase.

2. Injection of oöcytes

*Xenopus laevis* oöcytes were isolated and defolliculated by collagenase treatment and maintained in 100 mM NaCl, 2 mM KCl, 1.8 mM CaCl$_2$, 1 mM MgCl$_2$, 5 mM HEPES, pH 7.6, 20 μg/ml ampicillin and 25 μg/ml streptomycin at 19°–25° C. for 2 to 5 days after, injection and prior to recording. For each transcript that was injected into the oöcyte, 6 ng of the specific mRNA was injected per cell in a total volume of 50 nl.

3. Intracellular voltage recordings

Injected oöcytes were examined for voltage-dependent barium currents using two-electrode voltage clamp methods [Dascal, N. (1987) CRC Crit. *Rev. Biochem.* 22:317]. The pclamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM BaCl$_2$, 36 mM tetraethylammonium chloride (TEA-Cl), 2 mr KCl, 5 mM 4-aminopyridine, 0.15 mM niflumic acid, 5 mM HEPES, pH 7.6.

a. Electrophysiological analysis of oöcytes injected with transcripts encoding the human neuronal calcium channel $\alpha_1$, $\alpha_2$ and $\beta_1$-subunits Uninjected oöcytes were examined by two-electrode voltage clamp methods and a very small (25 nA) endogenous inward Ba$^{2+}$ current was detected in only one of seven analyzed cells.

Oöcytes coinjected with $\alpha_{1D}$, $\alpha_2$ and $\beta_1$ subunit transcripts expressed sustained inward barium currents upon depolarization of the membrane from a holding potential of –90 mV or –50 mV (154±129 nA, n=21). These currents typically showed little inactivation when test pulses ranging from 140 to 700 msec. were administered. Depolarization to a series of voltages revealed currents that first appeared at approximately –30 mV and peaked at approximately 0 mV.

Application of the DHP Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a lox concentrate directly into the CO μl bath while the perfusion pump was turned off. The DMSO concentration of the final diluted drug solutions in contact with the cell never exceeded 0.1%. Control experiments showed that 0.1% DMSO had no effect on membrane currents.

Application of the DHP antagonist nifedipine (stock solution prepared in DMSO and applied to the cell as described for application of Bay K 8644) blocked a substantial fraction (91±6%, n=7) of the inward barium current in oöcytes coinjected with transcripts of the $\alpha_{1D}$, $\beta_2$ and $\beta_1$ subunits. A residual inactivating component of the inward barium current typically remained- after nifedipine application. The inward barium current was blocked completely by 50 μM Cd$^{2+}$, but only approximately 15% by 100 μM Ni$^{2+}$.

The effect of ωCgTX on the inward barium currents in oöcytes co-injected with transcripts of the $\alpha_{1D}$, $\alpha_2$, and $\beta_1$ subunits was investigated. ωCgTX (Bachem, Inc., Torrance Calif.) was prepared in the 15 mM BaCd$_2$ bath solution plus 0.1% cytochrome C (sigma) to serve as a carrier protein.

Control experiments showed that cytochrome C had no effect on currents. A series of voltage pulses from a. −90 mV holding potential to 0 mV were recorded at 20 msec. intervals. To reduce the inhibition of ωCgTX binding by divalent cations, recordings were made in 15 mM BaCl$_2$, 73.5 mM tetraethylammonium chloride, and the remaining ingredients identical to the 40 mM Ba$^{2+}$ recording solution. Bay K 8644 was applied to the cell prior to addition to ωCgTX in order to determine the effect of ωCGTX on the DHP-sensitive current component that was distinguished by the prolonged tail currents. The inward, barium current was blocked weakly (54±29%, n=7) and reversibly by relatively high concentrations (10–15 μM) of ωCgTX. The test currents and the accompanying tail currents were blocked progressively within two to three minutes after application of ωCgTX, but both recovered partially as the ωcgTX was flushed from the bath.

b. Analysis of oöcytes injected with only a transcripts encoding the human neuronal calcium channel $\alpha_{1D}$ or transcripts encoding an $\alpha_{1D}$ and other subunits The contribution of the $\alpha_2$ and $\beta_1$ subunits to the inward barium current in oöcytes injected with transcripts encoding the $\alpha_{1D}$, $\beta_2$ and $\beta_1$ subunits was assessed by expression of the $\alpha_{1D}$ subunit alone or in combination with either the $\beta_1$ subunit or the $\alpha_2$ subunit. In oöcytes injected with only the transcript of a $\alpha_{1D}$ cDNA, no Ba$^{2+}$ currents were detected (n-3). In oöcytes injected with transcripts of $\alpha_{1D}$ and $\beta_1$ cDNAs, small (108±39 nA) Ba$^{2+}$ currents were detected upon depolarization of the membrane from a holding potential of −90 mV that resembled the currents observed in cells injected with transcripts of $\alpha_{1D}$, $\alpha_2$ and $\beta_1$ cDNAs, although the magnitude of the current was less. In two of the four oöcytes injected with transcripts of the $\alpha_{1D}$-encoding and $\beta_1$-encoding DNA, the Ba$^{2+}$ currents exhibited a sensitivity to Bay X 8644 that was similar to the Bay K 8644 sensitivity of Ba$^{2+}$ currents expressed in oöcytes injected with transcripts encoding the $\alpha_{1D}$ $\alpha_1$-, $\alpha_2$, and $\beta_1$ subunits.

Three of five o8cytes injected with transcripts encoding the $\alpha_{1D}$ and $\alpha_2$ subunits exhibited very small Ba$^{2+}$ currents (15–30 nA) upon depolarization of the membrane from a holding potential of −90 mV. These barium currents showed little or no response to Bay K 8644.

C. Analysis of oöcytes injected with transcripts encoding the human neuronal calcium channel $\alpha_2$ and/or $\beta_1$ subunit To evaluate the contribution of the $\alpha_{1D}$ $\alpha_1$-subunit to the inward barium currents detected in oöcytes co-injected with transcripts encoding the $\alpha_{1D}$, $\alpha_2$ and $\beta_1$ subunits, oöcytes injected with transcripts encoding the human neuronal calcium channel $\alpha_2$ and/or $\beta_1$ subunits were assayed for barium currents. Oöcytes injected with transcripts encoding the $\alpha_2$ subunit displayed no detectable inward barium currents (n-5). Oöcytes injected with transcripts encoding a $\beta_1$ subunit displayed measurable (54±23 nA, n=S) inward barium currents upon depolarization and oöcytes injected with transcripts encoding the $\alpha_2$ and $\beta_1$ subunits displayed inward barium currents that were approximately 50% larger (80±61 nA, n=18) than those detected in oöcytes injected with transcripts of the $\beta_1$-encoding DNA only.

The inward barium currents in oöcytes injected with transcripts encoding the $\beta_1$ subunit or $\alpha_2$ and $\beta_1$ subunits typically were first observed when the membrane was depolarized to −30 mV from a holding potential of −90 mV and peaked when the membrane was depolarized to 10 to 20 mV. Macroscopically, the currents in oöcytes injected with transcripts encoding the $\alpha_2$ and $\beta_1$ subunits or with transcripts encoding the $\beta_1$ subunit were indistinguishable. In contrast to the currents in oöcytes co-injected with transcripts of $\alpha_{1D}$, $\alpha_2$ and $\beta_1$ subunit cDNAs, these currents showed a significant inactivation during the test pulse and a strong sensitivity to the holding potential. The inward barium currents in oöcytes co-injected with transcripts encoding the $\alpha_2$ and $\beta_1$ subunits usually inactivated to 10–60% of the peak magnitude during a 140-msec pulse and were significantly more sensitive to holding potential than those in oöcytes co-injected with transcripts encoding the $\alpha_{1D}$, $\alpha_2$ and β1 subunits. Changing the holding potential of the membranes of oöcytes co-injected with transcripts encoding the $\alpha_2$ and $\beta_1$ subunits from −90 to −50 mV resulted in an approximately 81% (n=11) reduction in the magnitude of the inward barium current of these cells. In contrast, the inward barium current measured in oöcytes co-injected with transcripts encoding the $\alpha_{1D}$, $\alpha_2$ and $\beta_1$ subunits were reduced approximately 24% (n-11) when the holding potential was changed from −90 to −50 mV.

The inward barium currents detected in oöcytes injected with transcripts encoding the $\alpha_2$ and $\beta_1$ subunits were pharmacologically distinct from those observed in oöcytes co-injected with transcripts encoding the $\alpha_{1D}$, $\alpha_2$ and $\beta_1$ subunits. Oöcytes injected with transcripts encoding the $\alpha_2$ and $\beta_1$ subunits displayed inward barium currents that were insensitive to Bay K 8644 (n=11). Nifedipine sensitivity was difficult to measure because of the holding potential sensitivity of nifedipine and the current observed in oöcytes injected with transcripts encoding the $\beta_2$ and $\beta_1$ subunits. Nevertheless, two oöcytes that were co-injected with transcripts encoding the $\alpha_2$ and $\beta_1$ subunits displayed measurable (25 to 45 nA) inward barium currents when depolarized from a holding potential of −50 mV. These currents were insensitive to nifedipine (5 to 10 μM). The inward barium currents in oöcytes injected with transcripts encoding the $\alpha_2$ and $\beta_1$ subunits showed the same sensitivity to heavy metals as the currents detected in oöcytes injected with transcripts encoding the $\alpha_{1D}$, $\alpha_2$ and $\beta_1$ subunits.

The inward barium current detected in oöcytes injected with transcripts encoding the human neuronal $\alpha_2$ and $\beta_1$ subunits has pharmacological and biophysical properties that resemble calcium currents in uninjected Xenopus oöcytes. Because the amino acids of this human neuronal calcium channel $\beta_1$ subunit lack hydrophobic segments capable of forming transmembrane domains, it is unlikely that recombinant $\beta_1$ subunits alone can form an ion channel. It is more probable that a homologous endogenous $\alpha_1$ subunit exists in oöcytes and that the activity mediated by such an $\alpha_1$ subunit is enhanced by expression of a human neuronal $\beta_1$ subunit.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

What is claimed is:

1. A method for identifying a compound that modulates the activity of a calcium channel, comprising;
   suspending a eukaryotic cell which has a functional, heterologous calcium channel, in a solution containing a test compound and a calcium channel selective ion;
   depolarizing the cell membrane of said cell;
   detecting the current flowing into said cell; and
   comparing the current flowing into the cell with the current that flows into the same or a substantially identical cell suspended in the presence of the same calcium channel selective ion but in the absence of the compound, whereby test compounds that modulate the activity of a calcium channel are identified, wherein:
   the heterologous calcium channel includes one or more human calcium channel subunits expressed by nucleic acid that is heterologous to said cell;
   the only heterologous ion channels that are expressed by the cells are calcium channels;
   the current that is detected in the presence of a compound that modulates the activity of the heterologous calcium channel is different from that produced when the same or a substantially identical cell in the presence of the same calcium channel selective ion but in the absence of said compound is depolarized;
   the one or more subunits comprise $\alpha_1$-subunit selected from the group consisting of:
      an $\alpha_{1C}$-subunit comprising the sequence of amino acids encoded by the sequence nucleotides set forth in SEQ ID NO. 3;
      an $a_{1D}$ subunit comprising the sequence of amino acids encoded by the sequence of nucleotides set forth in SEQ ID NO: 1 or SEQ ID NO. 29;
      a human calcium channel $\alpha_1$-subunit that is encoded by a DNA molecule capable of hybridizing under conditions of high stringency with DNA that is fully complementary to an mRNA transcript native to a human cell that encodes one of the aforesaid human calcium channel $\alpha_1$-subunits, such that any probe that contains at least 14 contiguous bases from the coding portion of the $\alpha_1$-subunit-encoding DNA molecule is capable of hybridizing under conditions of high stringency to the DNA that is fully complementary to the mRNA transcript;

an $\alpha_{1C}$-subunit encoded by an mRNA transcript native to a human cell, wherein DNA that is fully complementary to the transcript is capable of hybridizing under conditions of high stringency to a probe having the sequence of nucleotides set forth in SEQ ID No. 4, SEQ ID No. 5 or SEQ ID No. 6; and an $\alpha_{1D}$-subunit encoded by an mRNA transcript native to a human cell, wherein DNA that is fully complementary to the transcript is capable of hybridizing under conditions of high stringency to a probe having the sequence of nucleotides set forth in SEQ ID No. 2.

2. The method of claim 1, wherein prior to the depolarization step the cell is maintained at a holding potential which substantially inactivates calcium channels which are endogenous to said cell.

3. The method of claim 1, wherein:

the cell is an amphibian oöcyte;

the heterologous nucleic acid is RNA that is injected into the oöcyte; and the one or more human calcium channel subunits further comprise a $\beta_2$-subunit.

4. The method of claim 1, wherein:

the cell is an amphibian oöcyte;

the heterologous nucleic acid is RNA that is injected into the oöcyte; and the one or more human calcium channel subunits further comprise a $\beta$-subunit, wherein:

the $\beta$-subunit is selected from the group consisting of:

a $\beta_{1-1}$-subunit comprising the sequence of amino acids encoded by the sequence of nucleotides set forth in SEQ ID NO. 26;

a $\beta_{1-2}$-subunit comprising the sequence of amino acids encoded by the sequence of nucleotides set forth in SEQ ID NO. 9;

a $\beta_{1-3}$-subunit comprising the sequence of amino acids encoded by the sequence of nucleotides set forth in SEQ ID NO. 10;

a $\beta_{1-4}$-subunit comprising the sequence of amino acids encoded by the sequence of nucleotides set forth in SEQ ID NO. 27;

a $\beta_{1-5}$-subunit comprising the sequence of amino acids encoded by the sequence of nucleotides set forth in SEQ ID NO. 28; and a human calcium channel $\beta$-subunit that is encoded by a DNA molecule capable of hybridizing under conditions of high stringency with DNA that is fully complementary to an mRNA transcript native to a human cell that encodes one of the aforesaid human calcium channel $\beta$-subunits.

5. The method of claim 4, wherein the subunits encoded by said RNA further comprise an $\alpha_2$-subunit, a γ-subunit or an $\alpha_2$-subunit and γ-subunit.

6. The method of claim 1, wherein the cell is an HEK cell and the heterologous nucleic acid is DNA.

7. A substantially pure $\alpha_1$-subunit of a human calcium channel, wherein:

the $\alpha_1$-subunit is selected from the group consisting of:

an $\alpha_{1C}$-subunit comprising the sequence of amino acids encoded by the sequence nucleotides set forth in SEQ ID NO. 3;

an $\alpha_{1D}$-subunit comprising the sequence of amino acids encoded by the sequence of nucleotides set forth in SEQ ID NO: 1 or SEQ ID NO. 29;

an $\alpha_{1A}$-subunit comprising the sequence of amino acids encoded by the $\alpha_{1A}$-encoding DNA in a phage having all of the identifying characteristics of the phage deposited as ATCC Accession No. 75293;

a human calcium channel $\alpha_1$-subunit that is encoded by a DNA molecule capable of hybridizing under conditions of high stringency with DNA that is fully complementary to an mRNA transcript native to a human cell that encodes one of the aforesaid human calcium channel $\alpha_1$-subunits, such that any probe that contains at least 14 contiguous bases from the coding portion of the $\alpha_1$-subunit-encoding DNA molecule is capable of hybridizing under conditions of high stringency to the DNA that is fully complementary to the mRNA transcripts;

an $\alpha_{1A}$-subunit encoded by an mRNA transcript native to a human cell, wherein DNA that is fully complementary to the transcript is capable of hybridizing under conditions of high stringency to a probe having the sequence of nucleotides set forth in SEQ ID No. 21;

an $\alpha_{1C}$-subunit encoded by an mRNA transcript native to a human cell, wherein DNA that is fully complementary to the transcript is capable of hybridizing under conditions of high stringency to a probe having the sequence of nucleotides set forth in SEQ ID No. 4, SEQ ID No. 5 or SEQ ID No. 6; and an $\alpha_{1D}$-Subunit encoded by an mRNA transcript native to a human cell, wherein DNA that is fully complementary to the transcript is capable of hybridizing under conditions of high stringency to a probe having the sequence of nucleotides set forth in SEQ ID No. 2.

8. The subunit of claim 7 that is an $\alpha_{1D}$-subunit.

9. The subunit of claim 8, comprising the sequence of amino acids encoded by the sequence of nucleotides set forth in SEQ ID NO. 1.

10. The subunit of claim 8, comprising the sequence of amino acids that is encoded by the sequence of nucleotides set forth in SEQ ID NO. 2.

11. The subunit of claim 7 that is an $\alpha_{1C}$-subunit.

12. The subunit of claim 11, comprising the sequence of amino acids encoded by the sequence of nucleotides set forth in SEQ ID NO. 3.

13. The subunit of claim 11, comprising the sequence of amino acids encoded by the sequence of nucleotides set forth in SEQ ID NO. 4.

14. The subunit of claim 11, comprising the sequence of amino acids that is encoded by the sequence of nucleotides set forth in SEQ ID NO. 5.

15. The subunit of claim 11, comprising the sequence of amino acids encoded by the sequence of nucleotides set forth in SEQ ID NO. 6.

16. The subunit of claim 7 that is an $\alpha_{1A}$-subunit.

17. The subunit of claim 16, comprising the sequence of amino acids encoded by the sequence of nucleotides set forth in SEQ ID NO. 21.

18. The subunit of claim 16 comprising the sequence of amino acids encoded by a sequence of nucleotides comprising the sequence of nucleotides of the $\alpha_{1a}$-encoding DNA in a phage having all of the identifying characteristics of the phage deposited under ATCC Accession No. 75293.

19. A substantially pure $\alpha_1$-subunit of a human calcium channel that is encoded by nucleic acid native to a human cell, wherein:

(a) the $\alpha_1$-subunit is selected from the group consisting of:

an $\alpha_{1c}$-subunit encoded by a DNA molecule comprising the sequence nucleotides set forth in SEQ ID NO. 3, SEQ ID NO. 4, SEQ ID NO. 5 or SEQ ID NO. 6;

an $\alpha_{1D}$ subunit comprising the sequence of amino acids encoded by the sequence of nucleotides set forth in SEQ ID NO: 1 or SEQ ID NO. 29;

an $\alpha_{1A}$-subunit encoded by a DNA molecule comprising the sequence of nucleotides set forth in SEQ ID NO. 21 or encoded by the $\alpha_{1A}$-encoding DNA in a phage having all of the identifying characteristics of the phage deposited as ATCC Accession No. 75293; and a human calcium channel $\alpha_1$-subunit that is encoded by DNA capable of hybridizing under conditions of high stringency with DNA that is fully complementary to the mRNA transcript native to a human cell; and (b) the $\alpha_1$-subunit binds to at least one compound selected from the group consisting of a dihydropyridines, a phenylalkylamines, $\omega$-CgTx, and a pyrazonoylguanidines.

20. A substantially pure $\alpha_2$-subunit of a human calcium channel selected from the group consisting of:

an $\alpha_{2a}$-subunit comprising the sequence of amino acids encoded by the sequence nucleotides set forth in SEQ ID NO. 22;

an $\alpha_{2c}$ subunit comprising the sequence of amino acids encoded by the sequence of nucleotides set forth in SEQ ID NO. 23;

an $\alpha_{2d}$ subunit comprising the sequence of amino acids encoded by the sequence of nucleotides set forth in SEQ ID NO. 24; and an $\alpha_{2e}$ subunit comprising the sequence of amino acids encoded by the sequence of nucleotides set forth in SEQ ID NO. 25.

21. The subunit of claim 20 that is an $\alpha_{2a}$-subunit.

22. The subunit of claim 21, comprising the sequence of amino acids encoded by the sequence of nucleotides set forth in SEQ ID NO. 22.

23. The subunit of claim 20 that is an $\alpha_{2c}$-subunit.

24. The subunit of claim 23, comprising the sequence of amino acids encoded by the sequence of nucleotides set forth in SEQ ID NO. 23.

25. The subunit of claim 20 that is an $\alpha_{2d}$-subunit.

26. The subunit of claim 25, comprising the sequence of amino acids encoded by the sequence of nucleotides set forth in SEQ ID NO. 24.

27. The subunit of claim 20 that is an $\alpha_{2e}$-subunit.

28. The subunit of claim 27 comprising the sequence of amino acids encoded by the sequence of nucleotides set forth in SEQ ID NO. 25.

29. An isolated $\alpha_{2b}$-subunit of a human calcium channel comprising the sequence of amino acids encoded by the sequence of nucleotides set forth in SEQ ID NO. 11.

30. A substantially pure $\beta_1$-subunit of a human calcium channel selected from the group consisting of:

a $\beta_{1-1}$-subunit comprising the sequence of amino acids encoded by the sequence of nucleotides set forth in SEQ ID NO. 26;

a $\beta_{1-2}$-subunit comprising the sequence of amino acids encoded by the sequence of nucleotides set forth in SEQ ID NO. 9;

a $\beta_{1-3}$-subunit comprising the sequence of amino acids encoded by the sequence of nucleotides set forth in SEQ ID NO.10;

a $\beta_{1-4}$-subunit comprising the sequence of amino acids encoded by the sequence of nucleotides set forth in SEQ ID NO. 27;

a $\beta_{1-5}$-subunit comprising the sequence of amino acids encoded by the sequence of nucleotides set forth in SEQ ID NO. 28; and a $\beta_1$ subunit encoded by an mRNA transcript native to a human cell, wherein DNA that is fully complementary to the transcript is capable of hybridizing under conditions of high stringency to a probe having a sequence corresponding to at least 30 contiguous nucleotides present in SEQ ID NO: 26. SEQ ID NO:9, SEQ ID NO:10, SEQ ID NO:27 or SEQ NO: 28; and a human calcium channel $\beta_1$-subunit that is encoded by a DNA molecule capable of hybridizing under conditions of high stringency with DNA that is fully complementary to an mRNA transcript native to a human cell that encodes one of the aforesaid human calcium channel $\beta_1$-subunits; such that any probe that contains at least 14 contiguous bases from the coding portion of the $\beta_1$-subunit-encoding DNA molecule is capable of hybridizing under conditions of high stringency to the DNA molecule that is fully complementary to the mRNA transcript.

31. The subunit of claim 30 that is an $\beta$1-1-subunit.

32. The subunit of claim 31 comprising the sequence of amino acids encoded by the sequence of nucleotides set forth in SEQ ID NO. 26.

33. The subunit of claim 30 that is an $\beta_{1-2}$-subunit.

34. The subunit of claim 33, comprising the sequence of amino acids encoded by the sequence of nucleotides set forth in SEQ ID NO. 9.

35. The subunit of claim 30 that is an $\beta_{1-3}$-subunit.

36. The subunit of claim 35, comprising the sequence of amino acids encoded by the sequence of nucleotides set forth in SEQ ID NO. 10.

37. The subunit of claim 30 that is an $\beta_{1-4}$-subunit.

38. The subunit of claim 37, comprising the sequence of amino acids encoded by the sequence of nucleotides set forth in SEQ ID NO. 27.

39. The subunit of claim 30 that is an $\beta_{1-5}$-subunit.

40. The subunit of claim 39, comprising the sequence of amino acids encoded by the sequence of nucleotides set forth in SEQ ID NO. 28.

41. A substantially pure peptide, comprising the sequence of amino acids encoded by SEQ ID No. 3 or 6.

42. A substantially pure peptide, comprising the sequence of amino acids encoded by SEQ ID No. 2.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
- ( A ) LENGTH: 7635 base pairs
- ( B ) TYPE: nucleic acid
- ( C ) STRANDEDNESS: double
- ( D ) TOPOLOGY: linear ( i i ) MOLECULE TYPE: DNA (genomic)

( i x ) FEATURE:
- ( A ) NAME/KEY: CDS
- ( B ) LOCATION: 511..6996

( i x ) FEATURE:
- ( A ) NAME/KEY: 5'UTR
- ( B ) LOCATION: 1..510

( i x ) FEATURE:
- ( A ) NAME/KEY: 3'UTR
- ( B ) LOCATION: 6994..7635

( x i ) SEQUENCE DESCRIPTION: SEQ ID NO:1:

```
GGGCGAGCGC CTCCGTCCCC GGATGTGAGC TCCGGCTGCC CGCGGTCCCG AGCCAGCGGC      60

GCGCGGGCGG CGGCGGCGGG CACCGGGCAC CGCGGCGGGC GGGCAGACGG GCGGGCATGG     120

GGGGAGCGCC GAGCGGCCCC GGCGGCCGGG CCGGCATCAC CGCGGCGTCT CTCCGCTAGA     180

GGAGGGGACA AGCCAGTTCT CCTTTGCAGC AAAAAATTAC ATGTATATAT TATTAAGATA     240

ATATATACAT TGGATTTTAT TTTTTAAAA  AGTTTATTTT GCTCCATTTT TGAAAAGAG      300

AGAGCTTGGG TGGCGAGCGG TTTTTTTTA  AAATCAATTA TCCTTATTTT CTGTTATTTG     360

TCCCCGTCCC TCCCCACCCC CCTGCTGAAG CGAGAATAAG GGCAGGGACC GCGGCTCCTA     420

CCTCTTGGTG ATCCCCTTCC CCATTCCGCC CCCGCCCCAA CGCCCAGCAC AGTGCCCTGC     480

ACACAGTAGT CGCTCAATAA ATGTTCGTGG ATG ATG ATG ATG ATG ATG ATG AAA     534
                                 Met Met Met Met Met Met Met Lys
                                  1               5

AAA ATG CAG CAT CAA CGG CAG CAG CAA GCG GAC CAC GCG AAC GAG GCA      582
Lys Met Gln His Gln Arg Gln Gln Gln Ala Asp His Ala Asn Glu Ala
     10              15                  20

AAC TAT GCA AGA GGC ACC AGA CTT CCT CTT TCT GGT GAA GGA CCA ACT      630
Asn Tyr Ala Arg Gly Thr Arg Leu Pro Leu Ser Gly Glu Gly Pro Thr
 25              30                  35                  40

TCT CAG CCG AAT AGC TCC AAG CAA ACT GTC CTG TCT TGG CAA GCT GCA      678
Ser Gln Pro Asn Ser Ser Lys Gln Thr Val Leu Ser Trp Gln Ala Ala
             45                  50                  55

ATC GAT GCT GCT AGA CAG GCC AAG GCT GCC CAA ACT ATG AGC ACC TCT      726
Ile Asp Ala Ala Arg Gln Ala Lys Ala Ala Gln Thr Met Ser Thr Ser
         60                  65                  70

GCA CCC CCA CCT GTA GGA TCT CTC TCC CAA AGA AAA CGT CAG CAA TAC      774
Ala Pro Pro Pro Val Gly Ser Leu Ser Gln Arg Lys Arg Gln Gln Tyr
             75                  80                  85

GCC AAG AGC AAA AAA CAG GGT AAC TCG TCC AAC AGC CGA CCT GCC CGC      822
Ala Lys Ser Lys Lys Gln Gly Asn Ser Ser Asn Ser Arg Pro Ala Arg
     90                  95                 100

GCC CTT TTC TGT TTA TCA CTC AAT AAC CCC ATC CGA AGA GCC TGC ATT      870
Ala Leu Phe Cys Leu Ser Leu Asn Asn Pro Ile Arg Arg Ala Cys Ile
105                 110                 115                 120
```

| | | | | | | | | | | | | | | | | |
|---|---|---|---|---|---|---|---|---|---|---|---|---|---|---|---|---|
| AGT | ATA | GTG | GAA | TGG | AAA | CCA | TTT | GAC | ATA | TTT | ATA | TTA | TTG | GCT | ATT | 918 |
| Ser | Ile | Val | Glu | Trp | Lys | Pro | Phe | Asp | Ile | Phe | Ile | Leu | Leu | Ala | Ile | |
| | 125 | | | | | | | 130 | | | | | | 135 | | |
| TTT | GCC | AAT | TGT | GTG | GCC | TTA | GCT | ATT | TAC | ATC | CCA | TTC | CCT | GAA | GAT | 966 |
| Phe | Ala | Asn | Cys | Val | Ala | Leu | Ala | Ile | Tyr | Ile | Pro | Phe | Pro | Glu | Asp | |
| | | 140 | | | | | 145 | | | | | 150 | | | | |
| GAT | TCT | AAT | TCA | ACA | AAT | CAT | AAC | TTG | GAA | AAA | GTA | GAA | TAT | GCC | TTC | 1014 |
| Asp | Ser | Asn | Ser | Thr | Asn | His | Asn | Leu | Glu | Lys | Val | Glu | Tyr | Ala | Phe | |
| | | 155 | | | | | 160 | | | | | 165 | | | | |
| CTG | ATT | ATT | TTT | ACA | GTC | GAG | ACA | TTT | TTG | AAG | ATT | ATA | GCG | TAT | GGA | 1062 |
| Leu | Ile | Ile | Phe | Thr | Val | Glu | Thr | Phe | Leu | Lys | Ile | Ile | Ala | Tyr | Gly | |
| | 170 | | | | | 175 | | | | | 180 | | | | | |
| TTA | TTG | CTA | CAT | CCT | AAT | GCT | TAT | GTT | AGG | AAT | GGA | TGG | AAT | TTA | CTG | 1110 |
| Leu | Leu | Leu | His | Pro | Asn | Ala | Tyr | Val | Arg | Asn | Gly | Trp | Asn | Leu | Leu | |
| 185 | | | | | 190 | | | | | 195 | | | | | 200 | |
| GAT | TTT | GTT | ATA | GTA | ATA | GTA | GGA | TTG | TTT | AGT | GTA | ATT | TTG | GAA | CAA | 1158 |
| Asp | Phe | Val | Ile | Val | Ile | Val | Gly | Leu | Phe | Ser | Val | Ile | Leu | Glu | Gln | |
| | | | | 205 | | | | | 210 | | | | | 215 | | |
| TTA | ACC | AAA | GAA | ACA | GAA | GGC | GGG | AAC | CAC | TCA | AGC | GGC | AAA | TCT | GGA | 1206 |
| Leu | Thr | Lys | Glu | Thr | Glu | Gly | Gly | Asn | His | Ser | Ser | Gly | Lys | Ser | Gly | |
| | | | 220 | | | | | 225 | | | | | 230 | | | |
| GGC | TTT | GAT | GTC | AAA | GCC | CTC | CGT | GCC | TTT | CGA | GTG | TTG | CGA | CCA | CTT | 1254 |
| Gly | Phe | Asp | Val | Lys | Ala | Leu | Arg | Ala | Phe | Arg | Val | Leu | Arg | Pro | Leu | |
| | | 235 | | | | | 240 | | | | | 245 | | | | |
| CGA | CTA | GTG | TCA | GGA | GTG | CCC | AGT | TTA | CAA | GTT | GTC | CTG | AAC | TCC | ATT | 1302 |
| Arg | Leu | Val | Ser | Gly | Val | Pro | Ser | Leu | Gln | Val | Val | Leu | Asn | Ser | Ile | |
| | 250 | | | | | 255 | | | | | 260 | | | | | |
| ATA | AAA | GCC | ATG | GTT | CCC | CTC | CTT | CAC | ATA | GCC | CTT | TTG | GTA | TTA | TTT | 1350 |
| Ile | Lys | Ala | Met | Val | Pro | Leu | Leu | His | Ile | Ala | Leu | Leu | Val | Leu | Phe | |
| 265 | | | | | 270 | | | | | 275 | | | | | 280 | |
| GTA | ATC | ATA | ATC | TAT | GCT | ATT | ATA | GGA | TTG | GAA | CTT | TTT | ATT | GGA | AAA | 1398 |
| Val | Ile | Ile | Ile | Tyr | Ala | Ile | Ile | Gly | Leu | Glu | Leu | Phe | Ile | Gly | Lys | |
| | | | | 285 | | | | | 290 | | | | | 295 | | |
| ATG | CAC | AAA | ACA | TGT | TTT | TTT | GCT | GAC | TCA | GAT | ATC | GTA | GCT | GAA | GAG | 1446 |
| Met | His | Lys | Thr | Cys | Phe | Phe | Ala | Asp | Ser | Asp | Ile | Val | Ala | Glu | Glu | |
| | | | 300 | | | | | 305 | | | | | 310 | | | |
| GAC | CCA | GCT | CCA | TGT | GCG | TTC | TCA | GGG | AAT | GGA | CGC | CAG | TGT | ACT | GCC | 1494 |
| Asp | Pro | Ala | Pro | Cys | Ala | Phe | Ser | Gly | Asn | Gly | Arg | Gln | Cys | Thr | Ala | |
| | | 315 | | | | | 320 | | | | | 325 | | | | |
| AAT | GGC | ACG | GAA | TGT | AGG | AGT | GGC | TGG | GTT | GGC | CCG | AAC | GGA | GGC | ATC | 1542 |
| Asn | Gly | Thr | Glu | Cys | Arg | Ser | Gly | Trp | Val | Gly | Pro | Asn | Gly | Gly | Ile | |
| | 330 | | | | | 335 | | | | | 340 | | | | | |
| ACC | AAC | TTT | GAT | AAC | TTT | GCC | TTT | GCC | ATG | CTT | ACT | GTG | TTT | CAG | TGC | 1590 |
| Thr | Asn | Phe | Asp | Asn | Phe | Ala | Phe | Ala | Met | Leu | Thr | Val | Phe | Gln | Cys | |
| 345 | | | | | 350 | | | | | 355 | | | | | 360 | |
| ATC | ACC | ATG | GAG | GGC | TGG | ACA | GAC | GTG | CTC | TAC | TGG | ATG | AAT | GAT | GCT | 1638 |
| Ile | Thr | Met | Glu | Gly | Trp | Thr | Asp | Val | Leu | Tyr | Trp | Met | Asn | Asp | Ala | |
| | | | | 365 | | | | | 370 | | | | | 375 | | |
| ATG | GGA | TTT | GAA | TTG | CCC | TGG | GTG | TAT | TTT | GTC | AGT | CTC | GTC | ATC | TTT | 1686 |
| Met | Gly | Phe | Glu | Leu | Pro | Trp | Val | Tyr | Phe | Val | Ser | Leu | Val | Ile | Phe | |
| | | | 380 | | | | | 385 | | | | | 390 | | | |
| GGG | TCA | TTT | TTC | GTA | CTA | AAT | CTT | GTA | CTT | GGT | GTA | TTG | AGC | GGA | GAA | 1734 |
| Gly | Ser | Phe | Phe | Val | Leu | Asn | Leu | Val | Leu | Gly | Val | Leu | Ser | Gly | Glu | |
| | | 395 | | | | | 400 | | | | | 405 | | | | |
| TTC | TCA | AAG | GAA | AGA | GAG | AAG | GCA | AAA | GCA | CGG | GGA | GAT | TTC | CAG | AAG | 1782 |
| Phe | Ser | Lys | Glu | Arg | Glu | Lys | Ala | Lys | Ala | Arg | Gly | Asp | Phe | Gln | Lys | |
| | | 410 | | | | | 415 | | | | | 420 | | | | |
| CTC | CGG | GAG | AAG | CAG | CAG | CTG | GAG | GAG | GAT | CTA | AAG | GGC | TAC | TTG | GAT | 1830 |
| Leu | Arg | Glu | Lys | Gln | Gln | Leu | Glu | Glu | Asp | Leu | Lys | Gly | Tyr | Leu | Asp | |
| 425 | | | | | 430 | | | | | 435 | | | | | 440 | |

-continued

| | | | | | | | | | | | | | | | | |
|---|---|---|---|---|---|---|---|---|---|---|---|---|---|---|---|---|
| TGG | ATC | ACC | CAA | GCT | GAG | GAC | ATC | GAT | CCG | GAG | AAT | GAG | GAA | GAA | GGA | 1878 |
| Trp | Ile | Thr | Gln | Ala | Glu | Asp | Ile | Asp | Pro | Glu | Asn | Glu | Glu | Glu | Gly | |
| | | | 445 | | | | | 450 | | | | | 455 | | | |
| GGA | GAG | GAA | GGC | AAA | CGA | AAT | ACT | AGC | ATG | CCC | ACC | AGC | GAG | ACT | GAG | 1926 |
| Gly | Glu | Glu | Gly | Lys | Arg | Asn | Thr | Ser | Met | Pro | Thr | Ser | Glu | Thr | Glu | |
| | | | 460 | | | | 465 | | | | | 470 | | | | |
| TCT | GTG | AAC | ACA | GAG | AAC | GTC | AGC | GGT | GAA | GGC | GAG | AAC | CGA | GGC | TGC | 1974 |
| Ser | Val | Asn | Thr | Glu | Asn | Val | Ser | Gly | Glu | Gly | Glu | Asn | Arg | Gly | Cys | |
| | | 475 | | | | | 480 | | | | | 485 | | | | |
| TGT | GGA | AGT | CTC | TGT | CAA | GCC | ATC | TCA | AAA | TCC | AAA | CTC | AGC | CGA | CGC | 2022 |
| Cys | Gly | Ser | Leu | Cys | Gln | Ala | Ile | Ser | Lys | Ser | Lys | Leu | Ser | Arg | Arg | |
| | 490 | | | | 495 | | | | | 500 | | | | | | |
| TGG | CGT | CGC | TGG | AAC | CGA | TTC | AAT | CGC | AGA | AGA | TGT | AGG | GCC | GCC | GTG | 2070 |
| Trp | Arg | Arg | Trp | Asn | Arg | Phe | Asn | Arg | Arg | Arg | Cys | Arg | Ala | Ala | Val | |
| 505 | | | | 510 | | | | | 515 | | | | | | 520 | |
| AAG | TCT | GTC | ACG | TTT | TAC | TGG | CTG | GTT | ATC | GTC | CTG | GTG | TTT | CTG | AAC | 2118 |
| Lys | Ser | Val | Thr | Phe | Tyr | Trp | Leu | Val | Ile | Val | Leu | Val | Phe | Leu | Asn | |
| | | | | 525 | | | | | 530 | | | | | 535 | | |
| ACC | TTA | ACC | ATT | TCC | TCT | GAG | CAC | TAC | AAT | CAG | CCA | GAT | TGG | TTG | ACA | 2166 |
| Thr | Leu | Thr | Ile | Ser | Ser | Glu | His | Tyr | Asn | Gln | Pro | Asp | Trp | Leu | Thr | |
| | | | 540 | | | | | 545 | | | | | 550 | | | |
| CAG | ATT | CAA | GAT | ATT | GCC | AAC | AAA | GTC | CTC | TTG | GCT | CTG | TTC | ACC | TGC | 2214 |
| Gln | Ile | Gln | Asp | Ile | Ala | Asn | Lys | Val | Leu | Leu | Ala | Leu | Phe | Thr | Cys | |
| | | 555 | | | | | 560 | | | | | 565 | | | | |
| GAG | ATG | CTG | GTA | AAA | ATG | TAC | AGC | TTG | GGC | CTC | CAA | GCA | TAT | TTC | GTC | 2262 |
| Glu | Met | Leu | Val | Lys | Met | Tyr | Ser | Leu | Gly | Leu | Gln | Ala | Tyr | Phe | Val | |
| | 570 | | | | 575 | | | | | 580 | | | | | | |
| TCT | CTT | TTC | AAC | CGG | TTT | GAT | TGC | TTC | GTG | GTG | TGT | GGT | GGA | ATC | ACT | 2310 |
| Ser | Leu | Phe | Asn | Arg | Phe | Asp | Cys | Phe | Val | Val | Cys | Gly | Gly | Ile | Thr | |
| 585 | | | | | 590 | | | | | 595 | | | | | 600 | |
| GAG | ACG | ATC | TTG | GTG | GAA | CTG | GAA | ATC | ATG | TCT | CCC | CTG | GGG | ATC | TCT | 2358 |
| Glu | Thr | Ile | Leu | Val | Glu | Leu | Glu | Ile | Met | Ser | Pro | Leu | Gly | Ile | Ser | |
| | | | | 605 | | | | 610 | | | | | 615 | | | |
| GTG | TTT | CGG | TGT | GTG | CGC | CTC | TTA | AGA | ATC | TTC | AAA | GTG | ACC | AGG | CAC | 2406 |
| Val | Phe | Arg | Cys | Val | Arg | Leu | Leu | Arg | Ile | Phe | Lys | Val | Thr | Arg | His | |
| | | | 620 | | | | | 625 | | | | | 630 | | | |
| TGG | ACT | TCC | CTG | AGC | AAC | TTA | GTG | GCA | TCC | TTA | TTA | AAC | TCC | ATG | AAG | 2454 |
| Trp | Thr | Ser | Leu | Ser | Asn | Leu | Val | Ala | Ser | Leu | Leu | Asn | Ser | Met | Lys | |
| | | 635 | | | | | 640 | | | | | 645 | | | | |
| TCC | ATC | GCT | TCG | CTG | TTG | CTT | CTG | CTT | TTT | CTC | TTC | ATT | ATC | ATC | TTT | 2502 |
| Ser | Ile | Ala | Ser | Leu | Leu | Leu | Leu | Leu | Phe | Leu | Phe | Ile | Ile | Ile | Phe | |
| | 650 | | | | 655 | | | | | 660 | | | | | | |
| TCC | TTG | CTT | GGG | ATG | CAG | CTG | TTT | GGC | GGC | AAG | TTT | AAT | TTT | GAT | GAA | 2550 |
| Ser | Leu | Leu | Gly | Met | Gln | Leu | Phe | Gly | Gly | Lys | Phe | Asn | Phe | Asp | Glu | |
| 665 | | | | | 670 | | | | | 675 | | | | | 680 | |
| ACG | CAA | ACC | AAG | CGG | AGC | ACC | TTT | GAC | AAT | TTC | CCT | CAA | GCA | CTT | CTC | 2598 |
| Thr | Gln | Thr | Lys | Arg | Ser | Thr | Phe | Asp | Asn | Phe | Pro | Gln | Ala | Leu | Leu | |
| | | | | 685 | | | | | 690 | | | | | 695 | | |
| ACA | GTG | TTC | CAG | ATC | CTG | ACA | GGC | GAA | GAC | TGG | AAT | GCT | GTG | ATG | TAC | 2646 |
| Thr | Val | Phe | Gln | Ile | Leu | Thr | Gly | Glu | Asp | Trp | Asn | Ala | Val | Met | Tyr | |
| | | | 700 | | | | | 705 | | | | | 710 | | | |
| GAT | GGC | ATC | ATG | GCT | TAC | GGG | GGC | CCA | TCC | TCT | TCA | GGA | ATG | ATC | GTC | 2694 |
| Asp | Gly | Ile | Met | Ala | Tyr | Gly | Gly | Pro | Ser | Ser | Ser | Gly | Met | Ile | Val | |
| | | 715 | | | | | 720 | | | | | 725 | | | | |
| TGC | ATC | TAC | TTC | ATC | ATC | CTC | TTC | ATT | TGT | GGT | AAC | TAT | ATT | CTA | CTG | 2742 |
| Cys | Ile | Tyr | Phe | Ile | Ile | Leu | Phe | Ile | Cys | Gly | Asn | Tyr | Ile | Leu | Leu | |
| | 730 | | | | 735 | | | | | 740 | | | | | | |
| AAT | GTC | TTC | TTG | GCC | ATC | GCT | GTA | GAC | AAT | TTG | GCT | GAT | GCT | GAA | AGT | 2790 |
| Asn | Val | Phe | Leu | Ala | Ile | Ala | Val | Asp | Asn | Leu | Ala | Asp | Ala | Glu | Ser | |
| 745 | | | | | 750 | | | | | 755 | | | | | 760 | |

-continued

| | | | | | | | | | | | | | | | | |
|---|---|---|---|---|---|---|---|---|---|---|---|---|---|---|---|---|
| CTG | AAC | ACT | GCT | CAG | AAA | GAA | GAA | GCG | GAA | GAA | AAG | GAG | AGG | AAA | AAG | 2838 |
| Leu | Asn | Thr | Ala | Gln<br>765 | Lys | Glu | Glu | Ala | Glu<br>770 | Glu | Lys | Glu | Arg | Lys<br>775 | Lys | |
| ATT | GCC | AGA | AAA | GAG | AGC | CTA | GAA | AAT | AAG | AAC | AAC | AAA | CCA | GAA | | 2886 |
| Ile | Ala | Arg | Lys<br>780 | Glu | Ser | Leu | Glu | Asn<br>785 | Lys | Lys | Asn | Asn | Lys<br>790 | Pro | Glu | |
| GTC | AAC | CAG | ATA | GCC | AAC | AGT | GAC | AAC | AAG | GTT | ACA | ATT | GAT | GAC | TAT | 2934 |
| Val | Asn | Gln<br>795 | Ile | Ala | Asn | Ser | Asp<br>800 | Asn | Lys | Val | Thr | Ile<br>805 | Asp | Asp | Tyr | |
| AGA | GAA | GAG | GAT | GAA | GAC | AAG | GAC | CCC | TAT | CCG | CCT | TGC | GAT | GTG | CCA | 2982 |
| Arg | Glu<br>810 | Glu | Asp | Glu | Asp | Lys<br>815 | Asp | Pro | Tyr | Pro | Pro<br>820 | Cys | Asp | Val | Pro | |
| GTA | GGG | GAA | GAG | GAA | GAG | GAA | GAG | GAG | GAG | GAT | GAA | CCT | GAG | GTT | CCT | 3030 |
| Val<br>825 | Gly | Glu | Glu | Glu | Glu<br>830 | Glu | Glu | Glu | Glu | Asp<br>835 | Glu | Pro | Glu | Val | Pro<br>840 | |
| GCC | GGA | CCC | CGT | CCT | CGA | AGG | ATC | TCG | GAG | TTG | AAC | ATG | AAG | GAA | AAA | 3078 |
| Ala | Gly | Pro | Arg | Pro<br>845 | Arg | Arg | Ile | Ser | Glu<br>850 | Leu | Asn | Met | Lys | Glu<br>855 | Lys | |
| ATT | GCC | CCC | ATC | CCT | GAA | GGG | AGC | GCT | TTC | TTC | ATT | CTT | AGC | AAG | ACC | 3126 |
| Ile | Ala | Pro | Ile | Pro<br>860 | Glu | Gly | Ser | Ala | Phe<br>865 | Phe | Ile | Leu | Ser | Lys<br>870 | Thr | |
| AAC | CCG | ATC | CGC | GTA | GGC | TGC | CAC | AAG | CTC | ATC | AAC | CAC | CAC | ATC | TTC | 3174 |
| Asn | Pro | Ile | Arg<br>875 | Val | Gly | Cys | His | Lys<br>880 | Leu | Ile | Asn | His | His<br>885 | Ile | Phe | |
| ACC | AAC | CTC | ATC | CTT | GTC | TTC | ATC | ATG | CTG | AGC | AGT | GCT | GCC | CTG | GCC | 3222 |
| Thr | Asn<br>890 | Leu | Ile | Leu | Val | Phe<br>895 | Ile | Met | Leu | Ser | Ser<br>900 | Ala | Ala | Leu | Ala | |
| GCA | GAG | GAC | CCC | ATC | CGC | AGC | CAC | TCC | TTC | CGG | AAC | ACG | ATA | CTG | GGT | 3270 |
| Ala<br>905 | Glu | Asp | Pro | Ile | Arg<br>910 | Ser | His | Ser | Phe | Arg<br>915 | Asn | Thr | Ile | Leu | Gly<br>920 | |
| TAC | TTT | GAC | TAT | GCC | TTC | ACA | GCC | ATC | TTT | ACT | GTT | GAG | ATC | CTG | TTG | 3318 |
| Tyr | Phe | Asp | Tyr | Ala<br>925 | Phe | Thr | Ala | Ile | Phe<br>930 | Thr | Val | Glu | Ile | Leu<br>935 | Leu | |
| AAG | ATG | ACA | ACT | TTT | GGA | GCT | TTC | CTC | CAC | AAA | GGG | GCC | TTC | TGC | AGG | 3366 |
| Lys | Met | Thr | Thr<br>940 | Phe | Gly | Ala | Phe | Leu<br>945 | His | Lys | Gly | Ala | Phe<br>950 | Cys | Arg | |
| AAC | TAC | TTC | AAT | TTG | CTG | GAT | ATG | CTG | GTG | GTT | GGG | GTG | TCT | CTG | GTG | 3414 |
| Asn | Tyr | Phe<br>955 | Asn | Leu | Leu | Asp | Met<br>960 | Leu | Val | Val | Gly | Val<br>965 | Ser | Leu | Val | |
| TCA | TTT | GGG | ATT | CAA | TCC | AGT | GCC | ATC | TCC | GTT | GTG | AAG | ATT | CTG | AGG | 3462 |
| Ser | Phe<br>970 | Gly | Ile | Gln | Ser | Ser<br>975 | Ala | Ile | Ser | Val | Val<br>980 | Lys | Ile | Leu | Arg | |
| GTC | TTA | AGG | GTC | CTG | CGT | CCC | CTC | AGG | GCC | ATC | AAC | AGA | GCA | AAA | GGA | 3510 |
| Val<br>985 | Leu | Arg | Val | Leu | Arg<br>990 | Pro | Leu | Arg | Ala | Ile<br>995 | Asn | Arg | Ala | Lys | Gly<br>1000 | |
| CTT | AAG | CAC | GTG | GTC | CAG | TGC | GTC | TTC | GTG | GCC | ATC | CGG | ACC | ATC | GGC | 3558 |
| Leu | Lys | His | Val | Val<br>1005 | Gln | Cys | Val | Phe | Val<br>1010 | Ala | Ile | Arg | Thr | Ile<br>1015 | Gly | |
| AAC | ATC | ATG | ATC | GTC | ACC | ACC | CTC | CTG | CAG | TTC | ATG | TTT | GCC | TGT | ATC | 3606 |
| Asn | Ile | Met | Ile<br>1020 | Val | Thr | Thr | Leu | Leu<br>1025 | Gln | Phe | Met | Phe | Ala<br>1030 | Cys | Ile | |
| GGG | GTC | CAG | TTG | TTC | AAG | GGG | AAG | TTC | TAT | CGC | TGT | ACG | GAT | GAA | GCC | 3654 |
| Gly | Val | Gln<br>1035 | Leu | Phe | Lys | Gly | Lys<br>1040 | Phe | Tyr | Arg | Cys | Thr<br>1045 | Asp | Glu | Ala | |
| AAA | AGT | AAC | CCT | GAA | GAA | TGC | AGG | GGA | CTT | TTC | ATC | CTC | TAC | AAG | GAT | 3702 |
| Lys | Ser | Asn | Pro<br>1050 | Glu | Glu | Cys | Arg | Gly<br>1055 | Leu | Phe | Ile | Leu | Tyr<br>1060 | Lys | Asp | |
| GGG | GAT | GTT | GAC | AGT | CCT | GTG | GTC | CGT | GAA | CGG | ATC | TGG | CAA | AAC | AGT | 3750 |
| Gly<br>1065 | Asp | Val | Asp | Ser | Pro<br>1070 | Val | Val | Arg | Glu | Arg<br>1075 | Ile | Trp | Gln | Asn | Ser<br>1080 | |

```
GAT TTC AAC TTC GAC AAC GTC CTC TCT GCT ATG ATG GCG CTC TTC ACA       3798
Asp Phe Asn Phe Asp Asn Val Leu Ser Ala Met Met Ala Leu Phe Thr
                    1085                1090                1095

GTC TCC ACG TTT GAG GGC TGG CCT GCG TTG CTG TAT AAA GCC ATC GAC       3846
Val Ser Thr Phe Glu Gly Trp Pro Ala Leu Leu Tyr Lys Ala Ile Asp
        1100                1105                1110

TCG AAT GGA GAG AAC ATC GGC CCA ATC TAC AAC CAC CGC GTG GAG ATC       3894
Ser Asn Gly Glu Asn Ile Gly Pro Ile Tyr Asn His Arg Val Glu Ile
            1115                1120                1125

TCC ATC TTC TTC ATC ATC TAC ATC ATC ATT GTA GCT TTC TTC ATG ATG       3942
Ser Ile Phe Phe Ile Ile Tyr Ile Ile Ile Val Ala Phe Phe Met Met
                1130                1135                1140

AAC ATC TTT GTG GGC TTT GTC ATC GTT ACA TTT CAG GAA CAA GGA GAA       3990
Asn Ile Phe Val Gly Phe Val Ile Val Thr Phe Gln Glu Gln Gly Glu
1145                1150                1155                1160

AAA GAG TAT AAG AAC TGT GAG CTG GAC AAA AAT CAG CGT CAG TGT GTT       4038
Lys Glu Tyr Lys Asn Cys Glu Leu Asp Lys Asn Gln Arg Gln Cys Val
                    1165                1170                1175

GAA TAC GCC TTG AAA GCA CGT CCC TTG CGG AGA TAC ATC CCC AAA AAC       4086
Glu Tyr Ala Leu Lys Ala Arg Pro Leu Arg Arg Tyr Ile Pro Lys Asn
                1180                1185                1190

CCC TAC CAG TAC AAG TTC TGG TAC GTG GTG AAC TCT TCG CCT TTC GAA       4134
Pro Tyr Gln Tyr Lys Phe Trp Tyr Val Val Asn Ser Ser Pro Phe Glu
            1195                1200                1205

TAC ATG ATG TTT GTC CTC ATC ATG CTC AAC ACA CTC TGC TTG GCC ATG       4182
Tyr Met Met Phe Val Leu Ile Met Leu Asn Thr Leu Cys Leu Ala Met
        1210                1215                1220

CAG CAC TAC GAG CAG TCC AAG ATG TTC AAT GAT GCC ATG GAC ATT CTG       4230
Gln His Tyr Glu Gln Ser Lys Met Phe Asn Asp Ala Met Asp Ile Leu
1225                1230                1235                1240

AAC ATG GTC TTC ACC GGG GTG TTC ACC GTC GAG ATG GTT TTG AAA GTC       4278
Asn Met Val Phe Thr Gly Val Phe Thr Val Glu Met Val Leu Lys Val
                    1245                1250                1255

ATC GCA TTT AAG CCT AAG GGG TAT TTT AGT GAC GCC TGG AAC ACG TTT       4326
Ile Ala Phe Lys Pro Lys Gly Tyr Phe Ser Asp Ala Trp Asn Thr Phe
                1260                1265                1270

GAC TCC CTC ATC GTA ATC GGC AGC ATT ATA GAC GTG GCC CTC AGC GAA       4374
Asp Ser Leu Ile Val Ile Gly Ser Ile Ile Asp Val Ala Leu Ser Glu
            1275                1280                1285

GCA GAC CCA ACT GAA AGT GAA AAT GTC CCT GTC CCA ACT GCT ACA CCT       4422
Ala Asp Pro Thr Glu Ser Glu Asn Val Pro Val Pro Thr Ala Thr Pro
        1290                1295                1300

GGG AAC TCT GAA GAG AGC AAT AGA ATC TCC ATC ACC TTT TTC CGT CTT       4470
Gly Asn Ser Glu Glu Ser Asn Arg Ile Ser Ile Thr Phe Phe Arg Leu
1305                1310                1315                1320

TTC CGA GTG ATG CGA TTG GTG AAG CTT CTC AGC AGG GGG GAA GGC ATC       4518
Phe Arg Val Met Arg Leu Val Lys Leu Leu Ser Arg Gly Glu Gly Ile
                    1325                1330                1335

CGG ACA TTG CTG TGG ACT TTT ATT AAG TTC TTT CAG GCG CTC CCG TAT       4566
Arg Thr Leu Leu Trp Thr Phe Ile Lys Phe Phe Gln Ala Leu Pro Tyr
                1340                1345                1350

GTG GCC CTC CTC ATA GCC ATG CTG TTC TTC ATC TAT GCG GTC ATT GGC       4614
Val Ala Leu Leu Ile Ala Met Leu Phe Phe Ile Tyr Ala Val Ile Gly
            1355                1360                1365

ATG CAG ATG TTT GGG AAA GTT GCC ATG AGA GAT AAC AAC CAG ATC AAT       4662
Met Gln Met Phe Gly Lys Val Ala Met Arg Asp Asn Asn Gln Ile Asn
        1370                1375                1380

AGG AAC AAT AAC TTC CAG ACG TTT CCC CAG GCG GTG CTG CTG CTC TTC       4710
Arg Asn Asn Asn Phe Gln Thr Phe Pro Gln Ala Val Leu Leu Leu Phe
1385                1390                1395                1400
```

| | | | | | | | | | | | | | | | | |
|---|---|---|---|---|---|---|---|---|---|---|---|---|---|---|---|---|
| AGG | TGT | GCA | ACA | GGT | GAG | GCC | TGG | CAG | GAG | ATC | ATG | CTG | GCC | TGT | CTC | 4758 |
| Arg | Cys | Ala | Thr | Gly | Glu | Ala | Trp | Gln | Glu | Ile | Met | Leu | Ala | Cys | Leu | |
| | | | 1405 | | | | | 1410 | | | | | | 1415 | | |
| CCA | GGG | AAG | CTC | TGT | GAC | CCT | GAG | TCA | GAT | TAC | AAC | CCC | GGG | GAG | GAG | 4806 |
| Pro | Gly | Lys | Leu | Cys | Asp | Pro | Glu | Ser | Asp | Tyr | Asn | Pro | Gly | Glu | Glu | |
| | | 1420 | | | | | 1425 | | | | | 1430 | | | | |
| CAT | ACA | TGT | GGG | AGC | AAC | TTT | GCC | ATT | GTC | TAT | TTC | ATC | AGT | TTT | TAC | 4854 |
| His | Thr | Cys | Gly | Ser | Asn | Phe | Ala | Ile | Val | Tyr | Phe | Ile | Ser | Phe | Tyr | |
| | | 1435 | | | | | 1440 | | | | | 1445 | | | | |
| ATG | CTC | TGT | GCA | TTT | CTG | ATC | ATC | AAT | CTG | TTT | GTG | GCT | GTC | ATC | ATG | 4902 |
| Met | Leu | Cys | Ala | Phe | Leu | Ile | Ile | Asn | Leu | Phe | Val | Ala | Val | Ile | Met | |
| | 1450 | | | | | 1455 | | | | | 1460 | | | | | |
| GAT | AAT | TTC | GAC | TAT | CTG | ACC | CGG | GAC | TGG | TCT | ATT | TTG | GGG | CCT | CAC | 4950 |
| Asp | Asn | Phe | Asp | Tyr | Leu | Thr | Arg | Asp | Trp | Ser | Ile | Leu | Gly | Pro | His | |
| 1465 | | | | 1470 | | | | | 1475 | | | | | 1480 | | |
| CAT | TTA | GAT | GAA | TTC | AAA | AGA | ATA | TGG | TCA | GAA | TAT | GAC | CCT | GAG | GCA | 4998 |
| His | Leu | Asp | Glu | Phe | Lys | Arg | Ile | Trp | Ser | Glu | Tyr | Asp | Pro | Glu | Ala | |
| | | | | 1485 | | | | | 1490 | | | | | 1495 | | |
| AAG | GGA | AGG | ATA | AAA | CAC | CTT | GAT | GTG | GTC | ACT | CTG | CTT | CGA | CGC | ATC | 5046 |
| Lys | Gly | Arg | Ile | Lys | His | Leu | Asp | Val | Val | Thr | Leu | Leu | Arg | Arg | Ile | |
| | | | | 1500 | | | | | 1505 | | | | | 1510 | | |
| CAG | CCT | CCC | CTG | GGG | TTT | GGG | AAG | TTA | TGT | CCA | CAC | AGG | GTA | GCG | TGC | 5094 |
| Gln | Pro | Pro | Leu | Gly | Phe | Gly | Lys | Leu | Cys | Pro | His | Arg | Val | Ala | Cys | |
| | | | 1515 | | | | | 1520 | | | | | 1525 | | | |
| AAG | AGA | TTA | GTT | GCC | ATG | AAC | ATG | CCT | CTC | AAC | AGT | GAC | GGG | ACA | GTC | 5142 |
| Lys | Arg | Leu | Val | Ala | Met | Asn | Met | Pro | Leu | Asn | Ser | Asp | Gly | Thr | Val | |
| | | 1530 | | | | | 1535 | | | | | 1540 | | | | |
| ATG | TTT | AAT | GCA | ACC | CTG | TTT | GCT | TTG | GTT | CGA | ACG | GCT | CTT | AAG | ATC | 5190 |
| Met | Phe | Asn | Ala | Thr | Leu | Phe | Ala | Leu | Val | Arg | Thr | Ala | Leu | Lys | Ile | |
| 1545 | | | | 1550 | | | | | 1555 | | | | | 1560 | | |
| AAG | ACC | GAA | GGG | AAC | CTG | GAG | CAA | GCT | AAT | GAA | GAA | CTT | CGG | GCT | GTG | 5238 |
| Lys | Thr | Glu | Gly | Asn | Leu | Glu | Gln | Ala | Asn | Glu | Glu | Leu | Arg | Ala | Val | |
| | | | | 1565 | | | | | 1570 | | | | | 1575 | | |
| ATA | AAG | AAA | ATT | TGG | AAG | AAA | ACC | AGC | ATG | AAA | TTA | CTT | GAC | CAA | GTT | 5286 |
| Ile | Lys | Lys | Ile | Trp | Lys | Lys | Thr | Ser | Met | Lys | Leu | Leu | Asp | Gln | Val | |
| | | | | 1580 | | | | | 1585 | | | | | 1590 | | |
| GTC | CCT | CCA | GCT | GGT | GAT | GAT | GAG | GTA | ACC | GTG | GGG | AAG | TTC | TAT | GCC | 5334 |
| Val | Pro | Pro | Ala | Gly | Asp | Asp | Glu | Val | Thr | Val | Gly | Lys | Phe | Tyr | Ala | |
| | | | 1595 | | | | | 1600 | | | | | 1605 | | | |
| ACT | TTC | CTG | ATA | CAG | GAC | TAC | TTT | AGG | AAA | TTC | AAG | AAA | CGG | AAA | GAA | 5382 |
| Thr | Phe | Leu | Ile | Gln | Asp | Tyr | Phe | Arg | Lys | Phe | Lys | Lys | Arg | Lys | Glu | |
| | | | 1610 | | | | | 1615 | | | | | 1620 | | | |
| CAA | GGA | CTG | GTG | GGA | AAG | TAC | CCT | GCG | AAG | AAC | ACC | ACA | ATT | GCC | CTA | 5430 |
| Gln | Gly | Leu | Val | Gly | Lys | Tyr | Pro | Ala | Lys | Asn | Thr | Thr | Ile | Ala | Leu | |
| 1625 | | | | 1630 | | | | | 1635 | | | | | 1640 | | |
| CAG | GCG | GGA | TTA | AGG | ACA | CTG | CAT | GAC | ATT | GGG | CCA | GAA | ATC | CGG | CGT | 5478 |
| Gln | Ala | Gly | Leu | Arg | Thr | Leu | His | Asp | Ile | Gly | Pro | Glu | Ile | Arg | Arg | |
| | | | 1645 | | | | | 1650 | | | | | 1655 | | | |
| GCT | ATA | TCG | TGT | GAT | TTG | CAA | GAT | GAC | GAG | CCT | GAG | GAA | ACA | AAA | CGA | 5526 |
| Ala | Ile | Ser | Cys | Asp | Leu | Gln | Asp | Asp | Glu | Pro | Glu | Glu | Thr | Lys | Arg | |
| | | | 1660 | | | | | 1665 | | | | | 1670 | | | |
| GAA | GAA | GAA | GAT | GAT | GTG | TTC | AAA | AGA | AAT | GGT | GCC | CTG | CTT | GGA | AAC | 5574 |
| Glu | Glu | Glu | Asp | Asp | Val | Phe | Lys | Arg | Asn | Gly | Ala | Leu | Leu | Gly | Asn | |
| | | | 1675 | | | | | 1680 | | | | | 1685 | | | |
| CAT | GTC | AAT | CAT | GTT | AAT | AGT | GAT | AGG | AGA | GAT | TCC | CTT | CAG | CAG | ACC | 5622 |
| His | Val | Asn | His | Val | Asn | Ser | Asp | Arg | Arg | Asp | Ser | Leu | Gln | Gln | Thr | |
| | | | 1690 | | | | | 1695 | | | | | 1700 | | | |
| AAT | ACC | ACC | CAC | CGT | CCC | CTG | CAT | GTC | CAA | AGG | CCT | TCA | ATT | CCA | CCT | 5670 |
| Asn | Thr | Thr | His | Arg | Pro | Leu | His | Val | Gln | Arg | Pro | Ser | Ile | Pro | Pro | |
| 1705 | | | | 1710 | | | | | 1715 | | | | | 1720 | | |

```
GCA  AGT  GAT  ACT  GAG  AAA  CCG  CTG  TTT  CCT  CCA  GCA  GGA  AAT  TCG  GTG      5718
Ala  Ser  Asp  Thr  Glu  Lys  Pro  Leu  Phe  Pro  Pro  Ala  Gly  Asn  Ser  Val
                    1725                1730                          1735

TGT  CAT  AAC  CAT  CAT  AAC  CAT  AAT  TCC  ATA  GGA  AAG  CAA  GTT  CCC  ACC      5766
Cys  His  Asn  His  His  Asn  His  Asn  Ser  Ile  Gly  Lys  Gln  Val  Pro  Thr
               1740                1745                     1750

TCA  ACA  AAT  GCC  AAT  CTC  AAT  AAT  GCC  AAT  ATG  TCC  AAA  GCT  GCC  CAT      5814
Ser  Thr  Asn  Ala  Asn  Leu  Asn  Asn  Ala  Asn  Met  Ser  Lys  Ala  Ala  His
          1755                     1760                     1765

GGA  AAG  CGG  CCC  AGC  ATT  GGG  AAC  CTT  GAG  CAT  GTG  TCT  GAA  AAT  GGG      5862
Gly  Lys  Arg  Pro  Ser  Ile  Gly  Asn  Leu  Glu  His  Val  Ser  Glu  Asn  Gly
     1770                     1775                     1780

CAT  CAT  TCT  TCC  CAC  AAG  CAT  GAC  CGG  GAG  CCT  CAG  AGA  AGG  TCC  AGT      5910
His  His  Ser  Ser  His  Lys  His  Asp  Arg  Glu  Pro  Gln  Arg  Arg  Ser  Ser
1785                1790                     1795                          1800

GTG  AAA  AGA  ACC  CGC  TAT  TAT  GAA  ACT  TAC  ATT  AGG  TCC  GAC  TCA  GGA      5958
Val  Lys  Arg  Thr  Arg  Tyr  Tyr  Glu  Thr  Tyr  Ile  Arg  Ser  Asp  Ser  Gly
                    1805                1810                          1815

GAT  GAA  CAG  CTC  CCA  ACT  ATT  TGC  CGG  GAA  GAC  CCA  GAG  ATA  CAT  GGC      6006
Asp  Glu  Gln  Leu  Pro  Thr  Ile  Cys  Arg  Glu  Asp  Pro  Glu  Ile  His  Gly
               1820                     1825                     1830

TAT  TTC  AGG  GAC  CCC  CAC  TGC  TTG  GGG  GAG  CAG  GAG  TAT  TTC  AGT  AGT      6054
Tyr  Phe  Arg  Asp  Pro  His  Cys  Leu  Gly  Glu  Gln  Glu  Tyr  Phe  Ser  Ser
          1835                     1840                     1845

GAG  GAA  TGC  TAC  GAG  GAT  GAC  AGC  TCG  CCC  ACC  TGG  AGC  AGG  CAA  AAC      6102
Glu  Glu  Cys  Tyr  Glu  Asp  Asp  Ser  Ser  Pro  Thr  Trp  Ser  Arg  Gln  Asn
     1850                     1855                     1860

TAT  GGC  TAC  TAC  AGC  AGA  TAC  CCA  GGC  AGA  AAC  ATC  GAC  TCT  GAG  AGG      6150
Tyr  Gly  Tyr  Tyr  Ser  Arg  Tyr  Pro  Gly  Arg  Asn  Ile  Asp  Ser  Glu  Arg
1865                1870                     1875                          1880

CCC  CGA  GGC  TAC  CAT  CAT  CCC  CAA  GGA  TTC  TTG  GAG  GAC  GAT  GAC  TCG      6198
Pro  Arg  Gly  Tyr  His  His  Pro  Gln  Gly  Phe  Leu  Glu  Asp  Asp  Asp  Ser
                    1885                1890                          1895

CCC  GTT  TGC  TAT  GAT  TCA  CGG  AGA  TCT  CCA  AGG  AGA  CGC  CTA  CTA  CCT      6246
Pro  Val  Cys  Tyr  Asp  Ser  Arg  Arg  Ser  Pro  Arg  Arg  Arg  Leu  Leu  Pro
               1900                     1905                     1910

CCC  ACC  CCA  GCA  TCC  CAC  CGG  AGA  TCC  TCC  TTC  AAC  TTT  GAG  TGC  CTG      6294
Pro  Thr  Pro  Ala  Ser  His  Arg  Arg  Ser  Ser  Phe  Asn  Phe  Glu  Cys  Leu
          1915                     1920                     1925

CGC  CGG  CAG  AGC  AGC  CAG  GAA  GAG  GTC  CCG  TCG  TCT  CCC  ATC  TTC  CCC      6342
Arg  Arg  Gln  Ser  Ser  Gln  Glu  Glu  Val  Pro  Ser  Ser  Pro  Ile  Phe  Pro
     1930                     1935                     1940

CAT  CGC  ACG  GCC  CTG  CCT  CTG  CAT  CTA  ATG  CAG  CAA  CAG  ATC  ATG  GCA      6390
His  Arg  Thr  Ala  Leu  Pro  Leu  His  Leu  Met  Gln  Gln  Gln  Ile  Met  Ala
1945                1950                     1955                          1960

GTT  GCC  GGC  CTA  GAT  TCA  AGT  AAA  GCC  CAG  AAG  TAC  TCA  CCG  AGT  CAC      6438
Val  Ala  Gly  Leu  Asp  Ser  Ser  Lys  Ala  Gln  Lys  Tyr  Ser  Pro  Ser  His
                    1965                1970                          1975

TCG  ACC  CGG  TCG  TGG  GCC  ACC  CCT  CCA  GCA  ACC  CCT  CCC  TAC  CGG  GAC      6486
Ser  Thr  Arg  Ser  Trp  Ala  Thr  Pro  Pro  Ala  Thr  Pro  Pro  Tyr  Arg  Asp
               1980                     1985                     1990

TGG  ACA  CCG  TGC  TAC  ACC  CCC  CTG  ATC  CAA  GTG  GAG  CAG  TCA  GAG  GCC      6534
Trp  Thr  Pro  Cys  Tyr  Thr  Pro  Leu  Ile  Gln  Val  Glu  Gln  Ser  Glu  Ala
          1995                     2000                     2005

CTG  GAC  CAG  GTG  AAC  GGC  AGC  CTG  CCG  TCC  CTG  CAC  CGC  AGC  TCC  TGG      6582
Leu  Asp  Gln  Val  Asn  Gly  Ser  Leu  Pro  Ser  Leu  His  Arg  Ser  Ser  Trp
     2010                     2015                     2020

TAC  ACA  GAC  GAG  CCC  GAC  ATC  TCC  TAC  CGG  ACT  TTC  ACA  CCA  GCC  AGC      6630
Tyr  Thr  Asp  Glu  Pro  Asp  Ile  Ser  Tyr  Arg  Thr  Phe  Thr  Pro  Ala  Ser
2025                2030                     2035                          2040
```

| | | | | | | | | | | | | | | | | |
|---|---|---|---|---|---|---|---|---|---|---|---|---|---|---|---|---|
| CTG | ACT | GTC | CCC | AGC | AGC | TTC | CGG | AAC | AAA | AAC | AGC | GAC | AAG | CAG | AGG | 6678 |
| Leu | Thr | Val | Pro | Ser | Ser | Phe | Arg | Asn | Lys | Asn | Ser | Asp | Lys | Gln | Arg | |
| | | | | 2045 | | | | | 2050 | | | | | 2055 | | |
| AGT | GCG | GAC | AGC | TTG | GTG | GAG | GCA | GTC | CTG | ATA | TCC | GAA | GGC | TTG | GGA | 6726 |
| Ser | Ala | Asp | Ser | Leu | Val | Glu | Ala | Val | Leu | Ile | Ser | Glu | Gly | Leu | Gly | |
| | | | | 2060 | | | | | 2065 | | | | | 2070 | | |
| CGC | TAT | GCA | AGG | GAC | CCA | AAA | TTT | GTG | TCA | GCA | ACA | AAA | CAC | GAA | ATC | 6774 |
| Arg | Tyr | Ala | Arg | Asp | Pro | Lys | Phe | Val | Ser | Ala | Thr | Lys | His | Glu | Ile | |
| | | | | 2075 | | | | | 2080 | | | | | 2085 | | |
| GCT | GAT | GCC | TGT | GAC | CTC | ACC | ATC | GAC | GAG | ATG | GAG | AGT | GCA | GCC | AGC | 6822 |
| Ala | Asp | Ala | Cys | Asp | Leu | Thr | Ile | Asp | Glu | Met | Glu | Ser | Ala | Ala | Ser | |
| | | | | 2090 | | | | | 2095 | | | | | 2100 | | |
| ACC | CTG | CTT | AAT | GGG | AAC | GTG | CGT | CCC | CGA | GCC | AAC | GGG | GAT | GTG | GGC | 6870 |
| Thr | Leu | Leu | Asn | Gly | Asn | Val | Arg | Pro | Arg | Ala | Asn | Gly | Asp | Val | Gly | |
| 2105 | | | | | 2110 | | | | | 2115 | | | | | 2120 | |
| CCC | CTC | TCA | CAC | CGG | CAG | GAC | TAT | GAG | CTA | CAG | GAC | TTT | GGT | CCT | GGC | 6918 |
| Pro | Leu | Ser | His | Arg | Gln | Asp | Tyr | Glu | Leu | Gln | Asp | Phe | Gly | Pro | Gly | |
| | | | | 2125 | | | | | 2130 | | | | | 2135 | | |
| TAC | AGC | GAC | GAA | GAG | CCA | GAC | CCT | GGG | AGG | GAT | GAG | GAG | GAC | CTG | GCG | 6966 |
| Tyr | Ser | Asp | Glu | Glu | Pro | Asp | Pro | Gly | Arg | Asp | Glu | Glu | Asp | Leu | Ala | |
| | | | | 2140 | | | | | 2145 | | | | | 2150 | | |
| GAT | GAA | ATG | ATA | TGC | ATC | ACC | ACC | TTG | TAGCCCCCAG | | CGAGGGGCAG | | | | | 7013 |
| Asp | Glu | Met | Ile | Cys | Ile | Thr | Thr | Leu | | | | | | | | |
| | | | | 2155 | | | | 2160 | | | | | | | | |

| | | | | | |
|---|---|---|---|---|---|
| ACTGGCTCTG | GCCTCAGGTG | GGGCGCAGGA | GAGCCAGGGG | AAAAGTGCCT | CATAGTTAGG | 7073 |
| AAAGTTTAGG | CACTAGTTGG | GAGTAATATT | CAATTAATTA | GACTTTTGTA | TAAGAGATGT | 7133 |
| CATGCCTCAA | GAAAGCCATA | AACCTGGTAG | GAACAGGTCC | CAAGCGGTTG | AGCCTGGCAG | 7193 |
| AGTACCATGC | GCTCGGCCCC | AGCTGCAGGA | AACAGCAGGC | CCCGCCTCT | CACAGAGGAT | 7253 |
| GGGTGAGGAG | GCCAGACCTG | CCCTGCCCCA | TTGTCCAGAT | GGGCACTGCT | GTGGAGTCTG | 7313 |
| CTTCTCCCAT | GTACCAGGGC | ACCAGGCCCA | CCCAACTGAA | GGCATGGCGG | CGGGGTGCAG | 7373 |
| GGGAAAGTTA | AAGGTGATGA | CGATCATCAC | ACCTGTGTCG | TTACCTCAGC | CATCGGTCTA | 7433 |
| GCATATCAGT | CACTGGGCCC | AACATATCCA | TTTTTAAACC | CTTTCCCCCA | AATACACTGC | 7493 |
| GTCCTGGTTC | CTGTTTAGCT | GTTCTGAAAT | ACGGTGTGTA | AGTAAGTCAG | AACCCAGCTA | 7553 |
| CCAGTGATTA | TTGCGAGGGC | AATGGGACCT | CATAAATAAG | GTTTTCTGTG | ATGTGACGCC | 7613 |
| AGTTTACATA | AGAGAATATC | AC | | | | 7635 |

( 2 ) INFORMATION FOR SEQ ID NO:2:

( i ) SEQUENCE CHARACTERISTICS:
        ( A ) LENGTH: 104 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..102

( i x ) FEATURE:
        ( A ) NAME/KEY: misc_feature
        ( B ) LOCATION: 1..104
        ( D ) OTHER INFORMATION: /note="A 104-nucleotide
            alternative exon of alpha-1D."

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| GTA | AAT | GAT | GCG | ATA | GGA | TGG | GAA | TGG | CCA | TGG | GTG | TAT | TTT | GTT | AGT | 48 |
| Val | Asn | Asp | Ala | Ile | Gly | Trp | Glu | Trp | Pro | Trp | Val | Tyr | Phe | Val | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CTG | ATC | ATC | CTT | GGC | TCA | TTT | TTC | GTC | CTT | AAC | CTG | GTT | CTT | GGT | GTC | 96 |
| Leu | Ile | Ile | Leu | Gly | Ser | Phe | Phe | Val | Leu | Asn | Leu | Val | Leu | Gly | Val | |
| | | | | 20 | | | | 25 | | | | | 30 | | | |
| CTT | AGT | GG | | | | | | | | | | | | | | 104 |
| Leu | Ser | | | | | | | | | | | | | | | |

( 2 ) INFORMATION FOR SEQ ID NO:3:

( i ) SEQUENCE CHARACTERISTICS:
        ( A ) LENGTH: 5904 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..5904

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GTC | AAT | GAG | AAT | ACG | AGG | ATG | TAC | ATT | CCA | GAG | GAA | AAC | CAC | CAA | 48 |
| Met | Val | Asn | Glu | Asn | Thr | Arg | Met | Tyr | Ile | Pro | Glu | Glu | Asn | His | Gln | |
| 1 | | | | 5 | | | | | 10 | | | | | 15 | | |
| GGT | TCC | AAC | TAT | GGG | AGC | CCA | CGC | CCC | GCC | CAT | GCC | AAC | ATG | AAT | GCC | 96 |
| Gly | Ser | Asn | Tyr | Gly | Ser | Pro | Arg | Pro | Ala | His | Ala | Asn | Met | Asn | Ala | |
| | | | 20 | | | | 25 | | | | | 30 | | | | |
| AAT | GCG | GCA | GCG | GGG | CTG | GCC | CCT | GAG | CAC | ATC | CCC | ACC | CCG | GGG | GCT | 144 |
| Asn | Ala | Ala | Ala | Gly | Leu | Ala | Pro | Glu | His | Ile | Pro | Thr | Pro | Gly | Ala | |
| | | 35 | | | | | 40 | | | | | 45 | | | | |
| GCC | CTG | TCG | TGG | CAG | GCG | GCC | ATC | GAC | GCA | GCC | CGG | CAG | GCT | AAG | CTG | 192 |
| Ala | Leu | Ser | Trp | Gln | Ala | Ala | Ile | Asp | Ala | Ala | Arg | Gln | Ala | Lys | Leu | |
| | 50 | | | | | 55 | | | | | 60 | | | | | |
| ATG | GGC | AGC | GCT | GGC | AAT | GCG | ACC | ATC | TCC | ACA | GTC | AGC | TCC | ACG | CAG | 240 |
| Met | Gly | Ser | Ala | Gly | Asn | Ala | Thr | Ile | Ser | Thr | Val | Ser | Ser | Thr | Gln | |
| 65 | | | | | 70 | | | | | 75 | | | | | 80 | |
| CGG | AAG | CGC | CAG | CAA | TAT | GGG | AAA | CCC | AAG | AAG | CAG | GGC | AGC | ACC | ACG | 288 |
| Arg | Lys | Arg | Gln | Gln | Tyr | Gly | Lys | Pro | Lys | Lys | Gln | Gly | Ser | Thr | Thr | |
| | | | | 85 | | | | | 90 | | | | | 95 | | |
| GCC | ACA | CGC | CCG | CCC | CGA | GCC | CTG | CTC | TGC | CTG | ACC | CTG | AAG | AAC | CCC | 336 |
| Ala | Thr | Arg | Pro | Pro | Arg | Ala | Leu | Leu | Cys | Leu | Thr | Leu | Lys | Asn | Pro | |
| | | | 100 | | | | | 105 | | | | | 110 | | | |
| ATC | CGG | AGG | GCC | TGC | ATC | AGC | ATT | GTC | GAA | TGG | AAA | CCA | TTT | GAA | ATA | 384 |
| Ile | Arg | Arg | Ala | Cys | Ile | Ser | Ile | Val | Glu | Trp | Lys | Pro | Phe | Glu | Ile | |
| | | 115 | | | | | 120 | | | | | 125 | | | | |
| ATT | ATT | TTA | CTG | ACT | ATT | TTT | GCC | AAT | TGT | GTG | GCC | TTA | GCG | ATC | TAT | 432 |
| Ile | Ile | Leu | Leu | Thr | Ile | Phe | Ala | Asn | Cys | Val | Ala | Leu | Ala | Ile | Tyr | |
| | 130 | | | | | 135 | | | | | 140 | | | | | |
| ATT | CCC | TTT | CCA | GAA | GAT | GAT | TCC | AAC | GCC | ACC | AAT | TCC | AAC | CTG | GAA | 480 |
| Ile | Pro | Phe | Pro | Glu | Asp | Asp | Ser | Asn | Ala | Thr | Asn | Ser | Asn | Leu | Glu | |
| 145 | | | | | 150 | | | | | 155 | | | | | 160 | |
| CGA | GTG | GAA | TAT | CTC | TTT | CTC | ATA | ATT | TTT | ACG | GTG | GAA | GCG | TTT | TTA | 528 |
| Arg | Val | Glu | Tyr | Leu | Phe | Leu | Ile | Ile | Phe | Thr | Val | Glu | Ala | Phe | Leu | |
| | | | | 165 | | | | | 170 | | | | | 175 | | |
| AAA | GTA | ATC | GCC | TAT | GGA | CTC | CTC | TTT | CAC | CCC | AAT | GCC | TAC | CTC | CGC | 576 |
| Lys | Val | Ile | Ala | Tyr | Gly | Leu | Leu | Phe | His | Pro | Asn | Ala | Tyr | Leu | Arg | |
| | | | 180 | | | | | 185 | | | | | 190 | | | |
| AAC | GGC | TGG | AAC | CTA | CTA | GAT | TTT | ATA | ATT | GTG | GTT | GTG | GGG | CTT | TTT | 624 |
| Asn | Gly | Trp | Asn | Leu | Leu | Asp | Phe | Ile | Ile | Val | Val | Val | Gly | Leu | Phe | |
| | | 195 | | | | | 200 | | | | | 205 | | | | |
| AGT | GCA | ATT | TTA | GAA | CAA | GCA | ACC | AAA | GCA | GAT | GGG | GCA | AAC | GCT | CTC | 672 |
| Ser | Ala | Ile | Leu | Glu | Gln | Ala | Thr | Lys | Ala | Asp | Gly | Ala | Asn | Ala | Leu | |
| | 210 | | | | | 215 | | | | | 220 | | | | | |

```
GGA GGG AAA GGG GCC GGA TTT GAT GTG AAG GCG CTG AGG GCC TTC CGC        720
Gly Gly Lys Gly Ala Gly Phe Asp Val Lys Ala Leu Arg Ala Phe Arg
225             230              235              240

GTG CTG CGC CCC CTG CGG CTG GTG TCC GGA GTC CCA AGT CTC CAG GTG        768
Val Leu Arg Pro Leu Arg Leu Val Ser Gly Val Pro Ser Leu Gln Val
            245              250              255

GTC CTG AAT TCC ATC ATC AAG GCC ATG GTC CCC CTG CTG CAC ATC GCC        816
Val Leu Asn Ser Ile Ile Lys Ala Met Val Pro Leu Leu His Ile Ala
            260              265              270

CTG CTT GTG CTG TTT GTC ATC ATC ATC TAC GCC ATC ATC GGC TTG GAG        864
Leu Leu Val Leu Phe Val Ile Ile Ile Tyr Ala Ile Ile Gly Leu Glu
            275              280              285

CTC TTC ATG GGG AAG ATG CAC AAG ACC TGC TAC AAC CAG GAG GGC ATA        912
Leu Phe Met Gly Lys Met His Lys Thr Cys Tyr Asn Gln Glu Gly Ile
    290              295              300

GCA GAT GTT CCA GCA GAA GAT GAC CCT TCC CCT TGT GCG CTG GAA ACG        960
Ala Asp Val Pro Ala Glu Asp Asp Pro Ser Pro Cys Ala Leu Glu Thr
305             310              315              320

GGC CAC GGG CGG CAG TGC CAG AAC GGC ACG GTG TGC AAG CCC GGC TGG       1008
Gly His Gly Arg Gln Cys Gln Asn Gly Thr Val Cys Lys Pro Gly Trp
            325              330              335

GAT GGT CCC AAG CAC GGC ATC ACC AAC TTT GAC AAC TTT GCC TTC GCC       1056
Asp Gly Pro Lys His Gly Ile Thr Asn Phe Asp Asn Phe Ala Phe Ala
            340              345              350

ATG CTC ACG GTG TTC CAG TGC ATC ACC ATG GAG GGC TGG ACG GAC GTG       1104
Met Leu Thr Val Phe Gln Cys Ile Thr Met Glu Gly Trp Thr Asp Val
            355              360              365

CTG TAC TGG GTC AAT GAT GCC GTA GGA AGG GAC TGG CCC TGG ATC TAT       1152
Leu Tyr Trp Val Asn Asp Ala Val Gly Arg Asp Trp Pro Trp Ile Tyr
    370              375              380

TTT GTT ACA CTA ATC ATC ATA GGG TCA TTT TTT GTA CTT AAC TTG GTT       1200
Phe Val Thr Leu Ile Ile Ile Gly Ser Phe Phe Val Leu Asn Leu Val
385             390              395              400

CTC GGT GTG CTT AGC GGA GAG TTT TCC AAA GAG AGG GAG AAG GCC AAG       1248
Leu Gly Val Leu Ser Gly Glu Phe Ser Lys Glu Arg Glu Lys Ala Lys
            405              410              415

GCC CGG GGA GAT TTC CAG AAG CTG CGG GAG AAG CAG CAG CTA GAA GAG       1296
Ala Arg Gly Asp Phe Gln Lys Leu Arg Glu Lys Gln Gln Leu Glu Glu
            420              425              430

GAT CTC AAA GGC TAC CTG GAT TGG ATC ACT CAG GCC GAA GAC ATC GNT       1344
Asp Leu Lys Gly Tyr Leu Asp Trp Ile Thr Gln Ala Glu Asp Ile Xaa
            435              440              445

CCT GAG AAT GAG GAC GAA GGC ATG GAT GAG GAG AAG CCC CGA AAC AGA       1392
Pro Glu Asn Glu Asp Glu Gly Met Asp Glu Glu Lys Pro Arg Asn Arg
    450              455              460

GGC ACT CCG GCG GGC ATG CTT GAT CAG AAG AAA GGG AAG TTT GCT TGG       1440
Gly Thr Pro Ala Gly Met Leu Asp Gln Lys Lys Gly Lys Phe Ala Trp
465             470              475              480

TTT AGT CAC TCC ACA GAA ACC CAT GTG AGC ATG CCC ACC AGT GAG ACC       1488
Phe Ser His Ser Thr Glu Thr His Val Ser Met Pro Thr Ser Glu Thr
            485              490              495

GAG TCC GTC AAC ACC GAA AAC GTG GCT GGA GGT GAC ATC GAG GGA GAA       1536
Glu Ser Val Asn Thr Glu Asn Val Ala Gly Gly Asp Ile Glu Gly Glu
            500              505              510

AAC TGC GGG GCC AGG CTG GCC CAC CGG ATC TCC AAG TCA AAG TTC AGC       1584
Asn Cys Gly Ala Arg Leu Ala His Arg Ile Ser Lys Ser Lys Phe Ser
            515              520              525

CGC TAC TGG CGC CGG TGG AAT CGG TTC TGC AGA AGG AAG TGC CGC GCC       1632
Arg Tyr Trp Arg Arg Trp Asn Arg Phe Cys Arg Arg Lys Cys Arg Ala
            530              535              540
```

| | | | | | | | | | | | | | | | | |
|---|---|---|---|---|---|---|---|---|---|---|---|---|---|---|---|---|
| GCA | GTC | AAG | TCT | AAT | GTC | TTC | TAC | TGG | CTG | GTG | ATT | TTC | CTG | GTG | TTC | 1680 |
| Ala | Val | Lys | Ser | Asn | Val | Phe | Tyr | Trp | Leu | Val | Ile | Phe | Leu | Val | Phe | |
| 545 | | | | 550 | | | | | 555 | | | | | 560 | | |
| CTC | AAC | ACG | CTC | ACC | ATT | GCC | TCT | GAG | CAC | TAC | AAC | CAG | CCC | AAC | TGG | 1728 |
| Leu | Asn | Thr | Leu | Thr | Ile | Ala | Ser | Glu | His | Tyr | Asn | Gln | Pro | Asn | Trp | |
| | | | | 565 | | | | | 570 | | | | | 575 | | |
| CTC | ACA | GAA | GTC | CAA | GAC | ACG | GCA | AAC | AAG | GCC | CTG | CTG | GCC | CTG | TTC | 1776 |
| Leu | Thr | Glu | Val | Gln | Asp | Thr | Ala | Asn | Lys | Ala | Leu | Leu | Ala | Leu | Phe | |
| | | | 580 | | | | | 585 | | | | | 590 | | | |
| ACG | GCA | GAG | ATG | CTC | CTG | AAG | ATG | TAC | AGC | CTG | GGC | CTG | CAG | GCC | TAC | 1824 |
| Thr | Ala | Glu | Met | Leu | Leu | Lys | Met | Tyr | Ser | Leu | Gly | Leu | Gln | Ala | Tyr | |
| | | | 595 | | | | | 600 | | | | | 605 | | | |
| TTC | GTG | TCC | CTC | TTC | AAC | CGC | TTT | GAC | TGC | TTC | GTC | GTG | TGT | GGC | GGC | 1872 |
| Phe | Val | Ser | Leu | Phe | Asn | Arg | Phe | Asp | Cys | Phe | Val | Val | Cys | Gly | Gly | |
| | | 610 | | | | | 615 | | | | | 620 | | | | |
| ATC | CTG | GAG | ACC | ATC | CTG | GTG | GAG | ACC | AAG | ATC | ATG | TCC | CCA | CTG | GGC | 1920 |
| Ile | Leu | Glu | Thr | Ile | Leu | Val | Glu | Thr | Lys | Ile | Met | Ser | Pro | Leu | Gly | |
| 625 | | | | | 630 | | | | | 635 | | | | | 640 | |
| ATC | TCC | GTG | CTC | AGA | TGC | GTC | CGG | CTG | CTG | AGG | ATT | TTC | AAG | ATC | ACG | 1968 |
| Ile | Ser | Val | Leu | Arg | Cys | Val | Arg | Leu | Leu | Arg | Ile | Phe | Lys | Ile | Thr | |
| | | | | 645 | | | | | 650 | | | | | 655 | | |
| AGG | TAC | TGG | AAC | TCC | TTG | AGC | AAC | CTG | GTG | GCA | TCC | TTG | CTG | AAC | TCT | 2016 |
| Arg | Tyr | Trp | Asn | Ser | Leu | Ser | Asn | Leu | Val | Ala | Ser | Leu | Leu | Asn | Ser | |
| | | | 660 | | | | | 665 | | | | | 670 | | | |
| GTG | CGC | TCC | ATC | GCC | TCC | CTG | CTC | CTT | CTC | CTC | TTC | CTC | TTC | ATC | ATC | 2064 |
| Val | Arg | Ser | Ile | Ala | Ser | Leu | Leu | Leu | Leu | Leu | Phe | Leu | Phe | Ile | Ile | |
| | | 675 | | | | | 680 | | | | | 685 | | | | |
| ATC | TTC | TCC | CTC | CTG | GGG | ATG | CAG | CTC | TTT | GGA | GGA | AAG | TTC | AAC | TTT | 2112 |
| Ile | Phe | Ser | Leu | Leu | Gly | Met | Gln | Leu | Phe | Gly | Gly | Lys | Phe | Asn | Phe | |
| | 690 | | | | | 695 | | | | | 700 | | | | | |
| GAT | GAG | ATG | CAG | ACC | CGG | AGG | AGC | ACA | TTC | GAT | AAC | TTC | CCC | CAG | TCC | 2160 |
| Asp | Glu | Met | Gln | Thr | Arg | Arg | Ser | Thr | Phe | Asp | Asn | Phe | Pro | Gln | Ser | |
| 705 | | | | | 710 | | | | | 715 | | | | | 720 | |
| CTC | CTC | ACT | GTG | TTT | CAG | ATC | CTG | ACC | GGG | GAG | GAC | TGG | AAT | TCG | GTG | 2208 |
| Leu | Leu | Thr | Val | Phe | Gln | Ile | Leu | Thr | Gly | Glu | Asp | Trp | Asn | Ser | Val | |
| | | | | 725 | | | | | 730 | | | | | 735 | | |
| ATG | TAT | GAT | GGG | ATC | ATG | GCT | TAT | GGG | GGC | CCC | TCT | TTT | CCA | GGG | ATG | 2256 |
| Met | Tyr | Asp | Gly | Ile | Met | Ala | Tyr | Gly | Gly | Pro | Ser | Phe | Pro | Gly | Met | |
| | | | 740 | | | | | 745 | | | | | 750 | | | |
| TTA | GTC | TGT | ATT | TAC | TTC | ATC | ATC | CTC | TTC | ATC | TCT | GGA | AAC | TAT | ATC | 2304 |
| Leu | Val | Cys | Ile | Tyr | Phe | Ile | Ile | Leu | Phe | Ile | Ser | Gly | Asn | Tyr | Ile | |
| | | 755 | | | | | 760 | | | | | 765 | | | | |
| CTA | CTG | AAT | GTG | TTC | TTG | GCC | ATT | GCT | GTG | GAC | AAC | CTG | GCT | GAT | GCT | 2352 |
| Leu | Leu | Asn | Val | Phe | Leu | Ala | Ile | Ala | Val | Asp | Asn | Leu | Ala | Asp | Ala | |
| | 770 | | | | | 775 | | | | | 780 | | | | | |
| GAG | AGC | CTC | ACA | TCT | GCC | CTA | AAG | GAG | GAG | GAA | GAG | GAG | AAG | GAG | AGA | 2400 |
| Glu | Ser | Leu | Thr | Ser | Ala | Leu | Lys | Glu | Glu | Glu | Glu | Glu | Lys | Glu | Arg | |
| 785 | | | | | 790 | | | | | 795 | | | | | 800 | |
| AAG | AAG | CTG | GCC | AGG | ACT | GCC | AGC | CCA | GAG | AAG | AAA | CAA | GAG | TTG | GTG | 2448 |
| Lys | Lys | Leu | Ala | Arg | Thr | Ala | Ser | Pro | Glu | Lys | Lys | Gln | Glu | Leu | Val | |
| | | | | 805 | | | | | 810 | | | | | 815 | | |
| GAG | AAG | CCG | GCA | GTG | GGG | GAA | TCC | AAG | GAG | GAG | AAG | ATT | GAG | CTG | AAA | 2496 |
| Glu | Lys | Pro | Ala | Val | Gly | Glu | Ser | Lys | Glu | Glu | Lys | Ile | Glu | Leu | Lys | |
| | | | 820 | | | | | 825 | | | | | 830 | | | |
| TCC | ATC | ACG | GCT | GAC | GGA | GAG | TCT | CCA | CCC | GCC | ACC | AAG | ATC | AAC | ATG | 2544 |
| Ser | Ile | Thr | Ala | Asp | Gly | Glu | Ser | Pro | Pro | Ala | Thr | Lys | Ile | Asn | Met | |
| | | 835 | | | | | 840 | | | | | 845 | | | | |
| GAT | GAC | CTC | CAG | CCC | AAT | GAA | AAT | GAG | GAT | AAG | AGC | CCC | TAC | CCC | AAC | 2592 |
| Asp | Asp | Leu | Gln | Pro | Asn | Glu | Asn | Glu | Asp | Lys | Ser | Pro | Tyr | Pro | Asn | |
| | 850 | | | | | 855 | | | | | 860 | | | | | |

```
CCA GAA ACT ACA GGA GAA GAG GAT GAG GAG GAG CCA GAG ATG CCT GTC    2640
Pro Glu Thr Thr Gly Glu Glu Asp Glu Glu Glu Pro Glu Met Pro Val
865                 870                 875                 880

GGC CCT CGC CCA CGA CCA CTC TCT GAG CTT CAC CTT AAG GAA AAG GCA    2688
Gly Pro Arg Pro Arg Pro Leu Ser Glu Leu His Leu Lys Glu Lys Ala
                885                 890                 895

GTG CCC ATG CCA GAA GCC AGC GCG TTT TTC ATC TTC AGC TCT AAC AAC    2736
Val Pro Met Pro Glu Ala Ser Ala Phe Phe Ile Phe Ser Ser Asn Asn
            900                 905                 910

AGG TTT CGC CTC CAG TGC CAC CGC ATT GTC AAT GAC ACG ATC TTC ACC    2784
Arg Phe Arg Leu Gln Cys His Arg Ile Val Asn Asp Thr Ile Phe Thr
        915                 920                 925

AAC CTG ATC CTC TTC TTC ATT CTG CTC AGC AGC ATT TCC CTG GCT GCT    2832
Asn Leu Ile Leu Phe Phe Ile Leu Leu Ser Ser Ile Ser Leu Ala Ala
    930                 935                 940

GAG GAC CCG GTC CAG CAC ACC TCC TTC AGG AAC CAT ATT CTG TTT TAT    2880
Glu Asp Pro Val Gln His Thr Ser Phe Arg Asn His Ile Leu Phe Tyr
945                 950                 955                 960

TTT GAT ATT GTT TTT ACC ACC ATT TTC ACC ATT GAA ATT GCT CTG AAG    2928
Phe Asp Ile Val Phe Thr Thr Ile Phe Thr Ile Glu Ile Ala Leu Lys
                965                 970                 975

ATG ACT GCT TAT GGG GCT TTC TTG CAC AAG GGT TCT TTC TGC CGG AAC    2976
Met Thr Ala Tyr Gly Ala Phe Leu His Lys Gly Ser Phe Cys Arg Asn
            980                 985                 990

TAC TTC AAC ATC CTG GAC CTG CTG GTG GTC AGC GTG TCC CTC ATC TCC    3024
Tyr Phe Asn Ile Leu Asp Leu Leu Val Val Ser Val Ser Leu Ile Ser
        995                 1000                1005

TTT GGC ATC CAG TCC AGT GCA ATC AAT GTC GTG AAG ATC TTG CGA GTC    3072
Phe Gly Ile Gln Ser Ser Ala Ile Asn Val Val Lys Ile Leu Arg Val
    1010                1015                1020

CTG CGA GTA CTC AGG CCC CTG AGG GCC ATC AAC AGG GCC AAG GGG CTA    3120
Leu Arg Val Leu Arg Pro Leu Arg Ala Ile Asn Arg Ala Lys Gly Leu
1025                1030                1035                1040

AAG CAT GTG GTT CAG TGT GTG TTT GTC GCC ATC CGG ACC ATC GGG AAC    3168
Lys His Val Val Gln Cys Val Phe Val Ala Ile Arg Thr Ile Gly Asn
                1045                1050                1055

ATC GTG ATT GTC ACC ACC CTG CTG CAG TTC ATG TTT GCC TGC ATC GGG    3216
Ile Val Ile Val Thr Thr Leu Leu Gln Phe Met Phe Ala Cys Ile Gly
            1060                1065                1070

GTC CAG CTC TTC AAG GGA AAG CTG TAC ACC TGT TCA GAC AGT TCC AAG    3264
Val Gln Leu Phe Lys Gly Lys Leu Tyr Thr Cys Ser Asp Ser Ser Lys
        1075                1080                1085

CAG ACA GAG GCG GAA TGC AAG GGC AAC TAC ATC ACG TAC AAA GAC GGG    3312
Gln Thr Glu Ala Glu Cys Lys Gly Asn Tyr Ile Thr Tyr Lys Asp Gly
    1090                1095                1100

GAG GTT GAC CAC CCC ATC ATC CAA CCC CGC AGC TGG GAG AAC AGC AAG    3360
Glu Val Asp His Pro Ile Ile Gln Pro Arg Ser Trp Glu Asn Ser Lys
1105                1110                1115                1120

TTT GAC TTT GAC AAT GTT CTG GCA GCC ATG ATG GCC CTC TTC ACC GTC    3408
Phe Asp Phe Asp Asn Val Leu Ala Ala Met Met Ala Leu Phe Thr Val
                1125                1130                1135

TCC ACC TTC GAA GGG TGG CCA GAG CTG CTG TAC CGC TCC ATC GAC TCC    3456
Ser Thr Phe Glu Gly Trp Pro Glu Leu Leu Tyr Arg Ser Ile Asp Ser
            1140                1145                1150

CAC ACG GAA GAC AAG GGC CCC ATC TAC AAC TAC CGT GTG GAG ATC TCC    3504
His Thr Glu Asp Lys Gly Pro Ile Tyr Asn Tyr Arg Val Glu Ile Ser
        1155                1160                1165

ATC TTC TTC ATC ATC TAC ATC ATC ATC ATC GCC TTC TTC ATG ATG AAC    3552
Ile Phe Phe Ile Ile Tyr Ile Ile Ile Ile Ala Phe Phe Met Met Asn
    1170                1175                1180
```

| | | | | | | | | | | | | | | | | |
|---|---|---|---|---|---|---|---|---|---|---|---|---|---|---|---|---|
| ATC | TTC | GTG | GGC | TTC | GTC | ATC | GTC | ACC | TTT | CAG | GAG | CAG | GGG | GAG | CAG | 3600 |
| Ile | Phe | Val | Gly | Phe | Val | Ile | Val | Thr | Phe | Gln | Glu | Gln | Gly | Glu | Gln | |
| 1185 | | | | | 1190 | | | | | 1195 | | | | | 1200 | |
| GAG | TAC | AAG | AAC | TGT | GAG | CTG | GAC | AAG | AAC | CAG | CGA | CAG | TGC | GTG | GAA | 3648 |
| Glu | Tyr | Lys | Asn | Cys | Glu | Leu | Asp | Lys | Asn | Gln | Arg | Gln | Cys | Val | Glu | |
| | | | | | 1205 | | | | | 1210 | | | | | 1215 | |
| TAC | GCC | CTC | AAG | GCC | CGG | CCC | CTG | CGG | AGG | TAC | ATC | CCC | AAG | AAC | CAG | 3696 |
| Tyr | Ala | Leu | Lys | Ala | Arg | Pro | Leu | Arg | Arg | Tyr | Ile | Pro | Lys | Asn | Gln | |
| | | | 1220 | | | | | 1225 | | | | | 1230 | | | |
| CAC | CAG | TAC | AAA | GTG | TGG | TAC | GTG | GTC | AAC | TCC | ACC | TAC | TTC | GAG | TAC | 3744 |
| His | Gln | Tyr | Lys | Val | Trp | Tyr | Val | Val | Asn | Ser | Thr | Tyr | Phe | Glu | Tyr | |
| | | 1235 | | | | | 1240 | | | | | 1245 | | | | |
| CTG | ATG | TTC | GTC | CTC | ATC | CTG | CTC | AAC | ACC | ATC | TGC | CTG | GCC | ATG | CAG | 3792 |
| Leu | Met | Phe | Val | Leu | Ile | Leu | Leu | Asn | Thr | Ile | Cys | Leu | Ala | Met | Gln | |
| | | 1250 | | | | | 1255 | | | | | 1260 | | | | |
| CAC | TAC | GGC | CAG | AGC | TGC | CTG | TTC | AAA | ATC | GCC | ATG | AAC | ATC | CTC | AAC | 3840 |
| His | Tyr | Gly | Gln | Ser | Cys | Leu | Phe | Lys | Ile | Ala | Met | Asn | Ile | Leu | Asn | |
| 1265 | | | | | 1270 | | | | | 1275 | | | | | 1280 | |
| ATG | CTC | TTC | ACT | GGC | CTC | TTC | ACC | GTG | GAG | ATG | ATC | CTG | AAG | CTC | ATT | 3888 |
| Met | Leu | Phe | Thr | Gly | Leu | Phe | Thr | Val | Glu | Met | Ile | Leu | Lys | Leu | Ile | |
| | | | | 1285 | | | | | 1290 | | | | | 1295 | | |
| GCC | TTC | AAA | CCC | AAG | GGT | TAC | TTT | AGT | GAT | CCC | TGG | AAT | GTT | TTT | GAC | 3936 |
| Ala | Phe | Lys | Pro | Lys | Gly | Tyr | Phe | Ser | Asp | Pro | Trp | Asn | Val | Phe | Asp | |
| | | | 1300 | | | | | 1305 | | | | | 1310 | | | |
| TTC | CTC | ATC | GTA | ATT | GGC | AGC | ATA | ATT | GAC | GTC | ATT | CTC | AGT | GAG | ACT | 3984 |
| Phe | Leu | Ile | Val | Ile | Gly | Ser | Ile | Ile | Asp | Val | Ile | Leu | Ser | Glu | Thr | |
| | | 1315 | | | | | 1320 | | | | | 1325 | | | | |
| AAT | CCA | GCT | GAA | CAT | ACC | CAA | TGC | TCT | CCC | TCT | ATG | AAC | GCA | GAG | GAA | 4032 |
| Asn | Pro | Ala | Glu | His | Thr | Gln | Cys | Ser | Pro | Ser | Met | Asn | Ala | Glu | Glu | |
| | 1330 | | | | | 1335 | | | | | 1340 | | | | | |
| AAC | TCC | CGC | ATC | TCC | ATC | ACC | TTC | TTC | CGC | CTG | TTC | CGG | GTC | ATG | CGT | 4080 |
| Asn | Ser | Arg | Ile | Ser | Ile | Thr | Phe | Phe | Arg | Leu | Phe | Arg | Val | Met | Arg | |
| 1345 | | | | | 1350 | | | | | 1355 | | | | | 1360 | |
| CTG | GTG | AAG | CTG | CTG | AGC | CGT | GGG | GAG | GGC | ATC | CGG | ACG | CTG | CTG | TGG | 4128 |
| Leu | Val | Lys | Leu | Leu | Ser | Arg | Gly | Glu | Gly | Ile | Arg | Thr | Leu | Leu | Trp | |
| | | | | 1365 | | | | | 1370 | | | | | 1375 | | |
| ACC | TTC | ATC | AAG | TCC | TTC | CAG | GCC | CTG | CCC | TAT | GTG | GCC | CTC | CTG | ATC | 4176 |
| Thr | Phe | Ile | Lys | Ser | Phe | Gln | Ala | Leu | Pro | Tyr | Val | Ala | Leu | Leu | Ile | |
| | | | 1380 | | | | | 1385 | | | | | 1390 | | | |
| GTG | ATG | CTG | TTC | TTC | ATC | TAC | GCG | GTG | ATC | GGG | ATG | CAG | GTG | TTT | GGG | 4224 |
| Val | Met | Leu | Phe | Phe | Ile | Tyr | Ala | Val | Ile | Gly | Met | Gln | Val | Phe | Gly | |
| | | | | 1395 | | | | | 1400 | | | | | 1405 | | |
| AAA | ATT | GCC | CTG | AAT | GAT | ACC | ACA | GAG | ATC | AAC | CGG | AAC | AAC | AAC | TTT | 4272 |
| Lys | Ile | Ala | Leu | Asn | Asp | Thr | Thr | Glu | Ile | Asn | Arg | Asn | Asn | Asn | Phe | |
| | | | 1410 | | | | | 1415 | | | | | 1420 | | | |
| CAG | ACC | TTC | CCC | CAG | GCC | GTG | CTC | CTC | TTC | AGG | TGT | GCC | ACC | GGG | | 4320 |
| Gln | Thr | Phe | Pro | Gln | Ala | Val | Leu | Leu | Leu | Phe | Arg | Cys | Ala | Thr | Gly | |
| 1425 | | | | | 1430 | | | | | 1435 | | | | | 1440 | |
| GAG | GCC | TGG | CAG | GAC | ATC | ATG | CTG | GCC | TGC | ATG | CCA | GGC | AAG | AAG | TGT | 4368 |
| Glu | Ala | Trp | Gln | Asp | Ile | Met | Leu | Ala | Cys | Met | Pro | Gly | Lys | Lys | Cys | |
| | | | | 1445 | | | | | 1450 | | | | | 1455 | | |
| GCC | CCA | GAG | TCC | GAG | CCC | AGC | AAC | AGC | ACG | GAG | GGT | GAA | ACA | CCC | TGT | 4416 |
| Ala | Pro | Glu | Ser | Glu | Pro | Ser | Asn | Ser | Thr | Glu | Gly | Glu | Thr | Pro | Cys | |
| | | | 1460 | | | | | 1465 | | | | | 1470 | | | |
| GGT | AGC | AGC | TTT | GCT | GTC | TTC | TAC | TTC | ATC | AGC | TTC | TAC | ATG | CGC | TGT | 4464 |
| Gly | Ser | Ser | Phe | Ala | Val | Phe | Tyr | Phe | Ile | Ser | Phe | Tyr | Met | Arg | Cys | |
| | | | 1475 | | | | | 1480 | | | | | 1485 | | | |
| GCC | TTC | CTG | ATC | ATC | AAC | CTC | TTT | GTA | GCT | GTC | ATC | ATG | GAC | AAC | TTT | 4512 |
| Ala | Phe | Leu | Ile | Ile | Asn | Leu | Phe | Val | Ala | Val | Ile | Met | Asp | Asn | Phe | |
| | | | 1490 | | | | | 1495 | | | | | 1500 | | | |

```
GAC TAC CTG ACA AGG GAC TGG TCC ATC CTT GGT CCC CAC CAC CTG GAT    4560
Asp Tyr Leu Thr Arg Asp Trp Ser Ile Leu Gly Pro His His Leu Asp
1505                1510                1515                1520

GAG TTT AAA AGA ATC TGG GCA GAG TAT GAC CCT GAA GCC AAG GGT CGT    4608
Glu Phe Lys Arg Ile Trp Ala Glu Tyr Asp Pro Glu Ala Lys Gly Arg
                1525                1530                1535

ATC AAA CAC CTG GAT GTG GTG ACC CTC CTC CGG CGG ATT CAG CCG CCA    4656
Ile Lys His Leu Asp Val Val Thr Leu Leu Arg Arg Ile Gln Pro Pro
        1540                1545                1550

CTA GGT TTT GGG AAG CTG TGC CCT CAC CGC GTG GCT TGC AAA CGC CTG    4704
Leu Gly Phe Gly Lys Leu Cys Pro His Arg Val Ala Cys Lys Arg Leu
1555                1560                1565

GTC TCC ATG AAC ATG CCT CTG AAC AGC GAC GGG ACA GTC ATG TTC AAT    4752
Val Ser Met Asn Met Pro Leu Asn Ser Asp Gly Thr Val Met Phe Asn
1570                1575                1580

GCC ACC CTG TTT GCC CTG GTC AGG ACG GCC CTG AGG ATC AAA ACA GAA    4800
Ala Thr Leu Phe Ala Leu Val Arg Thr Ala Leu Arg Ile Lys Thr Glu
1585                1590                1595                1600

GGG AAC CTA GAA CAA GCC AAT GAG GAG CTG CGG GCG ATC ATC AAG AAG    4848
Gly Asn Leu Glu Gln Ala Asn Glu Glu Leu Arg Ala Ile Ile Lys Lys
                1605                1610                1615

ATC TGG AAG CGG ACC AGC ATG AAG CTG CTG GAC CAG GTG GTG CCC CCT    4896
Ile Trp Lys Arg Thr Ser Met Lys Leu Leu Asp Gln Val Val Pro Pro
        1620                1625                1630

GCA GGT GAT GAT GAG GTC ACC GTT GGC AAG TTC TAC GCC ACG TTC CTG    4944
Ala Gly Asp Asp Glu Val Thr Val Gly Lys Phe Tyr Ala Thr Phe Leu
1635                1640                1645

ATC CAG GAG TAC TTC CGG AAG TTC AAG AAG CGC AAA GAG CAG GGC CTT    4992
Ile Gln Glu Tyr Phe Arg Lys Phe Lys Lys Arg Lys Glu Gln Gly Leu
1650                1655                1660

GTG GGC AAG CCC TCC CAG AGG AAC GCG CTG TCT CTG CAG GCT GGC TTG    5040
Val Gly Lys Pro Ser Gln Arg Asn Ala Leu Ser Leu Gln Ala Gly Leu
1665                1670                1675                1680

CGC ACA CTG CAT GAC ATC GGG CCT GAG ATC CGA CGG GCC ATC TCT GGA    5088
Arg Thr Leu His Asp Ile Gly Pro Glu Ile Arg Arg Ala Ile Ser Gly
                1685                1690                1695

GAT CTC ACC GCT GAG GAG GAG CTG GAC AAG GCC ATG AAG GAG GCT GTG    5136
Asp Leu Thr Ala Glu Glu Glu Leu Asp Lys Ala Met Lys Glu Ala Val
        1700                1705                1710

TCC GCT GCT TCT GAA GAT GAC ATC TTC AGG AGG GCC GGT GGC CTG TTC    5184
Ser Ala Ala Ser Glu Asp Asp Ile Phe Arg Arg Ala Gly Gly Leu Phe
1715                1720                1725

GGC AAC CAC GTC AGC TAC TAC CAA AGC GAC GGC CGG AGC GCC TTC CCC    5232
Gly Asn His Val Ser Tyr Tyr Gln Ser Asp Gly Arg Ser Ala Phe Pro
1730                1735                1740

CAG ACC TTC ACC ACT CAG CGC CCG CTG CAC ATC AAC AAG GCG GGC AGC    5280
Gln Thr Phe Thr Thr Gln Arg Pro Leu His Ile Asn Lys Ala Gly Ser
1745                1750                1755                1760

AGC CAG GGC GAC ACT GAG TCG CCA TCC CAC GAG AAG CTG GTG GAC TCC    5328
Ser Gln Gly Asp Thr Glu Ser Pro Ser His Glu Lys Leu Val Asp Ser
                1765                1770                1775

ACC TTC ACC CCG AGC AGC TAC TCG TCC ACC GGC TCC AAC GCC AAC ATC    5376
Thr Phe Thr Pro Ser Ser Tyr Ser Ser Thr Gly Ser Asn Ala Asn Ile
        1780                1785                1790

AAC AAC GCC AAC AAC ACC GCC CTG GGT CGC CTC CCT CGC CCC GCC GGC    5424
Asn Asn Ala Asn Asn Thr Ala Leu Gly Arg Leu Pro Arg Pro Ala Gly
1795                1800                1805

TAC CCC AGC ACA GTC AGC ACT GTG GAG GGC CAC GGG CCC CCC TTG TCC    5472
Tyr Pro Ser Thr Val Ser Thr Val Glu Gly His Gly Pro Pro Leu Ser
1810                1815                1820
```

| | | | | | | | | | | | | | | | | |
|---|---|---|---|---|---|---|---|---|---|---|---|---|---|---|---|---|
| CCT | GCC | ATC | CGG | GTG | CAG | GAG | GTG | GCG | TGG | AAG | CTC | AGC | TCC | AAC | AGG | 5520 |
| Pro | Ala | Ile | Arg | Val | Gln | Glu | Val | Ala | Trp | Lys | Leu | Ser | Ser | Asn | Arg | |
| 1825 | | | | 1830 | | | | 1835 | | | | | | | 1840 | |
| TGC | CAC | TCC | CGG | GAG | AGC | CAG | GCA | GCC | ATG | GCG | CGT | CAG | GAG | GAG | ACG | 5568 |
| Cys | His | Ser | Arg | Glu | Ser | Gln | Ala | Ala | Met | Ala | Arg | Gln | Glu | Glu | Thr | |
| | | | | 1845 | | | | | 1850 | | | | | | 1855 | |
| TCT | CAG | GAT | GAG | ACC | TAT | GAA | GTG | AAG | ATG | AAC | CAT | GAC | ACG | GAG | GCC | 5616 |
| Ser | Gln | Asp | Glu | Thr | Tyr | Glu | Val | Lys | Met | Asn | His | Asp | Thr | Glu | Ala | |
| | | | 1860 | | | | | 1865 | | | | | 1870 | | | |
| TGC | AGT | GAG | CCC | AGC | CTG | CTC | TCC | ACA | GAG | ATG | CTC | TCC | TAC | CAG | GAT | 5664 |
| Cys | Ser | Glu | Pro | Ser | Leu | Leu | Ser | Thr | Glu | Met | Leu | Ser | Tyr | Gln | Asp | |
| | | | 1875 | | | | | 1880 | | | | | 1885 | | | |
| GAC | GAA | AAT | CGG | CAA | CTG | ACG | CTC | CCA | GAG | GAG | GAC | AAG | AGG | GAC | ATC | 5712 |
| Asp | Glu | Asn | Arg | Gln | Leu | Thr | Leu | Pro | Glu | Glu | Asp | Lys | Arg | Asp | Ile | |
| | | | 1890 | | | | | 1895 | | | | | 1900 | | | |
| CGG | CAA | TCT | CCG | AAG | AGG | GGT | TTC | CTC | CGC | TCT | TCC | TCA | CTA | GGT | CGA | 5760 |
| Arg | Gln | Ser | Pro | Lys | Arg | Gly | Phe | Leu | Arg | Ser | Ser | Ser | Leu | Gly | Arg | |
| 1905 | | | | 1910 | | | | | 1915 | | | | | | 1920 | |
| AGG | GCC | TCC | TTC | CAC | CTG | GAA | TGT | CTG | AAG | CGA | CAG | AAG | GAC | CGA | GGG | 5808 |
| Arg | Ala | Ser | Phe | His | Leu | Glu | Cys | Leu | Lys | Arg | Gln | Lys | Asp | Arg | Gly | |
| | | | | 1925 | | | | | 1930 | | | | | 1935 | | |
| GGA | GAC | ATC | TCT | CAG | AAG | ACA | GTC | CTG | CCC | TTG | CAT | CTG | GTT | CAT | CAT | 5856 |
| Gly | Asp | Ile | Ser | Gln | Lys | Thr | Val | Leu | Pro | Leu | His | Leu | Val | His | His | |
| | | | 1940 | | | | | 1945 | | | | | 1950 | | | |
| CAG | GCA | TTG | GCA | GTG | GCA | GGC | CTG | AGC | CCC | CTC | CTC | CAG | AGA | AGC | CAT | 5904 |
| Gln | Ala | Leu | Ala | Val | Ala | Gly | Leu | Ser | Pro | Leu | Leu | Gln | Arg | Ser | His | |
| | | | 1955 | | | | | 1960 | | | | | 1965 | | | |

( 2 ) INFORMATION FOR SEQ ID NO:4:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| AGACCACGGC | TTCCTCGAAT | CTTGCGCGAA | GCCGCCGGCC | TCGGAGGAGG | GATTAATCCA | 60 |
| GACCCGCCGG | GGGGTGTTTT | CACATTTCTT | CCTCTTCGTG | GCTGCTCCTC | CTATTAAAAC | 120 |
| CATTTTTGGT | CC | | | | | 132 |

( 2 ) INFORMATION FOR SEQ ID NO:5:

( i ) SEQUENCE CHARACTERISTICS:
        ( A ) LENGTH: 89 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| CGCTGAGGGC | CTTCCGCGTG | CTGCGCCCCC | TGCGGCTGGT | GTCCGGAGTC | CCAAGTCTCC | 60 |
| AGGTGGTCCT | GAATTCCATC | ATCAAGGCC | | | | 89 |

( 2 ) INFORMATION FOR SEQ ID NO:6:

( i ) SEQUENCE CHARACTERISTICS:
        ( A ) LENGTH: 84 base pairs
        ( B ) TYPE: nucleic acid
        ( C ) STRANDEDNESS: double ( D ) TOPOLOGY: linear ( i i ) MOLECULE TYPE: DNA (genomic)

( i x ) FEATURE:
    ( A ) NAME/KEY: CDS
    ( B ) LOCATION: 1..84
    ( D ) OTHER INFORMATION: /note="An alternative exon of alpha-1C."

( x i ) SEQUENCE DESCRIPTION: SEQ ID NO:6:

```
CAC TAT TTC TGT GAT GCA TGG AAT ACA TTT GAC GCC TTG ATT GTT GTG      48
His Tyr Phe Cys Asp Ala Trp Asn Thr Phe Asp Ala Leu Ile Val Val
 1               5                  10                  15

GGT AGC ATT GTT GAT ATA GCA ATC ACC GAG GTA AAC                      84
Gly Ser Ile Val Asp Ile Ala Ile Thr Glu Val Asn
            20                  25
```

( 2 ) INFORMATION FOR SEQ ID NO:7:

( i ) SEQUENCE CHARACTERISTICS:
        ( A ) LENGTH: 7362 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 144..7163

( i x ) FEATURE:
        ( A ) NAME/KEY: 5'UTR
        ( B ) LOCATION: 1..143

( i x ) FEATURE:
        ( A ) NAME/KEY: 3'UTR
        ( B ) LOCATION: 7161..7362

( x i ) SEQUENCE DESCRIPTION: SEQ ID NO:7:

```
GCGGCGGCGG CTGCGGCGGT GGGGCCGGGC GAGGTCCGTG CGGTCCCGGC GGCTCCGTGG      60

CTGCTCCGCT CTGAGCGCCT GCGCGCCCCG CGCCCTCCCT GCCGGGGCCG CTGGGCCGGG     120

GATGCACGCG GGGCCCGGGA GCC ATG GTC CGC TTC GGG GAC GAG CTG GGC        170
                         Met Val Arg Phe Gly Asp Glu Leu Gly
                          1               5

GGC CGC TAT GGA GGC CCC GGC GGC GGA GAG CGG GCC CGG GGC GGC GGG      218
Gly Arg Tyr Gly Gly Pro Gly Gly Gly Glu Arg Ala Arg Gly Gly Gly
 10              15                  20                  25

GCC GGC GGG GCG GGG GGC CCG GGT CCC GGG GGG CTG CAG CCC GGC CAG      266
Ala Gly Gly Ala Gly Gly Pro Gly Pro Gly Gly Leu Gln Pro Gly Gln
             30                  35                  40

CGG GTC CTC TAC AAG CAA TCG ATC GCG CAG CGC GCG CGG ACC ATG GCG      314
Arg Val Leu Tyr Lys Gln Ser Ile Ala Gln Arg Ala Arg Thr Met Ala
             45                  50                  55

CTG TAC AAC CCC ATC CCG GTC AAG CAG AAC TGC TTC ACC GTC AAC CGC      362
Leu Tyr Asn Pro Ile Pro Val Lys Gln Asn Cys Phe Thr Val Asn Arg
         60                  65                  70

TCG CTC TTC GTC TTC AGC GAG GAC AAC GTC GTC CGC AAA TAC GCG AAG      410
Ser Leu Phe Val Phe Ser Glu Asp Asn Val Val Arg Lys Tyr Ala Lys
     75                  80                  85

CGC ATC ACC GAG TGG CCT CCA TTC GAG AAT ATG ATC CTG GCC ACC ATC      458
Arg Ile Thr Glu Trp Pro Pro Phe Glu Asn Met Ile Leu Ala Thr Ile
 90              95                  100                 105

ATC GCC AAC TGC ATC GTG CTG GCC CTG GAG CAG CAC CTC CCT GAT GGG      506
Ile Ala Asn Cys Ile Val Leu Ala Leu Glu Gln His Leu Pro Asp Gly
             110                 115                 120
```

| | | | | | | | | | | | | | | | | |
|---|---|---|---|---|---|---|---|---|---|---|---|---|---|---|---|---|
| GAC | AAA | ACG | CCC | ATG | TCC | GAG | CGG | CTG | GAC | GAC | ACG | GAG | CCC | TAT | TTC | 554 |
| Asp | Lys | Thr | Pro | Met | Ser | Glu | Arg | Leu | Asp | Asp | Thr | Glu | Pro | Tyr | Phe | |
| | | | 125 | | | | 130 | | | | | | 135 | | | |
| ATC | GGG | ATC | TTT | TGC | TTC | GAG | GCA | GGG | ATC | AAA | ATC | ATC | GCT | CTG | GGC | 602 |
| Ile | Gly | Ile | Phe | Cys | Phe | Glu | Ala | Gly | Ile | Lys | Ile | Ile | Ala | Leu | Gly | |
| | | 140 | | | | | 145 | | | | | 150 | | | | |
| TTT | GTC | TTC | CAC | AAG | GGC | TCT | TAC | CTG | CGG | AAC | GGC | TGG | AAC | GTC | ATG | 650 |
| Phe | Val | Phe | His | Lys | Gly | Ser | Tyr | Leu | Arg | Asn | Gly | Trp | Asn | Val | Met | |
| 155 | | | | | | | 160 | | | | | 165 | | | | |
| GAC | TTC | GTG | GTC | GTC | CTC | ACA | GGG | ATC | CTT | GCC | ACG | GCT | GGA | ACT | GAC | 698 |
| Asp | Phe | Val | Val | Val | Leu | Thr | Gly | Ile | Leu | Ala | Thr | Ala | Gly | Thr | Asp | |
| 170 | | | | | 175 | | | | | 180 | | | | | 185 | |
| TTC | GAC | CTG | CGA | ACA | CTG | AGG | GCT | GTG | CGT | GTG | CTG | AGG | CCC | CTG | AAG | 746 |
| Phe | Asp | Leu | Arg | Thr | Leu | Arg | Ala | Val | Arg | Val | Leu | Arg | Pro | Leu | Lys | |
| | | | | 190 | | | | | 195 | | | | | 200 | | |
| CTG | GTG | TCT | GGG | ATT | CCA | AGT | TTG | CAG | GTG | GTG | CTC | AAG | TCC | ATC | ATG | 794 |
| Leu | Val | Ser | Gly | Ile | Pro | Ser | Leu | Gln | Val | Val | Leu | Lys | Ser | Ile | Met | |
| | | | 205 | | | | | 210 | | | | | 215 | | | |
| AAG | GCC | ATG | GTT | CCA | CTC | CTG | CAG | ATT | GGG | CTG | CTT | CTC | TTC | TTT | GCC | 842 |
| Lys | Ala | Met | Val | Pro | Leu | Leu | Gln | Ile | Gly | Leu | Leu | Leu | Phe | Phe | Ala | |
| | | 220 | | | | | 225 | | | | | 230 | | | | |
| ATC | CTC | ATG | TTT | GCC | ATC | ATT | GGC | CTG | GAG | TTC | TAC | ATG | GGC | AAG | TTC | 890 |
| Ile | Leu | Met | Phe | Ala | Ile | Ile | Gly | Leu | Glu | Phe | Tyr | Met | Gly | Lys | Phe | |
| 235 | | | | | | 240 | | | | | 245 | | | | | |
| CAC | AAG | GCC | TGT | TTC | CCC | AAC | AGC | ACA | GAT | GCG | GAG | CCC | GTG | GGT | GAC | 938 |
| His | Lys | Ala | Cys | Phe | Pro | Asn | Ser | Thr | Asp | Ala | Glu | Pro | Val | Gly | Asp | |
| 250 | | | | | 255 | | | | | 260 | | | | | 265 | |
| TTC | CCC | TGT | GGC | AAG | GAG | GCC | CCA | GCC | CGG | CTG | TGC | GAG | GGC | GAC | ACT | 986 |
| Phe | Pro | Cys | Gly | Lys | Glu | Ala | Pro | Ala | Arg | Leu | Cys | Glu | Gly | Asp | Thr | |
| | | | | 270 | | | | | 275 | | | | | 280 | | |
| GAG | TGC | CGG | GAG | TAC | TGG | CCA | GGA | CCC | AAC | TTT | GGC | ATC | ACC | AAC | TTT | 1034 |
| Glu | Cys | Arg | Glu | Tyr | Trp | Pro | Gly | Pro | Asn | Phe | Gly | Ile | Thr | Asn | Phe | |
| | | | 285 | | | | | 290 | | | | | 295 | | | |
| GAC | AAT | ATC | CTG | TTT | GCC | ATC | TTG | ACG | GTG | TTC | CAG | TGC | ATC | ACC | ATG | 1082 |
| Asp | Asn | Ile | Leu | Phe | Ala | Ile | Leu | Thr | Val | Phe | Gln | Cys | Ile | Thr | Met | |
| | | 300 | | | | | 305 | | | | | 310 | | | | |
| GAG | GGC | TGG | ACT | GAC | ATC | CTC | TAT | AAT | ACA | AAC | GAT | GCG | GCC | GGC | AAC | 1130 |
| Glu | Gly | Trp | Thr | Asp | Ile | Leu | Tyr | Asn | Thr | Asn | Asp | Ala | Ala | Gly | Asn | |
| | 315 | | | | | 320 | | | | | 325 | | | | | |
| ACC | TGG | AAC | TGG | CTC | TAC | TTC | ATC | CCT | CTC | ATC | ATC | ATC | GGC | TCC | TTC | 1178 |
| Thr | Trp | Asn | Trp | Leu | Tyr | Phe | Ile | Pro | Leu | Ile | Ile | Ile | Gly | Ser | Phe | |
| 330 | | | | | 335 | | | | | 340 | | | | | 345 | |
| TTC | ATG | CTC | AAC | CTG | GTG | CTG | GGC | GTG | CTC | TCG | GGG | GAG | TTT | GCC | AAG | 1226 |
| Phe | Met | Leu | Asn | Leu | Val | Leu | Gly | Val | Leu | Ser | Gly | Glu | Phe | Ala | Lys | |
| | | | | 350 | | | | | 355 | | | | | 360 | | |
| GAG | CGA | GAG | AGG | GTG | GAG | AAC | CGC | CGC | GCC | TTC | CTG | AAG | CTG | CGC | CGG | 1274 |
| Glu | Arg | Glu | Arg | Val | Glu | Asn | Arg | Arg | Ala | Phe | Leu | Lys | Leu | Arg | Arg | |
| | | | 365 | | | | | 370 | | | | | 375 | | | |
| CAG | CAG | CAG | ATC | GAG | CGA | GAG | CTC | AAC | GGG | TAC | CTG | GAG | TGG | ATC | TTC | 1322 |
| Gln | Gln | Gln | Ile | Glu | Arg | Glu | Leu | Asn | Gly | Tyr | Leu | Glu | Trp | Ile | Phe | |
| | | 380 | | | | | 385 | | | | | 390 | | | | |
| AAG | GCG | GAG | GAA | GTC | ATG | CTG | GCC | GAG | GAG | GAC | AGG | AAT | GCA | GAG | GAG | 1370 |
| Lys | Ala | Glu | Glu | Val | Met | Leu | Ala | Glu | Glu | Asp | Arg | Asn | Ala | Glu | Glu | |
| | 395 | | | | | 400 | | | | | 405 | | | | | |
| AAG | TCC | CCT | TTG | GAC | GTG | CTG | AAG | AGA | GCG | GCC | ACC | AAG | AAG | AGC | AGA | 1418 |
| Lys | Ser | Pro | Leu | Asp | Val | Leu | Lys | Arg | Ala | Ala | Thr | Lys | Lys | Ser | Arg | |
| 410 | | | | | 415 | | | | | 420 | | | | | 425 | |
| AAT | GAC | CTG | ATC | CAC | GCA | GAG | GAG | GGA | GAG | GAC | CGG | TTT | GCA | GAT | CTC | 1466 |
| Asn | Asp | Leu | Ile | His | Ala | Glu | Glu | Gly | Glu | Asp | Arg | Phe | Ala | Asp | Leu | |
| | | | | 430 | | | | | 435 | | | | | 440 | | |

| | | | | | | | | | | | | | | | | |
|---|---|---|---|---|---|---|---|---|---|---|---|---|---|---|---|---|
| TGT | GCT | GTT | GGA | TCC | CCC | TTC | GCC | CGC | GCC | AGC | CTC | AAG | AGC | GGG | AAG | 1514 |
| Cys | Ala | Val | Gly | Ser | Pro | Phe | Ala | Arg | Ala | Ser | Leu | Lys | Ser | Gly | Lys | |
| | | | 445 | | | | | 450 | | | | | 455 | | | |
| ACA | GAG | AGC | TCG | TCA | TAC | TTC | CGG | AGG | AAG | GAG | AAG | ATG | TTC | CGG | TTT | 1562 |
| Thr | Glu | Ser | Ser | Ser | Tyr | Phe | Arg | Arg | Lys | Glu | Lys | Met | Phe | Arg | Phe | |
| | | | 460 | | | | | 465 | | | | | 470 | | | |
| TTT | ATC | CGG | CGC | ATG | GTG | AAG | GCT | CAG | AGC | TTC | TAC | TGG | GTG | GTG | CTG | 1610 |
| Phe | Ile | Arg | Arg | Met | Val | Lys | Ala | Gln | Ser | Phe | Tyr | Trp | Val | Val | Leu | |
| | | 475 | | | | | 480 | | | | | 485 | | | | |
| TGC | GTG | GTG | GCC | CTG | AAC | ACA | CTG | TGT | GTG | GCC | ATG | GTG | CAT | TAC | AAC | 1658 |
| Cys | Val | Val | Ala | Leu | Asn | Thr | Leu | Cys | Val | Ala | Met | Val | His | Tyr | Asn | |
| | 490 | | | | | 495 | | | | | 500 | | | | 505 | |
| CAG | CCG | CGG | CGG | CTT | ACC | ACG | ACC | CTG | TAT | TTT | GCA | GAG | TTT | GTT | TTC | 1706 |
| Gln | Pro | Arg | Arg | Leu | Thr | Thr | Thr | Leu | Tyr | Phe | Ala | Glu | Phe | Val | Phe | |
| | | | | 510 | | | | | 515 | | | | | 520 | | |
| CTG | GGT | CTC | TTC | CTC | ACA | GAG | ATG | TCC | CTG | AAG | ATG | TAT | GGC | CTG | GGG | 1754 |
| Leu | Gly | Leu | Phe | Leu | Thr | Glu | Met | Ser | Leu | Lys | Met | Tyr | Gly | Leu | Gly | |
| | | | 525 | | | | | 530 | | | | | 535 | | | |
| CCC | AGA | AGC | TAC | TTC | CGG | TCC | TCC | TTC | AAC | TGC | TTC | GAC | TTT | GGG | GTC | 1802 |
| Pro | Arg | Ser | Tyr | Phe | Arg | Ser | Ser | Phe | Asn | Cys | Phe | Asp | Phe | Gly | Val | |
| | | | 540 | | | | | 545 | | | | | 550 | | | |
| ATC | GTG | GGG | AGC | GTC | TTT | GAA | GTG | GTC | TGG | GCG | GCC | ATC | AAG | CCG | GGA | 1850 |
| Ile | Val | Gly | Ser | Val | Phe | Glu | Val | Val | Trp | Ala | Ala | Ile | Lys | Pro | Gly | |
| | | 555 | | | | | 560 | | | | | 565 | | | | |
| AGC | TCC | TTT | GGG | ATC | AGT | GTG | CTG | CGG | GCC | CTC | CGC | CTG | CTG | AGG | ATC | 1898 |
| Ser | Ser | Phe | Gly | Ile | Ser | Val | Leu | Arg | Ala | Leu | Arg | Leu | Leu | Arg | Ile | |
| 570 | | | | | 575 | | | | | 580 | | | | | 585 | |
| TTC | AAA | GTC | ACG | AAG | TAC | TGG | AGC | TCC | CTG | CGG | AAC | CTG | GTG | GTG | TCC | 1946 |
| Phe | Lys | Val | Thr | Lys | Tyr | Trp | Ser | Ser | Leu | Arg | Asn | Leu | Val | Val | Ser | |
| | | | | 590 | | | | | 595 | | | | | 600 | | |
| CTG | CTG | AAC | TCC | ATG | AAG | TCC | ATC | ATC | AGC | CTC | CTC | TTC | TTG | CTC | TTC | 1994 |
| Leu | Leu | Asn | Ser | Met | Lys | Ser | Ile | Ile | Ser | Leu | Leu | Phe | Leu | Leu | Phe | |
| | | | 605 | | | | | 610 | | | | | 615 | | | |
| CTG | TTC | ATT | GTG | GTC | TTC | GCC | CTG | CTG | GGG | ATG | CAG | CTG | TTT | GGG | GGA | 2042 |
| Leu | Phe | Ile | Val | Val | Phe | Ala | Leu | Leu | Gly | Met | Gln | Leu | Phe | Gly | Gly | |
| | | 620 | | | | | 625 | | | | | 630 | | | | |
| CAG | TTC | AAC | TTC | CAG | GAT | GAG | ACT | CCC | ACA | ACC | AAC | TTC | GAC | ACC | TTC | 2090 |
| Gln | Phe | Asn | Phe | Gln | Asp | Glu | Thr | Pro | Thr | Thr | Asn | Phe | Asp | Thr | Phe | |
| | 635 | | | | | 640 | | | | | 645 | | | | | |
| CCT | GCC | GCC | ATC | CTC | ACT | GTC | TTC | CAG | ATC | CTG | ACG | GGA | GAG | GAC | TGG | 2138 |
| Pro | Ala | Ala | Ile | Leu | Thr | Val | Phe | Gln | Ile | Leu | Thr | Gly | Glu | Asp | Trp | |
| 650 | | | | | 655 | | | | | 660 | | | | | 665 | |
| AAT | GCA | GTG | ATG | TAT | CAC | GGG | ATC | GAA | TCG | CAA | GGC | GGC | GTC | AGC | AAA | 2186 |
| Asn | Ala | Val | Met | Tyr | His | Gly | Ile | Glu | Ser | Gln | Gly | Gly | Val | Ser | Lys | |
| | | | | 670 | | | | | 675 | | | | | 680 | | |
| GGC | ATG | TTC | TCG | TCC | TTT | TAC | TTC | ATT | GTC | CTG | ACA | CTG | TTC | GGA | AAC | 2234 |
| Gly | Met | Phe | Ser | Ser | Phe | Tyr | Phe | Ile | Val | Leu | Thr | Leu | Phe | Gly | Asn | |
| | | | 685 | | | | | 690 | | | | | 695 | | | |
| TAC | ACT | CTG | CTG | AAT | GTC | TTT | CTG | GCC | ATC | GCT | GTG | GAC | AAC | CTG | GCC | 2282 |
| Tyr | Thr | Leu | Leu | Asn | Val | Phe | Leu | Ala | Ile | Ala | Val | Asp | Asn | Leu | Ala | |
| | | 700 | | | | | 705 | | | | | 710 | | | | |
| AAC | GCC | CAA | GAG | CTG | ACC | AAG | GAT | GAA | GAG | GAG | ATG | GAA | GAA | GCA | GCC | 2330 |
| Asn | Ala | Gln | Glu | Leu | Thr | Lys | Asp | Glu | Glu | Glu | Met | Glu | Glu | Ala | Ala | |
| | 715 | | | | | 720 | | | | | 725 | | | | | |
| AAT | CAG | AAG | CTT | GCT | CTG | CAA | AAG | GCC | AAA | GAA | GTG | GCT | GAA | GTC | AGC | 2378 |
| Asn | Gln | Lys | Leu | Ala | Leu | Gln | Lys | Ala | Lys | Glu | Val | Ala | Glu | Val | Ser | |
| 730 | | | | | 735 | | | | | 740 | | | | | 745 | |
| CCC | ATG | TCT | GCC | GCG | AAC | ATC | TCC | ATC | GCC | GCC | AGG | CAG | CAG | AAC | TCG | 2426 |
| Pro | Met | Ser | Ala | Ala | Asn | Ile | Ser | Ile | Ala | Ala | Arg | Gln | Gln | Asn | Ser | |
| | | | | 750 | | | | | 755 | | | | | 760 | | |

-continued

| | | | | | | | | | | | | | | | | |
|---|---|---|---|---|---|---|---|---|---|---|---|---|---|---|---|---|
| GCC | AAG | GCG | CGC | TCG | GTG | TGG | GAG | CAG | CGG | GCC | AGC | CAG | CTA | CGG | CTG | 2474 |
| Ala | Lys | Ala | Arg | Ser | Val | Trp | Glu | Gln | Arg | Ala | Ser | Gln | Leu | Arg | Leu | |
| | 765 | | | | | | 770 | | | | | 775 | | | | |
| CAG | AAC | CTG | CGG | GCC | AGC | TGC | GAG | GCG | CTG | TAC | AGC | GAG | ATG | GAC | CCC | 2522 |
| Gln | Asn | Leu | Arg | Ala | Ser | Cys | Glu | Ala | Leu | Tyr | Ser | Glu | Met | Asp | Pro | |
| | | 780 | | | | | 785 | | | | | | 790 | | | |
| GAG | GAG | CGG | CTG | CGC | TTC | GCC | ACT | ACG | CGC | CAC | CTG | CGG | CCC | GAC | ATG | 2570 |
| Glu | Glu | Arg | Leu | Arg | Phe | Ala | Thr | Thr | Arg | His | Leu | Arg | Pro | Asp | Met | |
| 795 | | | | | | 800 | | | | | | 805 | | | | |
| AAG | ACG | CAC | CTG | GAC | CGG | CCG | CTG | GTG | GTG | GAG | CTG | GGC | CGC | GAC | GGC | 2618 |
| Lys | Thr | His | Leu | Asp | Arg | Pro | Leu | Val | Val | Glu | Leu | Gly | Arg | Asp | Gly | |
| 810 | | | | | 815 | | | | | 820 | | | | | 825 | |
| GCG | CGG | GGG | CCC | GTG | GGA | GGC | AAA | GCC | CGA | CCT | GAG | GCT | GCG | GAG | GCC | 2666 |
| Ala | Arg | Gly | Pro | Val | Gly | Gly | Lys | Ala | Arg | Pro | Glu | Ala | Ala | Glu | Ala | |
| | | | | 830 | | | | | 835 | | | | | | 840 | |
| CCC | GAG | GGC | GTC | GAC | CCT | CCG | CGC | AGG | CAC | CAC | CGG | CAC | CGC | GAC | AAG | 2714 |
| Pro | Glu | Gly | Val | Asp | Pro | Pro | Arg | Arg | His | His | Arg | His | Arg | Asp | Lys | |
| | | | | 845 | | | | | 850 | | | | | 855 | | |
| GAC | AAG | ACC | CCC | GCG | GCG | GGG | GAC | CAG | GAC | CGA | GCA | GAG | GCC | CCG | AAG | 2762 |
| Asp | Lys | Thr | Pro | Ala | Ala | Gly | Asp | Gln | Asp | Arg | Ala | Glu | Ala | Pro | Lys | |
| | | | 860 | | | | | 865 | | | | | 870 | | | |
| GCG | GAG | AGC | GGG | GAG | CCC | GGT | GCC | CGG | GAG | GAG | CGG | CCG | CGG | CCG | CAC | 2810 |
| Ala | Glu | Ser | Gly | Glu | Pro | Gly | Ala | Arg | Glu | Glu | Arg | Pro | Arg | Pro | His | |
| 875 | | | | | 880 | | | | | 885 | | | | | | |
| CGC | AGC | CAC | AGC | AAG | GAG | GCC | GCG | GGG | CCC | CCG | GAG | GCG | CGG | AGC | GAG | 2858 |
| Arg | Ser | His | Ser | Lys | Glu | Ala | Ala | Gly | Pro | Pro | Glu | Ala | Arg | Ser | Glu | |
| 890 | | | | | 895 | | | | | 900 | | | | | 905 | |
| CGC | GGC | CGA | GGC | CCA | GGC | CCC | GAG | GGC | GGC | CGG | CGG | CAC | CAC | CGG | CGC | 2906 |
| Arg | Gly | Arg | Gly | Pro | Gly | Pro | Glu | Gly | Gly | Arg | Arg | His | His | Arg | Arg | |
| | | | | 910 | | | | | 915 | | | | | 920 | | |
| GGC | TCC | CCG | GAG | GAG | GCG | GCC | GAG | CGG | GAG | CCC | CGA | CGC | CAC | CGC | GCG | 2954 |
| Gly | Ser | Pro | Glu | Glu | Ala | Ala | Glu | Arg | Glu | Pro | Arg | Arg | His | Arg | Ala | |
| | | | 925 | | | | | 930 | | | | | 935 | | | |
| CAC | CGG | CAC | CAG | GAT | CCG | AGC | AAG | GAG | TGC | GCC | GGC | GCC | AAG | GGC | GAG | 3002 |
| His | Arg | His | Gln | Asp | Pro | Ser | Lys | Glu | Cys | Ala | Gly | Ala | Lys | Gly | Glu | |
| | | 940 | | | | | 945 | | | | | 950 | | | | |
| CGG | CGC | GCG | CGG | CAC | CGC | GGC | GGC | CCC | CGA | GCG | GGG | CCC | CGG | GAG | GCG | 3050 |
| Arg | Arg | Ala | Arg | His | Arg | Gly | Gly | Pro | Arg | Ala | Gly | Pro | Arg | Glu | Ala | |
| 955 | | | | | 960 | | | | | 965 | | | | | | |
| GAG | AGC | GGG | GAG | GAG | CCG | GCG | CGG | CGG | CAC | CGG | GCC | CGG | CAC | AAG | GCG | 3098 |
| Glu | Ser | Gly | Glu | Glu | Pro | Ala | Arg | Arg | His | Arg | Ala | Arg | His | Lys | Ala | |
| 970 | | | | | 975 | | | | | 980 | | | | | 985 | |
| CAG | CCT | GCT | CAC | GAG | GCT | GTG | GAG | AAG | GAG | ACC | ACG | GAG | AAG | GAG | GCC | 3146 |
| Gln | Pro | Ala | His | Glu | Ala | Val | Glu | Lys | Glu | Thr | Thr | Glu | Lys | Glu | Ala | |
| | | | | 990 | | | | 995 | | | | | | 1000 | | |
| ACG | GAG | AAG | GAG | GCT | GAG | ATA | GTG | GAA | GCC | GAC | AAG | GAA | AAG | GAG | CTC | 3194 |
| Thr | Glu | Lys | Glu | Ala | Glu | Ile | Val | Glu | Ala | Asp | Lys | Glu | Lys | Glu | Leu | |
| | | | | 1005 | | | | | 1010 | | | | | 1015 | | |
| CGG | AAC | CAC | CAG | CCC | CGG | GAG | CCA | CAC | TGT | GAC | CTG | GAG | ACC | AGT | GGG | 3242 |
| Arg | Asn | His | Gln | Pro | Arg | Glu | Pro | His | Cys | Asp | Leu | Glu | Thr | Ser | Gly | |
| | | | 1020 | | | | | 1025 | | | | | 1030 | | | |
| ACT | GTG | ACT | GTG | GGT | CCC | ATG | CAC | ACA | CTG | CCC | AGC | ACC | TGT | CTC | CAG | 3290 |
| Thr | Val | Thr | Val | Gly | Pro | Met | His | Thr | Leu | Pro | Ser | Thr | Cys | Leu | Gln | |
| | | | 1035 | | | | | 1040 | | | | | 1045 | | | |
| AAG | GTG | GAG | GAA | CAG | CCA | GAG | GAT | GCA | GAC | AAT | CAG | CGG | AAC | GTC | ACT | 3338 |
| Lys | Val | Glu | Glu | Gln | Pro | Glu | Asp | Ala | Asp | Asn | Gln | Arg | Asn | Val | Thr | |
| 1050 | | | | | 1055 | | | | | 1060 | | | | | 1065 | |
| CGC | ATG | GGC | AGT | CAG | CCC | CCA | GAC | CCG | AAC | ACT | ATT | GTA | CAT | ATC | CCA | 3386 |
| Arg | Met | Gly | Ser | Gln | Pro | Pro | Asp | Pro | Asn | Thr | Ile | Val | His | Ile | Pro | |
| | | | | 1070 | | | | | 1075 | | | | | 1080 | | |

```
GTG ATG CTG ACG GGC CCT CTT GGG GAA GCC ACG GTC GTT CCC AGT GGT     3434
Val Met Leu Thr Gly Pro Leu Gly Glu Ala Thr Val Val Pro Ser Gly
        1085                1090                1095

AAC GTG GAC CTG GAA AGC CAA GCA GAG GGG AAG AAG GAG GTG GAA GCG     3482
Asn Val Asp Leu Glu Ser Gln Ala Glu Gly Lys Lys Glu Val Glu Ala
1100                1105                1110

GAT GAC GTG ATG AGG AGC GGC CCC CGG CCT ATC GTC CCA TAC AGC TCC     3530
Asp Asp Val Met Arg Ser Gly Pro Arg Pro Ile Val Pro Tyr Ser Ser
        1115                1120                1125

ATG TTC TGT TTA AGC CCC ACC AAC CTG CTC CGC CGC TTC TGC CAC TAC     3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC     3626
Ile Val Thr Met Arg Tyr Phe Glu Val Val Ile Leu Val Val Ile Ala
        1150                1155                1160

TTG AGC AGC ATC GCC CTG GCT GCT GAG GAC CCA GTG CGC ACA GAC TCG     3674
Leu Ser Ser Ile Ala Leu Ala Ala Glu Asp Pro Val Arg Thr Asp Ser
1165                1170                1175

CCC AGG AAC AAC GCT CTG AAA TAC CTG GAT TAC ATT TTC ACT GGT GTC     3722
Pro Arg Asn Asn Ala Leu Lys Tyr Leu Asp Tyr Ile Phe Thr Gly Val
        1180                1185                1190

TTT ACC TTT GAG ATG GTG ATA AAG ATG ATC GAC TTG GGA CTG CTG CTT     3770
Phe Thr Phe Glu Met Val Ile Lys Met Ile Asp Leu Gly Leu Leu Leu
1195                1200                1205

CAC CCT GGA GCC TAT TTC CGG GAC TTG TGG AAC ATT CTG GAC TTC ATT     3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG     3866
Val Val Ser Gly Ala Leu Val Ala Phe Ala Phe Ser Gly Ser Lys Gly
        1230                1235                1240

AAA GAC ATC AAT ACC ATC AAG TCT CTG AGA GTC CTT CGT GTC CTG CGG     3914
Lys Asp Ile Asn Thr Ile Lys Ser Leu Arg Val Leu Arg Val Leu Arg
        1245                1250                1255

CCC CTC AAG ACC ATC AAA CGG CTG CCC AAG CTC AAG GCT GTG TTT GAC     3962
Pro Leu Lys Thr Ile Lys Arg Leu Pro Lys Leu Lys Ala Val Phe Asp
        1260                1265                1270

TGT GTG GTG AAC TCC CTG AAG AAT GTC CTC AAC ATC TTG ATT GTC TAC     4010
Cys Val Val Asn Ser Leu Lys Asn Val Leu Asn Ile Leu Ile Val Tyr
1275                1280                1285

ATG CTC TTC ATG TTC ATA TTT GCC GTC ATT GCG GTG CAG CTC TTC AAA     4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC     4106
Gly Lys Phe Phe Tyr Cys Thr Asp Glu Ser Lys Glu Leu Glu Arg Asp
                1310                1315                1320

TGC AGG GGT CAG TAT TTG GAT TAT GAG AAG GAG GAA GTG GAA GCT CAG     4154
Cys Arg Gly Gln Tyr Leu Asp Tyr Glu Lys Glu Glu Val Glu Ala Gln
        1325                1330                1335

CCC AGG CAG TGG AAG AAA TAC GAC TTT CAC TAC GAC AAT GTG CTC TGG     4202
Pro Arg Gln Trp Lys Lys Tyr Asp Phe His Tyr Asp Asn Val Leu Trp
        1340                1345                1350

GCT CTG CTG ACG CTG TTC ACA GTG TCC ACG GGA GAA GGC TGG CCC ATG     4250
Ala Leu Leu Thr Leu Phe Thr Val Ser Thr Gly Glu Gly Trp Pro Met
        1355                1360                1365

GTG CTG AAA CAC TCC GTG GAT GCC ACC TAT GAG GAG CAG GGT CCA AGC     4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG     4346
Pro Gly Tyr Arg Met Glu Leu Ser Ile Phe Tyr Val Val Tyr Phe Val
        1390                1395                1400
```

```
GTC  TTT  CCC  TTC  TTC  TTC  GTC  AAC  ATC  TTT  GTG  GCT  TTG  ATC  ATC  ATC      4394
Val  Phe  Pro  Phe  Phe  Phe  Val  Asn  Ile  Phe  Val  Ala  Leu  Ile  Ile  Ile
     1405                          1410                      1415

ACC  TTC  CAG  GAG  CAG  GGG  GAC  AAG  GTG  ATG  TCT  GAA  TGC  AGC  CTG  GAG      4442
Thr  Phe  Gln  Glu  Gln  Gly  Asp  Lys  Val  Met  Ser  Glu  Cys  Ser  Leu  Glu
     1420                          1425                      1430

AAG  AAC  GAG  AGG  GCT  TGC  ATT  GAC  TTC  GCC  ATC  AGC  GCC  AAA  CCC  CTG      4490
Lys  Asn  Glu  Arg  Ala  Cys  Ile  Asp  Phe  Ala  Ile  Ser  Ala  Lys  Pro  Leu
     1435                          1440                      1445

ACA  CGG  TAC  ATG  CCC  CAA  AAC  CGG  CAG  TCG  TTC  CAG  TAT  AAG  ACG  TGG      4538
Thr  Arg  Tyr  Met  Pro  Gln  Asn  Arg  Gln  Ser  Phe  Gln  Tyr  Lys  Thr  Trp
1450                     1455                     1460                     1465

ACA  TTT  GTG  GTC  TCC  CCG  CCC  TTT  GAA  TAC  TTC  ATC  ATG  GCC  ATG  ATA      4586
Thr  Phe  Val  Val  Ser  Pro  Pro  Phe  Glu  Tyr  Phe  Ile  Met  Ala  Met  Ile
                    1470                     1475                     1480

GCC  CTC  AAC  ACT  GTG  GTG  CTG  ATG  ATG  AAG  TTC  TAT  GAT  GCA  CCC  TAT      4634
Ala  Leu  Asn  Thr  Val  Val  Leu  Met  Met  Lys  Phe  Tyr  Asp  Ala  Pro  Tyr
               1485                     1490                     1495

GAG  TAC  GAG  CTG  ATG  CTG  AAA  TGC  CTG  AAC  ATC  GTG  TTC  ACA  TCC  ATG      4682
Glu  Tyr  Glu  Leu  Met  Leu  Lys  Cys  Leu  Asn  Ile  Val  Phe  Thr  Ser  Met
          1500                     1505                     1510

TTC  TCC  ATG  GAA  TGC  GTG  CTG  AAG  ATC  ATC  GCC  TTT  GGG  GTG  CTG  AAC      4730
Phe  Ser  Met  Glu  Cys  Val  Leu  Lys  Ile  Ile  Ala  Phe  Gly  Val  Leu  Asn
     1515                          1520                     1525

TAT  TTC  AGA  GAT  GCC  TGG  AAT  GTC  TTT  GAC  TTT  GTC  ACT  GTG  TTG  GGA      4778
Tyr  Phe  Arg  Asp  Ala  Trp  Asn  Val  Phe  Asp  Phe  Val  Thr  Val  Leu  Gly
1530                     1535                     1540                     1545

AGT  ATT  ACT  GAT  ATT  TTA  GTA  ACA  GAG  ATT  GCG  GAA  ACG  AAC  AAT  TTC      4826
Ser  Ile  Thr  Asp  Ile  Leu  Val  Thr  Glu  Ile  Ala  Glu  Thr  Asn  Asn  Phe
                    1550                     1555                     1560

ATC  AAC  CTC  AGC  TTC  CTC  CGC  CTC  TTT  CGA  GCT  GCG  CGG  CTG  ATC  AAG      4874
Ile  Asn  Leu  Ser  Phe  Leu  Arg  Leu  Phe  Arg  Ala  Ala  Arg  Leu  Ile  Lys
               1565                     1570                     1575

CTG  CTC  CGC  CAG  GGC  TAC  ACC  ATC  CGC  ATC  CTG  CTG  TGG  ACC  TTT  GTC      4922
Leu  Leu  Arg  Gln  Gly  Tyr  Thr  Ile  Arg  Ile  Leu  Leu  Trp  Thr  Phe  Val
          1580                     1585                     1590

CAG  TCC  TTC  AAG  GCC  CTG  CCC  TAC  GTG  TGT  CTG  CTC  ATT  GCC  ATG  CTG      4970
Gln  Ser  Phe  Lys  Ala  Leu  Pro  Tyr  Val  Cys  Leu  Leu  Ile  Ala  Met  Leu
     1595                     1600                     1605

TTC  TTC  ATC  TAC  GCC  ATC  ATC  GGC  ATG  CAG  GTG  TTT  GGG  AAT  ATT  GCC      5018
Phe  Phe  Ile  Tyr  Ala  Ile  Ile  Gly  Met  Gln  Val  Phe  Gly  Asn  Ile  Ala
1610                     1615                     1620                     1625

CTG  GAT  GAT  GAC  ACC  AGC  ATC  AAC  CGC  CAC  AAC  AAC  TTC  CGG  ACG  TTT      5066
Leu  Asp  Asp  Asp  Thr  Ser  Ile  Asn  Arg  His  Asn  Asn  Phe  Arg  Thr  Phe
                    1630                     1635                     1640

TTG  CAA  GCC  CTG  ATG  CTG  CTG  TTC  AGG  AGC  GCC  ACG  GGG  GAG  GCC  TGG      5114
Leu  Gln  Ala  Leu  Met  Leu  Leu  Phe  Arg  Ser  Ala  Thr  Gly  Glu  Ala  Trp
               1645                     1650                     1655

CAC  GAG  ATC  ATG  CTG  TCC  TGC  CTG  AGC  AAC  CAG  GCC  TGT  GAT  GAG  CAG      5162
His  Glu  Ile  Met  Leu  Ser  Cys  Leu  Ser  Asn  Gln  Ala  Cys  Asp  Glu  Gln
          1660                     1665                     1670

GCC  AAT  GCC  ACC  GAG  TGT  GGA  AGT  GAC  TTT  GCC  TAC  TTC  TAC  TTC  GTC      5210
Ala  Asn  Ala  Thr  Glu  Cys  Gly  Ser  Asp  Phe  Ala  Tyr  Phe  Tyr  Phe  Val
     1675                     1680                     1685

TCC  TTC  ATC  TTC  CTG  TGC  TCC  TTT  CTG  ATG  TTG  AAC  CTC  TTT  GTG  GCT      5258
Ser  Phe  Ile  Phe  Leu  Cys  Ser  Phe  Leu  Met  Leu  Asn  Leu  Phe  Val  Ala
1690                     1695                     1700                     1705

GTG  ATC  ATG  GAC  AAT  TTT  GAG  TAC  CTC  ACG  CGG  GAC  TCT  TCC  ATC  CTA      5306
Val  Ile  Met  Asp  Asn  Phe  Glu  Tyr  Leu  Thr  Arg  Asp  Ser  Ser  Ile  Leu
                    1710                     1715                     1720
```

```
GGT CCT CAC CAC TTG GAT GAG TTC ATC CGG GTC TGG GCT GAA TAC GAC      5354
Gly Pro His His Leu Asp Glu Phe Ile Arg Val Trp Ala Glu Tyr Asp
        1725                1730                1735

CCG GCT GCG TGT GGG CGC ATC AGT TAC AAT GAC ATG TTT GAG ATG CTG      5402
Pro Ala Ala Cys Gly Arg Ile Ser Tyr Asn Asp Met Phe Glu Met Leu
        1740                1745                1750

AAA CAC ATG TCC CCG CCT CTG GGG CTG GGG AAG AAA TGC CCT GCT CGA      5450
Lys His Met Ser Pro Pro Leu Gly Leu Gly Lys Lys Cys Pro Ala Arg
        1755                1760                1765

GTT GCT TAC AAG CGC CTG GTT CGC ATG AAC ATG CCC ATC TCC AAC GAG      5498
Val Ala Tyr Lys Arg Leu Val Arg Met Asn Met Pro Ile Ser Asn Glu
1770            1775                1780                1785

GAC ATG ACT GTT CAC TTC ACG TCC ACG CTG ATG GCC CTC ATC CGG ACG      5546
Asp Met Thr Val His Phe Thr Ser Thr Leu Met Ala Leu Ile Arg Thr
        1790                1795                1800

GCA CTG GAG ATC AAG CTG GCC CCA GCT GGG ACA AAG CAG CAT CAG TGT      5594
Ala Leu Glu Ile Lys Leu Ala Pro Ala Gly Thr Lys Gln His Gln Cys
        1805                1810                1815

GAC GCG GAG TTG AGG AAG GAG ATT TCC GTT GTG TGG GCC AAT CTG CCC      5642
Asp Ala Glu Leu Arg Lys Glu Ile Ser Val Val Trp Ala Asn Leu Pro
        1820                1825                1830

CAG AAG ACT TTG GAC TTG CTG GTA CCA CCC CAT AAG CCT GAT GAG ATG      5690
Gln Lys Thr Leu Asp Leu Leu Val Pro Pro His Lys Pro Asp Glu Met
        1835                1840                1845

ACA GTG GGG AAG GTT TAT GCA GCT CTG ATG ATA TTT GAC TTC TAC AAG      5738
Thr Val Gly Lys Val Tyr Ala Ala Leu Met Ile Phe Asp Phe Tyr Lys
1850            1855                1860                1865

CAG AAC AAA ACC ACC AGA GAC CAG ATG CAG CAG GCT CCT GGA GGC CTC      5786
Gln Asn Lys Thr Thr Arg Asp Gln Met Gln Gln Ala Pro Gly Gly Leu
        1870                1875                1880

TCC CAG ATG GGT CCT GTG TCC CTG TTC CAC CCT CTG AAG GCC ACC CTG      5834
Ser Gln Met Gly Pro Val Ser Leu Phe His Pro Leu Lys Ala Thr Leu
        1885                1890                1895

GAG CAG ACA CAG CCG GCT GTG CTC CGA GGA GCC CGG GTT TTC CTT CGA      5882
Glu Gln Thr Gln Pro Ala Val Leu Arg Gly Ala Arg Val Phe Leu Arg
        1900                1905                1910

CAG AAG AGT TCC ACC TCC CTC AGC AAT GGC GGG GCC ATA CAA AAC CAA      5930
Gln Lys Ser Ser Thr Ser Leu Ser Asn Gly Gly Ala Ile Gln Asn Gln
        1915                1920                1925

GAG AGT GGC ATC AAA GAG TCT GTC TCC TGG GGC ACT CAA AGG ACC CAG      5978
Glu Ser Gly Ile Lys Glu Ser Val Ser Trp Gly Thr Gln Arg Thr Gln
1930            1935                1940                1945

GAT GCA CCC CAT GAG GCC AGG CCA CCC CTG GAG CGT GGC CAC TCC ACA      6026
Asp Ala Pro His Glu Ala Arg Pro Pro Leu Glu Arg Gly His Ser Thr
        1950                1955                1960

GAG ATC CCT GTG GGG CGG TCA GGA GCA CTG GCT GTG GAC GTT CAG ATG      6074
Glu Ile Pro Val Gly Arg Ser Gly Ala Leu Ala Val Asp Val Gln Met
        1965                1970                1975

CAG AGC ATA ACC CGG AGG GGC CCT GAT GGG GAG CCC CAG CCT GGG CTG      6122
Gln Ser Ile Thr Arg Arg Gly Pro Asp Gly Glu Pro Gln Pro Gly Leu
        1980                1985                1990

GAG AGC CAG GGT CGA GCG GCC TCC ATG CCC CGC CTT GCG GCC GAG ACT      6170
Glu Ser Gln Gly Arg Ala Ala Ser Met Pro Arg Leu Ala Ala Glu Thr
        1995                2000                2005

CAG CCC GTC ACA GAT GCC AGC CCC ATG AAG CGC TCC ATC TCC ACG CTG      6218
Gln Pro Val Thr Asp Ala Ser Pro Met Lys Arg Ser Ile Ser Thr Leu
        2010                2015                2020                2025

GCC CAG CGG CCC CGT GGG ACT CAT CTT TGC AGC ACC ACC CCG GAC CGC      6266
Ala Gln Arg Pro Arg Gly Thr His Leu Cys Ser Thr Thr Pro Asp Arg
        2030                2035                2040
```

| | | | | | | | | | | | | | | | | |
|---|---|---|---|---|---|---|---|---|---|---|---|---|---|---|---|---|
| CCA | CCC | CCT | AGC | CAG | GCG | TCG | TCG | CAC | CAC | CAC | CAC | CAC | CGC | TGC | CAC | 6314 |
| Pro | Pro | Pro | Ser | Gln | Ala | Ser | Ser | His | His | His | His | His | Arg | Cys | His | |
| | | | 2045 | | | | | 2050 | | | | | 2055 | | | |
| CGC | CGC | AGG | GAC | AGG | AAG | CAG | AGG | TCC | CTG | GAG | AAG | GGG | CCC | AGC | CTG | 6362 |
| Arg | Arg | Arg | Asp | Arg | Lys | Gln | Arg | Ser | Leu | Glu | Lys | Gly | Pro | Ser | Leu | |
| | | | 2060 | | | | | 2065 | | | | | 2070 | | | |
| TCT | GCC | GAT | ATG | GAT | GGC | GCA | CCA | AGC | AGT | GCT | GTG | GGG | CCG | GGG | CTG | 6410 |
| Ser | Ala | Asp | Met | Asp | Gly | Ala | Pro | Ser | Ser | Ala | Val | Gly | Pro | Gly | Leu | |
| | | | 2075 | | | | | 2080 | | | | | 2085 | | | |
| CCC | CCG | GGA | GAG | GGG | CCT | ACA | GGC | TGC | CGG | CGG | GAA | CGA | GAG | CGC | CGG | 6458 |
| Pro | Pro | Gly | Glu | Gly | Pro | Thr | Gly | Cys | Arg | Arg | Glu | Arg | Glu | Arg | Arg | |
| 2090 | | | | | 2095 | | | | | 2100 | | | | | 2105 | |
| CAG | GAG | CGG | GGC | CGG | TCC | CAG | GAG | CGG | AGG | CAG | CCC | TCA | TCC | TCC | TCC | 6506 |
| Gln | Glu | Arg | Gly | Arg | Ser | Gln | Glu | Arg | Arg | Gln | Pro | Ser | Ser | Ser | Ser | |
| | | | | 2110 | | | | | 2115 | | | | | 2120 | | |
| TCG | GAG | AAG | CAG | CGC | TTC | TAC | TCC | TGC | GAC | CGC | TTT | GGG | GGC | CGT | GAG | 6554 |
| Ser | Glu | Lys | Gln | Arg | Phe | Tyr | Ser | Cys | Asp | Arg | Phe | Gly | Gly | Arg | Glu | |
| | | | | 2125 | | | | | 2130 | | | | | 2135 | | |
| CCC | CCG | AAG | CCC | AAG | CCC | TCC | CTC | AGC | AGC | CAC | CCA | ACG | TCG | CCA | ACA | 6602 |
| Pro | Pro | Lys | Pro | Lys | Pro | Ser | Leu | Ser | Ser | His | Pro | Thr | Ser | Pro | Thr | |
| | | | | 2140 | | | | | 2145 | | | | | 2150 | | |
| GCT | GGC | CAG | GAG | CCG | GGA | CCC | CAC | CCA | CAG | GGC | AGT | GGT | TCC | GTG | AAT | 6650 |
| Ala | Gly | Gln | Glu | Pro | Gly | Pro | His | Pro | Gln | Gly | Ser | Gly | Ser | Val | Asn | |
| | | | 2155 | | | | | 2160 | | | | | 2165 | | | |
| GGG | AGC | CCC | TTG | CTG | TCA | ACA | TCT | GGT | GCT | AGC | ACC | CCC | GGC | CGC | GGT | 6698 |
| Gly | Ser | Pro | Leu | Leu | Ser | Thr | Ser | Gly | Ala | Ser | Thr | Pro | Gly | Arg | Gly | |
| 2170 | | | | | 2175 | | | | | 2180 | | | | | 2185 | |
| GGG | CGG | AGG | CAG | CTC | CCC | CAG | ACG | CCC | CTG | ACT | CCC | CGC | CCC | AGC | ATC | 6746 |
| Gly | Arg | Arg | Gln | Leu | Pro | Gln | Thr | Pro | Leu | Thr | Pro | Arg | Pro | Ser | Ile | |
| | | | | 2190 | | | | | 2195 | | | | | 2200 | | |
| ACC | TAC | AAG | ACG | GCC | AAC | TCC | TCA | CCC | ATC | CAC | TTC | GCC | GGG | GCT | CAG | 6794 |
| Thr | Tyr | Lys | Thr | Ala | Asn | Ser | Ser | Pro | Ile | His | Phe | Ala | Gly | Ala | Gln | |
| | | | | 2205 | | | | | 2210 | | | | | 2215 | | |
| ACC | AGC | CTC | CCT | GCC | TTC | TCC | CCA | GGC | CGG | CTC | AGC | CGT | GGG | CTT | TCC | 6842 |
| Thr | Ser | Leu | Pro | Ala | Phe | Ser | Pro | Gly | Arg | Leu | Ser | Arg | Gly | Leu | Ser | |
| | | | 2220 | | | | | 2225 | | | | | 2230 | | | |
| GAA | CAC | AAC | GCC | CTG | CTG | CAG | AGA | GAC | CCC | CTC | AGC | CAG | CCC | CTG | GCC | 6890 |
| Glu | His | Asn | Ala | Leu | Leu | Gln | Arg | Asp | Pro | Leu | Ser | Gln | Pro | Leu | Ala | |
| | | | | 2235 | | | | | 2240 | | | | | 2245 | | |
| CCT | GGC | TCT | CGA | ATT | GGC | TCT | GAC | CCT | TAC | CTG | GGG | CAG | CGT | CTG | GAC | 6938 |
| Pro | Gly | Ser | Arg | Ile | Gly | Ser | Asp | Pro | Tyr | Leu | Gly | Gln | Arg | Leu | Asp | |
| 2250 | | | | | 2255 | | | | | 2260 | | | | | 2265 | |
| AGT | GAG | GCC | TCT | GTC | CAC | GCC | CTG | CCT | GAG | GAC | ACG | CTC | ACT | TTC | GAG | 6986 |
| Ser | Glu | Ala | Ser | Val | His | Ala | Leu | Pro | Glu | Asp | Thr | Leu | Thr | Phe | Glu | |
| | | | | 2270 | | | | | 2275 | | | | | 2280 | | |
| GAG | GCT | GTG | GCC | ACC | AAC | TCG | GGC | CGC | TCC | TCC | AGG | ACT | TCC | TAC | GTG | 7034 |
| Glu | Ala | Val | Ala | Thr | Asn | Ser | Gly | Arg | Ser | Ser | Arg | Thr | Ser | Tyr | Val | |
| | | | | 2285 | | | | | 2290 | | | | | 2295 | | |
| TCC | TCC | CTG | ACC | TCC | CAG | TCT | CAC | CCT | CTC | CGC | CGC | GTG | CCC | AAC | GGT | 7082 |
| Ser | Ser | Leu | Thr | Ser | Gln | Ser | His | Pro | Leu | Arg | Arg | Val | Pro | Asn | Gly | |
| | | | 2300 | | | | | 2305 | | | | | 2310 | | | |
| TAC | CAC | TGC | ACC | CTG | GGA | CTC | AGC | TCG | GGT | GGC | CGA | GCA | CGG | CAC | AGC | 7130 |
| Tyr | His | Cys | Thr | Leu | Gly | Leu | Ser | Ser | Gly | Gly | Arg | Ala | Arg | His | Ser | |
| | | | 2315 | | | | | 2320 | | | | | 2325 | | | |
| TAC | CAC | CAC | CCT | GAC | CAA | GAC | CAC | TGG | TGC | TAGCTGCACC | | GTGACCGCTC | | | | 7180 |
| Tyr | His | His | Pro | Asp | Gln | Asp | His | Trp | Cys | | | | | | | |
| 2330 | | | | | 2335 | | | | | | | | | | | |
| AGACGCCTGC | | ATGCAGCAGG | | CGTGTGTTCC | | AGTGGATGAG | | TTTTATCATC | | CACACGGGGC | | | | | | 7240 |
| AGTCGGCCCT | | CGGGGGAGGC | | CTTGCCCACC | | TTGGTGAGGC | | TCCTGTGGCC | | CCTCCCTCCC | | | | | | 7300 |

-continued

```
CCTCCTCCCC TCTTTTACTC TAGACGACGA ATAAAGCCCT GTTGCTTGAG TGTACGTACC      7360

GC                                                                     7362
```

( 2 ) INFORMATION FOR SEQ ID NO:8:

( i ) SEQUENCE CHARACTERISTICS:
        ( A ) LENGTH: 7175 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 144..6857

( i x ) FEATURE:
        ( A ) NAME/KEY: 5'UTR
        ( B ) LOCATION: 1..143

( i x ) FEATURE:
        ( A ) NAME/KEY: 3'UTR
        ( B ) LOCATION: 6855..7175

( x i ) SEQUENCE DESCRIPTION: SEQ ID NO:8:

```
GCGGCGGCGG CTGCGGCGGT GGGGCCGGGC GAGGTCCGTG CGGTCCCGGC GGCTCCGTGG        60

CTGCTCCGCT CTGAGCGCCT GCGCGCCCCG CGCCCTCCCT GCCGGGGCCG CTGGGCCGGG       120

GATGCACGCG GGGCCCGGGA GCC ATG GTC CGC TTC GGG GAC GAG CTG GGC          170
                         Met Val Arg Phe Gly Asp Glu Leu Gly
                          1               5

GGC CGC TAT GGA GGC CCC GGC GGC GGA GAG CGG GCC CGG GGC GGC GGG        218
Gly Arg Tyr Gly Gly Pro Gly Gly Gly Glu Arg Ala Arg Gly Gly Gly
 10              15                  20                  25

GCC GGC GGG GCG GGG GGC CCG GGT CCC GGG GGG CTG CAG CCC GGC CAG        266
Ala Gly Gly Ala Gly Gly Pro Gly Pro Gly Gly Leu Gln Pro Gly Gln
                 30                  35                  40

CGG GTC CTC TAC AAG CAA TCG ATC GCG CAG CGC GCG CGG ACC ATG GCG        314
Arg Val Leu Tyr Lys Gln Ser Ile Ala Gln Arg Ala Arg Thr Met Ala
                 45                  50                  55

CTG TAC AAC CCC ATC CCG GTC AAG CAG AAC TGC TTC ACC GTC AAC CGC        362
Leu Tyr Asn Pro Ile Pro Val Lys Gln Asn Cys Phe Thr Val Asn Arg
             60                  65                  70

TCG CTC TTC GTC TTC AGC GAG GAC AAC GTC GTC CGC AAA TAC GCG AAG        410
Ser Leu Phe Val Phe Ser Glu Asp Asn Val Val Arg Lys Tyr Ala Lys
         75                  80                  85

CGC ATC ACC GAG TGG CCT CCA TTC GAG AAT ATG ATC CTG GCC ACC ATC        458
Arg Ile Thr Glu Trp Pro Pro Phe Glu Asn Met Ile Leu Ala Thr Ile
 90                  95                 100                 105

ATC GCC AAC TGC ATC GTG CTG GCC CTG GAG CAG CAC CTC CCT GAT GGG        506
Ile Ala Asn Cys Ile Val Leu Ala Leu Glu Gln His Leu Pro Asp Gly
                110                 115                 120

GAC AAA ACG CCC ATG TCC GAG CGG CTG GAC GAC ACG GAG CCC TAT TTC        554
Asp Lys Thr Pro Met Ser Glu Arg Leu Asp Asp Thr Glu Pro Tyr Phe
            125                 130                 135

ATC GGG ATC TTT TGC TTC GAG GCA GGG ATC AAA ATC ATC GCT CTG GGC        602
Ile Gly Ile Phe Cys Phe Glu Ala Gly Ile Lys Ile Ile Ala Leu Gly
        140                 145                 150

TTT GTC TTC CAC AAG GGC TCT TAC CTG CGG AAC GGC TGG AAC GTC ATG        650
Phe Val Phe His Lys Gly Ser Tyr Leu Arg Asn Gly Trp Asn Val Met
    155                 160                 165

GAC TTC GTG GTC GTC CTC ACA GGG ATC CTT GCC ACG GCT GGA ACT GAC        698
Asp Phe Val Val Val Leu Thr Gly Ile Leu Ala Thr Ala Gly Thr Asp
```

|     |     |     |     |     | 170 |     |     |     | 175 |     |     |     |     | 180 |     |     |     |     | 185 |     |     |
|-----|-----|-----|-----|-----|-----|-----|-----|-----|-----|-----|-----|-----|-----|-----|-----|-----|-----|-----|-----|-----|-----|

```
TTC  GAC  CTG  CGA  ACA  CTG  AGG  GCT  GTG  CGT  GTG  CTG  AGG  CCC  CTG  AAG                746
Phe  Asp  Leu  Arg  Thr  Leu  Arg  Ala  Val  Arg  Val  Leu  Arg  Pro  Leu  Lys
               190                     195                          200

CTG  GTG  TCT  GGG  ATT  CCA  AGT  TTG  CAG  GTG  GTG  CTC  AAG  TCC  ATC  ATG                794
Leu  Val  Ser  Gly  Ile  Pro  Ser  Leu  Gln  Val  Val  Leu  Lys  Ser  Ile  Met
                    205                     210                          215

AAG  GCC  ATG  GTT  CCA  CTC  CTG  CAG  ATT  GGG  CTG  CTT  CTC  TTC  TTT  GCC                842
Lys  Ala  Met  Val  Pro  Leu  Leu  Gln  Ile  Gly  Leu  Leu  Leu  Phe  Phe  Ala
               220                     225                          230

ATC  CTC  ATG  TTT  GCC  ATC  ATT  GGC  CTG  GAG  TTC  TAC  ATG  GGC  AAG  TTC                890
Ile  Leu  Met  Phe  Ala  Ile  Ile  Gly  Leu  Glu  Phe  Tyr  Met  Gly  Lys  Phe
          235                          240                     245

CAC  AAG  GCC  TGT  TTC  CCC  AAC  AGC  ACA  GAT  GCG  GAG  CCC  GTG  GGT  GAC                938
His  Lys  Ala  Cys  Phe  Pro  Asn  Ser  Thr  Asp  Ala  Glu  Pro  Val  Gly  Asp
250                     255                     260                          265

TTC  CCC  TGT  GGC  AAG  GAG  GCC  CCA  GCC  CGG  CTG  TGC  GAG  GGC  GAC  ACT                986
Phe  Pro  Cys  Gly  Lys  Glu  Ala  Pro  Ala  Arg  Leu  Cys  Glu  Gly  Asp  Thr
                    270                     275                          280

GAG  TGC  CGG  GAG  TAC  TGG  CCA  GGA  CCC  AAC  TTT  GGC  ATC  ACC  AAC  TTT              1034
Glu  Cys  Arg  Glu  Tyr  Trp  Pro  Gly  Pro  Asn  Phe  Gly  Ile  Thr  Asn  Phe
          285                          290                     295

GAC  AAT  ATC  CTG  TTT  GCC  ATC  TTG  ACG  GTG  TTC  CAG  TGC  ATC  ACC  ATG              1082
Asp  Asn  Ile  Leu  Phe  Ala  Ile  Leu  Thr  Val  Phe  Gln  Cys  Ile  Thr  Met
     300                          305                          310

GAG  GGC  TGG  ACT  GAC  ATC  CTC  TAT  AAT  ACA  AAC  GAT  GCG  GCC  GGC  AAC              1130
Glu  Gly  Trp  Thr  Asp  Ile  Leu  Tyr  Asn  Thr  Asn  Asp  Ala  Ala  Gly  Asn
          315                          320                     325

ACC  TGG  AAC  TGG  CTC  TAC  TTC  ATC  CCT  CTC  ATC  ATC  ATC  GGC  TCC  TTC              1178
Thr  Trp  Asn  Trp  Leu  Tyr  Phe  Ile  Pro  Leu  Ile  Ile  Ile  Gly  Ser  Phe
330                          335                     340                     345

TTC  ATG  CTC  AAC  CTG  GTG  CTG  GGC  GTG  CTC  TCG  GGG  GAG  TTT  GCC  AAG              1226
Phe  Met  Leu  Asn  Leu  Val  Leu  Gly  Val  Leu  Ser  Gly  Glu  Phe  Ala  Lys
                    350                     355                          360

GAG  CGA  GAG  AGG  GTG  GAG  AAC  CGC  CGC  GCC  TTC  CTG  AAG  CTG  CGC  CGG              1274
Glu  Arg  Glu  Arg  Val  Glu  Asn  Arg  Arg  Ala  Phe  Leu  Lys  Leu  Arg  Arg
               365                     370                          375

CAG  CAG  CAG  ATC  GAG  CGA  GAG  CTC  AAC  GGG  TAC  CTG  GAG  TGG  ATC  TTC              1322
Gln  Gln  Gln  Ile  Glu  Arg  Glu  Leu  Asn  Gly  Tyr  Leu  Glu  Trp  Ile  Phe
     380                          385                          390

AAG  GCG  GAG  GAA  GTC  ATG  CTG  GCC  GAG  GAG  GAC  AGG  AAT  GCA  GAG  GAG              1370
Lys  Ala  Glu  Glu  Val  Met  Leu  Ala  Glu  Glu  Asp  Arg  Asn  Ala  Glu  Glu
     395                          400                     405

AAG  TCC  CCT  TTG  GAC  GTG  CTG  AAG  AGA  GCG  GCC  ACC  AAG  AAG  AGC  AGA              1418
Lys  Ser  Pro  Leu  Asp  Val  Leu  Lys  Arg  Ala  Ala  Thr  Lys  Lys  Ser  Arg
410                          415                     420                     425

AAT  GAC  CTG  ATC  CAC  GCA  GAG  GAG  GGA  GAG  GAC  CGG  TTT  GCA  GAT  CTC              1466
Asn  Asp  Leu  Ile  His  Ala  Glu  Glu  Gly  Glu  Asp  Arg  Phe  Ala  Asp  Leu
               430                     435                          440

TGT  GCT  GTT  GGA  TCC  CCC  TTC  GCC  CGC  GCC  AGC  CTC  AAG  AGC  GGG  AAG              1514
Cys  Ala  Val  Gly  Ser  Pro  Phe  Ala  Arg  Ala  Ser  Leu  Lys  Ser  Gly  Lys
               445                     450                          455

ACA  GAG  AGC  TCG  TCA  TAC  TTC  CGG  AGG  AAG  GAG  AAG  ATG  TTC  CGG  TTT              1562
Thr  Glu  Ser  Ser  Ser  Tyr  Phe  Arg  Arg  Lys  Glu  Lys  Met  Phe  Arg  Phe
          460                          465                     470

TTT  ATC  CGG  CGC  ATG  GTG  AAG  GCT  CAG  AGC  TTC  TAC  TGG  GTG  GTG  CTG              1610
Phe  Ile  Arg  Arg  Met  Val  Lys  Ala  Gln  Ser  Phe  Tyr  Trp  Val  Val  Leu
     475                          480                     485

TGC  GTG  GTG  GCC  CTG  AAC  ACA  CTG  TGT  GTG  GCC  ATG  GTG  CAT  TAC  AAC              1658
Cys  Val  Val  Ala  Leu  Asn  Thr  Leu  Cys  Val  Ala  Met  Val  His  Tyr  Asn
```

```
                490                             495                             500                             505
CAG   CCG   CGG   CGG   CTT   ACC   ACG   ACC   CTG   TAT   TTT   GCA   GAG   TTT   GTT   TTC    1706
Gln   Pro   Arg   Arg   Leu   Thr   Thr   Thr   Leu   Tyr   Phe   Ala   Glu   Phe   Val   Phe
                  510                             515                             520

CTG   GGT   CTC   TTC   CTC   ACA   GAG   ATG   TCC   CTG   AAG   ATG   TAT   GGC   CTG   GGG    1754
Leu   Gly   Leu   Phe   Leu   Thr   Glu   Met   Ser   Leu   Lys   Met   Tyr   Gly   Leu   Gly
                  525                             530                             535

CCC   AGA   AGC   TAC   TTC   CGG   TCC   TCC   TTC   AAC   TGC   TTC   GAC   TTT   GGG   GTC    1802
Pro   Arg   Ser   Tyr   Phe   Arg   Ser   Ser   Phe   Asn   Cys   Phe   Asp   Phe   Gly   Val
                  540                             545                             550

ATC   GTG   GGG   AGC   GTC   TTT   GAA   GTG   GTC   TGG   GCG   GCC   ATC   AAG   CCG   GGA    1850
Ile   Val   Gly   Ser   Val   Phe   Glu   Val   Val   Trp   Ala   Ala   Ile   Lys   Pro   Gly
      555                             560                             565

AGC   TCC   TTT   GGG   ATC   AGT   GTG   CTG   CGG   GCC   CTC   CGC   CTG   CTG   AGG   ATC    1898
Ser   Ser   Phe   Gly   Ile   Ser   Val   Leu   Arg   Ala   Leu   Arg   Leu   Leu   Arg   Ile
570                             575                             580                             585

TTC   AAA   GTC   ACG   AAG   TAC   TGG   AGC   TCC   CTG   CGG   AAC   CTG   GTG   GTG   TCC    1946
Phe   Lys   Val   Thr   Lys   Tyr   Trp   Ser   Ser   Leu   Arg   Asn   Leu   Val   Val   Ser
                  590                             595                             600

CTG   CTG   AAC   TCC   ATG   AAG   TCC   ATC   ATC   AGC   CTG   CTC   TTC   TTG   CTC   TTC    1994
Leu   Leu   Asn   Ser   Met   Lys   Ser   Ile   Ile   Ser   Leu   Leu   Phe   Leu   Leu   Phe
                  605                             610                             615

CTG   TTC   ATT   GTG   GTC   TTC   GCC   CTG   CTG   GGG   ATG   CAG   CTG   TTT   GGG   GGA    2042
Leu   Phe   Ile   Val   Val   Phe   Ala   Leu   Leu   Gly   Met   Gln   Leu   Phe   Gly   Gly
                  620                             625                             630

CAG   TTC   AAC   TTC   CAG   GAT   GAG   ACT   CCC   ACA   ACC   AAC   TTC   GAC   ACC   TTC    2090
Gln   Phe   Asn   Phe   Gln   Asp   Glu   Thr   Pro   Thr   Thr   Asn   Phe   Asp   Thr   Phe
                  635                             640                             645

CCT   GCC   GCC   ATC   CTC   ACT   GTC   TTC   CAG   ATC   CTG   ACG   GGA   GAG   GAC   TGG    2138
Pro   Ala   Ala   Ile   Leu   Thr   Val   Phe   Gln   Ile   Leu   Thr   Gly   Glu   Asp   Trp
650                             655                             660                             665

AAT   GCA   GTG   ATG   TAT   CAC   GGG   ATC   GAA   TCG   CAA   GGC   GGC   GTC   AGC   AAA    2186
Asn   Ala   Val   Met   Tyr   His   Gly   Ile   Glu   Ser   Gln   Gly   Gly   Val   Ser   Lys
                  670                             675                             680

GGC   ATG   TTC   TCG   TCC   TTT   TAC   TTC   ATT   GTC   CTG   ACA   CTG   TTC   GGA   AAC    2234
Gly   Met   Phe   Ser   Ser   Phe   Tyr   Phe   Ile   Val   Leu   Thr   Leu   Phe   Gly   Asn
                  685                             690                             695

TAC   ACT   CTG   CTG   AAT   GTC   TTT   CTG   GCC   ATC   GCT   GTG   GAC   AAC   CTG   GCC    2282
Tyr   Thr   Leu   Leu   Asn   Val   Phe   Leu   Ala   Ile   Ala   Val   Asp   Asn   Leu   Ala
            700                             705                             710

AAC   GCC   CAA   GAG   CTG   ACC   AAG   GAT   GAA   GAG   GAG   ATG   GAA   GAA   GCA   GCC    2330
Asn   Ala   Gln   Glu   Leu   Thr   Lys   Asp   Glu   Glu   Glu   Met   Glu   Glu   Ala   Ala
      715                             720                             725

AAT   CAG   AAG   CTT   GCT   CTG   CAA   AAG   GCC   AAA   GAA   GTG   GCT   GAA   GTC   AGC    2378
Asn   Gln   Lys   Leu   Ala   Leu   Gln   Lys   Ala   Lys   Glu   Val   Ala   Glu   Val   Ser
730                             735                             740                             745

CCC   ATG   TCT   GCC   GCG   AAC   ATC   TCC   ATC   GCC   GCC   AGG   CAG   CAG   AAC   TCG    2426
Pro   Met   Ser   Ala   Ala   Asn   Ile   Ser   Ile   Ala   Ala   Arg   Gln   Gln   Asn   Ser
                  750                             755                             760

GCC   AAG   GCG   CGC   TCG   GTG   TGG   GAG   CAG   CGG   GCC   AGC   CAG   CTA   CGG   CTG    2474
Ala   Lys   Ala   Arg   Ser   Val   Trp   Glu   Gln   Arg   Ala   Ser   Gln   Leu   Arg   Leu
                  765                             770                             775

CAG   AAC   CTG   CGG   GCC   AGC   TGC   GAG   GCG   CTG   TAC   AGC   GAG   ATG   GAC   CCC    2522
Gln   Asn   Leu   Arg   Ala   Ser   Cys   Glu   Ala   Leu   Tyr   Ser   Glu   Met   Asp   Pro
                  780                             785                             790

GAG   GAG   CGG   CTG   CGC   TTC   GCC   ACT   ACG   CGC   CAC   CTG   CGG   CCC   GAC   ATG    2570
Glu   Glu   Arg   Leu   Arg   Phe   Ala   Thr   Thr   Arg   His   Leu   Arg   Pro   Asp   Met
      795                             800                             805

AAG   ACG   CAC   CTG   GAC   CGG   CCG   CTG   GTG   GTG   GAG   CTG   GGC   CGC   GAC   GGC    2618
Lys   Thr   His   Leu   Asp   Arg   Pro   Leu   Val   Val   Glu   Leu   Gly   Arg   Asp   Gly
```

-continued

| | | | | | | | | | | | | | | | | |
|---|---|---|---|---|---|---|---|---|---|---|---|---|---|---|---|---|
| | 810 | | | | 815 | | | | 820 | | | | 825 | | | |
| GCG | CGG | GGG | CCC | GTG | GGA | GGC | AAA | GCC | CGA | CCT | GAG | GCT | GCG | GAG | GCC | 2666 |
| Ala | Arg | Gly | Pro | Val 830 | Gly | Gly | Lys | Ala | Arg 835 | Pro | Glu | Ala | Ala | Glu 840 | Ala | |
| CCC | GAG | GGC | GTC | GAC | CCT | CCG | CGC | AGG | CAC | CAC | CGG | CAC | CGC | GAC | AAG | 2714 |
| Pro | Glu | Gly | Val 845 | Asp | Pro | Pro | Arg | Arg 850 | His | His | Arg | His | Arg 855 | Asp | Lys | |
| GAC | AAG | ACC | CCC | GCG | GCG | GGG | GAC | CAG | GAC | CGA | GCA | GAG | GCC | CCG | AAG | 2762 |
| Asp | Lys | Thr 860 | Pro | Ala | Ala | Gly | Asp 865 | Gln | Asp | Arg | Ala | Glu 870 | Ala | Pro | Lys | |
| GCG | GAG | AGC | GGG | GAG | CCC | GGT | GCC | CGG | GAG | GAG | CGG | CCG | CGG | CCG | CAC | 2810 |
| Ala | Glu 875 | Ser | Gly | Glu | Pro | Gly 880 | Ala | Arg | Glu | Glu | Arg 885 | Pro | Arg | Pro | His | |
| CGC | AGC | CAC | AGC | AAG | GAG | GCC | GCG | GGG | CCC | CCG | GAG | GCG | CGG | AGC | GAG | 2858 |
| Arg | Ser | His | Ser | Lys | Glu 895 | Ala | Ala | Gly | Pro | Pro 900 | Glu | Ala | Arg | Ser | Glu 905 | |
| 890 | | | | | | | | | | | | | | | | |
| CGC | GGC | CGA | GGC | CCA | GGC | CCC | GAG | GGC | GGC | CGG | CGG | CAC | CAC | CGG | CGC | 2906 |
| Arg | Gly | Arg | Gly | Pro | Gly 910 | Pro | Glu | Gly | Gly | Arg 915 | Arg | His | His | Arg 920 | Arg | |
| GGC | TCC | CCG | GAG | GAG | GCG | GCC | GAG | CGG | GAG | CCC | CGA | CGC | CAC | CGC | GCG | 2954 |
| Gly | Ser | Pro | Glu 925 | Glu | Ala | Ala | Glu | Arg 930 | Glu | Pro | Arg | Arg | His 935 | Arg | Ala | |
| CAC | CGG | CAC | CAG | GAT | CCG | AGC | AAG | GAG | TGC | GCC | GGC | GCC | AAG | GGC | GAG | 3002 |
| His | Arg | His 940 | Gln | Asp | Pro | Ser | Lys 945 | Glu | Cys | Ala | Gly | Ala 950 | Lys | Gly | Glu | |
| CGG | CGC | GCG | CGG | CAC | CGC | GGC | GGC | CCC | CGA | GCG | GGG | CCC | CGG | GAG | GCG | 3050 |
| Arg | Arg | Ala 955 | Arg | His | Arg | Gly | Gly 960 | Pro | Arg | Ala | Gly | Pro 965 | Arg | Glu | Ala | |
| GAG | AGC | GGG | GAG | GAG | CCG | GCG | CGG | CGG | CAC | CGG | GCC | CGG | CAC | AAG | GCG | 3098 |
| Glu 970 | Ser | Gly | Glu | Glu | Pro 975 | Ala | Arg | Arg | His | Arg 980 | Ala | Arg | His | Lys | Ala 985 | |
| CAG | CCT | GCT | CAC | GAG | GCT | GTG | GAG | AAG | GAG | ACC | ACG | GAG | AAG | GAG | GCC | 3146 |
| Gln | Pro | Ala | His | Glu 990 | Ala | Val | Glu | Lys | Glu 995 | Thr | Thr | Glu | Lys | Glu 1000 | Ala | |
| ACG | GAG | AAG | GAG | GCT | GAG | ATA | GTG | GAA | GCC | GAC | AAG | GAA | AAG | GAG | CTC | 3194 |
| Thr | Glu | Lys | Glu | Ala 1005 | Glu | Ile | Val | Glu | Ala 1010 | Asp | Lys | Glu | Lys | Glu 1015 | Leu | |
| CGG | AAC | CAC | CAG | CCC | CGG | GAG | CCA | CAC | TGT | GAC | CTG | GAG | ACC | AGT | GGG | 3242 |
| Arg | Asn | His 1020 | Gln | Pro | Arg | Glu | Pro 1025 | His | Cys | Asp | Leu | Glu 1030 | Thr | Ser | Gly | |
| ACT | GTG | ACT | GTG | GGT | CCC | ATG | CAC | ACA | CTG | CCC | AGC | ACC | TGT | CTC | CAG | 3290 |
| Thr | Val | Thr 1035 | Val | Gly | Pro | Met | His 1040 | Thr | Leu | Pro | Ser | Thr 1045 | Cys | Leu | Gln | |
| AAG | GTG | GAG | GAA | CAG | CCA | GAG | GAT | GCA | GAC | AAT | CAG | CGG | AAC | GTC | ACT | 3338 |
| Lys | Val | Glu | Glu | Gln | Pro | Glu | Asp | Ala | Asp | Asn | Gln | Arg | Asn | Val | Thr | |
| 1050 | | | | | 1055 | | | | | 1060 | | | | | 1065 | |
| CGC | ATG | GGC | AGT | CAG | CCC | CCA | GAC | CCG | AAC | ACT | ATT | GTA | CAT | ATC | CCA | 3386 |
| Arg | Met | Gly | Ser | Gln 1070 | Pro | Pro | Asp | Pro | Asn 1075 | Thr | Ile | Val | His | Ile 1080 | Pro | |
| GTG | ATG | CTG | ACG | GGC | CCT | CTT | GGG | GAA | GCC | ACG | GTC | GTT | CCC | AGT | GGT | 3434 |
| Val | Met | Leu | Thr | Gly 1085 | Pro | Leu | Gly | Glu | Ala 1090 | Thr | Val | Val | Pro | Ser 1095 | Gly | |
| AAC | GTG | GAC | CTG | GAA | AGC | CAA | GCA | GAG | GGG | AAG | AAG | GAG | GTG | GAA | GCG | 3482 |
| Asn | Val | Asp | Leu | Glu | Ser | Gln | Ala | Glu | Gly | Lys | Lys | Glu | Val | Glu | Ala | |
| | | 1100 | | | | | 1105 | | | | | 1110 | | | | |
| GAT | GAC | GTG | ATG | AGG | AGC | GGC | CCC | CGG | CCT | ATC | GTC | CCA | TAC | AGC | TCC | 3530 |
| Asp | Asp | Val | Met | Arg | Ser | Gly | Pro | Arg | Pro | Ile | Val | Pro | Tyr | Ser | Ser | |
| | | 1115 | | | | 1120 | | | | | 1125 | | | | | |
| ATG | TTC | TGT | TTA | AGC | CCC | ACC | AAC | CTG | CTC | CGC | CGC | TTC | TGC | CAC | TAC | 3578 |
| Met | Phe | Cys | Leu | Ser | Pro | Thr | Asn | Leu | Leu | Arg | Arg | Phe | Cys | His | Tyr | |

-continued

|  | 1130 | | | 1135 | | | 1140 | | | 1145 | | |  |
|---|---|---|---|---|---|---|---|---|---|---|---|---|---|
| ATC | GTG | ACC | ATG | AGG | TAC | TTC | GAG | GTG | GTC | ATT | CTC | GTG | GTC | ATC | GCC | 3626 |
| Ile | Val | Thr | Met | Arg | Tyr | Phe | Glu | Val | Val | Ile | Leu | Val | Val | Ile | Ala | |
|  |  |  |  | 1150 |  |  |  | 1155 |  |  |  |  | 1160 |  |  |  |

```
ATC GTG ACC ATG AGG TAC TTC GAG GTG GTC ATT CTC GTG GTC ATC GCC    3626
Ile Val Thr Met Arg Tyr Phe Glu Val Val Ile Leu Val Val Ile Ala
            1150                1155                1160

TTG AGC AGC ATC GCC CTG GCT GCT GAG GAC CCA GTG CGC ACA GAC TCG    3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC    3722
Pro Arg Asn Asn Ala Leu Lys Tyr Leu Asp Tyr Ile Phe Thr Gly Val
            1180                1185                1190

TTT ACC TTT GAG ATG GTG ATA AAG ATG ATC GAC TTG GGA CTG CTG CTT    3770
Phe Thr Phe Glu Met Val Ile Lys Met Ile Asp Leu Gly Leu Leu Leu
        1195                1200                1205

CAC CCT GGA GCC TAT TTC CGG GAC TTG TGG AAC ATT CTG GAC TTC ATT    3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG    3866
Val Val Ser Gly Ala Leu Val Ala Phe Ala Phe Ser Gly Ser Lys Gly
                    1230                1235                1240

AAA GAC ATC AAT ACC ATC AAG TCT CTG AGA GTC CTT CGT GTC CTG CGG    3914
Lys Asp Ile Asn Thr Ile Lys Ser Leu Arg Val Leu Arg Val Leu Arg
            1245                1250                1255

CCC CTC AAG ACC ATC AAA CGG CTG CCC AAG CTC AAG GCT GTG TTT GAC    3962
Pro Leu Lys Thr Ile Lys Arg Leu Pro Lys Leu Lys Ala Val Phe Asp
            1260                1265                1270

TGT GTG GTG AAC TCC CTG AAG AAT GTC CTC AAC ATC TTG ATT GTC TAC    4010
Cys Val Val Asn Ser Leu Lys Asn Val Leu Asn Ile Leu Ile Val Tyr
        1275                1280                1285

ATG CTC TTC ATG TTC ATA TTT GCC GTC ATT GCG GTG CAG CTC TTC AAA    4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC    4106
Gly Lys Phe Phe Tyr Cys Thr Asp Glu Ser Lys Glu Leu Glu Arg Asp
                    1310                1315                1320

TGC AGG GGT CAG TAT TTG GAT TAT GAG AAG GAG GAA GTG GAA GCT CAG    4154
Cys Arg Gly Gln Tyr Leu Asp Tyr Glu Lys Glu Glu Val Glu Ala Gln
                1325                1330                1335

CCC AGG CAG TGG AAG AAA TAC GAC TTT CAC TAC GAC AAT GTG CTC TGG    4202
Pro Arg Gln Trp Lys Lys Tyr Asp Phe His Tyr Asp Asn Val Leu Trp
            1340                1345                1350

GCT CTG CTG ACG CTG TTC ACA GTG TCC ACG GGA GAA GGC TGG CCC ATG    4250
Ala Leu Leu Thr Leu Phe Thr Val Ser Thr Gly Glu Gly Trp Pro Met
            1355                1360                1365

GTG CTG AAA CAC TCC GTG GAT GCC ACC TAT GAG GAG CAG GGT CCA AGC    4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG    4346
Pro Gly Tyr Arg Met Glu Leu Ser Ile Phe Tyr Val Val Tyr Phe Val
                1390                1395                1400

GTC TTT CCC TTC TTC TTC GTC AAC ATC TTT GTG GCT TTG ATC ATC ATC    4394
Val Phe Pro Phe Phe Phe Val Asn Ile Phe Val Ala Leu Ile Ile Ile
                1405                1410                1415

ACC TTC CAG GAG CAG GGG GAC AAG GTG ATG TCT GAA TGC AGC CTG GAG    4442
Thr Phe Gln Glu Gln Gly Asp Lys Val Met Ser Glu Cys Ser Leu Glu
            1420                1425                1430

AAG AAC GAG AGG GCT TGC ATT GAC TTC GCC ATC AGC GCC AAA CCC CTG    4490
Lys Asn Glu Arg Ala Cys Ile Asp Phe Ala Ile Ser Ala Lys Pro Leu
            1435                1440                1445

ACA CGG TAC ATG CCC CAA AAC CGG CAG TCG TTC CAG TAT AAG ACG TGG    4538
Thr Arg Tyr Met Pro Gln Asn Arg Gln Ser Phe Gln Tyr Lys Thr Trp
```

-continued

| | | | | | | | | | | | | | | | | |
|---|---|---|---|---|---|---|---|---|---|---|---|---|---|---|---|---|
| 1450 | | | | | 1455 | | | | | 1460 | | | | | 1465 | |

```
ACA TTT GTG GTC TCC CCG CCC TTT GAA TAC TTC ATC ATG GCC ATG ATA      4586
Thr Phe Val Val Ser Pro Pro Phe Glu Tyr Phe Ile Met Ala Met Ile
            1470                1475                1480

GCC CTC AAC ACT GTG GTG CTG ATG ATG AAG TTC TAT GAT GCA CCC TAT      4634
Ala Leu Asn Thr Val Val Leu Met Met Lys Phe Tyr Asp Ala Pro Tyr
            1485                1490                1495

GAG TAC GAG CTG ATG CTG AAA TGC CTG AAC ATC GTG TTC ACA TCC ATG      4682
Glu Tyr Glu Leu Met Leu Lys Cys Leu Asn Ile Val Phe Thr Ser Met
            1500                1505                1510

TTC TCC ATG GAA TGC GTG CTG AAG ATC ATC GCC TTT GGG GTG CTG AAC      4730
Phe Ser Met Glu Cys Val Leu Lys Ile Ile Ala Phe Gly Val Leu Asn
    1515                1520                1525

TAT TTC AGA GAT GCC TGG AAT GTC TTT GAC TTT GTC ACT GTG TTG GGA      4778
Tyr Phe Arg Asp Ala Trp Asn Val Phe Asp Phe Val Thr Val Leu Gly
1530                1535                1540                1545

AGT ATT ACT GAT ATT TTA GTA ACA GAG ATT GCG GAA ACG AAC AAT TTC      4826
Ser Ile Thr Asp Ile Leu Val Thr Glu Ile Ala Glu Thr Asn Asn Phe
            1550                1555                1560

ATC AAC CTC AGC TTC CTC CGC CTC TTT CGA GCT GCG CGG CTG ATC AAG      4874
Ile Asn Leu Ser Phe Leu Arg Leu Phe Arg Ala Ala Arg Leu Ile Lys
        1565                1570                1575

CTG CTC CGC CAG GGC TAC ACC ATC CGC ATC CTG CTG TGG ACC TTT GTC      4922
Leu Leu Arg Gln Gly Tyr Thr Ile Arg Ile Leu Leu Trp Thr Phe Val
        1580                1585                1590

CAG TCC TTC AAG GCC CTG CCC TAC GTG TGT CTG CTC ATT GCC ATG CTG      4970
Gln Ser Phe Lys Ala Leu Pro Tyr Val Cys Leu Leu Ile Ala Met Leu
        1595                1600                1605

TTC TTC ATC TAC GCC ATC ATC GGC ATG CAG GTG TTT GGG AAT ATT GCC      5018
Phe Phe Ile Tyr Ala Ile Ile Gly Met Gln Val Phe Gly Asn Ile Ala
1610                1615                1620                1625

CTG GAT GAT GAC ACC AGC ATC AAC CGC CAC AAC AAC TTC CGG ACG TTT      5066
Leu Asp Asp Asp Thr Ser Ile Asn Arg His Asn Asn Phe Arg Thr Phe
            1630                1635                1640

TTG CAA GCC CTG ATG CTG CTG TTC AGG AGC GCC ACG GGG GAG GCC TGG      5114
Leu Gln Ala Leu Met Leu Leu Phe Arg Ser Ala Thr Gly Glu Ala Trp
            1645                1650                1655

CAC GAG ATC ATG CTG TCC TGC CTG AGC AAC CAG GCC TGT GAT GAG CAG      5162
His Glu Ile Met Leu Ser Cys Leu Ser Asn Gln Ala Cys Asp Glu Gln
            1660                1665                1670

GCC AAT GCC ACC GAG TGT GGA AGT GAC TTT GCC TAC TTC TAC TTC GTC      5210
Ala Asn Ala Thr Glu Cys Gly Ser Asp Phe Ala Tyr Phe Tyr Phe Val
            1675                1680                1685

TCC TTC ATC TTC CTG TGC TCC TTT CTG ATG TTG AAC CTC TTT GTG GCT      5258
Ser Phe Ile Phe Leu Cys Ser Phe Leu Met Leu Asn Leu Phe Val Ala
1690                1695                1700                1705

GTG ATC ATG GAC AAT TTT GAG TAC CTC ACG CGG GAC TCT TCC ATC CTA      5306
Val Ile Met Asp Asn Phe Glu Tyr Leu Thr Arg Asp Ser Ser Ile Leu
            1710                1715                1720

GGT CCT CAC CAC TTG GAT GAG TTC ATC CGG GTC TGG GCT GAA TAC GAC      5354
Gly Pro His His Leu Asp Glu Phe Ile Arg Val Trp Ala Glu Tyr Asp
            1725                1730                1735

CCG GCT GCG TGT GGG CGC ATC AGT TAC AAT GAC ATG TTT GAG ATG CTG      5402
Pro Ala Ala Cys Gly Arg Ile Ser Tyr Asn Asp Met Phe Glu Met Leu
            1740                1745                1750

AAA CAC ATG TCC CCG CCT CTG GGG CTG GGG AAG AAA TGC CCT GCT CGA      5450
Lys His Met Ser Pro Pro Leu Gly Leu Gly Lys Lys Cys Pro Ala Arg
            1755                1760                1765

GTT GCT TAC AAG CGC CTG GTT CGC ATG AAC ATG CCC ATC TCC AAC GAG      5498
Val Ala Tyr Lys Arg Leu Val Arg Met Asn Met Pro Ile Ser Asn Glu
```

```
1770                    1775                    1780                    1785

GAC  ATG  ACT  GTT  CAC  TTC  ACG  TCC  ACG  CTG  ATG  GCC  CTC  ATC  CGG  ACG         5546
Asp  Met  Thr  Val  His  Phe  Thr  Ser  Thr  Leu  Met  Ala  Leu  Ile  Arg  Thr
               1790                    1795                    1800

GCA  CTG  GAG  ATC  AAG  CTG  GCC  CCA  GCT  GGG  ACA  AAG  CAG  CAT  CAG  TGT         5594
Ala  Leu  Glu  Ile  Lys  Leu  Ala  Pro  Ala  Gly  Thr  Lys  Gln  His  Gln  Cys
               1805                    1810                    1815

GAC  GCG  GAG  TTG  AGG  AAG  GAG  ATT  TCC  GTT  GTG  TGG  GCC  AAT  CTG  CCC         5642
Asp  Ala  Glu  Leu  Arg  Lys  Glu  Ile  Ser  Val  Val  Trp  Ala  Asn  Leu  Pro
               1820                    1825                    1830

CAG  AAG  ACT  TTG  GAC  TTG  CTG  GTA  CCA  CCC  CAT  AAG  CCT  GAT  GAG  ATG         5690
Gln  Lys  Thr  Leu  Asp  Leu  Leu  Val  Pro  Pro  His  Lys  Pro  Asp  Glu  Met
               1835                    1840                    1845

ACA  GTG  GGG  AAG  GTT  TAT  GCA  GCT  CTG  ATG  ATA  TTT  GAC  TTC  TAC  AAG         5738
Thr  Val  Gly  Lys  Val  Tyr  Ala  Ala  Leu  Met  Ile  Phe  Asp  Phe  Tyr  Lys
1850                    1855                    1860                    1865

CAG  AAC  AAA  ACC  ACC  AGA  GAC  CAG  ATG  CAG  CAG  GCT  CCT  GGA  GGC  CTC         5786
Gln  Asn  Lys  Thr  Thr  Arg  Asp  Gln  Met  Gln  Gln  Ala  Pro  Gly  Gly  Leu
               1870                    1875                    1880

TCC  CAG  ATG  GGT  CCT  GTG  TCC  CTG  TTC  CAC  CCT  CTG  AAG  GCC  ACC  CTG         5834
Ser  Gln  Met  Gly  Pro  Val  Ser  Leu  Phe  His  Pro  Leu  Lys  Ala  Thr  Leu
               1885                    1890                    1895

GAG  CAG  ACA  CAG  CCG  GCT  GTG  CTC  CGA  GGA  GCC  CGG  GTT  TTC  CTT  CGA         5882
Glu  Gln  Thr  Gln  Pro  Ala  Val  Leu  Arg  Gly  Ala  Arg  Val  Phe  Leu  Arg
               1900                    1905                    1910

CAG  AAG  AGT  TCC  ACC  TCC  CTC  AGC  AAT  GGC  GGG  GCC  ATA  CAA  AAC  CAA         5930
Gln  Lys  Ser  Ser  Thr  Ser  Leu  Ser  Asn  Gly  Gly  Ala  Ile  Gln  Asn  Gln
               1915                    1920                    1925

GAG  AGT  GGC  ATC  AAA  GAG  TCT  GTC  TCC  TGG  GGC  ACT  CAA  AGG  ACC  CAG         5978
Glu  Ser  Gly  Ile  Lys  Glu  Ser  Val  Ser  Trp  Gly  Thr  Gln  Arg  Thr  Gln
1930                    1935                    1940                    1945

GAT  GCA  CCC  CAT  GAG  GCC  AGG  CCA  CCC  CTG  GAG  CGT  GGC  CAC  TCC  ACA         6026
Asp  Ala  Pro  His  Glu  Ala  Arg  Pro  Pro  Leu  Glu  Arg  Gly  His  Ser  Thr
               1950                    1955                    1960

GAG  ATC  CCT  GTG  GGG  CGG  TCA  GGA  GCA  CTG  GCT  GTG  GAC  GTT  CAG  ATG         6074
Glu  Ile  Pro  Val  Gly  Arg  Ser  Gly  Ala  Leu  Ala  Val  Asp  Val  Gln  Met
               1965                    1970                    1975

CAG  AGC  ATA  ACC  CGG  AGG  GGC  CCT  GAT  GGG  GAG  CCC  CAG  CCT  GGG  CTG         6122
Gln  Ser  Ile  Thr  Arg  Arg  Gly  Pro  Asp  Gly  Glu  Pro  Gln  Pro  Gly  Leu
               1980                    1985                    1990

GAG  AGC  CAG  GGT  CGA  GCG  GCC  TCC  ATG  CCC  CGC  CTT  GCG  GCC  GAG  ACT         6170
Glu  Ser  Gln  Gly  Arg  Ala  Ala  Ser  Met  Pro  Arg  Leu  Ala  Ala  Glu  Thr
               1995                    2000                    2005

CAG  CCC  GTC  ACA  GAT  GCC  AGC  CCC  ATG  AAG  CGC  TCC  ATC  TCC  ACG  CTG         6218
Gln  Pro  Val  Thr  Asp  Ala  Ser  Pro  Met  Lys  Arg  Ser  Ile  Ser  Thr  Leu
2010                    2015                    2020                    2025

GCC  CAG  CGG  CCC  CGT  GGG  ACT  CAT  CTT  TGC  AGC  ACC  ACC  CCG  GAC  CGC         6266
Ala  Gln  Arg  Pro  Arg  Gly  Thr  His  Leu  Cys  Ser  Thr  Thr  Pro  Asp  Arg
               2030                    2035                    2040

CCA  CCC  CCT  AGC  CAG  GCG  TCG  TCG  CAC  CAC  CAC  CAC  CAC  CGC  TGC  CAC         6314
Pro  Pro  Pro  Ser  Gln  Ala  Ser  Ser  His  His  His  His  His  Arg  Cys  His
               2045                    2050                    2055

CGC  CGC  AGG  GAC  AGG  AAG  CAG  AGG  TCC  CTG  GAG  AAG  GGG  CCC  AGC  CTG         6362
Arg  Arg  Arg  Asp  Arg  Lys  Gln  Arg  Ser  Leu  Glu  Lys  Gly  Pro  Ser  Leu
               2060                    2065                    2070

TCT  GCC  GAT  ATG  GAT  GGC  GCA  CCA  AGC  AGT  GCT  GTG  GGG  CCG  GGG  CTG         6410
Ser  Ala  Asp  Met  Asp  Gly  Ala  Pro  Ser  Ser  Ala  Val  Gly  Pro  Gly  Leu
               2075                    2080                    2085

CCC  CCG  GGA  GAG  GGG  CCT  ACA  GGC  TGC  CGG  CGG  GAA  CGA  GAG  CGC  CGG         6458
Pro  Pro  Gly  Glu  Gly  Pro  Thr  Gly  Cys  Arg  Arg  Glu  Arg  Glu  Arg  Arg
```

```
       2090                    2095                   2100                     2105
CAG  GAG  CGG  GGC  CGG  TCC  CAG  GAG  CGG  AGG  CAG  CCC  TCA  TCC  TCC  TCC            6506
Gln  Glu  Arg  Gly  Arg  Ser  Gln  Glu  Arg  Arg  Gln  Pro  Ser  Ser  Ser  Ser
                    2110                    2115                    2120

TCG  GAG  AAG  CAG  CGC  TTC  TAC  TCC  TGC  GAC  CGC  TTT  GGG  GGC  CGT  GAG            6554
Ser  Glu  Lys  Gln  Arg  Phe  Tyr  Ser  Cys  Asp  Arg  Phe  Gly  Gly  Arg  Glu
                    2125                    2130                    2135

CCC  CCG  AAG  CCC  AAG  CCC  TCC  CTC  AGC  AGC  CAC  CCA  ACG  TCG  CCA  ACA            6602
Pro  Pro  Lys  Pro  Lys  Pro  Ser  Leu  Ser  Ser  His  Pro  Thr  Ser  Pro  Thr
                    2140                    2145                    2150

GCT  GGC  CAG  GAG  CCG  GGA  CCC  CAC  CCA  CAG  GCC  GGC  TCA  GCC  GTG  GGC            6650
Ala  Gly  Gln  Glu  Pro  Gly  Pro  His  Pro  Gln  Ala  Gly  Ser  Ala  Val  Gly
          2155                    2160                    2165

TTT  CCG  AAC  ACA  ACG  CCC  TGC  TGC  AGA  GAG  ACC  CCC  TCA  GCC  AGC  CCC            6698
Phe  Pro  Asn  Thr  Thr  Pro  Cys  Cys  Arg  Glu  Thr  Pro  Ser  Ala  Ser  Pro
2170                    2175                    2180                    2185

TGG  CCC  CTG  GCT  CTC  GAA  TTG  GCT  CTG  ACC  CTT  ACC  TGG  GGC  AGC  GTC            6746
Trp  Pro  Leu  Ala  Leu  Glu  Leu  Ala  Leu  Thr  Leu  Thr  Trp  Gly  Ser  Val
                    2190                    2195                    2200

TGG  ACA  GTG  AGG  CCT  CTG  TCC  ACG  CCC  TGC  CTG  AGG  ACA  CGC  TCA  CTT            6794
Trp  Thr  Val  Arg  Pro  Leu  Ser  Thr  Pro  Cys  Leu  Arg  Thr  Arg  Ser  Leu
               2205                    2210                    2215

TCG  AGG  AGG  CTG  TGG  CCA  CCA  ACT  CGG  GCC  GCT  CCT  CCA  GGA  CTT  CCT            6842
Ser  Arg  Arg  Leu  Trp  Pro  Pro  Thr  Arg  Ala  Ala  Pro  Pro  Gly  Leu  Pro
          2220                    2225                    2230

ACG  TGT  CCT  CCC  TGACCTCCCA  GTCTCACCCT  CTCCGCCGCG  TGCCCAACGG                        6894
Thr  Cys  Pro  Pro
          2235

TTACCACTGC  ACCCTGGGAC  TCAGCTCGGG  TGGCCGAGCA  CGGCACAGCT  ACCACCACCC                    6954

TGACCAAGAC  CACTGGTGCT  AGCTGCACCG  TGACCGCTCA  GACGCCTGCA  TGCAGCAGGC                    7014

GTGTGTTCCA  GTGGATGAGT  TTTATCATCC  ACACGGGGCA  GTCGGCCCTC  GGGGGAGGCC                    7074

TTGCCCACCT  TGGTGAGGCT  CCTGTGGCCC  CTCCCTCCCC  CTCCTCCCCT  CTTTTACTCT                    7134

AGACGACGAA  TAAAGCCCTG  TTGCTTGAGT  GTACGTACCG  C                                         7175
```

( 2 ) INFORMATION FOR SEQ ID NO:9:

( i ) SEQUENCE CHARACTERISTICS:
        ( A ) LENGTH: 1546 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1437

( i x ) FEATURE:
        ( A ) NAME/KEY: 3'UTR
        ( B ) LOCATION: 1435..1546
        ( D ) OTHER INFORMATION: /standard_name="Beta 1-2"

( x i ) SEQUENCE DESCRIPTION: SEQ ID NO:9:

```
ATG  GTC  CAG  AAG  ACC  AGC  ATG  TCC  CGG  GGC  CCT  TAC  CCA  CCC  TCC  CAG             48
Met  Val  Gln  Lys  Thr  Ser  Met  Ser  Arg  Gly  Pro  Tyr  Pro  Pro  Ser  Gln
  1                 5                        10                      15

GAG  ATC  CCC  ATG  GAG  GTC  TTC  GAC  CCC  AGC  CCG  CAG  GGC  AAA  TAC  AGC             96
Glu  Ile  Pro  Met  Glu  Val  Phe  Asp  Pro  Ser  Pro  Gln  Gly  Lys  Tyr  Ser
               20                      25                      30

AAG  AGG  AAA  GGG  CGA  TTC  AAA  CGG  TCA  GAT  GGG  AGC  ACG  TCC  TCG  GAT            144
Lys  Arg  Lys  Gly  Arg  Phe  Lys  Arg  Ser  Asp  Gly  Ser  Thr  Ser  Ser  Asp
```

-continued

| | 35 | | | | | 40 | | | | | 45 | | | | |
|---|---|---|---|---|---|---|---|---|---|---|---|---|---|---|---|
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | | 70 | | | | | 75 | | | | | 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |
| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |
| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |
| | | | 260 | | | | | 265 | | | | | 270 | | | |
| ATT | TCC | CTG | GCT | AAG | CGC | TCA | GTT | CTC | AAC | AAC | CCC | AGC | AAA | CAC | ATC | 864 |
| Ile | Ser | Leu | Ala | Lys | Arg | Ser | Val | Leu | Asn | Asn | Pro | Ser | Lys | His | Ile | |
| | | 275 | | | | | 280 | | | | | 285 | | | | |
| ATC | ATT | GAG | CGC | TCC | AAC | ACA | CGC | TCC | AGC | CTG | GCT | GAG | GTG | CAG | AGT | 912 |
| Ile | Ile | Glu | Arg | Ser | Asn | Thr | Arg | Ser | Ser | Leu | Ala | Glu | Val | Gln | Ser | |
| | 290 | | | | | 295 | | | | | 300 | | | | | |
| GAA | ATC | GAG | CGA | ATC | TTC | GAG | CTG | GCC | CGG | ACC | CTT | CAG | TTG | GTC | GCT | 960 |
| Glu | Ile | Glu | Arg | Ile | Phe | Glu | Leu | Ala | Arg | Thr | Leu | Gln | Leu | Val | Ala | |
| 305 | | | | | 310 | | | | | 315 | | | | | 320 | |
| CTG | GAT | GCT | GAC | ACC | ATC | AAT | CAC | CCA | GCC | CAG | CTG | TCC | AAG | ACC | TCG | 1008 |
| Leu | Asp | Ala | Asp | Thr | Ile | Asn | His | Pro | Ala | Gln | Leu | Ser | Lys | Thr | Ser | |
| | | | | 325 | | | | | 330 | | | | | 335 | | |
| CTG | GCC | CCC | ATC | ATT | GTT | TAC | ATC | AAG | ATC | ACC | TCT | CCC | AAG | GTA | CTT | 1056 |
| Leu | Ala | Pro | Ile | Ile | Val | Tyr | Ile | Lys | Ile | Thr | Ser | Pro | Lys | Val | Leu | |
| | | | 340 | | | | | 345 | | | | | 350 | | | |
| CAA | AGG | CTC | ATC | AAG | TCC | CGA | GGA | AAG | TCT | CAG | TCC | AAA | CAC | CTC | AAT | 1104 |
| Gln | Arg | Leu | Ile | Lys | Ser | Arg | Gly | Lys | Ser | Gln | Ser | Lys | His | Leu | Asn | |

-continued

|  |  | 355 |  |  |  |  | 360 |  |  |  |  | 365 |  |  |  |
|---|---|---|---|---|---|---|---|---|---|---|---|---|---|---|---|
| GTC | CAA | ATA | GCG | GCC | TCG | GAA | AAG | CTG | GCA | CAG | TGC | CCC | CCT | GAA | ATG | 1152
| Val | Gln | Ile | Ala | Ala | Ser | Glu | Lys | Leu | Ala | Gln | Cys | Pro | Pro | Glu | Met |
|  | 370 |  |  |  | 375 |  |  |  |  | 380 |  |  |  |  |  |
| TTT | GAC | ATC | ATC | CTG | GAT | GAG | AAC | CAA | TTG | GAG | GAT | GCC | TGC | GAG | CAT | 1200
| Phe | Asp | Ile | Ile | Leu | Asp | Glu | Asn | Gln | Leu | Glu | Asp | Ala | Cys | Glu | His |
| 385 |  |  |  |  | 390 |  |  |  |  | 395 |  |  |  |  | 400 |
| CTG | GCG | GAG | TAC | TTG | GAA | GCC | TAT | TGG | AAG | GCC | ACA | CAC | CCG | CCC | AGC | 1248
| Leu | Ala | Glu | Tyr | Leu | Glu | Ala | Tyr | Trp | Lys | Ala | Thr | His | Pro | Pro | Ser |
|  |  |  |  | 405 |  |  |  |  | 410 |  |  |  |  | 415 |  |
| AGC | ACG | CCA | CCC | AAT | CCG | CTG | CTG | AAC | CGC | ACC | ATG | GCT | ACC | GCA | GCC | 1296
| Ser | Thr | Pro | Pro | Asn | Pro | Leu | Leu | Asn | Arg | Thr | Met | Ala | Thr | Ala | Ala |
|  |  |  | 420 |  |  |  |  | 425 |  |  |  |  | 430 |  |  |
| CTG | GCT | GCC | AGC | CCT | GCC | CCT | GTC | TCC | AAC | CTC | CAG | GTA | CAG | GTG | CTC | 1344
| Leu | Ala | Ala | Ser | Pro | Ala | Pro | Val | Ser | Asn | Leu | Gln | Val | Gln | Val | Leu |
|  |  | 435 |  |  |  |  | 440 |  |  |  |  | 445 |  |  |  |
| ACC | TCG | CTC | AGG | AGA | AAC | CTC | GGC | TTC | TGG | GGC | GGG | CTG | GAG | TCC | TCA | 1392
| Thr | Ser | Leu | Arg | Arg | Asn | Leu | Gly | Phe | Trp | Gly | Gly | Leu | Glu | Ser | Ser |
|  | 450 |  |  |  |  | 455 |  |  |  |  | 460 |  |  |  |  |
| CAG | CGG | GGC | AGT | GTG | GTG | CCC | CAG | GAG | CAG | GAA | CAT | GCC | ATG | TAGTGGGCGC |  | 1444
| Gln | Arg | Gly | Ser | Val | Val | Pro | Gln | Glu | Gln | Glu | His | Ala | Met |  |  |
| 465 |  |  |  | 470 |  |  |  |  | 475 |  |  |  |  |  |  |

CCTGCCCGTC TTCCCTCCTG CTCTGGGGTC GGAACTGGAG TGCAGGGAAC ATGGAGGAGG 1504

AAGGGAAGAG CTTTATTTTG TAAAAAAATA AGATGAGCGG CA 1546

(2) INFORMATION FOR SEQ ID NO:10:

( i ) SEQUENCE CHARACTERISTICS:
        ( A ) LENGTH: 1851 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1797
        ( D ) OTHER INFORMATION: /standard_name="Beta1-3"

( i x ) FEATURE:
        ( A ) NAME/KEY: 3'UTR
        ( B ) LOCATION: 1795..1851

( x i ) SEQUENCE DESCRIPTION: SEQ ID NO:10:

| ATG | GTC | CAG | AAG | ACC | AGC | ATG | TCC | CGG | GGC | CCT | TAC | CCA | CCC | TCC | CAG | 48
| Met | Val | Gln | Lys | Thr | Ser | Met | Ser | Arg | Gly | Pro | Tyr | Pro | Pro | Ser | Gln |
| 1 |  |  |  | 5 |  |  |  |  | 10 |  |  |  |  | 15 |  |
| GAG | ATC | CCC | ATG | GGA | GTC | TTC | GAC | CCC | AGC | CCG | CAG | GGC | AAA | TAC | AGC | 96
| Glu | Ile | Pro | Met | Gly | Val | Phe | Asp | Pro | Ser | Pro | Gln | Gly | Lys | Tyr | Ser |
|  |  |  | 20 |  |  |  |  | 25 |  |  |  |  | 30 |  |  |
| AAG | AGG | AAA | GGG | CGA | TTC | AAA | CGG | TCA | GAT | GGG | AGC | ACG | TCC | TCG | GAT | 144
| Lys | Arg | Lys | Gly | Arg | Phe | Lys | Arg | Ser | Asp | Gly | Ser | Thr | Ser | Ser | Asp |
|  |  | 35 |  |  |  |  | 40 |  |  |  |  | 45 |  |  |  |
| ACC | ACA | TCC | AAC | AGC | TTT | GTC | CGC | CAG | GGC | TCA | GCG | GAG | TCC | TAC | ACC | 192
| Thr | Thr | Ser | Asn | Ser | Phe | Val | Arg | Gln | Gly | Ser | Ala | Glu | Ser | Tyr | Thr |
|  | 50 |  |  |  |  | 55 |  |  |  |  | 60 |  |  |  |  |
| AGC | CGT | CCA | TCA | GAC | TCT | GAT | GTA | TCT | CTG | GAG | GAG | GAC | CGG | GAA | GCC | 240
| Ser | Arg | Pro | Ser | Asp | Ser | Asp | Val | Ser | Leu | Glu | Glu | Asp | Arg | Glu | Ala |
| 65 |  |  |  |  | 70 |  |  |  |  | 75 |  |  |  |  | 80 |
| TTA | AGG | AAG | GAA | GCA | GAG | CGC | CAG | GCA | TTA | GCG | CAG | CTC | GAG | AAG | GCC | 288
| Leu | Arg | Lys | Glu | Ala | Glu | Arg | Gln | Ala | Leu | Ala | Gln | Leu | Glu | Lys | Ala |
|  |  |  |  | 85 |  |  |  |  | 90 |  |  |  |  | 95 |  |

| | | | | | | | | | | | | | | | | |
|---|---|---|---|---|---|---|---|---|---|---|---|---|---|---|---|---|
| AAG | ACC | AAG | CCA | GTG | GCA | TTT | GCT | GTG | CGG | ACA | AAT | GTT | GGC | TAC | AAT | 336 |
| Lys | Thr | Lys | Pro 100 | Val | Ala | Phe | Ala | Val 105 | Arg | Thr | Asn | Val | Gly 110 | Tyr | Asn | |
| CCG | TCT | CCA | GGG | GAT | GAG | GTG | CCT | GTG | CAG | GGA | GTG | GCC | ATC | ACC | TTC | 384 |
| Pro | Ser | Pro 115 | Gly | Asp | Glu | Val | Pro 120 | Val | Gln | Gly | Val | Ala 125 | Ile | Thr | Phe | |
| GAG | CCC | AAA | GAC | TTC | CTG | CAC | ATC | AAG | GAG | AAA | TAC | AAT | AAT | GAC | TGG | 432 |
| Glu | Pro 130 | Lys | Asp | Phe | Leu | His 135 | Ile | Lys | Glu | Lys | Tyr 140 | Asn | Asn | Asp | Trp | |
| TGG | ATC | GGG | CGG | CTG | GTG | AAG | GAG | GGC | TGT | GAG | GTT | GGC | TTC | ATT | CCC | 480 |
| Trp 145 | Ile | Gly | Arg | Leu | Val 150 | Lys | Glu | Gly | Cys | Glu 155 | Val | Gly | Phe | Ile | Pro 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu 165 | Asp | Ser | Leu | Arg | Leu 170 | Leu | Gln | Glu | Gln | Lys 175 | Leu | |
| CGC | CAG | AAC | CGC | CTC | GGC | TCC | AGC | AAA | TCA | GGC | GAT | AAC | TCC | AGT | TCC | 576 |
| Arg | Gln | Asn | Arg 180 | Leu | Gly | Ser | Ser | Lys 185 | Ser | Gly | Asp | Asn | Ser 190 | Ser | Ser | |
| AGT | CTG | GGA | GAT | GTG | GTG | ACT | GGC | ACC | CGC | CGC | CCC | ACA | CCC | CCT | GCC | 624 |
| Ser | Leu | Gly 195 | Asp | Val | Val | Thr | Gly 200 | Thr | Arg | Arg | Pro | Thr 205 | Pro | Pro | Ala | |
| AGT | GCC | AAA | CAG | AAG | CAG | AAG | TCG | ACA | GAG | CAT | GTG | CCC | CCC | TAT | GAC | 672 |
| Ser | Ala 210 | Lys | Gln | Lys | Gln | Lys 215 | Ser | Thr | Glu | His | Val 220 | Pro | Pro | Tyr | Asp | |
| GTG | GTG | CCT | TCC | ATG | AGG | CCC | ATC | ATC | CTG | GTG | GGA | CCG | TCG | CTC | AAG | 720 |
| Val | Val 225 | Pro | Ser | Met | Arg | Pro 230 | Ile | Ile | Leu | Val | Gly 235 | Pro | Ser | Leu | Lys 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr 245 | Asp | Met | Met | Gln | Lys 250 | Ala | Leu | Phe | Asp | Phe 255 | Leu | |
| AAG | CAT | CGG | TTT | GAT | GGC | AGG | ATC | TCC | ATC | ACT | CGT | GTG | ACG | GCA | GAT | 816 |
| Lys | His | Arg | Phe 260 | Asp | Gly | Arg | Ile | Ser 265 | Ile | Thr | Arg | Val | Thr 270 | Ala | Asp | |
| ATT | TCC | CTG | GCT | AAG | CGC | TCA | GTT | CTC | AAC | AAC | CCC | AGC | AAA | CAC | ATC | 864 |
| Ile | Ser | Leu 275 | Ala | Lys | Arg | Ser | Val 280 | Leu | Asn | Asn | Pro | Ser 285 | Lys | His | Ile | |
| ATC | ATT | GAG | CGC | TCC | AAC | ACA | CGC | TCC | AGC | CTG | GCT | GAG | GTG | CAG | AGT | 912 |
| Ile | Ile | Glu 290 | Arg | Ser | Asn | Thr 295 | Arg | Ser | Ser | Leu | Ala 300 | Glu | Val | Gln | Ser | |
| GAA | ATC | GAG | CGA | ATC | TTC | GAG | CTG | GCC | CGG | ACC | CTT | CAG | TTG | GTC | GCT | 960 |
| Glu | Ile | Glu 305 | Arg | Ile | Phe | Glu 310 | Leu | Ala | Arg | Thr | Leu 315 | Gln | Leu | Val | Ala 320 | |
| CTG | GAT | GCT | GAC | ACC | ATC | AAT | CAC | CCA | GCC | CAG | CTG | TCC | AAG | ACC | TCG | 1008 |
| Leu | Asp | Ala | Asp | Thr 325 | Ile | Asn | His | Pro | Ala 330 | Gln | Leu | Ser | Lys | Thr 335 | Ser | |
| CTG | GCC | CCC | ATC | ATT | GTT | TAC | ATC | AAG | ATC | ACC | TCT | CCC | AAG | GTA | CTT | 1056 |
| Leu | Ala | Pro | Ile 340 | Ile | Val | Tyr | Ile | Lys 345 | Ile | Thr | Ser | Pro | Lys 350 | Val | Leu | |
| CAA | AGG | CTC | ATC | AAG | TCC | CGA | GGA | AAG | TCT | CAG | TCC | AAA | CAC | CTC | AAT | 1104 |
| Gln | Arg | Leu | Ile 355 | Lys | Ser | Arg | Gly | Lys 360 | Ser | Gln | Ser | Lys | His 365 | Leu | Asn | |
| GTC | CAA | ATA | GCG | GCC | TCG | GAA | AAG | CTG | GCA | CAG | TGC | CCC | CCT | GAA | ATG | 1152 |
| Val | Gln | Ile | Ala 370 | Ala | Ser | Glu | Lys 375 | Leu | Ala | Gln | Cys | Pro 380 | Pro | Glu | Met | |
| TTT | GAC | ATC | ATC | CTG | GAT | GAG | AAC | CAA | TTG | GAG | GAT | GCC | TGC | GAG | CAT | 1200 |
| Phe 385 | Asp | Ile | Ile | Leu | Asp 390 | Glu | Asn | Gln | Leu | Glu 395 | Asp | Ala | Cys | Glu | His 400 | |
| CTG | GCG | GAG | TAC | TTG | GAA | GCC | TAT | TGG | AAG | GCC | ACA | CAC | CCG | CCC | AGC | 1248 |
| Leu | Ala | Glu | Tyr | Leu 405 | Glu | Ala | Tyr | Trp | Lys 410 | Ala | Thr | His | Pro | Pro 415 | Ser | |

| | | | | | | | | | | | | | | | | |
|---|---|---|---|---|---|---|---|---|---|---|---|---|---|---|---|---|
| AGC | ACG | CCA | CCC | AAT | CCG | CTG | CTG | AAC | CGC | ACC | ATG | GCT | ACC | GCA | GCC | 1296 |
| Ser | Thr | Pro | Pro | Asn | Pro | Leu | Leu | Asn | Arg | Thr | Met | Ala | Thr | Ala | Ala | |
| | | | 420 | | | | | 425 | | | | | 430 | | | |
| CTG | GCT | GCC | AGC | CCT | GCC | CCT | GTC | TCC | AAC | CTC | CAG | GGA | CCC | TAC | CTT | 1344 |
| Leu | Ala | Ala | Ser | Pro | Ala | Pro | Val | Ser | Asn | Leu | Gln | Gly | Pro | Tyr | Leu | |
| | | 435 | | | | | 440 | | | | | 445 | | | | |
| GCT | TCC | GGG | GAC | CAG | CCA | CTG | GAA | CGG | GCC | ACC | GGG | GAG | CAC | GCC | AGC | 1392 |
| Ala | Ser | Gly | Asp | Gln | Pro | Leu | Glu | Arg | Ala | Thr | Gly | Glu | His | Ala | Ser | |
| | | 450 | | | | | 455 | | | | | 460 | | | | |
| ATG | CAC | GAG | TAC | CCA | GGG | GAG | CTG | GGC | CAG | CCC | CCA | GGC | CTT | TAC | CCC | 1440 |
| Met | His | Glu | Tyr | Pro | Gly | Glu | Leu | Gly | Gln | Pro | Pro | Gly | Leu | Tyr | Pro | |
| 465 | | | | | 470 | | | | | 475 | | | | | 480 | |
| AGC | AGC | CAC | CCA | CCA | GGC | CGG | GCA | GGC | ACG | CTA | CGG | GCA | CTG | TCC | CGC | 1488 |
| Ser | Ser | His | Pro | Pro | Gly | Arg | Ala | Gly | Thr | Leu | Arg | Ala | Leu | Ser | Arg | |
| | | | | 485 | | | | | 490 | | | | | 495 | | |
| CAA | GAC | ACT | TTT | GAT | GCC | GAC | ACC | CCC | GGC | AGC | CGA | AAC | TCT | GCC | TAC | 1536 |
| Gln | Asp | Thr | Phe | Asp | Ala | Asp | Thr | Pro | Gly | Ser | Arg | Asn | Ser | Ala | Tyr | |
| | | | 500 | | | | 505 | | | | | 510 | | | | |
| ACG | GAG | CTG | GGA | GAC | TCA | TGT | GTG | GAC | ATG | GAG | ACT | GAC | CCC | TCA | GAG | 1584 |
| Thr | Glu | Leu | Gly | Asp | Ser | Cys | Val | Asp | Met | Glu | Thr | Asp | Pro | Ser | Glu | |
| | | 515 | | | | 520 | | | | | 525 | | | | | |
| GGG | CCA | GGG | CTT | GGA | GAC | CCT | GCA | GGG | GGC | GGC | ACG | CCC | CCA | GCC | CGA | 1632 |
| Gly | Pro | Gly | Leu | Gly | Asp | Pro | Ala | Gly | Gly | Gly | Thr | Pro | Pro | Ala | Arg | |
| | 530 | | | | | 535 | | | | | 540 | | | | | |
| CAG | GGA | TCC | TGG | GAG | GAC | GAG | GAA | GAA | GAC | TAT | GAG | GAA | GAG | CTG | ACC | 1680 |
| Gln | Gly | Ser | Trp | Glu | Asp | Glu | Glu | Glu | Asp | Tyr | Glu | Glu | Glu | Leu | Thr | |
| 545 | | | | | 550 | | | | | 555 | | | | | 560 | |
| GAC | AAC | CGG | AAC | CGG | GGC | CGG | AAT | AAG | GCC | CGC | TAC | TGC | GCT | GAG | GGT | 1728 |
| Asp | Asn | Arg | Asn | Arg | Gly | Arg | Asn | Lys | Ala | Arg | Tyr | Cys | Ala | Glu | Gly | |
| | | | | 565 | | | | | 570 | | | | | 575 | | |
| GGG | GGT | CCA | GTT | TTG | GGG | CGC | AAC | AAG | AAT | GAG | CTG | GAG | GGC | TGG | GGA | 1776 |
| Gly | Gly | Pro | Val | Leu | Gly | Arg | Asn | Lys | Asn | Glu | Leu | Glu | Gly | Trp | Gly | |
| | | | 580 | | | | | 585 | | | | | 590 | | | |
| CGA | GGC | GTC | TAC | ATT | CGC | TGAGAGGCAG | GGGCCACACG | GCGGGAGGAA | | | | | | | | 1824 |
| Arg | Gly | Val | Tyr | Ile | Arg | | | | | | | | | | | |
| | | | 595 | | | | | | | | | | | | | |

GGGCTCTGAG CCCAGGGGAG GGGAGGG        1851

( 2 ) INFORMATION FOR SEQ ID NO:11:

( i ) SEQUENCE CHARACTERISTICS:
        ( A ) LENGTH: 3600 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 35..3310
        ( D ) OTHER INFORMATION: /standard_name="Alpha-2b"

( i x ) FEATURE:
        ( A ) NAME/KEY: 5'UTR
        ( B ) LOCATION: 1..34

( i x ) FEATURE:
        ( A ) NAME/KEY: 3'UTR
        ( B ) LOCATION: 3308..3600

( x i ) SEQUENCE DESCRIPTION: SEQ ID NO:11:

| | | | | | | | | |
|---|---|---|---|---|---|---|---|---|
| GCGGGGGAGG | GGGCATTGAT | CTTCGATCGC | GAAG | ATG | GCT | GCT | GGC | TGC | CTG | 52 |
| | | | | Met | Ala | Ala | Gly | Cys | Leu | |
| | | | | 1 | | | | 5 | | |

```
CTG  GCC  TTG  ACT  CTG  ACA  CTT  TTC  CAA  TCT  TTG  CTC  ATC  GGC  CCC  TCG    100
Leu  Ala  Leu  Thr  Leu  Thr  Leu  Phe  Gln  Ser  Leu  Leu  Ile  Gly  Pro  Ser
               10                  15                       20

TCG  GAG  GAG  CCG  TTC  CCT  TCG  GCC  GTC  ACT  ATC  AAA  TCA  TGG  GTG  GAT    148
Ser  Glu  Glu  Pro  Phe  Pro  Ser  Ala  Val  Thr  Ile  Lys  Ser  Trp  Val  Asp
               25                  30                       35

AAG  ATG  CAA  GAA  GAC  CTT  GTC  ACA  CTG  GCA  AAA  ACA  GCA  AGT  GGA  GTC    196
Lys  Met  Gln  Glu  Asp  Leu  Val  Thr  Leu  Ala  Lys  Thr  Ala  Ser  Gly  Val
     40                       45                       50

AAT  CAG  CTT  GTT  GAT  ATT  TAT  GAG  AAA  TAT  CAA  GAT  TTG  TAT  ACT  GTG    244
Asn  Gln  Leu  Val  Asp  Ile  Tyr  Glu  Lys  Tyr  Gln  Asp  Leu  Tyr  Thr  Val
55                       60                       65                       70

GAA  CCA  AAT  AAT  GCA  CGC  CAG  CTG  GTA  GAA  ATT  GCA  GCC  AGG  GAT  ATT    292
Glu  Pro  Asn  Asn  Ala  Arg  Gln  Leu  Val  Glu  Ile  Ala  Ala  Arg  Asp  Ile
                    75                  80                       85

GAG  AAA  CTT  CTG  AGC  AAC  AGA  TCT  AAA  GCC  CTG  GTG  AGC  CTG  GCA  TTG    340
Glu  Lys  Leu  Leu  Ser  Asn  Arg  Ser  Lys  Ala  Leu  Val  Ser  Leu  Ala  Leu
                    90                  95                       100

GAA  GCG  GAG  AAA  GTT  CAA  GCA  GCT  CAC  CAG  TGG  AGA  GAA  GAT  TTT  GCA    388
Glu  Ala  Glu  Lys  Val  Gln  Ala  Ala  His  Gln  Trp  Arg  Glu  Asp  Phe  Ala
               105                      110                      115

AGC  AAT  GAA  GTT  GTC  TAC  TAC  AAT  GCA  AAG  GAT  GAT  CTC  GAT  CCT  GAG    436
Ser  Asn  Glu  Val  Val  Tyr  Tyr  Asn  Ala  Lys  Asp  Asp  Leu  Asp  Pro  Glu
     120                      125                      130

AAA  AAT  GAC  AGT  GAG  CCA  GGC  AGC  CAG  AGG  ATA  AAA  CCT  GTT  TTC  ATT    484
Lys  Asn  Asp  Ser  Glu  Pro  Gly  Ser  Gln  Arg  Ile  Lys  Pro  Val  Phe  Ile
135                      140                      145                      150

GAA  GAT  GCT  AAT  TTT  GGA  CGA  CAA  ATA  TCT  TAT  CAG  CAC  GCA  GCA  GTC    532
Glu  Asp  Ala  Asn  Phe  Gly  Arg  Gln  Ile  Ser  Tyr  Gln  His  Ala  Ala  Val
                    155                      160                      165

CAT  ATT  CCT  ACT  GAC  ATC  TAT  GAG  GGC  TCA  ACA  ATT  GTG  TTA  AAT  GAA    580
His  Ile  Pro  Thr  Asp  Ile  Tyr  Glu  Gly  Ser  Thr  Ile  Val  Leu  Asn  Glu
               170                      175                      180

CTC  AAC  TGG  ACA  AGT  GCC  TTA  GAT  GAA  GTT  TTC  AAA  AAG  AAT  CGC  GAG    628
Leu  Asn  Trp  Thr  Ser  Ala  Leu  Asp  Glu  Val  Phe  Lys  Lys  Asn  Arg  Glu
               185                      190                      195

GAA  GAC  CCT  TCA  TTA  TTG  TGG  CAG  GTT  TTT  GGC  AGT  GCC  ACT  GGC  CTA    676
Glu  Asp  Pro  Ser  Leu  Leu  Trp  Gln  Val  Phe  Gly  Ser  Ala  Thr  Gly  Leu
     200                      205                      210

GCT  CGA  TAT  TAT  CCA  GCT  TCA  CCA  TGG  GTT  GAT  AAT  AGT  AGA  ACT  CCA    724
Ala  Arg  Tyr  Tyr  Pro  Ala  Ser  Pro  Trp  Val  Asp  Asn  Ser  Arg  Thr  Pro
215                      220                      225                      230

AAT  AAG  ATT  GAC  CTT  TAT  GAT  GTA  CGC  AGA  AGA  CCA  TGG  TAC  ATC  CAA    772
Asn  Lys  Ile  Asp  Leu  Tyr  Asp  Val  Arg  Arg  Arg  Pro  Trp  Tyr  Ile  Gln
                    235                      240                      245

GGA  GCT  GCA  TCT  CCT  AAA  GAC  ATG  CTT  ATT  CTG  GTG  GAT  GTG  AGT  GGA    820
Gly  Ala  Ala  Ser  Pro  Lys  Asp  Met  Leu  Ile  Leu  Val  Asp  Val  Ser  Gly
               250                      255                      260

AGT  GTT  AGT  GGA  TTG  ACA  CTT  AAA  CTG  ATC  CGA  ACA  TCT  GTC  TCC  GAA    868
Ser  Val  Ser  Gly  Leu  Thr  Leu  Lys  Leu  Ile  Arg  Thr  Ser  Val  Ser  Glu
               265                      270                      275

ATG  TTA  GAA  ACC  CTC  TCA  GAT  GAT  GAT  TTC  GTG  AAT  GTA  GCT  TCA  TTT    916
Met  Leu  Glu  Thr  Leu  Ser  Asp  Asp  Asp  Phe  Val  Asn  Val  Ala  Ser  Phe
     280                      285                      290

AAC  AGC  AAT  GCT  CAG  GAT  GTA  AGC  TGT  TTT  CAG  CAC  CTT  GTC  CAA  GCA    964
Asn  Ser  Asn  Ala  Gln  Asp  Val  Ser  Cys  Phe  Gln  His  Leu  Val  Gln  Ala
295                      300                      305                      310

AAT  GTA  AGA  AAT  AAA  AAA  GTG  TTG  AAA  GAC  GCG  GTG  AAT  AAT  ATC  ACA    1012
Asn  Val  Arg  Asn  Lys  Lys  Val  Leu  Lys  Asp  Ala  Val  Asn  Asn  Ile  Thr
                    315                      320                      325
```

```
GCC  AAA  GGA  ATT  ACA  GAT  TAT  AAG  AAG  GGC  TTT  AGT  TTT  GCT  TTT  GAA     1060
Ala  Lys  Gly  Ile  Thr  Asp  Tyr  Lys  Lys  Gly  Phe  Ser  Phe  Ala  Phe  Glu
               330                 335                      340

CAG  CTG  CTT  AAT  TAT  AAT  GTT  TCC  AGA  GCA  AAC  TGC  AAT  AAG  ATT  ATT     1108
Gln  Leu  Leu  Asn  Tyr  Asn  Val  Ser  Arg  Ala  Asn  Cys  Asn  Lys  Ile  Ile
          345                      350                      355

ATG  CTA  TTC  ACG  GAT  GGA  GGA  GAA  GAG  AGA  GCC  CAG  GAG  ATA  TTT  AAC     1156
Met  Leu  Phe  Thr  Asp  Gly  Gly  Glu  Glu  Arg  Ala  Gln  Glu  Ile  Phe  Asn
360                           365                      370

AAA  TAC  AAT  AAA  GAT  AAA  AAA  GTA  CGT  GTA  TTC  AGG  TTT  TCA  GTT  GGT     1204
Lys  Tyr  Asn  Lys  Asp  Lys  Lys  Val  Arg  Val  Phe  Arg  Phe  Ser  Val  Gly
375                      380                      385                      390

CAA  CAC  AAT  TAT  GAG  AGA  GGA  CCT  ATT  CAG  TGG  ATG  GCC  TGT  GAA  AAC     1252
Gln  His  Asn  Tyr  Glu  Arg  Gly  Pro  Ile  Gln  Trp  Met  Ala  Cys  Glu  Asn
               395                      400                      405

AAA  GGT  TAT  TAT  TAT  GAA  ATT  CCT  TCC  ATT  GGT  GCA  ATA  AGA  ATC  AAT     1300
Lys  Gly  Tyr  Tyr  Tyr  Glu  Ile  Pro  Ser  Ile  Gly  Ala  Ile  Arg  Ile  Asn
                    410                      415                      420

ACT  CAG  GAA  TAT  TTG  GAT  GTT  TTG  GGA  AGA  CCA  ATG  GTT  TTA  GCA  GGA     1348
Thr  Gln  Glu  Tyr  Leu  Asp  Val  Leu  Gly  Arg  Pro  Met  Val  Leu  Ala  Gly
               425                      430                      435

GAC  AAA  GCT  AAG  CAA  GTC  CAA  TGG  ACA  AAT  GTG  TAC  CTG  GAT  GCA  TTG     1396
Asp  Lys  Ala  Lys  Gln  Val  Gln  Trp  Thr  Asn  Val  Tyr  Leu  Asp  Ala  Leu
     440                      445                      450

GAA  CTG  GGA  CTT  GTC  ATT  ACT  GGA  ACT  CTT  CCG  GTC  TTC  AAC  ATA  ACC     1444
Glu  Leu  Gly  Leu  Val  Ile  Thr  Gly  Thr  Leu  Pro  Val  Phe  Asn  Ile  Thr
455                      460                      465                      470

GGC  CAA  TTT  GAA  AAT  AAG  ACA  AAC  TTA  AAG  AAC  CAG  CTG  ATT  CTT  GGT     1492
Gly  Gln  Phe  Glu  Asn  Lys  Thr  Asn  Leu  Lys  Asn  Gln  Leu  Ile  Leu  Gly
                    475                      480                      485

GTG  ATG  GGA  GTA  GAT  GTG  TCT  TTG  GAA  GAT  ATT  AAA  AGA  CTG  ACA  CCA     1540
Val  Met  Gly  Val  Asp  Val  Ser  Leu  Glu  Asp  Ile  Lys  Arg  Leu  Thr  Pro
               490                      495                      500

CGT  TTT  ACA  CTG  TGC  CCC  AAT  GGG  TAT  TAC  TTT  GCA  ATC  GAT  CCT  AAT     1588
Arg  Phe  Thr  Leu  Cys  Pro  Asn  Gly  Tyr  Tyr  Phe  Ala  Ile  Asp  Pro  Asn
          505                      510                      515

GGT  TAT  GTT  TTA  TTA  CAT  CCA  AAT  CTT  CAG  CCA  AAG  AAC  CCC  AAA  TCT     1636
Gly  Tyr  Val  Leu  Leu  His  Pro  Asn  Leu  Gln  Pro  Lys  Asn  Pro  Lys  Ser
     520                      525                      530

CAG  GAG  CCA  GTA  ACA  TTG  GAT  TTC  CTT  GAT  GCA  GAG  TTA  GAG  AAT  GAT     1684
Gln  Glu  Pro  Val  Thr  Leu  Asp  Phe  Leu  Asp  Ala  Glu  Leu  Glu  Asn  Asp
535                      540                      545                      550

ATT  AAA  GTG  GAG  ATT  CGA  AAT  AAG  ATG  ATT  GAT  GGG  GAA  AGT  GGA  GAA     1732
Ile  Lys  Val  Glu  Ile  Arg  Asn  Lys  Met  Ile  Asp  Gly  Glu  Ser  Gly  Glu
               555                      560                      565

AAA  ACA  TTC  AGA  ACT  CTG  GTT  AAA  TCT  CAA  GAT  GAG  AGA  TAT  ATT  GAC     1780
Lys  Thr  Phe  Arg  Thr  Leu  Val  Lys  Ser  Gln  Asp  Glu  Arg  Tyr  Ile  Asp
          570                      575                      580

AAA  GGA  AAC  AGG  ACA  TAC  ACA  TGG  ACA  CCT  GTC  AAT  GGC  ACA  GAT  TAC     1828
Lys  Gly  Asn  Arg  Thr  Tyr  Thr  Trp  Thr  Pro  Val  Asn  Gly  Thr  Asp  Tyr
     585                      590                      595

AGT  TTG  GCC  TTG  GTA  TTA  CCA  ACC  TAC  AGT  TTT  TAC  TAT  ATA  AAA  GCC     1876
Ser  Leu  Ala  Leu  Val  Leu  Pro  Thr  Tyr  Ser  Phe  Tyr  Tyr  Ile  Lys  Ala
600                      605                      610

AAA  CTA  GAA  GAG  ACA  ATA  ACT  CAG  GCC  AGA  TCA  AAA  AAG  GGC  AAA  ATG     1924
Lys  Leu  Glu  Glu  Thr  Ile  Thr  Gln  Ala  Arg  Ser  Lys  Lys  Gly  Lys  Met
615                      620                      625                      630

AAG  GAT  TCG  GAA  ACC  CTG  AAG  CCA  GAT  AAT  TTT  GAA  GAA  TCT  GGC  TAT     1972
Lys  Asp  Ser  Glu  Thr  Leu  Lys  Pro  Asp  Asn  Phe  Glu  Glu  Ser  Gly  Tyr
               635                      640                      645
```

```
ACA TTC ATA GCA CCA AGA GAT TAC TGC AAT GAC CTG AAA ATA TCG GAT      2020
Thr Phe Ile Ala Pro Arg Asp Tyr Cys Asn Asp Leu Lys Ile Ser Asp
            650                 655                 660

AAT AAC ACT GAA TTT CTT TTA AAT TTC AAC GAG TTT ATT GAT AGA AAA      2068
Asn Asn Thr Glu Phe Leu Leu Asn Phe Asn Glu Phe Ile Asp Arg Lys
        665                 670                 675

ACT CCA AAC AAC CCA TCA TGT AAC GCG GAT TTG ATT AAT AGA GTC TTG      2116
Thr Pro Asn Asn Pro Ser Cys Asn Ala Asp Leu Ile Asn Arg Val Leu
    680                 685                 690

CTT GAT GCA GGC TTT ACA AAT GAA CTT GTC CAA AAT TAC TGG AGT AAG      2164
Leu Asp Ala Gly Phe Thr Asn Glu Leu Val Gln Asn Tyr Trp Ser Lys
695                 700                 705                 710

CAG AAA AAT ATC AAG GGA GTG AAA GCA CGA TTT GTT GTG ACT GAT GGT      2212
Gln Lys Asn Ile Lys Gly Val Lys Ala Arg Phe Val Val Thr Asp Gly
                715                 720                 725

GGG ATT ACC AGA GTT TAT CCC AAA GAG GCT GGA GAA AAT TGG CAA GAA      2260
Gly Ile Thr Arg Val Tyr Pro Lys Glu Ala Gly Glu Asn Trp Gln Glu
730                 735                 740

AAC CCA GAG ACA TAT GAG GAC AGC TTC TAT AAA AGG AGC CTA GAT AAT      2308
Asn Pro Glu Thr Tyr Glu Asp Ser Phe Tyr Lys Arg Ser Leu Asp Asn
        745                 750                 755

GAT AAC TAT GTT TTC ACT GCT CCC TAC TTT AAC AAA AGT GGA CCT GGT      2356
Asp Asn Tyr Val Phe Thr Ala Pro Tyr Phe Asn Lys Ser Gly Pro Gly
760                 765                 770

GCC TAT GAA TCG GGC ATT ATG GTA AGC AAA GCT GTA GAA ATA TAT ATT      2404
Ala Tyr Glu Ser Gly Ile Met Val Ser Lys Ala Val Glu Ile Tyr Ile
775                 780                 785                 790

CAA GGG AAA CTT CTT AAA CCT GCA GTT GTT GGA ATT AAA ATT GAT GTA      2452
Gln Gly Lys Leu Leu Lys Pro Ala Val Val Gly Ile Lys Ile Asp Val
                795                 800                 805

AAT TCC TGG ATA GAG AAT TTC ACC AAA ACC TCA ATC AGA GAT CCG TGT      2500
Asn Ser Trp Ile Glu Asn Phe Thr Lys Thr Ser Ile Arg Asp Pro Cys
            810                 815                 820

GCT GGT CCA GTT TGT GAC TGC AAA AGA AAC AGT GAC GTA ATG GAT TGT      2548
Ala Gly Pro Val Cys Asp Cys Lys Arg Asn Ser Asp Val Met Asp Cys
        825                 830                 835

GTG ATT CTG GAT GAT GGT GGG TTT CTT CTG ATG GCA AAT CAT GAT GAT      2596
Val Ile Leu Asp Asp Gly Gly Phe Leu Leu Met Ala Asn His Asp Asp
    840                 845                 850

TAT ACT AAT CAG ATT GGA AGA TTT TTT GGA GAG ATT GAT CCC AGC TTG      2644
Tyr Thr Asn Gln Ile Gly Arg Phe Phe Gly Glu Ile Asp Pro Ser Leu
855                 860                 865                 870

ATG AGA CAC CTG GTT AAT ATA TCA GTT TAT GCT TTT AAC AAA TCT TAT      2692
Met Arg His Leu Val Asn Ile Ser Val Tyr Ala Phe Asn Lys Ser Tyr
                875                 880                 885

GAT TAT CAG TCA GTA TGT GAG CCC GGT GCT GCA CCA AAA CAA GGA GCA      2740
Asp Tyr Gln Ser Val Cys Glu Pro Gly Ala Ala Pro Lys Gln Gly Ala
            890                 895                 900

GGA CAT CGC TCA GCA TAT GTG CCA TCA GTA GCA GAC ATA TTA CAA ATT      2788
Gly His Arg Ser Ala Tyr Val Pro Ser Val Ala Asp Ile Leu Gln Ile
        905                 910                 915

GGC TGG TGG GCC ACT GCT GCT GCC TGG TCT ATT CTA CAG CAG TTT CTC      2836
Gly Trp Trp Ala Thr Ala Ala Ala Trp Ser Ile Leu Gln Gln Phe Leu
    920                 925                 930

TTG AGT TTG ACC TTT CCA CGA CTC CTT GAG GCA GTT GAG ATG GAG GAT      2884
Leu Ser Leu Thr Phe Pro Arg Leu Leu Glu Ala Val Glu Met Glu Asp
935                 940                 945                 950

GAT GAC TTC ACG GCC TCC CTG TCC AAG CAG AGC TGC ATT ACT GAA CAA      2932
Asp Asp Phe Thr Ala Ser Leu Ser Lys Gln Ser Cys Ile Thr Glu Gln
                955                 960                 965
```

| | | | | | | | | | | | | | | | |
|---|---|---|---|---|---|---|---|---|---|---|---|---|---|---|---|
| ACC | CAG | TAT | TTC | TTC | GAT | AAC | GAC | AGT | AAA | TCA | TTC | AGT | GGT | GTA | TTA | 2980
| Thr | Gln | Tyr | Phe | Phe | Asp | Asn | Asp | Ser | Lys | Ser | Phe | Ser | Gly | Val | Leu |
| | | | 970 | | | | | 975 | | | | | 980 | | |
| GAC | TGT | GGA | AAC | TGT | TCC | AGA | ATC | TTT | CAT | GGA | GAA | AAG | CTT | ATG | AAC | 3028
| Asp | Cys | Gly | Asn | Cys | Ser | Arg | Ile | Phe | His | Gly | Glu | Lys | Leu | Met | Asn |
| | | 985 | | | | | 990 | | | | | 995 | | | |
| ACC | AAC | TTA | ATA | TTC | ATA | ATG | GTT | GAG | AGC | AAA | GGG | ACA | TGT | CCA | TGT | 3076
| Thr | Asn | Leu | Ile | Phe | Ile | Met | Val | Glu | Ser | Lys | Gly | Thr | Cys | Pro | Cys |
| | 1000 | | | | | 1005 | | | | | 1010 | | | | |
| GAC | ACA | CGA | CTG | CTC | ATA | CAA | GCG | GAG | CAG | ACT | TCT | GAC | GGT | CCA | AAT | 3124
| Asp | Thr | Arg | Leu | Leu | Ile | Gln | Ala | Glu | Gln | Thr | Ser | Asp | Gly | Pro | Asn |
| 1015 | | | | | 1020 | | | | | 1025 | | | | | 1030 |
| CCT | TGT | GAC | ATG | GTT | AAG | CAA | CCT | AGA | TAC | CGA | AAA | GGG | CCT | GAT | GTC | 3172
| Pro | Cys | Asp | Met | Val | Lys | Gln | Pro | Arg | Tyr | Arg | Lys | Gly | Pro | Asp | Val |
| | | | | 1035 | | | | | 1040 | | | | | 1045 | |
| TGC | TTT | GAT | AAC | AAT | GTC | TTG | GAG | GAT | TAT | ACT | GAC | TGT | GGT | GGT | GTT | 3220
| Cys | Phe | Asp | Asn | Asn | Val | Leu | Glu | Asp | Tyr | Thr | Asp | Cys | Gly | Gly | Val |
| | | | | 1050 | | | | | 1055 | | | | | 1060 | |
| TCT | GGA | TTA | AAT | CCC | TCC | CTG | TGG | TAT | ATC | ATT | GGA | ATC | CAG | TTT | CTA | 3268
| Ser | Gly | Leu | Asn | Pro | Ser | Leu | Trp | Tyr | Ile | Ile | Gly | Ile | Gln | Phe | Leu |
| | | 1065 | | | | | 1070 | | | | | 1075 | | | |
| CTA | CTT | TGG | CTG | GTA | TCT | GGC | AGC | ACA | CAC | CGG | CTG | TTA | TGACCTTCTA | | | 3317
| Leu | Leu | Trp | Leu | Val | Ser | Gly | Ser | Thr | His | Arg | Leu | Leu | | | |
| | 1080 | | | | | 1085 | | | | | 1090 | | | | |

| | | | | |
|---|---|---|---|---|
| AAAACCAAAT | CTGCATAGTT | AAACTCCAGA | CCCTGCCAAA | ACATGAGCCC | TGCCCTCAAT | 3377
| TACAGTAACG | TAGGGTCAGC | TATAAAATCA | GACAAACATT | AGCTGGGCCT | GTTCCATGGC | 3437
| ATAACACTAA | GGCGCAGACT | CCTAAGGCAC | CCACTGGCTG | CATGTCAGGG | TGTCAGATCC | 3497
| TTAAACGTGT | GTGAATGCTG | CATCATCTAT | GTGTAACATC | AAAGCAAAAT | CCTATACGTG | 3557
| TCCTCTATTG | GAAAATTTGG | GCGTTTGTTG | TTGCATTGTT | GGT | | 3600

( 2 ) INFORMATION FOR SEQ ID NO:12:

( i ) SEQUENCE CHARACTERISTICS:
        ( A ) LENGTH: 323 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| CCCCCTGCCA | GTGGCCAAAC | AGAAGCAGAA | GTCGGGTAAT | GAAATGACTA | ACTTAGCCTT | 60
| TGAACTAGAC | CCCCTAGAGT | TAGAGGAGGA | AGAGGCTGAG | CTTGGTGAGC | AGAGTGGCTC | 120
| TGCCAAGACT | AGTGTTAGCA | GTGTCACCAC | CCCGCCACCC | CATGGCAAAC | GCATCCCCTT | 180
| CTTTAAGAAG | ACAGAGCATG | TGCCCCCCTA | TGACGTGGTG | CCTTCCATGA | GGCCCATCAT | 240
| CCTGGTGGGA | CCGTCGCTCA | AGGGCTACGA | GGTTACAGAC | ATGATGCAGA | AAGCTTTATT | 300
| TGACTTCTTG | AAGCATCGGT | TTG | | | | 323

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

CCTATTGGTG TAGGTATACC AACAATTAAT TTAAGAAAAA GGAGACCCAA TATCCAG          57

(2) INFORMATION FOR SEQ ID NO:14:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..132

(xi) SEQUENCE DESCRIPTION: SEQ ID NO:14:

```
TGG  TCC  TTT  GCC  TGC  GCC  TGT  GCC  GCC  TTC  ATC  CTC  CTC  TTT  CTC  GGC      48
Trp  Ser  Phe  Ala  Cys  Ala  Cys  Ala  Ala  Phe  Ile  Leu  Leu  Phe  Leu  Gly
 1              5                        10                       15

GGT  CTC  GCC  CTC  CTG  CTG  TTC  TCC  CTG  CCT  CGA  ATG  CCC  CGG  AAC  CCA      96
Gly  Leu  Ala  Leu  Leu  Leu  Phe  Ser  Leu  Pro  Arg  Met  Pro  Arg  Asn  Pro
               20                        25                       30

TGG  GAG  TCC  TGC  ATG  GAT  GCT  GAG  CCC  GAG  CAC  TAACCCTCCT  GCGGCCCTAG      149
Trp  Glu  Ser  Cys  Met  Asp  Ala  Glu  Pro  Glu  His
               35                        40
```

CGACCCTCAG GCTTCTTCCC AGGAAGCGGG G          180

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:15:

AATTCGGTAC GTACACTCGA GC          22

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:16:

GCTCGAGTGT ACGTACCG          18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:17:

CCATGGTACC TTCGTTGACG          20

( 2 ) INFORMATION FOR SEQ ID NO:18:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Oligonucleotide ( x i ) SEQUENCE DESCRIPTION: SEQ ID NO:18:

| | | |
|---|---|---|
| AATTCGTCAA CGAAGGTACC ATGG | | 24 |

( 2 ) INFORMATION FOR SEQ ID NO:19:

( i ) SEQUENCE CHARACTERISTICS:
    ( A ) LENGTH: 249 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:19:

| | |
|---|---|
| CGGTACGTAC ACTCGAGCGA CTGTGTCATG ATGTTTATTA GTGATGACAG TGAGGTGAGG | 60 |
| CAGGGGCTTG TGGAGCATGC TCTGTAGGTC ACACACTAGA GCCATAAGGC AAGAGTAGGC | 120 |
| GGGGAGACAG GTCCTCTGTG CCCTGTCTCT CCCCATCTAA CCCTAACCTA ACAAGCGGTA | 180 |
| GTTATGAGTC AGGGAACAAC GTCTGGAGCC CCGTCCTCCA AAGATGTTTG AGGGACAAGA | 240 |
| ACAGAAATG | 249 |

( 2 ) INFORMATION FOR SEQ ID NO:20:

( i ) SEQUENCE CHARACTERISTICS:
    ( A ) LENGTH: 402 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:20:

| | |
|---|---|
| CCACCTAGCA CGGGTTCGTT CCCCTCTCCC GGCCTGGCCC GGGCTCCCCG GTGGCCGCCG | 60 |
| CCCCCTCGCC GCCCATCTCT GGACTCAGAC GTCTCCCTGG AGGAGGACCG GGAGAGTGCC | 120 |
| CGGCGTGAAG TAGAGAGCCA GGCTCAGCAG CAGCTCGAAA GGGCCAAGCA CAAACCTGTG | 180 |
| GCATTTGCGG TGAGGACCAA TGTCAGCTAC TGTGGCGTAC TGGATGAGGA GTGCCCAGTC | 240 |
| CAGGGCTCTG GAGTCAACTT TGAGGCCAAA GATTTTCTGC ACATTAAAGA GAAGTACAGC | 300 |
| AATGACTGGT GGATCGGGCG GCTAGTGAAA GAGGGCGGGG ACATCGCCTT CATCCCCAGC | 360 |
| CCCCAGTGCC TGGTGAGCAT CCGCTCAAAC AGGAGCAGAA GG | 402 |

( 2 ) INFORMATION FOR SEQ ID NO:21:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Oligonucleotide ( x i ) SEQUENCE DESCRIPTION: SEQ ID NO:21:

CTCAGTACCA TCTCTGATAC CAGCCCCA 28

( 2 ) INFORMATION FOR SEQ ID NO:22:

( i ) SEQUENCE CHARACTERISTICS:
        ( A ) LENGTH: 3636 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 35..3346
        ( D ) OTHER INFORMATION: /standard_name="Alpha-2a"

( i x ) FEATURE:
        ( A ) NAME/KEY: 5'UTR
        ( B ) LOCATION: 1..34

( i x ) FEATURE:
        ( A ) NAME/KEY: 3'UTR
        ( B ) LOCATION: 3347..3636

( x i ) SEQUENCE DESCRIPTION: SEQ ID NO:22:

```
GCGGGGGAGG GGGCATTGAT CTTCGATCGC GAAG ATG GCT GCT GGC TGC CTG      52
                                     Met Ala Ala Gly Cys Leu
                                      1               5

CTG GCC TTG ACT CTG ACA CTT TTC CAA TCT TTG CTC ATC GGC CCC TCG   100
Leu Ala Leu Thr Leu Thr Leu Phe Gln Ser Leu Leu Ile Gly Pro Ser
             10              15                  20

TCG GAG GAG CCG TTC CCT TCG GCC GTC ACT ATC AAA TCA TGG GTG GAT   148
Ser Glu Glu Pro Phe Pro Ser Ala Val Thr Ile Lys Ser Trp Val Asp
         25              30              35

AAG ATG CAA GAA GAC CTT GTC ACA CTG GCA AAA ACA GCA AGT GGA GTC   196
Lys Met Gln Glu Asp Leu Val Thr Leu Ala Lys Thr Ala Ser Gly Val
     40              45              50

AAT CAG CTT GTT GAT ATT TAT GAG AAA TAT CAA GAT TTG TAT ACT GTG   244
Asn Gln Leu Val Asp Ile Tyr Glu Lys Tyr Gln Asp Leu Tyr Thr Val
 55              60              65                  70

GAA CCA AAT AAT GCA CGC CAG CTG GTA GAA ATT GCA GCC AGG GAT ATT   292
Glu Pro Asn Asn Ala Arg Gln Leu Val Glu Ile Ala Ala Arg Asp Ile
                 75              80                  85

GAG AAA CTT CTG AGC AAC AGA TCT AAA GCC CTG GTG AGC CTG GCA TTG   340
Glu Lys Leu Leu Ser Asn Arg Ser Lys Ala Leu Val Ser Leu Ala Leu
             90              95              100

GAA GCG GAG AAA GTT CAA GCA GCT CAC CAG TGG AGA GAA GAT TTT GCA   388
Glu Ala Glu Lys Val Gln Ala Ala His Gln Trp Arg Glu Asp Phe Ala
         105             110             115

AGC AAT GAA GTT GTC TAC TAC AAT GCA AAG GAT GAT CTC GAT CCT GAG   436
Ser Asn Glu Val Val Tyr Tyr Asn Ala Lys Asp Asp Leu Asp Pro Glu
     120             125             130

AAA AAT GAC AGT GAG CCA GGC AGC CAG AGG ATA AAA CCT GTT TTC ATT   484
Lys Asn Asp Ser Glu Pro Gly Ser Gln Arg Ile Lys Pro Val Phe Ile
135             140             145             150

GAA GAT GCT AAT TTT GGA CGA CAA ATA TCT TAT CAG CAC GCA GCA GTC   532
Glu Asp Ala Asn Phe Gly Arg Gln Ile Ser Tyr Gln His Ala Ala Val
                 155             160             165

CAT ATT CCT ACT GAC ATC TAT GAG GGC TCA ACA ATT GTG TTA AAT GAA   580
His Ile Pro Thr Asp Ile Tyr Glu Gly Ser Thr Ile Val Leu Asn Glu
             170             175             180

CTC AAC TGG ACA AGT GCC TTA GAT GAA GTT TTC AAA AAG AAT CGC GAG   628
Leu Asn Trp Thr Ser Ala Leu Asp Glu Val Phe Lys Lys Asn Arg Glu
         185             190             195
```

```
GAA  GAC  CCT  TCA  TTA  TTG  TGG  CAG  GTT  TTT  GGC  AGT  GCC  ACT  GGC  CTA      676
Glu  Asp  Pro  Ser  Leu  Leu  Trp  Gln  Val  Phe  Gly  Ser  Ala  Thr  Gly  Leu
     200                 205                      210

GCT  CGA  TAT  TAT  CCA  GCT  TCA  CCA  TGG  GTT  GAT  AAT  AGT  AGA  ACT  CCA      724
Ala  Arg  Tyr  Tyr  Pro  Ala  Ser  Pro  Trp  Val  Asp  Asn  Ser  Arg  Thr  Pro
215                      220                      225                      230

AAT  AAG  ATT  GAC  CTT  TAT  GAT  GTA  CGC  AGA  AGA  CCA  TGG  TAC  ATC  CAA      772
Asn  Lys  Ile  Asp  Leu  Tyr  Asp  Val  Arg  Arg  Arg  Pro  Trp  Tyr  Ile  Gln
                    235                      240                      245

GGA  GCT  GCA  TCT  CCT  AAA  GAC  ATG  CTT  ATT  CTG  GTG  GAT  GTG  AGT  GGA      820
Gly  Ala  Ala  Ser  Pro  Lys  Asp  Met  Leu  Ile  Leu  Val  Asp  Val  Ser  Gly
               250                      255                      260

AGT  GTT  AGT  GGA  TTG  ACA  CTT  AAA  CTG  ATC  CGA  ACA  TCT  GTC  TCC  GAA      868
Ser  Val  Ser  Gly  Leu  Thr  Leu  Lys  Leu  Ile  Arg  Thr  Ser  Val  Ser  Glu
          265                      270                      275

ATG  TTA  GAA  ACC  CTC  TCA  GAT  GAT  GAT  TTC  GTG  AAT  GTA  GCT  TCA  TTT      916
Met  Leu  Glu  Thr  Leu  Ser  Asp  Asp  Asp  Phe  Val  Asn  Val  Ala  Ser  Phe
     280                      285                      290

AAC  AGC  AAT  GCT  CAG  GAT  GTA  AGC  TGT  TTT  CAG  CAC  CTT  GTC  CAA  GCA      964
Asn  Ser  Asn  Ala  Gln  Asp  Val  Ser  Cys  Phe  Gln  His  Leu  Val  Gln  Ala
295                      300                      305                      310

AAT  GTA  AGA  AAT  AAA  AAA  GTG  TTG  AAA  GAC  GCG  GTG  AAT  AAT  ATC  ACA     1012
Asn  Val  Arg  Asn  Lys  Lys  Val  Leu  Lys  Asp  Ala  Val  Asn  Asn  Ile  Thr
                    315                      320                      325

GCC  AAA  GGA  ATT  ACA  GAT  TAT  AAG  AAG  GGC  TTT  AGT  TTT  GCT  TTT  GAA     1060
Ala  Lys  Gly  Ile  Thr  Asp  Tyr  Lys  Lys  Gly  Phe  Ser  Phe  Ala  Phe  Glu
               330                      335                      340

CAG  CTG  CTT  AAT  TAT  AAT  GTT  TCC  AGA  GCA  AAC  TGC  AAT  AAG  ATT  ATT     1108
Gln  Leu  Leu  Asn  Tyr  Asn  Val  Ser  Arg  Ala  Asn  Cys  Asn  Lys  Ile  Ile
          345                      350                      355

ATG  CTA  TTC  ACG  GAT  GGA  GGA  GAA  GAG  AGA  GCC  CAG  GAG  ATA  TTT  AAC     1156
Met  Leu  Phe  Thr  Asp  Gly  Gly  Glu  Glu  Arg  Ala  Gln  Glu  Ile  Phe  Asn
     360                      365                      370

AAA  TAC  AAT  AAA  GAT  AAA  AAA  GTA  CGT  GTA  TTC  AGG  TTT  TCA  GTT  GGT     1204
Lys  Tyr  Asn  Lys  Asp  Lys  Lys  Val  Arg  Val  Phe  Arg  Phe  Ser  Val  Gly
375                      380                      385                      390

CAA  CAC  AAT  TAT  GAG  AGA  GGA  CCT  ATT  CAG  TGG  ATG  GCC  TGT  GAA  AAC     1252
Gln  His  Asn  Tyr  Glu  Arg  Gly  Pro  Ile  Gln  Trp  Met  Ala  Cys  Glu  Asn
                    395                      400                      405

AAA  GGT  TAT  TAT  TAT  GAA  ATT  CCT  TCC  ATT  GGT  GCA  ATA  AGA  ATC  AAT     1300
Lys  Gly  Tyr  Tyr  Tyr  Glu  Ile  Pro  Ser  Ile  Gly  Ala  Ile  Arg  Ile  Asn
               410                      415                      420

ACT  CAG  GAA  TAT  TTG  GAT  GTT  TTG  GGA  AGA  CCA  ATG  GTT  TTA  GCA  GGA     1348
Thr  Gln  Glu  Tyr  Leu  Asp  Val  Leu  Gly  Arg  Pro  Met  Val  Leu  Ala  Gly
     425                      430                      435

GAC  AAA  GCT  AAG  CAA  GTC  CAA  TGG  ACA  AAT  GTG  TAC  CTG  GAT  GCA  TTG     1396
Asp  Lys  Ala  Lys  Gln  Val  Gln  Trp  Thr  Asn  Val  Tyr  Leu  Asp  Ala  Leu
440                      445                      450

GAA  CTG  GGA  CTT  GTC  ATT  ACT  GGA  ACT  CTT  CCG  GTC  TTC  AAC  ATA  ACC     1444
Glu  Leu  Gly  Leu  Val  Ile  Thr  Gly  Thr  Leu  Pro  Val  Phe  Asn  Ile  Thr
455                      460                      465                      470

GGC  CAA  TTT  GAA  AAT  AAG  ACA  AAC  TTA  AAG  AAC  CAG  CTG  ATT  CTT  GGT     1492
Gly  Gln  Phe  Glu  Asn  Lys  Thr  Asn  Leu  Lys  Asn  Gln  Leu  Ile  Leu  Gly
                    475                      480                      485

GTG  ATG  GGA  GTA  GAT  GTG  TCT  TTG  GAA  GAT  ATT  AAA  AGA  CTG  ACA  CCA     1540
Val  Met  Gly  Val  Asp  Val  Ser  Leu  Glu  Asp  Ile  Lys  Arg  Leu  Thr  Pro
               490                      495                      500

CGT  TTT  ACA  CTG  TGC  CCC  AAT  GGG  TAT  TAC  TTT  GCA  ATC  GAT  CCT  AAT     1588
Arg  Phe  Thr  Leu  Cys  Pro  Asn  Gly  Tyr  Tyr  Phe  Ala  Ile  Asp  Pro  Asn
     505                      510                      515
```

| | | | | | | | | | | | | | | | | |
|---|---|---|---|---|---|---|---|---|---|---|---|---|---|---|---|---|
| GGT | TAT | GTT | TTA | TTA | CAT | CCA | AAT | CTT | CAG | CCA | AAG | CCT | ATT | GGT | GTA | 1636 |
| Gly | Tyr | Val | Leu | Leu | His | Pro | Asn | Leu | Gln | Pro | Lys | Pro | Ile | Gly | Val | |
| | 520 | | | | 525 | | | | | 530 | | | | | | |
| GGT | ATA | CCA | ACA | ATT | AAT | TTA | AGA | AAA | AGG | AGA | CCC | AAT | ATC | CAG | AAC | 1684 |
| Gly | Ile | Pro | Thr | Ile | Asn | Leu | Arg | Lys | Arg | Arg | Pro | Asn | Ile | Gln | Asn | |
| 535 | | | | | 540 | | | | | 545 | | | | | 550 | |
| CCC | AAA | TCT | CAG | GAG | CCA | GTA | ACA | TTG | GAT | TTC | CTT | GAT | GCA | GAG | TTA | 1732 |
| Pro | Lys | Ser | Gln | Glu | Pro | Val | Thr | Leu | Asp | Phe | Leu | Asp | Ala | Glu | Leu | |
| | | | 555 | | | | | 560 | | | | | 565 | | | |
| GAG | AAT | GAT | ATT | AAA | GTG | GAG | ATT | CGA | AAT | AAG | ATG | ATT | GAT | GGG | GAA | 1780 |
| Glu | Asn | Asp | Ile | Lys | Val | Glu | Ile | Arg | Asn | Lys | Met | Ile | Asp | Gly | Glu | |
| | | | 570 | | | | 575 | | | | | 580 | | | | |
| AGT | GGA | GAA | AAA | ACA | TTC | AGA | ACT | CTG | GTT | AAA | TCT | CAA | GAT | GAG | AGA | 1828 |
| Ser | Gly | Glu | Lys | Thr | Phe | Arg | Thr | Leu | Val | Lys | Ser | Gln | Asp | Glu | Arg | |
| | | 585 | | | | | 590 | | | | | 595 | | | | |
| TAT | ATT | GAC | AAA | GGA | AAC | AGG | ACA | TAC | ACA | TGG | ACA | CCT | GTC | AAT | GGC | 1876 |
| Tyr | Ile | Asp | Lys | Gly | Asn | Arg | Thr | Tyr | Thr | Trp | Thr | Pro | Val | Asn | Gly | |
| | 600 | | | | 605 | | | | | 610 | | | | | | |
| ACA | GAT | TAC | AGT | TTG | GCC | TTG | GTA | TTA | CCA | ACC | TAC | AGT | TTT | TAC | TAT | 1924 |
| Thr | Asp | Tyr | Ser | Leu | Ala | Leu | Val | Leu | Pro | Thr | Tyr | Ser | Phe | Tyr | Tyr | |
| 615 | | | | | 620 | | | | | 625 | | | | | 630 | |
| ATA | AAA | GCC | AAA | CTA | GAA | GAG | ACA | ATA | ACT | CAG | GCC | AGA | TAT | TCG | GAA | 1972 |
| Ile | Lys | Ala | Lys | Leu | Glu | Glu | Thr | Ile | Thr | Gln | Ala | Arg | Tyr | Ser | Glu | |
| | | | | 635 | | | | | 640 | | | | | 645 | | |
| ACC | CTG | AAG | CCA | GAT | AAT | TTT | GAA | GAA | TCT | GGC | TAT | ACA | TTC | ATA | GCA | 2020 |
| Thr | Leu | Lys | Pro | Asp | Asn | Phe | Glu | Glu | Ser | Gly | Tyr | Thr | Phe | Ile | Ala | |
| | | | 650 | | | | | 655 | | | | | 660 | | | |
| CCA | AGA | GAT | TAC | TGC | AAT | GAC | CTG | AAA | ATA | TCG | GAT | AAT | AAC | ACT | GAA | 2068 |
| Pro | Arg | Asp | Tyr | Cys | Asn | Asp | Leu | Lys | Ile | Ser | Asp | Asn | Asn | Thr | Glu | |
| | | 665 | | | | | 670 | | | | | 675 | | | | |
| TTT | CTT | TTA | AAT | TTC | AAC | GAG | TTT | ATT | GAT | AGA | AAA | ACT | CCA | AAC | AAC | 2116 |
| Phe | Leu | Leu | Asn | Phe | Asn | Glu | Phe | Ile | Asp | Arg | Lys | Thr | Pro | Asn | Asn | |
| | 680 | | | | | 685 | | | | | 690 | | | | | |
| CCA | TCA | TGT | AAC | GCG | GAT | TTG | ATT | AAT | AGA | GTC | TTG | CTT | GAT | GCA | GGC | 2164 |
| Pro | Ser | Cys | Asn | Ala | Asp | Leu | Ile | Asn | Arg | Val | Leu | Leu | Asp | Ala | Gly | |
| 695 | | | | | 700 | | | | | 705 | | | | | 710 | |
| TTT | ACA | AAT | GAA | CTT | GTC | CAA | AAT | TAC | TGG | AGT | AAG | CAG | AAA | AAT | ATC | 2212 |
| Phe | Thr | Asn | Glu | Leu | Val | Gln | Asn | Tyr | Trp | Ser | Lys | Gln | Lys | Asn | Ile | |
| | | | | 715 | | | | | 720 | | | | | 725 | | |
| AAG | GGA | GTG | AAA | GCA | CGA | TTT | GTT | GTG | ACT | GAT | GGT | GGG | ATT | ACC | AGA | 2260 |
| Lys | Gly | Val | Lys | Ala | Arg | Phe | Val | Val | Thr | Asp | Gly | Gly | Ile | Thr | Arg | |
| | | | 730 | | | | | 735 | | | | | 740 | | | |
| GTT | TAT | CCC | AAA | GAG | GCT | GGA | GAA | AAT | TGG | CAA | GAA | AAC | CCA | GAG | ACA | 2308 |
| Val | Tyr | Pro | Lys | Glu | Ala | Gly | Glu | Asn | Trp | Gln | Glu | Asn | Pro | Glu | Thr | |
| | | 745 | | | | | 750 | | | | | 755 | | | | |
| TAT | GAG | GAC | AGC | TTC | TAT | AAA | AGG | AGC | CTA | GAT | AAT | GAT | AAC | TAT | GTT | 2356 |
| Tyr | Glu | Asp | Ser | Phe | Tyr | Lys | Arg | Ser | Leu | Asp | Asn | Asp | Asn | Tyr | Val | |
| | 760 | | | | | 765 | | | | | 770 | | | | | |
| TTC | ACT | GCT | CCC | TAC | TTT | AAC | AAA | AGT | GGA | CCT | GGT | GCC | TAT | GAA | TCG | 2404 |
| Phe | Thr | Ala | Pro | Tyr | Phe | Asn | Lys | Ser | Gly | Pro | Gly | Ala | Tyr | Glu | Ser | |
| 775 | | | | | 780 | | | | | 785 | | | | | 790 | |
| GGC | ATT | ATG | GTA | AGC | AAA | GCT | GTA | GAA | ATA | TAT | ATT | CAA | GGG | AAA | CTT | 2452 |
| Gly | Ile | Met | Val | Ser | Lys | Ala | Val | Glu | Ile | Tyr | Ile | Gln | Gly | Lys | Leu | |
| | | | | 795 | | | | | 800 | | | | | 805 | | |
| CTT | AAA | CCT | GCA | GTT | GTT | GGA | ATT | AAA | ATT | GAT | GTA | AAT | TCC | TGG | ATA | 2500 |
| Leu | Lys | Pro | Ala | Val | Val | Gly | Ile | Lys | Ile | Asp | Val | Asn | Ser | Trp | Ile | |
| | | | 810 | | | | | 815 | | | | | 820 | | | |
| GAG | AAT | TTC | ACC | AAA | ACC | TCA | ATC | AGA | GAT | CCG | TGT | GCT | GGT | CCA | GTT | 2548 |
| Glu | Asn | Phe | Thr | Lys | Thr | Ser | Ile | Arg | Asp | Pro | Cys | Ala | Gly | Pro | Val | |
| | | 825 | | | | | 830 | | | | | 835 | | | | |

| | | | | | | | | | | | | | | | | |
|---|---|---|---|---|---|---|---|---|---|---|---|---|---|---|---|---|
| TGT | GAC | TGC | AAA | AGA | AAC | AGT | GAC | GTA | ATG | GAT | TGT | GTG | ATT | CTG | GAT | 2596 |
| Cys | Asp | Cys | Lys | Arg | Asn | Ser | Asp | Val | Met | Asp | Cys | Val | Ile | Leu | Asp | |
| 840 | | | | | 845 | | | | | 850 | | | | | | |
| GAT | GGT | GGG | TTT | CTT | CTG | ATG | GCA | AAT | CAT | GAT | GAT | TAT | ACT | AAT | CAG | 2644 |
| Asp | Gly | Gly | Phe | Leu | Leu | Met | Ala | Asn | His | Asp | Asp | Tyr | Thr | Asn | Gln | |
| 855 | | | | | 860 | | | | | 865 | | | | | 870 | |
| ATT | GGA | AGA | TTT | TTT | GGA | GAG | ATT | GAT | CCC | AGC | TTG | ATG | AGA | CAC | CTG | 2692 |
| Ile | Gly | Arg | Phe | Phe | Gly | Glu | Ile | Asp | Pro | Ser | Leu | Met | Arg | His | Leu | |
| | | | | 875 | | | | | 880 | | | | | 885 | | |
| GTT | AAT | ATA | TCA | GTT | TAT | GCT | TTT | AAC | AAA | TCT | TAT | GAT | TAT | CAG | TCA | 2740 |
| Val | Asn | Ile | Ser | Val | Tyr | Ala | Phe | Asn | Lys | Ser | Tyr | Asp | Tyr | Gln | Ser | |
| | | | 890 | | | | | 895 | | | | | 900 | | | |
| GTA | TGT | GAG | CCC | GGT | GCT | GCA | CCA | AAA | CAA | GGA | GCA | GGA | CAT | CGC | TCA | 2788 |
| Val | Cys | Glu | Pro | Gly | Ala | Ala | Pro | Lys | Gln | Gly | Ala | Gly | His | Arg | Ser | |
| | | 905 | | | | | 910 | | | | | 915 | | | | |
| GCA | TAT | GTG | CCA | TCA | GTA | GCA | GAC | ATA | TTA | CAA | ATT | GGC | TGG | TGG | GCC | 2836 |
| Ala | Tyr | Val | Pro | Ser | Val | Ala | Asp | Ile | Leu | Gln | Ile | Gly | Trp | Trp | Ala | |
| 920 | | | | | 925 | | | | | 930 | | | | | | |
| ACT | GCT | GCT | GCC | TGG | TCT | ATT | CTA | CAG | CAG | TTT | CTC | TTG | AGT | TTG | ACC | 2884 |
| Thr | Ala | Ala | Ala | Trp | Ser | Ile | Leu | Gln | Gln | Phe | Leu | Leu | Ser | Leu | Thr | |
| 935 | | | | | 940 | | | | | 945 | | | | | 950 | |
| TTT | CCA | CGA | CTC | CTT | GAG | GCA | GTT | GAG | ATG | GAG | GAT | GAT | GAC | TTC | ACG | 2932 |
| Phe | Pro | Arg | Leu | Leu | Glu | Ala | Val | Glu | Met | Glu | Asp | Asp | Asp | Phe | Thr | |
| | | | | 955 | | | | | 960 | | | | | 965 | | |
| GCC | TCC | CTG | TCC | AAG | CAG | AGC | TGC | ATT | ACT | GAA | CAA | ACC | CAG | TAT | TTC | 2980 |
| Ala | Ser | Leu | Ser | Lys | Gln | Ser | Cys | Ile | Thr | Glu | Gln | Thr | Gln | Tyr | Phe | |
| | | | 970 | | | | | 975 | | | | | 980 | | | |
| TTC | GAT | AAC | GAC | AGT | AAA | TCA | TTC | AGT | GGT | GTA | TTA | GAC | TGT | GGA | AAC | 3028 |
| Phe | Asp | Asn | Asp | Ser | Lys | Ser | Phe | Ser | Gly | Val | Leu | Asp | Cys | Gly | Asn | |
| | | 985 | | | | | 990 | | | | | 995 | | | | |
| TGT | TCC | AGA | ATC | TTT | CAT | GGA | GAA | AAG | CTT | ATG | AAC | ACC | AAC | TTA | ATA | 3076 |
| Cys | Ser | Arg | Ile | Phe | His | Gly | Glu | Lys | Leu | Met | Asn | Thr | Asn | Leu | Ile | |
| 1000 | | | | | 1005 | | | | | 1010 | | | | | | |
| TTC | ATA | ATG | GTT | GAG | AGC | AAA | GGG | ACA | TGT | CCA | TGT | GAC | ACA | CGA | CTG | 3124 |
| Phe | Ile | Met | Val | Glu | Ser | Lys | Gly | Thr | Cys | Pro | Cys | Asp | Thr | Arg | Leu | |
| 1015 | | | | | 1020 | | | | | 1025 | | | | | 1030 | |
| CTC | ATA | CAA | GCG | GAG | CAG | ACT | TCT | GAC | GGT | CCA | AAT | CCT | TGT | GAC | ATG | 3172 |
| Leu | Ile | Gln | Ala | Glu | Gln | Thr | Ser | Asp | Gly | Pro | Asn | Pro | Cys | Asp | Met | |
| | | | | 1035 | | | | | 1040 | | | | | 1045 | | |
| GTT | AAG | CAA | CCT | AGA | TAC | CGA | AAA | GGG | CCT | GAT | GTC | TGC | TTT | GAT | AAC | 3220 |
| Val | Lys | Gln | Pro | Arg | Tyr | Arg | Lys | Gly | Pro | Asp | Val | Cys | Phe | Asp | Asn | |
| | | | 1050 | | | | | 1055 | | | | | 1060 | | | |
| AAT | GTC | TTG | GAG | GAT | TAT | ACT | GAC | TGT | GGT | GGT | GTT | TCT | GGA | TTA | AAT | 3268 |
| Asn | Val | Leu | Glu | Asp | Tyr | Thr | Asp | Cys | Gly | Gly | Val | Ser | Gly | Leu | Asn | |
| | | 1065 | | | | | 1070 | | | | | 1075 | | | | |
| CCC | TCC | CTG | TGG | TAT | ATC | ATT | GGA | ATC | CAG | TTT | CTA | CTA | CTT | TGG | CTG | 3316 |
| Pro | Ser | Leu | Trp | Tyr | Ile | Ile | Gly | Ile | Gln | Phe | Leu | Leu | Leu | Trp | Leu | |
| | | 1080 | | | | | 1085 | | | | | 1090 | | | | |
| GTA | TCT | GGC | AGC | ACA | CAC | CGG | CTG | TTA | TGACCTTCTA | | AAAACCAAAT | | | | | 3363 |
| Val | Ser | Gly | Ser | Thr | His | Arg | Leu | Leu | | | | | | | | |
| 1095 | | | | | 1100 | | | | | | | | | | | |

| | |
|---|---|
| CTGCATAGTT AAACTCCAGA CCCTGCCAAA ACATGAGCCC TGCCCTCAAT TACAGTAACG | 3423 |
| TAGGGTCAGC TATAAAATCA GACAAACATT AGCTGGGCCT GTTCCATGGC ATAACACTAA | 3483 |
| GGCGCAGACT CCTAAGGCAC CCACTGGCTG CATGTCAGGG TGTCAGATCC TTAAACGTGT | 3543 |
| GTGAATGCTG CATCATCTAT GTGTAACATC AAAGCAAAAT CCTATACGTG TCCTCTATTG | 3603 |
| GAAAATTTGG GCGTTTGTTG TTGCATTGTT GGT | 3636 |

( 2 ) INFORMATION FOR SEQ ID NO:23:

( i ) SEQUENCE CHARACTERISTICS:
        ( A ) LENGTH: 3585 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 35..3295
        ( D ) OTHER INFORMATION: /standard_name="Alpha-2c"

( i x ) FEATURE:
        ( A ) NAME/KEY: 5'UTR
        ( B ) LOCATION: 1..34

( i x ) FEATURE:
        ( A ) NAME/KEY: 3'UTR
        ( B ) LOCATION: 3296..3585

( x i ) SEQUENCE DESCRIPTION: SEQ ID NO:23:

```
GCGGGGAGG  GGGCATTGAT  CTTCGATCGC  GAAG ATG GCT GCT GGC TGC CTG           52
                                        Met Ala Ala Gly Cys Leu
                                         1               5

CTG GCC TTG ACT CTG ACA CTT TTC CAA TCT TTG CTC ATC GGC CCC TCG          100
Leu Ala Leu Thr Leu Thr Leu Phe Gln Ser Leu Leu Ile Gly Pro Ser
            10              15                      20

TCG GAG GAG CCG TTC CCT TCG GCC GTC ACT ATC AAA TCA TGG GTG GAT          148
Ser Glu Glu Pro Phe Pro Ser Ala Val Thr Ile Lys Ser Trp Val Asp
        25              30                      35

AAG ATG CAA GAA GAC CTT GTC ACA CTG GCA AAA ACA GCA AGT GGA GTC          196
Lys Met Gln Glu Asp Leu Val Thr Leu Ala Lys Thr Ala Ser Gly Val
    40              45                      50

AAT CAG CTT GTT GAT ATT TAT GAG AAA TAT CAA GAT TTG TAT ACT GTG          244
Asn Gln Leu Val Asp Ile Tyr Glu Lys Tyr Gln Asp Leu Tyr Thr Val
55              60                      65                      70

GAA CCA AAT AAT GCA CGC CAG CTG GTA GAA ATT GCA GCC AGG GAT ATT          292
Glu Pro Asn Asn Ala Arg Gln Leu Val Glu Ile Ala Ala Arg Asp Ile
                    75                      80                      85

GAG AAA CTT CTG AGC AAC AGA TCT AAA GCC CTG GTG AGC CTG GCA TTG          340
Glu Lys Leu Leu Ser Asn Arg Ser Lys Ala Leu Val Ser Leu Ala Leu
            90                      95                     100

GAA GCG GAG AAA GTT CAA GCA GCT CAC CAG TGG AGA GAA GAT TTT GCA          388
Glu Ala Glu Lys Val Gln Ala Ala His Gln Trp Arg Glu Asp Phe Ala
        105                     110                     115

AGC AAT GAA GTT GTC TAC TAC AAT GCA AAG GAT GAT CTC GAT CCT GAG          436
Ser Asn Glu Val Val Tyr Tyr Asn Ala Lys Asp Asp Leu Asp Pro Glu
    120                     125                     130

AAA AAT GAC AGT GAG CCA GGC AGC CAG AGG ATA AAA CCT GTT TTC ATT          484
Lys Asn Asp Ser Glu Pro Gly Ser Gln Arg Ile Lys Pro Val Phe Ile
135                     140                     145                 150

GAA GAT GCT AAT TTT GGA CGA CAA ATA TCT TAT CAG CAC GCA GCA GTC          532
Glu Asp Ala Asn Phe Gly Arg Gln Ile Ser Tyr Gln His Ala Ala Val
                155                     160                     165

CAT ATT CCT ACT GAC ATC TAT GAG GGC TCA ACA ATT GTG TTA AAT GAA          580
His Ile Pro Thr Asp Ile Tyr Glu Gly Ser Thr Ile Val Leu Asn Glu
            170                     175                     180

CTC AAC TGG ACA AGT GCC TTA GAT GAA GTT TTC AAA AAG AAT CGC GAG          628
Leu Asn Trp Thr Ser Ala Leu Asp Glu Val Phe Lys Lys Asn Arg Glu
        185                     190                     195

GAA GAC CCT TCA TTA TTG TGG CAG GTT TTT GGC AGT GCC ACT GGC CTA          676
Glu Asp Pro Ser Leu Leu Trp Gln Val Phe Gly Ser Ala Thr Gly Leu
    200                     205                     210
```

```
GCT  CGA  TAT  TAT  CCA  GCT  TCA  CCA  TGG  GTT  GAT  AAT  AGT  AGA  ACT  CCA      724
Ala  Arg  Tyr  Tyr  Pro  Ala  Ser  Pro  Trp  Val  Asp  Asn  Ser  Arg  Thr  Pro
215                 220                 225                 230

AAT  AAG  ATT  GAC  CTT  TAT  GAT  GTA  CGC  AGA  AGA  CCA  TGG  TAC  ATC  CAA      772
Asn  Lys  Ile  Asp  Leu  Tyr  Asp  Val  Arg  Arg  Arg  Pro  Trp  Tyr  Ile  Gln
                    235                 240                 245

GGA  GCT  GCA  TCT  CCT  AAA  GAC  ATG  CTT  ATT  CTG  GTG  GAT  GTG  AGT  GGA      820
Gly  Ala  Ala  Ser  Pro  Lys  Asp  Met  Leu  Ile  Leu  Val  Asp  Val  Ser  Gly
               250                 255                 260

AGT  GTT  AGT  GGA  TTG  ACA  CTT  AAA  CTG  ATC  CGA  ACA  TCT  GTC  TCC  GAA      868
Ser  Val  Ser  Gly  Leu  Thr  Leu  Lys  Leu  Ile  Arg  Thr  Ser  Val  Ser  Glu
          265                 270                 275

ATG  TTA  GAA  ACC  CTC  TCA  GAT  GAT  GAT  TTC  GTG  AAT  GTA  GCT  TCA  TTT      916
Met  Leu  Glu  Thr  Leu  Ser  Asp  Asp  Asp  Phe  Val  Asn  Val  Ala  Ser  Phe
     280                 285                 290

AAC  AGC  AAT  GCT  CAG  GAT  GTA  AGC  TGT  TTT  CAG  CAC  CTT  GTC  CAA  GCA      964
Asn  Ser  Asn  Ala  Gln  Asp  Val  Ser  Cys  Phe  Gln  His  Leu  Val  Gln  Ala
295                 300                 305                 310

AAT  GTA  AGA  AAT  AAA  AAA  GTG  TTG  AAA  GAC  GCG  GTG  AAT  AAT  ATC  ACA     1012
Asn  Val  Arg  Asn  Lys  Lys  Val  Leu  Lys  Asp  Ala  Val  Asn  Asn  Ile  Thr
                    315                 320                 325

GCC  AAA  GGA  ATT  ACA  GAT  TAT  AAG  AAG  GGC  TTT  AGT  TTT  GCT  TTT  GAA     1060
Ala  Lys  Gly  Ile  Thr  Asp  Tyr  Lys  Lys  Gly  Phe  Ser  Phe  Ala  Phe  Glu
               330                 335                 340

CAG  CTG  CTT  AAT  TAT  AAT  GTT  TCC  AGA  GCA  AAC  TGC  AAT  AAG  ATT  ATT     1108
Gln  Leu  Leu  Asn  Tyr  Asn  Val  Ser  Arg  Ala  Asn  Cys  Asn  Lys  Ile  Ile
          345                 350                 355

ATG  CTA  TTC  ACG  GAT  GGA  GGA  GAA  GAG  AGA  GCC  CAG  GAG  ATA  TTT  AAC     1156
Met  Leu  Phe  Thr  Asp  Gly  Gly  Glu  Glu  Arg  Ala  Gln  Glu  Ile  Phe  Asn
     360                 365                 370

AAA  TAC  AAT  AAA  GAT  AAA  AAA  GTA  CGT  GTA  TTC  AGG  TTT  TCA  GTT  GGT     1204
Lys  Tyr  Asn  Lys  Asp  Lys  Lys  Val  Arg  Val  Phe  Arg  Phe  Ser  Val  Gly
375                 380                 385                 390

CAA  CAC  AAT  TAT  GAG  AGA  GGA  CCT  ATT  CAG  TGG  ATG  GCC  TGT  GAA  AAC     1252
Gln  His  Asn  Tyr  Glu  Arg  Gly  Pro  Ile  Gln  Trp  Met  Ala  Cys  Glu  Asn
                    395                 400                 405

AAA  GGT  TAT  TAT  TAT  GAA  ATT  CCT  TCC  ATT  GGT  GCA  ATA  AGA  ATC  AAT     1300
Lys  Gly  Tyr  Tyr  Tyr  Glu  Ile  Pro  Ser  Ile  Gly  Ala  Ile  Arg  Ile  Asn
               410                 415                 420

ACT  CAG  GAA  TAT  TTG  GAT  GTT  TTG  GGA  AGA  CCA  ATG  GTT  TTA  GCA  GGA     1348
Thr  Gln  Glu  Tyr  Leu  Asp  Val  Leu  Gly  Arg  Pro  Met  Val  Leu  Ala  Gly
          425                 430                 435

GAC  AAA  GCT  AAG  CAA  GTC  CAA  TGG  ACA  AAT  GTG  TAC  CTG  GAT  GCA  TTG     1396
Asp  Lys  Ala  Lys  Gln  Val  Gln  Trp  Thr  Asn  Val  Tyr  Leu  Asp  Ala  Leu
     440                 445                 450

GAA  CTG  GGA  CTT  GTC  ATT  ACT  GGA  ACT  CTT  CCG  GTC  TTC  AAC  ATA  ACC     1444
Glu  Leu  Gly  Leu  Val  Ile  Thr  Gly  Thr  Leu  Pro  Val  Phe  Asn  Ile  Thr
455                 460                 465                 470

GGC  CAA  TTT  GAA  AAT  AAG  ACA  AAC  TTA  AAG  AAC  CAG  CTG  ATT  CTT  GGT     1492
Gly  Gln  Phe  Glu  Asn  Lys  Thr  Asn  Leu  Lys  Asn  Gln  Leu  Ile  Leu  Gly
               475                 480                 485

GTG  ATG  GGA  GTA  GAT  GTG  TCT  TTG  GAA  GAT  ATT  AAA  AGA  CTG  ACA  CCA     1540
Val  Met  Gly  Val  Asp  Val  Ser  Leu  Glu  Asp  Ile  Lys  Arg  Leu  Thr  Pro
          490                 495                 500

CGT  TTT  ACA  CTG  TGC  CCC  AAT  GGG  TAT  TAC  TTT  GCA  ATC  GAT  CCT  AAT     1588
Arg  Phe  Thr  Leu  Cys  Pro  Asn  Gly  Tyr  Tyr  Phe  Ala  Ile  Asp  Pro  Asn
     505                 510                 515

GGT  TAT  GTT  TTA  TTA  CAT  CCA  AAT  CTT  CAG  CCA  AAG  GAG  CCA  GTA  ACA     1636
Gly  Tyr  Val  Leu  Leu  His  Pro  Asn  Leu  Gln  Pro  Lys  Glu  Pro  Val  Thr
520                 525                 530
```

| | | | | | | | | | | | | | | | | |
|---|---|---|---|---|---|---|---|---|---|---|---|---|---|---|---|---|
| TTG | GAT | TTC | CTT | GAT | GCA | GAG | TTA | GAG | AAT | GAT | ATT | AAA | GTG | GAG | ATT | 1684 |
| Leu | Asp | Phe | Leu | Asp | Ala | Glu | Leu | Glu | Asn | Asp | Ile | Lys | Val | Glu | Ile | |
| 535 | | | | 540 | | | | | 545 | | | | | 550 | | |
| CGA | AAT | AAG | ATG | ATT | GAT | GGG | GAA | AGT | GGA | GAA | AAA | ACA | TTC | AGA | ACT | 1732 |
| Arg | Asn | Lys | Met | Ile | Asp | Gly | Glu | Ser | Gly | Glu | Lys | Thr | Phe | Arg | Thr | |
| | | | | 555 | | | | 560 | | | | | 565 | | | |
| CTG | GTT | AAA | TCT | CAA | GAT | GAG | AGA | TAT | ATT | GAC | AAA | GGA | AAC | AGG | ACA | 1780 |
| Leu | Val | Lys | Ser | Gln | Asp | Glu | Arg | Tyr | Ile | Asp | Lys | Gly | Asn | Arg | Thr | |
| | | | 570 | | | | | 575 | | | | | 580 | | | |
| TAC | ACA | TGG | ACA | CCT | GTC | AAT | GGC | ACA | GAT | TAC | AGT | TTG | GCC | TTG | GTA | 1828 |
| Tyr | Thr | Trp | Thr | Pro | Val | Asn | Gly | Thr | Asp | Tyr | Ser | Leu | Ala | Leu | Val | |
| | | 585 | | | | | 590 | | | | | 595 | | | | |
| TTA | CCA | ACC | TAC | AGT | TTT | TAC | TAT | ATA | AAA | GCC | AAA | CTA | GAA | GAG | ACA | 1876 |
| Leu | Pro | Thr | Tyr | Ser | Phe | Tyr | Tyr | Ile | Lys | Ala | Lys | Leu | Glu | Glu | Thr | |
| 600 | | | | | 605 | | | | | 610 | | | | | | |
| ATA | ACT | CAG | GCC | AGA | TCA | AAA | AAG | GGC | AAA | ATG | AAG | GAT | TCG | GAA | ACC | 1924 |
| Ile | Thr | Gln | Ala | Arg | Ser | Lys | Lys | Gly | Lys | Met | Lys | Asp | Ser | Glu | Thr | |
| 615 | | | | | 620 | | | | | 625 | | | | | 630 | |
| CTG | AAG | CCA | GAT | AAT | TTT | GAA | GAA | TCT | GGC | TAT | ACA | TTC | ATA | GCA | CCA | 1972 |
| Leu | Lys | Pro | Asp | Asn | Phe | Glu | Glu | Ser | Gly | Tyr | Thr | Phe | Ile | Ala | Pro | |
| | | | | 635 | | | | 640 | | | | | 645 | | | |
| AGA | GAT | TAC | TGC | AAT | GAC | CTG | AAA | ATA | TCG | GAT | AAT | AAC | ACT | GAA | TTT | 2020 |
| Arg | Asp | Tyr | Cys | Asn | Asp | Leu | Lys | Ile | Ser | Asp | Asn | Asn | Thr | Glu | Phe | |
| | | | 650 | | | | | 655 | | | | | 660 | | | |
| CTT | TTA | AAT | TTC | AAC | GAG | TTT | ATT | GAT | AGA | AAA | ACT | CCA | AAC | AAC | CCA | 2068 |
| Leu | Leu | Asn | Phe | Asn | Glu | Phe | Ile | Asp | Arg | Lys | Thr | Pro | Asn | Asn | Pro | |
| | | 665 | | | | | 670 | | | | | 675 | | | | |
| TCA | TGT | AAC | GCG | GAT | TTG | ATT | AAT | AGA | GTC | TTG | CTT | GAT | GCA | GGC | TTT | 2116 |
| Ser | Cys | Asn | Ala | Asp | Leu | Ile | Asn | Arg | Val | Leu | Leu | Asp | Ala | Gly | Phe | |
| | 680 | | | | | 685 | | | | | 690 | | | | | |
| ACA | AAT | GAA | CTT | GTC | CAA | AAT | TAC | TGG | AGT | AAG | CAG | AAA | AAT | ATC | AAG | 2164 |
| Thr | Asn | Glu | Leu | Val | Gln | Asn | Tyr | Trp | Ser | Lys | Gln | Lys | Asn | Ile | Lys | |
| 695 | | | | | 700 | | | | | 705 | | | | | 710 | |
| GGA | GTG | AAA | GCA | CGA | TTT | GTT | GTG | ACT | GAT | GGT | GGG | ATT | ACC | AGA | GTT | 2212 |
| Gly | Val | Lys | Ala | Arg | Phe | Val | Val | Thr | Asp | Gly | Gly | Ile | Thr | Arg | Val | |
| | | | | 715 | | | | 720 | | | | | 725 | | | |
| TAT | CCC | AAA | GAG | GCT | GGA | GAA | AAT | TGG | CAA | GAA | AAC | CCA | GAG | ACA | TAT | 2260 |
| Tyr | Pro | Lys | Glu | Ala | Gly | Glu | Asn | Trp | Gln | Glu | Asn | Pro | Glu | Thr | Tyr | |
| | | | 730 | | | | | 735 | | | | | 740 | | | |
| GAG | GAC | AGC | TTC | TAT | AAA | AGG | AGC | CTA | GAT | AAT | GAT | AAC | TAT | GTT | TTC | 2308 |
| Glu | Asp | Ser | Phe | Tyr | Lys | Arg | Ser | Leu | Asp | Asn | Asp | Asn | Tyr | Val | Phe | |
| | | 745 | | | | | 750 | | | | | 755 | | | | |
| ACT | GCT | CCC | TAC | TTT | AAC | AAA | AGT | GGA | CCT | GGT | GCC | TAT | GAA | TCG | GGC | 2356 |
| Thr | Ala | Pro | Tyr | Phe | Asn | Lys | Ser | Gly | Pro | Gly | Ala | Tyr | Glu | Ser | Gly | |
| | 760 | | | | | 765 | | | | | 770 | | | | | |
| ATT | ATG | GTA | AGC | AAA | GCT | GTA | GAA | ATA | TAT | ATT | CAA | GGG | AAA | CTT | CTT | 2404 |
| Ile | Met | Val | Ser | Lys | Ala | Val | Glu | Ile | Tyr | Ile | Gln | Gly | Lys | Leu | Leu | |
| 775 | | | | | 780 | | | | | 785 | | | | | 790 | |
| AAA | CCT | GCA | GTT | GTT | GGA | ATT | AAA | ATT | GAT | GTA | AAT | TCC | TGG | ATA | GAG | 2452 |
| Lys | Pro | Ala | Val | Val | Gly | Ile | Lys | Ile | Asp | Val | Asn | Ser | Trp | Ile | Glu | |
| | | | | 795 | | | | 800 | | | | | 805 | | | |
| AAT | TTC | ACC | AAA | ACC | TCA | ATC | AGA | GAT | CCG | TGT | GCT | GGT | CCA | GTT | TGT | 2500 |
| Asn | Phe | Thr | Lys | Thr | Ser | Ile | Arg | Asp | Pro | Cys | Ala | Gly | Pro | Val | Cys | |
| | | | 810 | | | | | 815 | | | | | 820 | | | |
| GAC | TGC | AAA | AGA | AAC | AGT | GAC | GTA | ATG | GAT | TGT | GTG | ATT | CTG | GAT | GAT | 2548 |
| Asp | Cys | Lys | Arg | Asn | Ser | Asp | Val | Met | Asp | Cys | Val | Ile | Leu | Asp | Asp | |
| | | 825 | | | | | 830 | | | | | 835 | | | | |
| GGT | GGG | TTT | CTT | CTG | ATG | GCA | AAT | CAT | GAT | GAT | TAT | ACT | AAT | CAG | ATT | 2596 |
| Gly | Gly | Phe | Leu | Leu | Met | Ala | Asn | His | Asp | Asp | Tyr | Thr | Asn | Gln | Ile | |
| | 840 | | | | | 845 | | | | | 850 | | | | | |

| | | | | | | | | | | | | | | | | |
|---|---|---|---|---|---|---|---|---|---|---|---|---|---|---|---|---|
| GGA | AGA | TTT | TTT | GGA | GAG | ATT | GAT | CCC | AGC | TTG | ATG | AGA | CAC | CTG | GTT | 2644 |
| Gly | Arg | Phe | Phe | Gly | Glu | Ile | Asp | Pro | Ser | Leu | Met | Arg | His | Leu | Val | |
| 855 | | | | 860 | | | | | 865 | | | | | | 870 | |
| AAT | ATA | TCA | GTT | TAT | GCT | TTT | AAC | AAA | TCT | TAT | GAT | TAT | CAG | TCA | GTA | 2692 |
| Asn | Ile | Ser | Val | Tyr | Ala | Phe | Asn | Lys | Ser | Tyr | Asp | Tyr | Gln | Ser | Val | |
| | | | | 875 | | | | | 880 | | | | | 885 | | |
| TGT | GAG | CCC | GGT | GCT | GCA | CCA | AAA | CAA | GGA | GCA | GGA | CAT | CGC | TCA | GCA | 2740 |
| Cys | Glu | Pro | Gly | Ala | Ala | Pro | Lys | Gln | Gly | Ala | Gly | His | Arg | Ser | Ala | |
| | | | 890 | | | | | 895 | | | | | 900 | | | |
| TAT | GTG | CCA | TCA | GTA | GCA | GAC | ATA | TTA | CAA | ATT | GGC | TGG | TGG | GCC | ACT | 2788 |
| Tyr | Val | Pro | Ser | Val | Ala | Asp | Ile | Leu | Gln | Ile | Gly | Trp | Trp | Ala | Thr | |
| | | 905 | | | | | 910 | | | | | 915 | | | | |
| GCT | GCT | GCC | TGG | TCT | ATT | CTA | CAG | CAG | TTT | CTC | TTG | AGT | TTG | ACC | TTT | 2836 |
| Ala | Ala | Ala | Trp | Ser | Ile | Leu | Gln | Gln | Phe | Leu | Leu | Ser | Leu | Thr | Phe | |
| | 920 | | | | | 925 | | | | | 930 | | | | | |
| CCA | CGA | CTC | CTT | GAG | GCA | GTT | GAG | ATG | GAG | GAT | GAT | GAC | TTC | ACG | GCC | 2884 |
| Pro | Arg | Leu | Leu | Glu | Ala | Val | Glu | Met | Glu | Asp | Asp | Asp | Phe | Thr | Ala | |
| 935 | | | | | 940 | | | | | 945 | | | | | 950 | |
| TCC | CTG | TCC | AAG | CAG | AGC | TGC | ATT | ACT | GAA | CAA | ACC | CAG | TAT | TTC | TTC | 2932 |
| Ser | Leu | Ser | Lys | Gln | Ser | Cys | Ile | Thr | Glu | Gln | Thr | Gln | Tyr | Phe | Phe | |
| | | | | 955 | | | | | 960 | | | | | 965 | | |
| GAT | AAC | GAC | AGT | AAA | TCA | TTC | AGT | GGT | GTA | TTA | GAC | TGT | GGA | AAC | TGT | 2980 |
| Asp | Asn | Asp | Ser | Lys | Ser | Phe | Ser | Gly | Val | Leu | Asp | Cys | Gly | Asn | Cys | |
| | | | 970 | | | | | 975 | | | | | 980 | | | |
| TCC | AGA | ATC | TTT | CAT | GGA | GAA | AAG | CTT | ATG | AAC | ACC | AAC | TTA | ATA | TTC | 3028 |
| Ser | Arg | Ile | Phe | His | Gly | Glu | Lys | Leu | Met | Asn | Thr | Asn | Leu | Ile | Phe | |
| | | 985 | | | | | 990 | | | | | 995 | | | | |
| ATA | ATG | GTT | GAG | AGC | AAA | GGG | ACA | TGT | CCA | TGT | GAC | ACA | CGA | CTG | CTC | 3076 |
| Ile | Met | Val | Glu | Ser | Lys | Gly | Thr | Cys | Pro | Cys | Asp | Thr | Arg | Leu | Leu | |
| | 1000 | | | | | 1005 | | | | | 1010 | | | | | |
| ATA | CAA | GCG | GAG | CAG | ACT | TCT | GAC | GGT | CCA | AAT | CCT | TGT | GAC | ATG | GTT | 3124 |
| Ile | Gln | Ala | Glu | Gln | Thr | Ser | Asp | Gly | Pro | Asn | Pro | Cys | Asp | Met | Val | |
| 1015 | | | | | 1020 | | | | | 1025 | | | | | 1030 | |
| AAG | CAA | CCT | AGA | TAC | CGA | AAA | GGG | CCT | GAT | GTC | TGC | TTT | GAT | AAC | AAT | 3172 |
| Lys | Gln | Pro | Arg | Tyr | Arg | Lys | Gly | Pro | Asp | Val | Cys | Phe | Asp | Asn | Asn | |
| | | | | 1035 | | | | | 1040 | | | | | 1045 | | |
| GTC | TTG | GAG | GAT | TAT | ACT | GAC | TGT | GGT | GGT | GTT | TCT | GGA | TTA | AAT | CCC | 3220 |
| Val | Leu | Glu | Asp | Tyr | Thr | Asp | Cys | Gly | Gly | Val | Ser | Gly | Leu | Asn | Pro | |
| | | | 1050 | | | | | 1055 | | | | | 1060 | | | |
| TCC | CTG | TGG | TAT | ATC | ATT | GGA | ATC | CAG | TTT | CTA | CTA | CTT | TGG | CTG | GTA | 3268 |
| Ser | Leu | Trp | Tyr | Ile | Ile | Gly | Ile | Gln | Phe | Leu | Leu | Leu | Trp | Leu | Val | |
| | | | 1065 | | | | | 1070 | | | | | 1075 | | | |
| TCT | GGC | AGC | ACA | CAC | CGG | CTG | TTA | TGACTTCTA | AAAACCAAAT | CTGCATAGTT | | | | | | 3322 |
| Ser | Gly | Ser | Thr | His | Arg | Leu | Leu | | | | | | | | | |
| | 1080 | | | | | 1085 | | | | | | | | | | |

| | | |
|---|---|---|
| AAACTCCAGA CCCTGCCAAA ACATGAGCCC TGCCCTCAAT TACAGTAACG TAGGGTCAGC | | 3382 |
| TATAAAATCA GACAAACATT AGCTGGGCCT GTTCCATGGC ATAACACTAA GGCGCAGACT | | 3442 |
| CCTAAGGCAC CCACTGGCTG CATGTCAGGG TGTCAGATCC TTAAACGTGT GTGAATGCTG | | 3502 |
| CATCATCTAT GTGTAACATC AAAGCAAAAT CCTATACGTG TCCTCTATTG GAAAATTTGG | | 3562 |
| GCGTTTGTTG TTGCATTGTT GGT | | 3585 |

(2) INFORMATION FOR SEQ ID NO:24:

(i) SEQUENCE CHARACTERISTICS:
        (A) LENGTH: 3564 base pairs
        (B) TYPE: nucleic acid
        (C) STRANDEDNESS: double
        (D) TOPOLOGY: linear -continued ( i i ) MOLECULE TYPE: DNA (genomic)

( i x ) FEATURE:
  ( A ) NAME/KEY: CDS
  ( B ) LOCATION: 35..3374 ([00fc]1625 to 1639 & [00fc]1908 to 1928)
  ( D ) OTHER INFORMATION: /standard_name="Alpha-2d"

( i x ) FEATURE:
  ( A ) NAME/KEY: 5'UTR
  ( B ) LOCATION: 1..34

( i x ) FEATURE:
  ( A ) NAME/KEY: 3'UTR
  ( B ) LOCATION: 3375..3565

( x i ) SEQUENCE DESCRIPTION: SEQ ID NO:24:

```
GCGGGGAGG  GGGCATTGAT  CTTCGATCGC  GAAG ATG GCT GCT GGC TGC CTG                    52
                                        Met Ala Ala Gly Cys Leu
                                         1               5

CTG GCC TTG ACT CTG ACA CTT TTC CAA TCT TTG CTC ATC GGC CCC TCG                   100
Leu Ala Leu Thr Leu Thr Leu Phe Gln Ser Leu Leu Ile Gly Pro Ser
             10              15                  20

TCG GAG GAG CCG TTC CCT TCG GCC GTC ACT ATC AAA TCA TGG GTG GAT                   148
Ser Glu Glu Pro Phe Pro Ser Ala Val Thr Ile Lys Ser Trp Val Asp
         25              30              35

AAG ATG CAA GAA GAC CTT GTC ACA CTG GCA AAA ACA GCA AGT GGA GTC                   196
Lys Met Gln Glu Asp Leu Val Thr Leu Ala Lys Thr Ala Ser Gly Val
     40              45              50

AAT CAG CTT GTT GAT ATT TAT GAG AAA TAT CAA GAT TTG TAT ACT GTG                   244
Asn Gln Leu Val Asp Ile Tyr Glu Lys Tyr Gln Asp Leu Tyr Thr Val
 55              60              65                  70

GAA CCA AAT AAT GCA CGC CAG CTG GTA GAA ATT GCA GCC AGG GAT ATT                   292
Glu Pro Asn Asn Ala Arg Gln Leu Val Glu Ile Ala Ala Arg Asp Ile
                 75              80              85

GAG AAA CTT CTG AGC AAC AGA TCT AAA GCC CTG GTG AGC CTG GCA TTG                   340
Glu Lys Leu Leu Ser Asn Arg Ser Lys Ala Leu Val Ser Leu Ala Leu
             90              95              100

GAA GCG GAG AAA GTT CAA GCA GCT CAC CAG TGG AGA GAA GAT TTT GCA                   388
Glu Ala Glu Lys Val Gln Ala Ala His Gln Trp Arg Glu Asp Phe Ala
         105             110             115

AGC AAT GAA GTT GTC TAC TAC AAT GCA AAG GAT GAT CTC GAT CCT GAG                   436
Ser Asn Glu Val Val Tyr Tyr Asn Ala Lys Asp Asp Leu Asp Pro Glu
     120             125             130

AAA AAT GAC AGT GAG CCA GGC AGC CAG AGG ATA AAA CCT GTT TTC ATT                   484
Lys Asn Asp Ser Glu Pro Gly Ser Gln Arg Ile Lys Pro Val Phe Ile
 135             140             145             150

GAA GAT GCT AAT TTT GGA CGA CAA ATA TCT TAT CAG CAC GCA GCA GTC                   532
Glu Asp Ala Asn Phe Gly Arg Gln Ile Ser Tyr Gln His Ala Ala Val
             155             160             165

CAT ATT CCT ACT GAC ATC TAT GAG GGC TCA ACA ATT GTG TTA AAT GAA                   580
His Ile Pro Thr Asp Ile Tyr Glu Gly Ser Thr Ile Val Leu Asn Glu
         170             175             180

CTC AAC TGG ACA AGT GCC TTA GAT GAA GTT TTC AAA AAG AAT CGC GAG                   628
Leu Asn Trp Thr Ser Ala Leu Asp Glu Val Phe Lys Lys Asn Arg Glu
     185             190             195

GAA GAC CCT TCA TTA TTG TGG CAG GTT TTT GGC AGT GCC ACT GGC CTA                   676
Glu Asp Pro Ser Leu Leu Trp Gln Val Phe Gly Ser Ala Thr Gly Leu
 200             205             210

GCT CGA TAT TAT CCA GCT TCA CCA TGG GTT GAT AAT AGT AGA ACT CCA                   724
Ala Arg Tyr Tyr Pro Ala Ser Pro Trp Val Asp Asn Ser Arg Thr Pro
 215             220             225             230

AAT AAG ATT GAC CTT TAT GAT GTA CGC AGA AGA CCA TGG TAC ATC CAA                   772
Asn Lys Ile Asp Leu Tyr Asp Val Arg Arg Pro Trp Tyr Ile Gln
             235             240             245
```

| | | | | | | | | | | | | | | | | |
|---|---|---|---|---|---|---|---|---|---|---|---|---|---|---|---|---|
| GGA | GCT | GCA | TCT | CCT | AAA | GAC | ATG | CTT | ATT | CTG | GTG | GAT | GTG | AGT | GGA | 820 |
| Gly | Ala | Ala | Ser 250 | Pro | Lys | Asp | Met | Leu 255 | Ile | Leu | Val | Asp | Val 260 | Ser | Gly | |
| AGT | GTT | AGT | GGA | TTG | ACA | CTT | AAA | CTG | ATC | CGA | ACA | TCT | GTC | TCC | GAA | 868 |
| Ser | Val | Ser 265 | Gly | Leu | Thr | Leu | Lys 270 | Leu | Ile | Arg | Thr | Ser 275 | Val | Ser | Glu | |
| ATG | TTA | GAA | ACC | CTC | TCA | GAT | GAT | GAT | TTC | GTG | AAT | GTA | GCT | TCA | TTT | 916 |
| Met | Leu 280 | Glu | Thr | Leu | Ser | Asp | Asp 285 | Asp | Phe | Val | Asn | Val 290 | Ala | Ser | Phe | |
| AAC | AGC | AAT | GCT | CAG | GAT | GTA | AGC | TGT | TTT | CAG | CAC | CTT | GTC | CAA | GCA | 964 |
| Asn | Ser 295 | Asn | Ala | Gln | Asp 300 | Val | Ser | Cys | Phe | Gln 305 | His | Leu | Val | Gln | Ala 310 | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys 315 | Lys | Val | Leu | Lys | Asp 320 | Ala | Val | Asn | Asn | Ile 325 | Thr | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile 330 | Thr | Asp | Tyr | Lys | Lys 335 | Gly | Phe | Ser | Phe | Ala 340 | Phe | Glu | |
| CAG | CTG | CTT | AAT | TAT | AAT | GTT | TCC | AGA | GCA | AAC | TGC | AAT | AAG | ATT | ATT | 1108 |
| Gln | Leu | Leu 345 | Asn | Tyr | Asn | Val | Ser 350 | Arg | Ala | Asn | Cys | Asn 355 | Lys | Ile | Ile | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly 365 | Gly | Glu | Glu | Arg | Ala | Gln 370 | Glu | Ile | Phe | Asn | |
| | | | | 360 | | | | | | | | | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys 375 | Asp | Lys | Lys | Val 380 | Arg | Val | Phe | Arg 385 | Phe | Ser | Val | Gly 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu 395 | Arg | Gly | Pro | Ile | Gln 400 | Trp | Met | Ala | Cys | Glu 405 | Asn | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr 410 | Tyr | Glu | Ile | Pro | Ser 415 | Ile | Gly | Ala | Ile | Arg 420 | Ile | Asn | |
| ACT | CAG | GAA | TAT | TTG | GAT | GTT | TTG | GGA | AGA | CCA | ATG | GTT | TTA | GCA | GGA | 1348 |
| Thr | Gln | Glu 425 | Tyr | Leu | Asp | Val | Leu 430 | Gly | Arg | Pro | Met | Val 435 | Leu | Ala | Gly | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys 440 | Gln | Val | Gln | Trp | Thr 445 | Asn | Val | Tyr | Leu | Asp 450 | Ala | Leu | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val 460 | Ile | Thr | Gly | Thr | Leu 465 | Pro | Val | Phe | Asn | Ile 470 | Thr | |
| | 455 | | | | | | | | | | | | | | | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn 475 | Lys | Thr | Asn | Leu | Lys 480 | Asn | Gln | Leu | Ile | Leu 485 | Gly | |
| GTG | ATG | GGA | GTA | GAT | GTG | TCT | TTG | GAA | GAT | ATT | AAA | AGA | CTG | ACA | CCA | 1540 |
| Val | Met | Gly | Val 490 | Asp | Val | Ser | Leu | Glu 495 | Asp | Ile | Lys | Arg | Leu 500 | Thr | Pro | |
| CGT | TTT | ACA | CTG | TGC | CCC | AAT | GGG | TAT | TAC | TTT | GCA | ATC | GAT | CCT | AAT | 1588 |
| Arg | Phe | Thr 505 | Leu | Cys | Pro | Asn | Gly 510 | Tyr | Tyr | Phe | Ala | Ile 515 | Asp | Pro | Asn | |
| GGT | TAT | GTT | TTA | TTA | CAT | CCA | AAT | CTT | CAG | CCA | AAG | GAG | CCA | GTA | ACA | 1636 |
| Gly | Tyr 520 | Val | Leu | Leu | His | Pro 525 | Asn | Leu | Gln | Pro | Lys 530 | Glu | Pro | Val | Thr | |
| TTG | GAT | TTC | CTT | GAT | GCA | GAG | TTA | GAG | AAT | GAT | ATT | AAA | GTG | GAG | ATT | 1684 |
| Leu | Asp | Phe | Leu | Asp | Ala 540 | Glu | Leu | Glu | Asn | Asp 545 | Ile | Lys | Val | Glu | Ile 550 | |
| | 535 | | | | | | | | | | | | | | | |
| CGA | AAT | AAG | ATG | ATT | GAT | GGG | GAA | AGT | GGA | GAA | AAA | ACA | TTC | AGA | ACT | 1732 |
| Arg | Asn | Lys | Met | Ile 555 | Asp | Gly | Glu | Ser | Gly 560 | Glu | Lys | Thr | Phe | Arg 565 | Thr | |

| | | | | | | | | | | | | | | | | |
|---|---|---|---|---|---|---|---|---|---|---|---|---|---|---|---|---|
| CTG | GTT | AAA | TCT | CAA | GAT | GAG | AGA | TAT | ATT | GAC | AAA | GGA | AAC | AGG | ACA | 1780 |
| Leu | Val | Lys | Ser | Gln | Asp | Glu | Arg | Tyr | Ile | Asp | Lys | Gly | Asn | Arg | Thr | |
| | | | 570 | | | | 575 | | | | | 580 | | | | |
| TAC | ACA | TGG | ACA | CCT | GTC | AAT | GGC | ACA | GAT | TAC | AGT | TTG | GCC | TTG | GTA | 1828 |
| Tyr | Thr | Trp | Thr | Pro | Val | Asn | Gly | Thr | Asp | Tyr | Ser | Leu | Ala | Leu | Val | |
| | | 585 | | | | | 590 | | | | | 595 | | | | |
| TTA | CCA | ACC | TAC | AGT | TTT | TAC | TAT | ATA | AAA | GCC | AAA | CTA | GAA | GAG | ACA | 1876 |
| Leu | Pro | Thr | Tyr | Ser | Phe | Tyr | Tyr | Ile | Lys | Ala | Lys | Leu | Glu | Glu | Thr | |
| | 600 | | | | | 605 | | | | | 610 | | | | | |
| ATA | ACT | CAG | GCC | AGA | TAT | TCG | GAA | ACC | CTG | AAG | CCA | GAT | AAT | TTT | GAA | 1924 |
| Ile | Thr | Gln | Ala | Arg | Tyr | Ser | Glu | Thr | Leu | Lys | Pro | Asp | Asn | Phe | Glu | |
| 615 | | | | | 620 | | | | | 625 | | | | | 630 | |
| GAA | TCT | GGC | TAT | ACA | TTC | ATA | GCA | CCA | AGA | GAT | TAC | TGC | AAT | GAC | CTG | 1972 |
| Glu | Ser | Gly | Tyr | Thr | Phe | Ile | Ala | Pro | Arg | Asp | Tyr | Cys | Asn | Asp | Leu | |
| | | | | 635 | | | | | 640 | | | | | | 645 | |
| AAA | ATA | TCG | GAT | AAT | AAC | ACT | GAA | TTT | CTT | TTA | AAT | TTC | AAC | GAG | TTT | 2020 |
| Lys | Ile | Ser | Asp | Asn | Asn | Thr | Glu | Phe | Leu | Leu | Asn | Phe | Asn | Glu | Phe | |
| | | | 650 | | | | | 655 | | | | | 660 | | | |
| ATT | GAT | AGA | AAA | ACT | CCA | AAC | AAC | CCA | TCA | TGT | AAC | GCG | GAT | TTG | ATT | 2068 |
| Ile | Asp | Arg | Lys | Thr | Pro | Asn | Asn | Pro | Ser | Cys | Asn | Ala | Asp | Leu | Ile | |
| | | 665 | | | | | 670 | | | | | 675 | | | | |
| AAT | AGA | GTC | TTG | CTT | GAT | GCA | GGC | TTT | ACA | AAT | GAA | CTT | GTC | CAA | AAT | 2116 |
| Asn | Arg | Val | Leu | Leu | Asp | Ala | Gly | Phe | Thr | Asn | Glu | Leu | Val | Gln | Asn | |
| | 680 | | | | | 685 | | | | | 690 | | | | | |
| TAC | TGG | AGT | AAG | CAG | AAA | AAT | ATC | AAG | GGA | GTG | AAA | GCA | CGA | TTT | GTT | 2164 |
| Tyr | Trp | Ser | Lys | Gln | Lys | Asn | Ile | Lys | Gly | Val | Lys | Ala | Arg | Phe | Val | |
| 695 | | | | | 700 | | | | | 705 | | | | | 710 | |
| GTG | ACT | GAT | GGT | GGG | ATT | ACC | AGA | GTT | TAT | CCC | AAA | GAG | GCT | GGA | GAA | 2212 |
| Val | Thr | Asp | Gly | Gly | Ile | Thr | Arg | Val | Tyr | Pro | Lys | Glu | Ala | Gly | Glu | |
| | | | | 715 | | | | | 720 | | | | | 725 | | |
| AAT | TGG | CAA | GAA | AAC | CCA | GAG | ACA | TAT | GAG | GAC | AGC | TTC | TAT | AAA | AGG | 2260 |
| Asn | Trp | Gln | Glu | Asn | Pro | Glu | Thr | Tyr | Glu | Asp | Ser | Phe | Tyr | Lys | Arg | |
| | | | 730 | | | | | 735 | | | | | 740 | | | |
| AGC | CTA | GAT | AAT | GAT | AAC | TAT | GTT | TTC | ACT | GCT | CCC | TAC | TTT | AAC | AAA | 2308 |
| Ser | Leu | Asp | Asn | Asp | Asn | Tyr | Val | Phe | Thr | Ala | Pro | Tyr | Phe | Asn | Lys | |
| | | 745 | | | | | 750 | | | | | 755 | | | | |
| AGT | GGA | CCT | GGT | GCC | TAT | GAA | TCG | GGC | ATT | ATG | GTA | AGC | AAA | GCT | GTA | 2356 |
| Ser | Gly | Pro | Gly | Ala | Tyr | Glu | Ser | Gly | Ile | Met | Val | Ser | Lys | Ala | Val | |
| | 760 | | | | | 765 | | | | | 770 | | | | | |
| GAA | ATA | TAT | ATT | CAA | GGG | AAA | CTT | CTT | AAA | CCT | GCA | GTT | GTT | GGA | ATT | 2404 |
| Glu | Ile | Tyr | Ile | Gln | Gly | Lys | Leu | Leu | Lys | Pro | Ala | Val | Val | Gly | Ile | |
| 775 | | | | | 780 | | | | | 785 | | | | | 790 | |
| AAA | ATT | GAT | GTA | AAT | TCC | TGG | ATA | GAG | AAT | TTC | ACC | AAA | ACC | TCA | ATC | 2452 |
| Lys | Ile | Asp | Val | Asn | Ser | Trp | Ile | Glu | Asn | Phe | Thr | Lys | Thr | Ser | Ile | |
| | | | | 795 | | | | | 800 | | | | | 805 | | |
| AGA | GAT | CCG | TGT | GCT | GGT | CCA | GTT | TGT | GAC | TGC | AAA | AGA | AAC | AGT | GAC | 2500 |
| Arg | Asp | Pro | Cys | Ala | Gly | Pro | Val | Cys | Asp | Cys | Lys | Arg | Asn | Ser | Asp | |
| | | | 810 | | | | | 815 | | | | | 820 | | | |
| GTA | ATG | GAT | TGT | GTG | ATT | CTG | GAT | GAT | GGT | GGG | TTT | CTT | CTG | ATG | GCA | 2548 |
| Val | Met | Asp | Cys | Val | Ile | Leu | Asp | Asp | Gly | Gly | Phe | Leu | Leu | Met | Ala | |
| | | 825 | | | | | 830 | | | | | 835 | | | | |
| AAT | CAT | GAT | GAT | TAT | ACT | AAT | CAG | ATT | GGA | AGA | TTT | TTT | GGA | GAG | ATT | 2596 |
| Asn | His | Asp | Asp | Tyr | Thr | Asn | Gln | Ile | Gly | Arg | Phe | Phe | Gly | Glu | Ile | |
| | 840 | | | | | 845 | | | | | 850 | | | | | |
| GAT | CCC | AGC | TTG | ATG | AGA | CAC | CTG | GTT | AAT | ATA | TCA | GTT | TAT | GCT | TTT | 2644 |
| Asp | Pro | Ser | Leu | Met | Arg | His | Leu | Val | Asn | Ile | Ser | Val | Tyr | Ala | Phe | |
| 855 | | | | | 860 | | | | | 865 | | | | | 870 | |
| AAC | AAA | TCT | TAT | GAT | TAT | CAG | TCA | GTA | TGT | GAG | CCC | GGT | GCT | GCA | CCA | 2692 |
| Asn | Lys | Ser | Tyr | Asp | Tyr | Gln | Ser | Val | Cys | Glu | Pro | Gly | Ala | Ala | Pro | |
| | | | | 875 | | | | | 880 | | | | | 885 | | |

| | | | | | | | | | | | | | | | |
|---|---|---|---|---|---|---|---|---|---|---|---|---|---|---|---|
| AAA | CAA | GGA | GCA | GGA | CAT | CGC | TCA | GCA | TAT | GTG | CCA | TCA | GTA | GCA | GAC | 2740 |
| Lys | Gln | Gly | Ala | Gly | His | Arg | Ser | Ala | Tyr | Val | Pro | Ser | Val | Ala | Asp | |
| | | | 890 | | | | | 895 | | | | | 900 | | | |
| ATA | TTA | CAA | ATT | GGC | TGG | TGG | GCC | ACT | GCT | GCT | GCC | TGG | TCT | ATT | CTA | 2788 |
| Ile | Leu | Gln | Ile | Gly | Trp | Trp | Ala | Thr | Ala | Ala | Ala | Trp | Ser | Ile | Leu | |
| | | 905 | | | | | 910 | | | | | 915 | | | | |
| CAG | CAG | TTT | CTC | TTG | AGT | TTG | ACC | TTT | CCA | CGA | CTC | CTT | GAG | GCA | GTT | 2836 |
| Gln | Gln | Phe | Leu | Leu | Ser | Leu | Thr | Phe | Pro | Arg | Leu | Leu | Glu | Ala | Val | |
| 920 | | | | | | 925 | | | | | 930 | | | | | |
| GAG | ATG | GAG | GAT | GAT | GAC | TTC | ACG | GCC | TCC | CTG | TCC | AAG | CAG | AGC | TGC | 2884 |
| Glu | Met | Glu | Asp | Asp | Asp | Phe | Thr | Ala | Ser | Leu | Ser | Lys | Gln | Ser | Cys | |
| 935 | | | | | 940 | | | | 945 | | | | | 950 | | |
| ATT | ACT | GAA | CAA | ACC | CAG | TAT | TTC | TTC | GAT | AAC | GAC | AGT | AAA | TCA | TTC | 2932 |
| Ile | Thr | Glu | Gln | Thr | Gln | Tyr | Phe | Phe | Asp | Asn | Asp | Ser | Lys | Ser | Phe | |
| | | | | 955 | | | | | 960 | | | | | 965 | | |
| AGT | GGT | GTA | TTA | GAC | TGT | GGA | AAC | TGT | TCC | AGA | ATC | TTT | CAT | GGA | GAA | 2980 |
| Ser | Gly | Val | Leu | Asp | Cys | Gly | Asn | Cys | Ser | Arg | Ile | Phe | His | Gly | Glu | |
| | | | 970 | | | | | 975 | | | | | 980 | | | |
| AAG | CTT | ATG | AAC | ACC | AAC | TTA | ATA | TTC | ATA | ATG | GTT | GAG | AGC | AAA | GGG | 3028 |
| Lys | Leu | Met | Asn | Thr | Asn | Leu | Ile | Phe | Ile | Met | Val | Glu | Ser | Lys | Gly | |
| | | 985 | | | | | 990 | | | | | 995 | | | | |
| ACA | TGT | CCA | TGT | GAC | ACA | CGA | CTG | CTC | ATA | CAA | GCG | GAG | CAG | ACT | TCT | 3076 |
| Thr | Cys | Pro | Cys | Asp | Thr | Arg | Leu | Leu | Ile | Gln | Ala | Glu | Gln | Thr | Ser | |
| 1000 | | | | | 1005 | | | | | 1010 | | | | | | |
| GAC | GGT | CCA | AAT | CCT | TGT | GAC | ATG | GTT | AAG | CAA | CCT | AGA | TAC | CGA | AAA | 3124 |
| Asp | Gly | Pro | Asn | Pro | Cys | Asp | Met | Val | Lys | Gln | Pro | Arg | Tyr | Arg | Lys | |
| 1015 | | | | | 1020 | | | | 1025 | | | | | 1030 | | |
| GGG | CCT | GAT | GTC | TGC | TTT | GAT | AAC | AAT | GTC | TTG | GAG | GAT | TAT | ACT | GAC | 3172 |
| Gly | Pro | Asp | Val | Cys | Phe | Asp | Asn | Asn | Val | Leu | Glu | Asp | Tyr | Thr | Asp | |
| | | | | 1035 | | | | 1040 | | | | | 1045 | | | |
| TGT | GGT | GGT | GTT | TCT | GGA | TTA | AAT | CCC | TCC | CTG | TGG | TAT | ATC | ATT | GGA | 3220 |
| Cys | Gly | Gly | Val | Ser | Gly | Leu | Asn | Pro | Ser | Leu | Trp | Tyr | Ile | Ile | Gly | |
| | | | 1050 | | | | | 1055 | | | | | 1060 | | | |
| ATC | CAG | TTT | CTA | CTA | CTT | TGG | CTG | GTA | TCT | GGC | AGC | ACA | CAC | CGG | CTG | 3268 |
| Ile | Gln | Phe | Leu | Leu | Leu | Trp | Leu | Val | Ser | Gly | Ser | Thr | His | Arg | Leu | |
| | | 1065 | | | | | 1070 | | | | | 1075 | | | | |

| | | | | | |
|---|---|---|---|---|---|
| TTA | TGACCTTCTA | AAAACCAAAT | CTGCATAGTT | AAACTCCAGA | CCCTGCCAAA | 3321 |
| Leu | | | | | | |
| ACATGAGCCC | TGCCCTCAAT | TACAGTAACG | TAGGGTCAGC | TATAAAATCA | GACAAACATT | 3381 |
| AGCTGGGCCT | GTTCCATGGC | ATAACACTAA | GGCGCAGACT | CCTAAGGCAC | CCACTGGCTG | 3441 |
| CATGTCAGGG | TGTCAGATCC | TTAAACGTGT | GTGAATGCTG | CATCATCTAT | GTGTAACATC | 3501 |
| AAAGCAAAAT | CCTATACGTG | TCCTCTATTG | GAAAATTTGG | GCGTTTGTTG | TTGCATTGTT | 3561 |
| GGT | | | | | | 3564 |

( 2 ) INFORMATION FOR SEQ ID NO:25:

( i ) SEQUENCE CHARACTERISTICS:
        ( A ) LENGTH: 3579 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 35..3289
        ( D ) OTHER INFORMATION: /standard_name="Alpha-2e"

( i x ) FEATURE:
        ( A ) NAME/KEY: 5'UTR (B) LOCATION: 1..34

(ix) FEATURE:
    (A) NAME/KEY: 3'UTR
    (B) LOCATION: 3289..3579

(xi) SEQUENCE DESCRIPTION: SEQ ID NO:25:

| | | | | | | | | | | | | | | | |
|---|---|---|---|---|---|---|---|---|---|---|---|---|---|---|---|
| GCGGGGGAGG | | GGGCATTGAT | | CTTCGATCGC | | GAAG | ATG | GCT | GCT | GGC | TGC | CTG | | | 52 |
| | | | | | | | Met | Ala | Ala | Gly | Cys | Leu | | | |
| | | | | | | | 1 | | | | 5 | | | | |
| CTG | GCC | TTG | ACT | CTG | ACA | CTT | TTC | CAA | TCT | TTG | CTC | ATC | GGC | CCC | TCG | 100 |
| Leu | Ala | Leu | Thr | Leu | Thr | Leu | Phe | Gln | Ser | Leu | Leu | Ile | Gly | Pro | Ser |
| | | | 10 | | | | 15 | | | | | 20 | | | |
| TCG | GAG | GAG | CCG | TTC | CCT | TCG | GCC | GTC | ACT | ATC | AAA | TCA | TGG | GTG | GAT | 148 |
| Ser | Glu | Glu | Pro | Phe | Pro | Ser | Ala | Val | Thr | Ile | Lys | Ser | Trp | Val | Asp |
| | | 25 | | | | | 30 | | | | | 35 | | | |
| AAG | ATG | CAA | GAA | GAC | CTT | GTC | ACA | CTG | GCA | AAA | ACA | GCA | AGT | GGA | GTC | 196 |
| Lys | Met | Gln | Glu | Asp | Leu | Val | Thr | Leu | Ala | Lys | Thr | Ala | Ser | Gly | Val |
| | 40 | | | | | 45 | | | | | 50 | | | | |
| AAT | CAG | CTT | GTT | GAT | ATT | TAT | GAG | AAA | TAT | CAA | GAT | TTG | TAT | ACT | GTG | 244 |
| Asn | Gln | Leu | Val | Asp | Ile | Tyr | Glu | Lys | Tyr | Gln | Asp | Leu | Tyr | Thr | Val |
| 55 | | | | | 60 | | | | | 65 | | | | | 70 |
| GAA | CCA | AAT | AAT | GCA | CGC | CAG | CTG | GTA | GAA | ATT | GCA | GCC | AGG | GAT | ATT | 292 |
| Glu | Pro | Asn | Asn | Ala | Arg | Gln | Leu | Val | Glu | Ile | Ala | Ala | Arg | Asp | Ile |
| | | | | 75 | | | | | 80 | | | | | 85 | |
| GAG | AAA | CTT | CTG | AGC | AAC | AGA | TCT | AAA | GCC | CTG | GTG | AGC | CTG | GCA | TTG | 340 |
| Glu | Lys | Leu | Leu | Ser | Asn | Arg | Ser | Lys | Ala | Leu | Val | Ser | Leu | Ala | Leu |
| | | | 90 | | | | | 95 | | | | | 100 | | |
| GAA | GCG | GAG | AAA | GTT | CAA | GCA | GCT | CAC | CAG | TGG | AGA | GAA | GAT | TTT | GCA | 388 |
| Glu | Ala | Glu | Lys | Val | Gln | Ala | Ala | His | Gln | Trp | Arg | Glu | Asp | Phe | Ala |
| | | 105 | | | | | 110 | | | | | 115 | | | |
| AGC | AAT | GAA | GTT | GTC | TAC | TAC | AAT | GCA | AAG | GAT | GAT | CTC | GAT | CCT | GAG | 436 |
| Ser | Asn | Glu | Val | Val | Tyr | Tyr | Asn | Ala | Lys | Asp | Asp | Leu | Asp | Pro | Glu |
| | 120 | | | | | 125 | | | | | 130 | | | | |
| AAA | AAT | GAC | AGT | GAG | CCA | GGC | AGC | CAG | AGG | ATA | AAA | CCT | GTT | TTC | ATT | 484 |
| Lys | Asn | Asp | Ser | Glu | Pro | Gly | Ser | Gln | Arg | Ile | Lys | Pro | Val | Phe | Ile |
| 135 | | | | | 140 | | | | | 145 | | | | | 150 |
| GAA | GAT | GCT | AAT | TTT | GGA | CGA | CAA | ATA | TCT | TAT | CAG | CAC | GCA | GCA | GTC | 532 |
| Glu | Asp | Ala | Asn | Phe | Gly | Arg | Gln | Ile | Ser | Tyr | Gln | His | Ala | Ala | Val |
| | | | | 155 | | | | | 160 | | | | | 165 | |
| CAT | ATT | CCT | ACT | GAC | ATC | TAT | GAG | GGC | TCA | ACA | ATT | GTG | TTA | AAT | GAA | 580 |
| His | Ile | Pro | Thr | Asp | Ile | Tyr | Glu | Gly | Ser | Thr | Ile | Val | Leu | Asn | Glu |
| | | | 170 | | | | | 175 | | | | | 180 | | |
| CTC | AAC | TGG | ACA | AGT | GCC | TTA | GAT | GAA | GTT | TTC | AAA | AAG | AAT | CGC | GAG | 628 |
| Leu | Asn | Trp | Thr | Ser | Ala | Leu | Asp | Glu | Val | Phe | Lys | Lys | Asn | Arg | Glu |
| | | | 185 | | | | | 190 | | | | | 195 | | |
| GAA | GAC | CCT | TCA | TTA | TTG | TGG | CAG | GTT | TTT | GGC | AGT | GCC | ACT | GGC | CTA | 676 |
| Glu | Asp | Pro | Ser | Leu | Leu | Trp | Gln | Val | Phe | Gly | Ser | Ala | Thr | Gly | Leu |
| | 200 | | | | | 205 | | | | | 210 | | | | |
| GCT | CGA | TAT | TAT | CCA | GCT | TCA | CCA | TGG | GTT | GAT | AAT | AGT | AGA | ACT | CCA | 724 |
| Ala | Arg | Tyr | Tyr | Pro | Ala | Ser | Pro | Trp | Val | Asp | Asn | Ser | Arg | Thr | Pro |
| 215 | | | | | 220 | | | | | 225 | | | | | 230 |
| AAT | AAG | ATT | GAC | CTT | TAT | GAT | GTA | CGC | AGA | AGA | CCA | TGG | TAC | ATC | CAA | 772 |
| Asn | Lys | Ile | Asp | Leu | Tyr | Asp | Val | Arg | Arg | Arg | Pro | Trp | Tyr | Ile | Gln |
| | | | | 235 | | | | | 240 | | | | | 245 | |
| GGA | GCT | GCA | TCT | CCT | AAA | GAC | ATG | CTT | ATT | CTG | GTG | GAT | GTG | AGT | GGA | 820 |
| Gly | Ala | Ala | Ser | Pro | Lys | Asp | Met | Leu | Ile | Leu | Val | Asp | Val | Ser | Gly |
| | | | 250 | | | | | 255 | | | | | 260 | | |
| AGT | GTT | AGT | GGA | TTG | ACA | CTT | AAA | CTG | ATC | CGA | ACA | TCT | GTC | TCC | GAA | 868 |
| Ser | Val | Ser | Gly | Leu | Thr | Leu | Lys | Leu | Ile | Arg | Thr | Ser | Val | Ser | Glu |
| | | 265 | | | | | 270 | | | | | 275 | | | |

| | | | | | | | | | | | | | | | | |
|---|---|---|---|---|---|---|---|---|---|---|---|---|---|---|---|---|
| ATG | TTA | GAA | ACC | CTC | TCA | GAT | GAT | GAT | TTC | GTG | AAT | GTA | GCT | TCA | TTT | 916 |
| Met | Leu | Glu | Thr | Leu | Ser | Asp | Asp | Asp | Phe | Val | Asn | Val | Ala | Ser | Phe | |
| | 280 | | | | 285 | | | | | 290 | | | | | | |
| AAC | AGC | AAT | GCT | CAG | GAT | GTA | AGC | TGT | TTT | CAG | CAC | CTT | GTC | CAA | GCA | 964 |
| Asn | Ser | Asn | Ala | Gln | Asp | Val | Ser | Cys | Phe | Gln | His | Leu | Val | Gln | Ala | |
| 295 | | | | 300 | | | | | 305 | | | | | | 310 | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys | Lys | Val | Leu | Lys | Asp | Ala | Val | Asn | Asn | Ile | Thr | |
| | | | | 315 | | | | | 320 | | | | | 325 | | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile | Thr | Asp | Tyr | Lys | Lys | Gly | Phe | Ser | Phe | Ala | Phe | Glu | |
| | | | 330 | | | | | 335 | | | | | 340 | | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | 345 | | | | | 350 | | | | | 355 | | | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| 360 | | | | | 365 | | | | | 370 | | | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | 380 | | | | | 385 | | | | | | 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | | 400 | | | | | 405 | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | 410 | | | | | 415 | | | | | 420 | | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | 425 | | | | | 430 | | | | | 435 | | | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| 440 | | | | | 445 | | | | | 450 | | | | | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | | 460 | | | | | 465 | | | | | 470 | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | | 475 | | | | | 480 | | | | | 485 | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | 490 | | | | | 495 | | | | | 500 | | | |
| CGT | TTT | ACA | CTG | TGC | CCC | AAT | GGG | TAT | TAC | TTT | GCA | ATC | GAT | CCT | AAT | 1588 |
| Arg | Phe | Thr | Leu | Cys | Pro | Asn | Gly | Tyr | Tyr | Phe | Ala | Ile | Asp | Pro | Asn | |
| | | 505 | | | | | 510 | | | | | 515 | | | | |
| GGT | TAT | GTT | TTA | TTA | CAT | CCA | AAT | CTT | CAG | CCA | AAG | AAC | CCC | AAA | TCT | 1636 |
| Gly | Tyr | Val | Leu | Leu | His | Pro | Asn | Leu | Gln | Pro | Lys | Asn | Pro | Lys | Ser | |
| | 520 | | | | | 525 | | | | | 530 | | | | | |
| CAG | GAG | CCA | GTA | ACA | TTG | GAT | TTC | CTT | GAT | GCA | GAG | TTA | GAG | AAT | GAT | 1684 |
| Gln | Glu | Pro | Val | Thr | Leu | Asp | Phe | Leu | Asp | Ala | Glu | Leu | Glu | Asn | Asp | |
| 535 | | | | | 540 | | | | | 545 | | | | | 550 | |
| ATT | AAA | GTG | GAG | ATT | CGA | AAT | AAG | ATG | ATT | GAT | GGG | GAA | AGT | GGA | GAA | 1732 |
| Ile | Lys | Val | Glu | Ile | Arg | Asn | Lys | Met | Ile | Asp | Gly | Glu | Ser | Gly | Glu | |
| | | | | 555 | | | | | 560 | | | | | 565 | | |
| AAA | ACA | TTC | AGA | ACT | CTG | GTT | AAA | TCT | CAA | GAT | GAG | AGA | TAT | ATT | GAC | 1780 |
| Lys | Thr | Phe | Arg | Thr | Leu | Val | Lys | Ser | Gln | Asp | Glu | Arg | Tyr | Ile | Asp | |
| | | | 570 | | | | | 575 | | | | | 580 | | | |
| AAA | GGA | AAC | AGG | ACA | TAC | ACA | TGG | ACA | CCT | GTC | AAT | GGC | ACA | GAT | TAC | 1828 |
| Lys | Gly | Asn | Arg | Thr | Tyr | Thr | Trp | Thr | Pro | Val | Asn | Gly | Thr | Asp | Tyr | |
| | | 585 | | | | | 590 | | | | | 595 | | | | |

| | | | | | | | | | | | | | | | | |
|---|---|---|---|---|---|---|---|---|---|---|---|---|---|---|---|---|
| AGT | TTG | GCC | TTG | GTA | TTA | CCA | ACC | TAC | AGT | TTT | TAC | TAT | ATA | AAA | GCC | 1876 |
| Ser | Leu | Ala | Leu | Val | Leu | Pro | Thr | Tyr | Ser | Phe | Tyr | Tyr | Ile | Lys | Ala | |
| 600 | | | | | 605 | | | | | 610 | | | | | | |
| AAA | CTA | GAA | GAG | ACA | ATA | ACT | CAG | GCC | AGA | TAT | TCG | GAA | ACC | CTG | AAG | 1924 |
| Lys | Leu | Glu | Glu | Thr | Ile | Thr | Gln | Ala | Arg | Tyr | Ser | Glu | Thr | Leu | Lys | |
| 615 | | | | 620 | | | | | 625 | | | | | | 630 | |
| CCA | GAT | AAT | TTT | GAA | GAA | TCT | GGC | TAT | ACA | TTC | ATA | GCA | CCA | AGA | GAT | 1972 |
| Pro | Asp | Asn | Phe | Glu | Glu | Ser | Gly | Tyr | Thr | Phe | Ile | Ala | Pro | Arg | Asp | |
| | | | 635 | | | | | 640 | | | | | 645 | | | |
| TAC | TGC | AAT | GAC | CTG | AAA | ATA | TCG | GAT | AAT | AAC | ACT | GAA | TTT | CTT | TTA | 2020 |
| Tyr | Cys | Asn | Asp | Leu | Lys | Ile | Ser | Asp | Asn | Asn | Thr | Glu | Phe | Leu | Leu | |
| | | | 650 | | | | 655 | | | | | 660 | | | | |
| AAT | TTC | AAC | GAG | TTT | ATT | GAT | AGA | AAA | ACT | CCA | AAC | AAC | CCA | TCA | TGT | 2068 |
| Asn | Phe | Asn | Glu | Phe | Ile | Asp | Arg | Lys | Thr | Pro | Asn | Asn | Pro | Ser | Cys | |
| | | 665 | | | | | 670 | | | | | 675 | | | | |
| AAC | GCG | GAT | TTG | ATT | AAT | AGA | GTC | TTG | CTT | GAT | GCA | GGC | TTT | ACA | AAT | 2116 |
| Asn | Ala | Asp | Leu | Ile | Asn | Arg | Val | Leu | Leu | Asp | Ala | Gly | Phe | Thr | Asn | |
| | 680 | | | | | 685 | | | | | 690 | | | | | |
| GAA | CTT | GTC | CAA | AAT | TAC | TGG | AGT | AAG | CAG | AAA | AAT | ATC | AAG | GGA | GTG | 2164 |
| Glu | Leu | Val | Gln | Asn | Tyr | Trp | Ser | Lys | Gln | Lys | Asn | Ile | Lys | Gly | Val | |
| 695 | | | | | 700 | | | | | 705 | | | | | 710 | |
| AAA | GCA | CGA | TTT | GTT | GTG | ACT | GAT | GGT | GGG | ATT | ACC | AGA | GTT | TAT | CCC | 2212 |
| Lys | Ala | Arg | Phe | Val | Val | Thr | Asp | Gly | Gly | Ile | Thr | Arg | Val | Tyr | Pro | |
| | | | | 715 | | | | 720 | | | | | | 725 | | |
| AAA | GAG | GCT | GGA | GAA | AAT | TGG | CAA | GAA | AAC | CCA | GAG | ACA | TAT | GAG | GAC | 2260 |
| Lys | Glu | Ala | Gly | Glu | Asn | Trp | Gln | Glu | Asn | Pro | Glu | Thr | Tyr | Glu | Asp | |
| | | | 730 | | | | | 735 | | | | | 740 | | | |
| AGC | TTC | TAT | AAA | AGG | AGC | CTA | GAT | AAT | GAT | AAC | TAT | GTT | TTC | ACT | GCT | 2308 |
| Ser | Phe | Tyr | Lys | Arg | Ser | Leu | Asp | Asn | Asp | Asn | Tyr | Val | Phe | Thr | Ala | |
| | | 745 | | | | | 750 | | | | | 755 | | | | |
| CCC | TAC | TTT | AAC | AAA | AGT | GGA | CCT | GGT | GCC | TAT | GAA | TCG | GGC | ATT | ATG | 2356 |
| Pro | Tyr | Phe | Asn | Lys | Ser | Gly | Pro | Gly | Ala | Tyr | Glu | Ser | Gly | Ile | Met | |
| | 760 | | | | | 765 | | | | | 770 | | | | | |
| GTA | AGC | AAA | GCT | GTA | GAA | ATA | TAT | ATT | CAA | GGG | AAA | CTT | CTT | AAA | CCT | 2404 |
| Val | Ser | Lys | Ala | Val | Glu | Ile | Tyr | Ile | Gln | Gly | Lys | Leu | Leu | Lys | Pro | |
| 775 | | | | | 780 | | | | | 785 | | | | | 790 | |
| GCA | GTT | GTT | GGA | ATT | AAA | ATT | GAT | GTA | AAT | TCC | TGG | ATA | GAG | AAT | TTC | 2452 |
| Ala | Val | Val | Gly | Ile | Lys | Ile | Asp | Val | Asn | Ser | Trp | Ile | Glu | Asn | Phe | |
| | | | | 795 | | | | 800 | | | | | | 805 | | |
| ACC | AAA | ACC | TCA | ATC | AGA | GAT | CCG | TGT | GCT | GGT | CCA | GTT | TGT | GAC | TGC | 2500 |
| Thr | Lys | Thr | Ser | Ile | Arg | Asp | Pro | Cys | Ala | Gly | Pro | Val | Cys | Asp | Cys | |
| | | | 810 | | | | | 815 | | | | | 820 | | | |
| AAA | AGA | AAC | AGT | GAC | GTA | ATG | GAT | TGT | GTG | ATT | CTG | GAT | GAT | GGT | GGG | 2548 |
| Lys | Arg | Asn | Ser | Asp | Val | Met | Asp | Cys | Val | Ile | Leu | Asp | Asp | Gly | Gly | |
| | | 825 | | | | 830 | | | | | 835 | | | | | |
| TTT | CTT | CTG | ATG | GCA | AAT | CAT | GAT | GAT | TAT | ACT | AAT | CAG | ATT | GGA | AGA | 2596 |
| Phe | Leu | Leu | Met | Ala | Asn | His | Asp | Asp | Tyr | Thr | Asn | Gln | Ile | Gly | Arg | |
| | 840 | | | | | 845 | | | | | 850 | | | | | |
| TTT | TTT | GGA | GAG | ATT | GAT | CCC | AGC | TTG | ATG | AGA | CAC | CTG | GTT | AAT | ATA | 2644 |
| Phe | Phe | Gly | Glu | Ile | Asp | Pro | Ser | Leu | Met | Arg | His | Leu | Val | Asn | Ile | |
| 855 | | | | | 860 | | | | | 865 | | | | | 870 | |
| TCA | GTT | TAT | GCT | TTT | AAC | AAA | TCT | TAT | GAT | TAT | CAG | TCA | GTA | TGT | GAG | 2692 |
| Ser | Val | Tyr | Ala | Phe | Asn | Lys | Ser | Tyr | Asp | Tyr | Gln | Ser | Val | Cys | Glu | |
| | | | | 875 | | | | 880 | | | | | 885 | | | |
| CCC | GGT | GCT | GCA | CCA | AAA | CAA | GGA | GCA | GGA | CAT | CGC | TCA | GCA | TAT | GTG | 2740 |
| Pro | Gly | Ala | Ala | Pro | Lys | Gln | Gly | Ala | Gly | His | Arg | Ser | Ala | Tyr | Val | |
| | | | 890 | | | | | 895 | | | | | 900 | | | |
| CCA | TCA | GTA | GCA | GAC | ATA | TTA | CAA | ATT | GGC | TGG | TGG | GCC | ACT | GCT | GCT | 2788 |
| Pro | Ser | Val | Ala | Asp | Ile | Leu | Gln | Ile | Gly | Trp | Trp | Ala | Thr | Ala | Ala | |
| | | 905 | | | | | 910 | | | | | 915 | | | | |

| | | | | | | | | | | | | | | | | |
|---|---|---|---|---|---|---|---|---|---|---|---|---|---|---|---|---|
| GCC | TGG | TCT | ATT | CTA | CAG | CAG | TTT | CTC | TTG | AGT | TTG | ACC | TTT | CCA | CGA | 2836 |
| Ala | Trp | Ser | Ile | Leu | Gln | Gln | Phe | Leu | Leu | Ser | Leu | Thr | Phe | Pro | Arg | |
| 920 | | | | | 925 | | | | | | 930 | | | | | |
| CTC | CTT | GAG | GCA | GTT | GAG | ATG | GAG | GAT | GAT | GAC | TTC | ACG | GCC | TCC | CTG | 2884 |
| Leu | Leu | Glu | Ala | Val | Glu | Met | Glu | Asp | Asp | Asp | Phe | Thr | Ala | Ser | Leu | |
| 935 | | | | 940 | | | | | 945 | | | | | | 950 | |
| TCC | AAG | CAG | AGC | TGC | ATT | ACT | GAA | CAA | ACC | CAG | TAT | TTC | TTC | GAT | AAC | 2932 |
| Ser | Lys | Gln | Ser | Cys | Ile | Thr | Glu | Gln | Thr | Gln | Tyr | Phe | Phe | Asp | Asn | |
| | | | | 955 | | | | | 960 | | | | | 965 | | |
| GAC | AGT | AAA | TCA | TTC | AGT | GGT | GTA | TTA | GAC | TGT | GGA | AAC | TGT | TCC | AGA | 2980 |
| Asp | Ser | Lys | Ser | Phe | Ser | Gly | Val | Leu | Asp | Cys | Gly | Asn | Cys | Ser | Arg | |
| | | | 970 | | | | | 975 | | | | | 980 | | | |
| ATC | TTT | CAT | GGA | GAA | AAG | CTT | ATG | AAC | ACC | AAC | TTA | ATA | TTC | ATA | ATG | 3028 |
| Ile | Phe | His | Gly | Glu | Lys | Leu | Met | Asn | Thr | Asn | Leu | Ile | Phe | Ile | Met | |
| | | 985 | | | | | 990 | | | | | 995 | | | | |
| GTT | GAG | AGC | AAA | GGG | ACA | TGT | CCA | TGT | GAC | ACA | CGA | CTG | CTC | ATA | CAA | 3076 |
| Val | Glu | Ser | Lys | Gly | Thr | Cys | Pro | Cys | Asp | Thr | Arg | Leu | Leu | Ile | Gln | |
| 1000 | | | | | | 1005 | | | | | 1010 | | | | | |
| GCG | GAG | CAG | ACT | TCT | GAC | GGT | CCA | AAT | CCT | TGT | GAC | ATG | GTT | AAG | CAA | 3124 |
| Ala | Glu | Gln | Thr | Ser | Asp | Gly | Pro | Asn | Pro | Cys | Asp | Met | Val | Lys | Gln | |
| 1015 | | | | | 1020 | | | | 1025 | | | | | 1030 | | |
| CCT | AGA | TAC | CGA | AAA | GGG | CCT | GAT | GTC | TGC | TTT | GAT | AAC | AAT | GTC | TTG | 3172 |
| Pro | Arg | Tyr | Arg | Lys | Gly | Pro | Asp | Val | Cys | Phe | Asp | Asn | Asn | Val | Leu | |
| | | | | 1035 | | | | | 1040 | | | | | 1045 | | |
| GAG | GAT | TAT | ACT | GAC | TGT | GGT | GGT | GTT | TCT | GGA | TTA | AAT | CCC | TCC | CTG | 3220 |
| Glu | Asp | Tyr | Thr | Asp | Cys | Gly | Gly | Val | Ser | Gly | Leu | Asn | Pro | Ser | Leu | |
| | | | | 1050 | | | | | 1055 | | | | | 1060 | | |
| TGG | TAT | ATC | ATT | GGA | ATC | CAG | TTT | CTA | CTA | CTT | TGG | CTG | GTA | TCT | GGC | 3268 |
| Trp | Tyr | Ile | Ile | Gly | Ile | Gln | Phe | Leu | Leu | Leu | Trp | Leu | Val | Ser | Gly | |
| | | | 1065 | | | | 1070 | | | | | 1075 | | | | |
| AGC | ACA | CAC | CGG | CTG | TTA | TGACCTTCTA | AAAACCAAAT | CTGCATAGTT | | | | | | | | 3316 |
| Ser | Thr | His | Arg | Leu | Leu | | | | | | | | | | | |
| | | | 1080 | | | 108 | | | | | | | | | | |
| AAACTCCAGA | CCCTGCCAAA | ACATGAGCCC | TGCCCTCAAT | TACAGTAACG | TAGGGTCAGC | | | | | | | | | | | 3376 |
| TATAAAATCA | GACAAACATT | AGCTGGGCCT | GTTCCATGGC | ATAACACTAA | GGCGCAGACT | | | | | | | | | | | 3436 |
| CCTAAGGCAC | CCACTGGCTG | CATGTCAGGG | TGTCAGATCC | TTAAACGTGT | GTGAATGCTG | | | | | | | | | | | 3496 |
| CATCATCTAT | GTGTAACATC | AAAGCAAAAT | CCTATACGTG | TCCTCTATTG | GAAAATTTGG | | | | | | | | | | | 3556 |
| GCGTTTGTTG | TTGCATTGTT | GGT | | | | | | | | | | | | | | 3579 |

( 2 ) INFORMATION FOR SEQ ID NO:26:

( i ) SEQUENCE CHARACTERISTICS:
        ( A ) LENGTH: 1681 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1437
        ( D ) OTHER INFORMATION: /standard_name="Beta-1-1"

( i x ) FEATURE:
        ( A ) NAME/KEY: 3'UTR
        ( B ) LOCATION: 1435..1681

( x i ) SEQUENCE DESCRIPTION: SEQ ID NO:26:

| | | | | | | | | | | | | | | | | |
|---|---|---|---|---|---|---|---|---|---|---|---|---|---|---|---|---|
| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAG | ATC | CCC | ATG | GAG | GTC | TTC | GAC | CCC | AGC | CCG | CAG | GGC | AAA | TAC | AGC | 96 |
| Glu | Ile | Pro | Met 20 | Glu | Val | Phe | Asp | Pro 25 | Ser | Pro | Gln | Gly | Lys 30 | Tyr | Ser | |
| AAG | AGG | AAA | GGG | CGA | TTC | AAA | CGG | TCA | GAT | GGG | AGC | ACG | TCC | TCG | GAT | 144 |
| Lys | Arg | Lys 35 | Gly | Arg | Phe | Lys | Arg 40 | Ser | Asp | Gly | Ser | Thr 45 | Ser | Ser | Asp | |
| ACC | ACA | TCC | AAC | AGC | TTT | GTC | CGC | CAG | GGC | TCA | GCG | GAG | TCC | TAC | ACC | 192 |
| Thr | Thr 50 | Ser | Asn | Ser | Phe | Val 55 | Arg | Gln | Gly | Ser | Ala 60 | Glu | Ser | Tyr | Thr | |
| AGC | CGT | CCA | TCA | GAC | TCT | GAT | GTA | TCT | CTG | GAG | GAG | GAC | CGG | GAA | GCC | 240 |
| Ser 65 | Arg | Pro | Ser | Asp | Ser 70 | Asp | Val | Ser | Leu | Glu 75 | Glu | Asp | Arg | Glu | Ala 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala 85 | Glu | Arg | Gln | Ala | Leu 90 | Ala | Gln | Leu | Glu | Lys 95 | Ala | |
| AAG | ACC | AAG | CCA | GTG | GCA | TTT | GCT | GTG | CGG | ACA | AAT | GTT | GGC | TAC | AAT | 336 |
| Lys | Thr | Lys | Pro 100 | Val | Ala | Phe | Ala | Val 105 | Arg | Thr | Asn | Val | Gly 110 | Tyr | Asn | |
| CCG | TCT | CCA | GGG | GAT | GAG | GTG | CCT | GTG | CAG | GGA | GTG | GCC | ATC | ACC | TTC | 384 |
| Pro | Ser | Pro 115 | Gly | Asp | Glu | Val | Pro 120 | Val | Gln | Gly | Val | Ala 125 | Ile | Thr | Phe | |
| GAG | CCC | AAA | GAC | TTC | CTG | CAC | ATC | AAG | GAG | AAA | TAC | AAT | AAT | GAC | TGG | 432 |
| Glu | Pro 130 | Lys | Asp | Phe | Leu | His 135 | Ile | Lys | Glu | Lys | Tyr 140 | Asn | Asn | Asp | Trp | |
| TGG | ATC | GGG | CGG | CTG | GTG | AAG | GAG | GGC | TGT | GAG | GTT | GGC | TTC | ATT | CCC | 480 |
| Trp 145 | Ile | Gly | Arg | Leu | Val 150 | Lys | Glu | Gly | Cys | Glu 155 | Val | Gly | Phe | Ile | Pro 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu 165 | Asp | Ser | Leu | Arg | Leu 170 | Leu | Gln | Glu | Gln | Lys 175 | Leu | |
| CGC | CAG | AAC | CGC | CTC | GGC | TCC | AGC | AAA | TCA | GGC | GAT | AAC | TCC | AGT | TCC | 576 |
| Arg | Gln | Asn | Arg 180 | Leu | Gly | Ser | Ser | Lys 185 | Ser | Gly | Asp | Asn | Ser 190 | Ser | Ser | |
| AGT | CTG | GGA | GAT | GTG | GTG | ACT | GGC | ACC | CGC | CGC | CCC | ACA | CCC | CCT | GCC | 624 |
| Ser | Leu | Gly | Asp 195 | Val | Val | Thr | Gly | Thr 200 | Arg | Arg | Pro | Thr | Pro 205 | Pro | Ala | |
| AGT | GGT | AAT | GAA | ATG | ACT | AAC | TTA | GCC | TTT | GAA | CTA | GAC | CCC | CTA | GAG | 672 |
| Ser | Gly 210 | Asn | Glu | Met | Thr | Asn 215 | Leu | Ala | Phe | Glu | Leu 220 | Asp | Pro | Leu | Glu | |
| TTA | GAG | GAG | GAA | GAG | GCT | GAG | CTT | GGT | GAG | CAG | AGT | GGC | TCT | GCC | AAG | 720 |
| Leu 225 | Glu | Glu | Glu | Glu | Ala 230 | Glu | Leu | Gly | Glu | Gln 235 | Ser | Gly | Ser | Ala | Lys 240 | |
| ACT | AGT | GTT | AGC | AGT | GTC | ACC | ACC | CCG | CCA | CCC | CAT | GGC | AAA | CGC | ATC | 768 |
| Thr | Ser | Val | Ser | Ser 245 | Val | Thr | Thr | Pro | Pro 250 | Pro | His | Gly | Lys | Arg 255 | Ile | |
| CCC | TTC | TTT | AAG | AAG | ACA | GAG | CAT | GTG | CCC | CCC | TAT | GAC | GTG | GTG | CCT | 816 |
| Pro | Phe | Phe | Lys 260 | Lys | Thr | Glu | His | Val 265 | Pro | Pro | Tyr | Asp | Val 270 | Val | Pro | |
| TCC | ATG | AGG | CCC | ATC | ATC | CTG | GTG | GGA | CCG | TCG | CTC | AAG | GGC | TAC | GAG | 864 |
| Ser | Met | Arg 275 | Pro | Ile | Ile | Leu | Val 280 | Gly | Pro | Ser | Leu | Lys 285 | Gly | Tyr | Glu | |
| GTT | ACA | GAC | ATG | ATG | CAG | AAA | GCT | TTA | TTT | GAC | TTC | TTG | AAG | CAT | CGG | 912 |
| Val | Thr | Asp 290 | Met | Met | Gln | Lys | Ala 295 | Leu | Phe | Asp | Phe | Leu 300 | Lys | His | Arg | |
| TTT | GAT | GGC | AGG | ATC | TCC | ATC | ACT | CGT | GTG | ACG | GCA | GAT | ATT | TCC | CTG | 960 |
| Phe 305 | Asp | Gly | Arg | Ile | Ser 310 | Ile | Thr | Arg | Val | Thr 315 | Ala | Asp | Ile | Ser | Leu 320 | |
| GCT | AAG | CGC | TCA | GTT | CTC | AAC | AAC | CCC | AGC | AAA | CAC | ATC | ATC | ATT | GAG | 1008 |
| Ala | Lys | Arg | Ser | Val 325 | Leu | Asn | Asn | Pro | Ser 330 | Lys | His | Ile | Ile | Ile 335 | Glu | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| CGC | TCC | AAC | ACA | CGC | TCC | AGC | CTG | GCT | GAG | GTG | CAG | AGT | GAA | ATC | GAG | 1056 |
| Arg | Ser | Asn | Thr | Arg | Ser | Ser | Leu | Ala | Glu | Val | Gln | Ser | Glu | Ile | Glu |      |
|     |     |     | 340 |     |     |     | 345 |     |     |     |     |     | 350 |     |     |      |
| CGA | ATC | TTC | GAG | CTG | GCC | CGG | ACC | CTT | CAG | TTG | GTC | GCT | CTG | GAT | GCT | 1104 |
| Arg | Ile | Phe | Glu | Leu | Ala | Arg | Thr | Leu | Gln | Leu | Val | Ala | Leu | Asp | Ala |      |
|     |     | 355 |     |     |     |     | 360 |     |     |     |     |     | 365 |     |     |      |
| GAC | ACC | ATC | AAT | CAC | CCA | GCC | CAG | CTG | TCC | AAG | ACC | TCG | CTG | GCC | CCC | 1152 |
| Asp | Thr | Ile | Asn | His | Pro | Ala | Gln | Leu | Ser | Lys | Thr | Ser | Leu | Ala | Pro |      |
|     | 370 |     |     |     |     | 375 |     |     |     |     | 380 |     |     |     |     |      |
| ATC | ATT | GTT | TAC | ATC | AAG | ATC | ACC | TCT | CCC | AAG | GTA | CTT | CAA | AGG | CTC | 1200 |
| Ile | Ile | Val | Tyr | Ile | Lys | Ile | Thr | Ser | Pro | Lys | Val | Leu | Gln | Arg | Leu |      |
| 385 |     |     |     |     | 390 |     |     |     |     | 395 |     |     |     |     | 400 |      |
| ATC | AAG | TCC | CGA | GGA | AAG | TCT | CAG | TCC | AAA | CAC | CTC | AAT | GTC | CAA | ATA | 1248 |
| Ile | Lys | Ser | Arg | Gly | Lys | Ser | Gln | Ser | Lys | His | Leu | Asn | Val | Gln | Ile |      |
|     |     |     |     | 405 |     |     |     |     | 410 |     |     |     |     | 415 |     |      |
| GCG | GCC | TCG | GAA | AAG | CTG | GCA | CAG | TGC | CCC | CCT | GAA | ATG | TTT | GAC | ATC | 1296 |
| Ala | Ala | Ser | Glu | Lys | Leu | Ala | Gln | Cys | Pro | Pro | Glu | Met | Phe | Asp | Ile |      |
|     |     |     | 420 |     |     |     |     | 425 |     |     |     |     | 430 |     |     |      |
| ATC | CTG | GAT | GAG | AAC | CAA | TTG | GAG | GAT | GCC | TGC | GAG | CAT | CTG | GCG | GAG | 1344 |
| Ile | Leu | Asp | Glu | Asn | Gln | Leu | Glu | Asp | Ala | Cys | Glu | His | Leu | Ala | Glu |      |
|     |     | 435 |     |     |     |     | 440 |     |     |     |     | 445 |     |     |     |      |
| TAC | TTG | GAA | GCC | TAT | TGG | AAG | GCC | ACA | CAC | CCG | CCC | AGC | AGC | ACG | CCA | 1392 |
| Tyr | Leu | Glu | Ala | Tyr | Trp | Lys | Ala | Thr | His | Pro | Pro | Ser | Ser | Thr | Pro |      |
|     | 450 |     |     |     |     | 455 |     |     |     |     | 460 |     |     |     |     |      |
| CCC | AAT | CCG | CTG | CTG | AAC | CGC | ACC | ATG | GCT | ACC | GCA | GCC | CTG | GCT |     | 1437 |
| Pro | Asn | Pro | Leu | Leu | Asn | Arg | Thr | Met | Ala | Thr | Ala | Ala | Leu | Ala |     |      |
| 465 |     |     |     |     | 470 |     |     |     |     | 475 |     |     |     |     |     |      |

```
GCCAGCCCTG CCCCTGTCTC CAACCTCCAG GTACAGGTGC TCACCTCGCT CAGGAGAAAC   1497
CTCGGCTTCT GGGGCGGGCT GGAGTCCTCA CAGCGGGGCA GTGTGGTGCC CCAGGAGCAG   1557
GAACATGCCA TGTAGTGGGC GCCCTGCCCG TCTTCCCTCC TGCTCTGGGG TCGGAACTGG   1617
AGTGCAGGGA ACATGGAGGA GGAAGGGAAG AGCTTTATTT TGTAAAAAAA TAAGATGAGC   1677
GGCA                                                                1681
```

( 2 ) INFORMATION FOR SEQ ID NO:27:

( i ) SEQUENCE CHARACTERISTICS:
        ( A ) LENGTH: 1526 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..651
        ( D ) OTHER INFORMATION: /standard_name="Beta 1-4"

( x i ) SEQUENCE DESCRIPTION: SEQ ID NO:27:

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| ATG | GTC | CAG | AAG | ACC | AGC | ATG | TCC | CGG | GGC | CCT | TAC | CCA | CCC | TCC | CAG | 48  |
| Met | Val | Gln | Lys | Thr | Ser | Met | Ser | Arg | Gly | Pro | Tyr | Pro | Pro | Ser | Gln |     |
| 1   |     |     |     | 5   |     |     |     |     | 10  |     |     |     |     | 15  |     |     |
| GAG | ATC | CCC | ATG | GAG | GTC | TTC | GAC | CCC | AGC | CCG | CAG | GGC | AAA | TAC | AGC | 96  |
| Glu | Ile | Pro | Met | Glu | Val | Phe | Asp | Pro | Ser | Pro | Gln | Gly | Lys | Tyr | Ser |     |
|     |     |     | 20  |     |     |     |     | 25  |     |     |     |     | 30  |     |     |     |
| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp |     |
|     |     | 35  |     |     |     |     | 40  |     |     |     |     | 45  |     |     |     |     |
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr |     |
|     | 50  |     |     |     |     | 55  |     |     |     |     | 60  |     |     |     |     |     |

| | | | | | | | | | | | | | | | | |
|---|---|---|---|---|---|---|---|---|---|---|---|---|---|---|---|---|
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | 70 | | | | | 75 | | | | | | 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GAC | AGA | GCA | TGT | GCC | CCC | CTA | TGACGTGGTG | CCTTCCATGA | GGCCCATCAT | | | | | | 678 |
| Ser | Asp | Arg | Ala | Cys | Ala | Pro | Leu | | | | | | | | | |
| | 210 | | | | | 215 | | | | | | | | | | |

| | | | | | |
|---|---|---|---|---|---|
| CCTGGTGGGA | CCGTCGCTCA | AGGGCTACGA | GGTTACAGAC | ATGATGCAGA | AGCTTTATT | 738 |
| TGACTTCTTG | AAGCATCGGT | TTGATGGCAG | GATCTCCATC | ACTCGTGTGA | CGGCAGATAT | 798 |
| TTCCCTGGCT | AAGCGCTCAG | TTCTCAACAA | CCCCAGCAAA | CACATCATCA | TTGAGCGCTC | 858 |
| CAACACACGC | TCCAGCCTGG | CTGAGGTGCA | GAGTGAAATC | GAGCGAATCT | TCGAGCTGGC | 918 |
| CCGGACCCTT | CAGTTGGTCG | CTCTGGATGC | TGACACCATC | AATCACCCAG | CCCAGCTGTC | 978 |
| CAAGACCTCG | CTGGCCCCCA | TCATTGTTTA | CATCAAGATC | ACCTCTCCCA | AGGTACTTCA | 1038 |
| AAGGCTCATC | AAGTCCCGAG | GAAAGTCTCA | GTCCAAACAC | CTCAATGTCC | AAATAGCGGC | 1098 |
| CTCGGAAAAG | CTGGCACAGT | GCCCCCTGA  | AATGTTTGAC | ATCATCCTGG | ATGAGAACCA | 1158 |
| ATTGGAGGAT | GCCTGCGAGC | ATCTGGCGGA | GTACTTGGAA | GCCTATTGGA | AGGCCACACA | 1218 |
| CCCGCCCAGC | AGCACGCCAC | CCAATCCGCT | GCTGAACCGC | ACCATGGCTA | CCGCAGCCCT | 1278 |
| GGCTGCCAGC | CCTGCCCCTG | TCTCCAACCT | CCAGGTACAG | GTGCTCACCT | CGCTCAGGAG | 1338 |
| AAACCTCGGC | TTCTGGGGCG | GGCTGGAGTC | CTCACAGCGG | GGCAGTGTGG | TGCCCCAGGA | 1398 |
| GCAGGAACAT | GCCATGTAGT | GGGCGCCCTG | CCCGTCTTCC | CTCCTGCTCT | GGGGTCGGAA | 1458 |
| CTGGAGTGCA | GGGAACATGG | AGGAGGAAGG | GAAGAGCTTT | ATTTTGTAAA | AAAATAAGAT | 1518 |
| GAGCGGCA | | | | | | 1526 |

( 2 ) INFORMATION FOR SEQ ID NO:28:

( i ) SEQUENCE CHARACTERISTICS:
        ( A ) LENGTH: 1393 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: 1..660
    ( D ) OTHER INFORMATION: /standard_name="Beta-1-5"

( x i ) SEQUENCE DESCRIPTION: SEQ ID NO:28:

```
ATG GTC CAG AAG ACC AGC ATG TCC CGG GGC CCT TAC CCA CCC TCC CAG     48
Met Val Gln Lys Thr Ser Met Ser Arg Gly Pro Tyr Pro Pro Ser Gln
 1               5                  10                  15

GAG ATC CCC ATG GAG GTC TTC GAC CCC AGC CCG CAG GGC AAA TAC AGC     96
Glu Ile Pro Met Glu Val Phe Asp Pro Ser Pro Gln Gly Lys Tyr Ser
                 20                  25                  30

AAG AGG AAA GGG CGA TTC AAA CGG TCA GAT GGG AGC ACG TCC TCG GAT    144
Lys Arg Lys Gly Arg Phe Lys Arg Ser Asp Gly Ser Thr Ser Ser Asp
             35                  40                  45

ACC ACA TCC AAC AGC TTT GTC CGC CAG GGC TCA GCG GAG TCC TAC ACC    192
Thr Thr Ser Asn Ser Phe Val Arg Gln Gly Ser Ala Glu Ser Tyr Thr
 50                  55                  60

AGC CGT CCA TCA GAC TCT GAT GTA TCT CTG GAG GAG GAC CGG GAA GCC    240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC    288
Leu Arg Lys Glu Ala Glu Arg Gln Ala Leu Ala Gln Leu Glu Lys Ala
                 85                  90                  95

AAG ACC AAG CCA GTG GCA TTT GCT GTG CGG ACA AAT GTT GGC TAC AAT    336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC    384
Pro Ser Pro Gly Asp Glu Val Pro Val Gln Gly Val Ala Ile Thr Phe
            115                 120                 125

GAG CCC AAA GAC TTC CTG CAC ATC AAG GAG AAA TAC AAT AAT GAC TGG    432
Glu Pro Lys Asp Phe Leu His Ile Lys Glu Lys Tyr Asn Asn Asp Trp
130                 135                 140

TGG ATC GGG CGG CTG GTG AAG GAG GGC TGT GAG GTT GGC TTC ATT CCC    480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG    528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC    576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC    624
Ser Leu Gly Asp Val Val Thr Gly Thr Arg Arg Pro Thr Pro Pro Ala
            195                 200                 205

AGT GGT TAC AGA CAT GAT GCA GAA AGC TTT ATT TGACTTCTTG AAGCATCGGT  677
Ser Gly Tyr Arg His Asp Ala Glu Ser Phe Ile
210                 215                 220

TTGATGGCAG GATCTCCATC ACTCGTGTGA CGGCAGATAT TTCCCTGGCT AAGCGCTCAG  737

TTCTCAACAA CCCCAGCAAA CACATCATCA TTGAGCGCTC CAACACACGC TCCAGCCTGG  797

CTGAGGTGCA GAGTGAAATC GAGCGAATCT TCGAGCTGGC CCGGACCCTT CAGTTGGTCG  857

CTCTGGATGC TGACACCATC AATCACCCAG CCCAGCTGTC CAAGACCTCG CTGGCCCCCA  917

TCATTGTTTA CATCAAGATC ACCTCTCCCA AGGTACTTCA AAGGCTCATC AAGTCCCGAG  977

GAAAGTCTCA GTCCAAACAC CTCAATGTCC AAATAGCGGC CTCGGAAAAG CTGGCACAGT 1037

GCCCCCCTGA AATGTTTGAC ATCATCCTGG ATGAGAACCA ATTGGAGGAT GCCTGCGAGC 1097

ATCTGGCGGA GTACTTGGAA GCCTATTGGA AGGCCACACA CCCGCCCAGC AGCACGCCAC 1157
```

-continued

| | | | | | |
|---|---|---|---|---|---|
| CCAATCCGCT | GCTGAACCGC | ACCATGGCTA | CCGCAGCCCT | GGCTGCCAGC | CCTGCCCCTG | 1217 |
| TCTCCAACCT | CCAGGTACAG | GTGCTCACCT | CGCTCAGGAG | AAACCTCGGC | TTCTGGGGCG | 1277 |
| GGCTGGAGTC | CTCACAGCGG | GGCAGTGTGG | TGCCCCAGGA | GCAGGAACAT | GCCATGTAGT | 1337 |
| GGGCGCCCTG | CCCGTCTTCC | CTCCTGCTCT | GGGGTCGGAA | CTGGAGTGCA | GGGAAC | 1393 |

( 2 ) INFORMATION FOR SEQ ID NO: 29:

( i ) SEQUENCE CHARACTERISTICS:
        ( A ) LENGTH: 7635 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 511..6996

( i x ) FEATURE:
        ( A ) NAME/KEY: 5'UTR
        ( B ) LOCATION: 1..510

( i x ) FEATURE:
        ( A ) NAME/KEY: 3'UTR
        ( B ) LOCATION: 6994..7635

( x i ) SEQUENCE DESCRIPTION: SEQ ID NO:29:

```
GGGCGAGCGC CTCCGTCCCC GGATGTGAGC TCCGGCTGCC CGCGGTCCCG AGCCAGCGGC      60

GCGCGGGCGG CGGCGGCGGG CACCGGGCAC CGCGGCGGGC GGGCAGACGG GCGGGCATGG     120

GGGGAGCGCC GAGCGGCCCC GGCGGCCGGG CCGGCATCAC CGCGGCGTCT CTCCGCTAGA     180

GGAGGGGACA AGCCAGTTCT CCTTTGCAGC AAAAAATTAC ATGTATATAT TATTAAGATA     240

ATATATACAT TGGATTTTAT TTTTTAAAA AGTTTATTTT GCTCCATTTT TGAAAAGAG       300

AGAGCTTGGG TGGCGAGCGG TTTTTTTTA AAATCAATTA TCCTTATTTT CTGTTATTTG      360

TCCCCGTCCC TCCCCACCCC CCTGCTGAAG CGAGAATAAG GGCAGGGACC GCGGCTCCTA     420

CCTCTTGGTG ATCCCCTTCC CCATTCCGCC CCGCCCCAA CGCCCAGCAC AGTGCCCTGC      480

ACACAGTAGT CGCTCAATAA ATGTTCGTGG ATG ATG ATG ATG ATG ATG ATG AAA      534
                                 Met Met Met Met Met Met Met Lys
                                  1               5

AAA ATG CAG CAT CAA CGG CAG CAG CAA GCG GAC CAC GCG AAC GAG GCA       582
Lys Met Gln His Gln Arg Gln Gln Gln Ala Asp His Ala Asn Glu Ala
         10              15                  20

AAC TAT GCA AGA GGC ACC AGA CTT CCT CTT TCT GGT GAA GGA CCA ACT       630
Asn Tyr Ala Arg Gly Thr Arg Leu Pro Leu Ser Gly Glu Gly Pro Thr
 25              30                  35                  40

TCT CAG CCG AAT AGC TCC AAG CAA ACT GTC CTG TCT TGG CAA GCT GCA       678
Ser Gln Pro Asn Ser Ser Lys Gln Thr Val Leu Ser Trp Gln Ala Ala
             45                  50                  55

ATC GAT GCT GCT AGA CAG GCC AAG GCT GCC CAA ACT ATG AGC ACC TCT       726
Ile Asp Ala Ala Arg Gln Ala Lys Ala Ala Gln Thr Met Ser Thr Ser
             60                  65                  70

GCA CCC CCA CCT GTA GGA TCT CTC TCC CAA AGA AAA CGT CAG CAA TAC       774
Ala Pro Pro Pro Val Gly Ser Leu Ser Gln Arg Lys Arg Gln Gln Tyr
         75                  80                  85

GCC AAG AGC AAA AAA CAG GGT AAC TCG TCC AAC AGC CGA CCT GCC CGC       822
Ala Lys Ser Lys Lys Gln Gly Asn Ser Ser Asn Ser Arg Pro Ala Arg
         90                  95                 100

GCC CTT TTC TGT TTA TCA CTC AAT AAC CCC ATC CGA AGA GCC TGC ATT       870
Ala Leu Phe Cys Leu Ser Leu Asn Asn Pro Ile Arg Arg Ala Cys Ile
105                 110                 115                 120
```

-continued

| | | | | | | | | | | | | | | | | |
|---|---|---|---|---|---|---|---|---|---|---|---|---|---|---|---|---|
| AGT | ATA | GTG | GAA | TGG | AAA | CCA | TTT | GAC | ATA | TTT | ATA | TTA | TTG | GCT | ATT | 918 |
| Ser | Ile | Val | Glu | Trp | Lys | Pro | Phe | Asp | Ile | Phe | Ile | Leu | Leu | Ala | Ile | |
| | | | 125 | | | | | 130 | | | | | | 135 | | |
| TTT | GCC | AAT | TGT | GTG | GCC | TTA | GCT | ATT | TAC | ATC | CCA | TTC | CCT | GAA | GAT | 966 |
| Phe | Ala | Asn | Cys | Val | Ala | Leu | Ala | Ile | Tyr | Ile | Pro | Phe | Pro | Glu | Asp | |
| | | | 140 | | | | | 145 | | | | | 150 | | | |
| GAT | TCT | AAT | TCA | ACA | AAT | CAT | AAC | TTG | GAA | AAA | GTA | GAA | TAT | GCC | TTC | 1014 |
| Asp | Ser | Asn | Ser | Thr | Asn | His | Asn | Leu | Glu | Lys | Val | Glu | Tyr | Ala | Phe | |
| | | | 155 | | | | | 160 | | | | | 165 | | | |
| CTG | ATT | ATT | TTT | ACA | GTC | GAG | ACA | TTT | TTG | AAG | ATT | ATA | GCG | TAT | GGA | 1062 |
| Leu | Ile | Ile | Phe | Thr | Val | Glu | Thr | Phe | Leu | Lys | Ile | Ile | Ala | Tyr | Gly | |
| | | 170 | | | | | 175 | | | | | 180 | | | | |
| TTA | TTG | CTA | CAT | CCT | AAT | GCT | TAT | GTT | AGG | AAT | GGA | TGG | AAT | TTA | CTG | 1110 |
| Leu | Leu | Leu | His | Pro | Asn | Ala | Tyr | Val | Arg | Asn | Gly | Trp | Asn | Leu | Leu | |
| 185 | | | | | 190 | | | | | 195 | | | | | 200 | |
| GAT | TTT | GTT | ATA | GTA | ATA | GTA | GGA | TTG | TTT | AGT | GTA | ATT | TTG | GAA | CAA | 1158 |
| Asp | Phe | Val | Ile | Val | Ile | Val | Gly | Leu | Phe | Ser | Val | Ile | Leu | Glu | Gln | |
| | | | | 205 | | | | | 210 | | | | | 215 | | |
| TTA | ACC | AAA | GAA | ACA | GAA | GGC | GGG | AAC | CAC | TCA | AGC | GGC | AAA | TCT | GGA | 1206 |
| Leu | Thr | Lys | Glu | Thr | Glu | Gly | Gly | Asn | His | Ser | Ser | Gly | Lys | Ser | Gly | |
| | | | 220 | | | | | 225 | | | | | 230 | | | |
| GGC | TTT | GAT | GTC | AAA | GCC | CTC | CGT | GCC | TTT | CGA | GTG | TTG | CGA | CCA | CTT | 1254 |
| Gly | Phe | Asp | Val | Lys | Ala | Leu | Arg | Ala | Phe | Arg | Val | Leu | Arg | Pro | Leu | |
| | | 235 | | | | | 240 | | | | | 245 | | | | |
| CGA | CTA | GTG | TCA | GGA | GTG | CCC | AGT | TTA | CAA | GTT | GTC | CTG | AAC | TCC | ATT | 1302 |
| Arg | Leu | Val | Ser | Gly | Val | Pro | Ser | Leu | Gln | Val | Val | Leu | Asn | Ser | Ile | |
| | | 250 | | | | | 255 | | | | | 260 | | | | |
| ATA | AAA | GCC | ATG | GTT | CCC | CTC | CTT | CAC | ATA | GCC | CTT | TGT | GTA | TTA | TTT | 1350 |
| Ile | Lys | Ala | Met | Val | Pro | Leu | Leu | His | Ile | Ala | Leu | Leu | Val | Leu | Phe | |
| 265 | | | | | 270 | | | | | 275 | | | | | 280 | |
| GTA | ATC | ATA | ATC | TAT | GCT | ATT | ATA | GGA | TTG | GAA | CTT | TTT | ATT | GGA | AAA | 1398 |
| Val | Ile | Ile | Ile | Tyr | Ala | Ile | Ile | Gly | Leu | Glu | Leu | Phe | Ile | Gly | Lys | |
| | | | | 285 | | | | | 290 | | | | | 295 | | |
| ATG | CAC | AAA | ACA | TGT | TTT | TTT | GCT | GAC | TCA | GAT | ATC | GTA | GCT | GAA | GAG | 1446 |
| Met | His | Lys | Thr | Cys | Phe | Phe | Ala | Asp | Ser | Asp | Ile | Val | Ala | Glu | Glu | |
| | | | 300 | | | | | 305 | | | | | 310 | | | |
| GAC | CCA | GCT | CCA | TGT | GCG | TTC | TCA | GGG | AAT | GGA | CGC | CAG | TGT | ACT | GCC | 1494 |
| Asp | Pro | Ala | Pro | Cys | Ala | Phe | Ser | Gly | Asn | Gly | Arg | Gln | Cys | Thr | Ala | |
| | | | 315 | | | | | 320 | | | | | 325 | | | |
| AAT | GGC | ACG | GAA | TGT | AGG | AGT | GGC | TGG | GTT | GGC | CCG | AAC | GGA | GGC | ATC | 1542 |
| Asn | Gly | Thr | Glu | Cys | Arg | Ser | Gly | Trp | Val | Gly | Pro | Asn | Gly | Gly | Ile | |
| | 330 | | | | | 335 | | | | | 340 | | | | | |
| ACC | AAC | TTT | GAT | AAC | TTT | GCC | TTT | GCC | ATG | CTT | ACT | GTG | TTT | CAG | TGC | 1590 |
| Thr | Asn | Phe | Asp | Asn | Phe | Ala | Phe | Ala | Met | Leu | Thr | Val | Phe | Gln | Cys | |
| 345 | | | | | 350 | | | | | 355 | | | | | 360 | |
| ATC | ACC | ATG | GAG | GGC | TGG | ACA | GAC | GTG | CTC | TAC | TGG | GTA | AAT | GAT | GCG | 1638 |
| Ile | Thr | Met | Glu | Gly | Trp | Thr | Asp | Val | Leu | Tyr | Trp | Val | Asn | Asp | Ala | |
| | | | | 365 | | | | | 370 | | | | | 375 | | |
| ATA | GGA | TGG | GAA | TGG | CCA | TGG | GTG | TAT | TTT | GTT | AGT | CTG | ATC | ATC | CTT | 1686 |
| Ile | Gly | Trp | Glu | Trp | Pro | Trp | Val | Tyr | Phe | Val | Ser | Leu | Ile | Ile | Leu | |
| | | | | 380 | | | | | 385 | | | | | 390 | | |
| GGC | TCA | TTT | TTC | GTC | CTT | AAC | CTG | GTT | CTT | GGT | GTC | CTT | AGT | GGA | GAA | 1734 |
| Gly | Ser | Phe | Phe | Val | Leu | Asn | Leu | Val | Leu | Gly | Val | Leu | Ser | Gly | Glu | |
| | | 395 | | | | | 400 | | | | | 405 | | | | |
| TTC | TCA | AAG | GAA | AGA | GAG | AAG | GCA | AAA | GCA | CGG | GGA | GAT | TTC | CAG | AAG | 1782 |
| Phe | Ser | Lys | Glu | Arg | Glu | Lys | Ala | Lys | Ala | Arg | Gly | Asp | Phe | Gln | Lys | |
| | | 410 | | | | | 415 | | | | | 420 | | | | |
| CTC | CGG | GAG | AAG | CAG | CAG | CTG | GAG | GAG | GAT | CTA | AAG | GGC | TAC | TTG | GAT | 1830 |
| Leu | Arg | Glu | Lys | Gln | Gln | Leu | Glu | Glu | Asp | Leu | Lys | Gly | Tyr | Leu | Asp | |
| 425 | | | | | 430 | | | | | 435 | | | | | 440 | |

| | | | | | | | | | | | | | | | | |
|---|---|---|---|---|---|---|---|---|---|---|---|---|---|---|---|---|
| TGG | ATC | ACC | CAA | GCT | GAG | GAC | ATC | GAT | CCG | GAG | AAT | GAG | GAA | GAA | GGA | 1878 |
| Trp | Ile | Thr | Gln | Ala | Glu | Asp | Ile | Asp | Pro | Glu | Asn | Glu | Glu | Glu | Gly | |
| | | | 445 | | | | | 450 | | | | | 455 | | | |
| GGA | GAG | GAA | GGC | AAA | CGA | AAT | ACT | AGC | ATG | CCC | ACC | AGC | GAG | ACT | GAG | 1926 |
| Gly | Glu | Glu | Gly | Lys | Arg | Asn | Thr | Ser | Met | Pro | Thr | Ser | Glu | Thr | Glu | |
| | | | 460 | | | | | 465 | | | | | 470 | | | |
| TCT | GTG | AAC | ACA | GAG | AAC | GTC | AGC | GGT | GAA | GGC | GAG | AAC | CGA | GGC | TGC | 1974 |
| Ser | Val | Asn | Thr | Glu | Asn | Val | Ser | Gly | Glu | Gly | Glu | Asn | Arg | Gly | Cys | |
| | | 475 | | | | | 480 | | | | | 485 | | | | |
| TGT | GGA | AGT | CTC | TGT | CAA | GCC | ATC | TCA | AAA | TCC | AAA | CTC | AGC | CGA | CGC | 2022 |
| Cys | Gly | Ser | Leu | Cys | Gln | Ala | Ile | Ser | Lys | Ser | Lys | Leu | Ser | Arg | Arg | |
| | 490 | | | | 495 | | | | | 500 | | | | | | |
| TGG | CGT | CGC | TGG | AAC | CGA | TTC | AAT | CGC | AGA | AGA | TGT | AGG | GCC | GCC | GTG | 2070 |
| Trp | Arg | Arg | Trp | Asn | Arg | Phe | Asn | Arg | Arg | Arg | Cys | Arg | Ala | Ala | Val | |
| 505 | | | | 510 | | | | | 515 | | | | | 520 | | |
| AAG | TCT | GTC | ACG | TTT | TAC | TGG | CTG | GTT | ATC | GTC | CTG | GTG | TTT | CTG | AAC | 2118 |
| Lys | Ser | Val | Thr | Phe | Tyr | Trp | Leu | Val | Ile | Val | Leu | Val | Phe | Leu | Asn | |
| | | | | 525 | | | | | 530 | | | | | 535 | | |
| ACC | TTA | ACC | ATT | TCC | TCT | GAG | CAC | TAC | AAT | CAG | CCA | GAT | TGG | TTG | ACA | 2166 |
| Thr | Leu | Thr | Ile | Ser | Ser | Glu | His | Tyr | Asn | Gln | Pro | Asp | Trp | Leu | Thr | |
| | | | 540 | | | | | 545 | | | | | 550 | | | |
| CAG | ATT | CAA | GAT | ATT | GCC | AAC | AAA | GTC | CTC | TTG | GCT | CTG | TTC | ACC | TGC | 2214 |
| Gln | Ile | Gln | Asp | Ile | Ala | Asn | Lys | Val | Leu | Leu | Ala | Leu | Phe | Thr | Cys | |
| | | 555 | | | | | 560 | | | | | 565 | | | | |
| GAG | ATG | CTG | GTA | AAA | ATG | TAC | AGC | TTG | GGC | CTC | CAA | GCA | TAT | TTC | GTC | 2262 |
| Glu | Met | Leu | Val | Lys | Met | Tyr | Ser | Leu | Gly | Leu | Gln | Ala | Tyr | Phe | Val | |
| 570 | | | | | 575 | | | | | 580 | | | | | | |
| TCT | CTT | TTC | AAC | CGG | TTT | GAT | TGC | TTC | GTG | GTG | TGT | GGT | GGA | ATC | ACT | 2310 |
| Ser | Leu | Phe | Asn | Arg | Phe | Asp | Cys | Phe | Val | Val | Cys | Gly | Gly | Ile | Thr | |
| 585 | | | | | 590 | | | | | 595 | | | | | 600 | |
| GAG | ACG | ATC | TTG | GTG | GAA | CTG | GAA | ATC | ATG | TCT | CCC | CTG | GGG | ATC | TCT | 2358 |
| Glu | Thr | Ile | Leu | Val | Glu | Leu | Glu | Ile | Met | Ser | Pro | Leu | Gly | Ile | Ser | |
| | | | | 605 | | | | | 610 | | | | | 615 | | |
| GTG | TTT | CGG | TGT | GTG | CGC | CTC | TTA | AGA | ATC | TTC | AAA | GTG | ACC | AGG | CAC | 2406 |
| Val | Phe | Arg | Cys | Val | Arg | Leu | Leu | Arg | Ile | Phe | Lys | Val | Thr | Arg | His | |
| | | | 620 | | | | | 625 | | | | | 630 | | | |
| TGG | ACT | TCC | CTG | AGC | AAC | TTA | GTG | GCA | TCC | TTA | TTA | AAC | TCC | ATG | AAG | 2454 |
| Trp | Thr | Ser | Leu | Ser | Asn | Leu | Val | Ala | Ser | Leu | Leu | Asn | Ser | Met | Lys | |
| | | 635 | | | | | 640 | | | | | 645 | | | | |
| TCC | ATC | GCT | TCG | CTG | TTG | CTT | CTG | CTT | TTT | CTC | TTC | ATT | ATC | ATC | TTT | 2502 |
| Ser | Ile | Ala | Ser | Leu | Leu | Leu | Leu | Leu | Phe | Leu | Phe | Ile | Ile | Ile | Phe | |
| | 650 | | | | | 655 | | | | | 660 | | | | | |
| TCC | TTG | CTT | GGG | ATG | CAG | CTG | TTT | GGC | GGC | AAG | TTT | AAT | TTT | GAT | GAA | 2550 |
| Ser | Leu | Leu | Gly | Met | Gln | Leu | Phe | Gly | Gly | Lys | Phe | Asn | Phe | Asp | Glu | |
| 665 | | | | | 670 | | | | | 675 | | | | | 680 | |
| ACG | CAA | ACC | AAG | CGG | AGC | ACC | TTT | GAC | AAT | TTC | CCT | CAA | GCA | CTT | CTC | 2598 |
| Thr | Gln | Thr | Lys | Arg | Ser | Thr | Phe | Asp | Asn | Phe | Pro | Gln | Ala | Leu | Leu | |
| | | | | 685 | | | | | 690 | | | | | 695 | | |
| ACA | GTG | TTC | CAG | ATC | CTG | ACA | GGC | GAA | GAC | TGG | AAT | GCT | GTG | ATG | TAC | 2646 |
| Thr | Val | Phe | Gln | Ile | Leu | Thr | Gly | Glu | Asp | Trp | Asn | Ala | Val | Met | Tyr | |
| | | | 700 | | | | | 705 | | | | | 710 | | | |
| GAT | GGC | ATC | ATG | GCT | TAC | GGG | GGC | CCA | TCC | TCT | TCA | GGA | ATG | ATC | GTC | 2694 |
| Asp | Gly | Ile | Met | Ala | Tyr | Gly | Gly | Pro | Ser | Ser | Ser | Gly | Met | Ile | Val | |
| | | 715 | | | | | 720 | | | | | 725 | | | | |
| TGC | ATC | TAC | TTC | ATC | ATC | CTC | TTC | ATT | TGT | GGT | AAC | TAT | ATT | CTA | CTG | 2742 |
| Cys | Ile | Tyr | Phe | Ile | Ile | Leu | Phe | Ile | Cys | Gly | Asn | Tyr | Ile | Leu | Leu | |
| | 730 | | | | | 735 | | | | | 740 | | | | | |
| AAT | GTC | TTC | TTG | GCC | ATC | GCT | GTA | GAC | AAT | TTG | GCT | GAT | GCT | GAA | AGT | 2790 |
| Asn | Val | Phe | Leu | Ala | Ile | Ala | Val | Asp | Asn | Leu | Ala | Asp | Ala | Glu | Ser | |
| 745 | | | | | 750 | | | | | 755 | | | | | 760 | |

| | | | | | | | | | | | | | | | | |
|---|---|---|---|---|---|---|---|---|---|---|---|---|---|---|---|---|
| CTG | AAC | ACT | GCT | CAG | AAA | GAA | GAA | GCG | GAA | GAA | AAG | GAG | AGG | AAA | AAG | 2838 |
| Leu | Asn | Thr | Ala | Gln | Lys | Glu | Glu | Ala | Glu | Glu | Lys | Glu | Arg | Lys | Lys | |
| | | | | 765 | | | | | 770 | | | | | 775 | | |
| ATT | GCC | AGA | AAA | GAG | AGC | CTA | GAA | AAT | AAA | AAG | AAC | AAC | AAA | CCA | GAA | 2886 |
| Ile | Ala | Arg | Lys | Glu | Ser | Leu | Glu | Asn | Lys | Lys | Asn | Asn | Lys | Pro | Glu | |
| | | | 780 | | | | | 785 | | | | | 790 | | | |
| GTC | AAC | CAG | ATA | GCC | AAC | AGT | GAC | AAC | AAG | GTT | ACA | ATT | GAT | GAC | TAT | 2934 |
| Val | Asn | Gln | Ile | Ala | Asn | Ser | Asp | Asn | Lys | Val | Thr | Ile | Asp | Asp | Tyr | |
| | | 795 | | | | | 800 | | | | | 805 | | | | |
| AGA | GAA | GAG | GAT | GAA | GAC | AAG | GAC | CCC | TAT | CCG | CCT | TGC | GAT | GTG | CCA | 2982 |
| Arg | Glu | Glu | Asp | Glu | Asp | Lys | Asp | Pro | Tyr | Pro | Pro | Cys | Asp | Val | Pro | |
| | 810 | | | | | 815 | | | | | 820 | | | | | |
| GTA | GGG | GAA | GAG | GAA | GAG | GAA | GAG | GAG | GAG | GAT | GAA | CCT | GAG | GTT | CCT | 3030 |
| Val | Gly | Glu | Glu | Glu | Glu | Glu | Glu | Glu | Glu | Asp | Glu | Pro | Glu | Val | Pro | |
| 825 | | | | | 830 | | | | | 835 | | | | | 840 | |
| GCC | GGA | CCC | CGT | CCT | CGA | AGG | ATC | TCG | GAG | TTG | AAC | ATG | AAG | GAA | AAA | 3078 |
| Ala | Gly | Pro | Arg | Pro | Arg | Arg | Ile | Ser | Glu | Leu | Asn | Met | Lys | Glu | Lys | |
| | | | | 845 | | | | | 850 | | | | | 855 | | |
| ATT | GCC | CCC | ATC | CCT | GAA | GGG | AGC | GCT | TTC | TTC | ATT | CTT | AGC | AAG | ACC | 3126 |
| Ile | Ala | Pro | Ile | Pro | Glu | Gly | Ser | Ala | Phe | Phe | Ile | Leu | Ser | Lys | Thr | |
| | | | 860 | | | | | 865 | | | | | 870 | | | |
| AAC | CCG | ATC | CGC | GTA | GGC | TGC | CAC | AAG | CTC | ATC | AAC | CAC | CAC | ATC | TTC | 3174 |
| Asn | Pro | Ile | Arg | Val | Gly | Cys | His | Lys | Leu | Ile | Asn | His | His | Ile | Phe | |
| | | 875 | | | | | 880 | | | | | 885 | | | | |
| ACC | AAC | CTC | ATC | CTT | GTC | TTC | ATC | ATG | CTG | AGC | AGT | GCT | GCC | CTG | GCC | 3222 |
| Thr | Asn | Leu | Ile | Leu | Val | Phe | Ile | Met | Leu | Ser | Ser | Ala | Ala | Leu | Ala | |
| | 890 | | | | | 895 | | | | | 900 | | | | | |
| GCA | GAG | GAC | CCC | ATC | CGC | AGC | CAC | TCC | TTC | CGG | AAC | ACG | ATA | CTG | GGT | 3270 |
| Ala | Glu | Asp | Pro | Ile | Arg | Ser | His | Ser | Phe | Arg | Asn | Thr | Ile | Leu | Gly | |
| 905 | | | | | 910 | | | | | 915 | | | | | 920 | |
| TAC | TTT | GAC | TAT | GCC | TTC | ACA | GCC | ATC | TTT | ACT | GTT | GAG | ATC | CTG | TTG | 3318 |
| Tyr | Phe | Asp | Tyr | Ala | Phe | Thr | Ala | Ile | Phe | Thr | Val | Glu | Ile | Leu | Leu | |
| | | | | 925 | | | | | 930 | | | | | 935 | | |
| AAG | ATG | ACA | ACT | TTT | GGA | GCT | TTC | CTC | CAC | AAA | GGG | GCC | TTC | TGC | AGG | 3366 |
| Lys | Met | Thr | Thr | Phe | Gly | Ala | Phe | Leu | His | Lys | Gly | Ala | Phe | Cys | Arg | |
| | | | 940 | | | | | 945 | | | | | 950 | | | |
| AAC | TAC | TTC | AAT | TTG | CTG | GAT | ATG | CTG | GTG | GTT | GGG | GTG | TCT | CTG | GTG | 3414 |
| Asn | Tyr | Phe | Asn | Leu | Leu | Asp | Met | Leu | Val | Val | Gly | Val | Ser | Leu | Val | |
| | | 955 | | | | | 960 | | | | | 965 | | | | |
| TCA | TTT | GGG | ATT | CAA | TCC | AGT | GCC | ATC | TCC | GTT | GTG | AAG | ATT | CTG | AGG | 3462 |
| Ser | Phe | Gly | Ile | Gln | Ser | Ser | Ala | Ile | Ser | Val | Val | Lys | Ile | Leu | Arg | |
| | 970 | | | | | 975 | | | | | 980 | | | | | |
| GTC | TTA | AGG | GTC | CTG | CGT | CCC | CTC | AGG | GCC | ATC | AAC | AGA | GCA | AAA | GGA | 3510 |
| Val | Leu | Arg | Val | Leu | Arg | Pro | Leu | Arg | Ala | Ile | Asn | Arg | Ala | Lys | Gly | |
| 985 | | | | | 990 | | | | | 995 | | | | | 1000 | |
| CTT | AAG | CAC | GTG | GTC | CAG | TGC | GTC | TTC | GTG | GCC | ATC | CGG | ACC | ATC | GGC | 3558 |
| Leu | Lys | His | Val | Val | Gln | Cys | Val | Phe | Val | Ala | Ile | Arg | Thr | Ile | Gly | |
| | | | | 1005 | | | | | 1010 | | | | | 1015 | | |
| AAC | ATC | ATG | ATC | GTC | ACC | ACC | CTC | CTG | CAG | TTC | ATG | TTT | GCC | TGT | ATC | 3606 |
| Asn | Ile | Met | Ile | Val | Thr | Thr | Leu | Leu | Gln | Phe | Met | Phe | Ala | Cys | Ile | |
| | | | 1020 | | | | | 1025 | | | | | 1030 | | | |
| GGG | GTC | CAG | TTG | TTC | AAG | GGG | AAG | TTC | TAT | CGC | TGT | ACG | GAT | GAA | GCC | 3654 |
| Gly | Val | Gln | Leu | Phe | Lys | Gly | Lys | Phe | Tyr | Arg | Cys | Thr | Asp | Glu | Ala | |
| | | | 1035 | | | | | 1040 | | | | | 1045 | | | |
| AAA | AGT | AAC | CCT | GAA | GAA | TGC | AGG | GGA | CTT | TTC | ATC | CTC | TAC | AAG | GAT | 3702 |
| Lys | Ser | Asn | Pro | Glu | Glu | Cys | Arg | Gly | Leu | Phe | Ile | Leu | Tyr | Lys | Asp | |
| | | | 1050 | | | | | 1055 | | | | | 1060 | | | |
| GGG | GAT | GTT | GAC | AGT | CCT | GTG | GTC | CGT | GAA | CGG | ATC | TGG | CAA | AAC | AGT | 3750 |
| Gly | Asp | Val | Asp | Ser | Pro | Val | Val | Arg | Glu | Arg | Ile | Trp | Gln | Asn | Ser | |
| 1065 | | | | | 1070 | | | | | 1075 | | | | | 1080 | |

```
GAT TTC AAC TTC GAC AAC GTC CTC TCT GCT ATG ATG GCG CTC TTC ACA                3798
Asp Phe Asn Phe Asp Asn Val Leu Ser Ala Met Met Ala Leu Phe Thr
            1085                1090                1095

GTC TCC ACG TTT GAG GGC TGG CCT GCG TTG CTG TAT AAA GCC ATC GAC                3846
Val Ser Thr Phe Glu Gly Trp Pro Ala Leu Leu Tyr Lys Ala Ile Asp
    1100                1105                1110

TCG AAT GGA GAG AAC ATC GGC CCA ATC TAC AAC CAC CGC GTG GAG ATC                3894
Ser Asn Gly Glu Asn Ile Gly Pro Ile Tyr Asn His Arg Val Glu Ile
1115                1120                1125

TCC ATC TTC TTC ATC ATC TAC ATC ATC ATT GTA GCT TTC TTC ATG ATG                3942
Ser Ile Phe Phe Ile Ile Tyr Ile Ile Ile Val Ala Phe Phe Met Met
        1130                1135                1140

AAC ATC TTT GTG GGC TTT GTC ATC GTT ACA TTT CAG GAA CAA GGA GAA                3990
Asn Ile Phe Val Gly Phe Val Ile Val Thr Phe Gln Glu Gln Gly Glu
1145                1150                1155                1160

AAA GAG TAT AAG AAC TGT GAG CTG GAC AAA AAT CAG CGT CAG TGT GTT                4038
Lys Glu Tyr Lys Asn Cys Glu Leu Asp Lys Asn Gln Arg Gln Cys Val
                1165                1170                1175

GAA TAC GCC TTG AAA GCA CGT CCC TTG CGG AGA TAC ATC CCC AAA AAC                4086
Glu Tyr Ala Leu Lys Ala Arg Pro Leu Arg Arg Tyr Ile Pro Lys Asn
            1180                1185                1190

CCC TAC CAG TAC AAG TTC TGG TAC GTG GTG AAC TCT TCG CCT TTC GAA                4134
Pro Tyr Gln Tyr Lys Phe Trp Tyr Val Val Asn Ser Ser Pro Phe Glu
        1195                1200                1205

TAC ATG ATG TTT GTC CTC ATC ATG CTC AAC ACA CTC TGC TTG GCC ATG                4182
Tyr Met Met Phe Val Leu Ile Met Leu Asn Thr Leu Cys Leu Ala Met
    1210                1215                1220

CAG CAC TAC GAG CAG TCC AAG ATG TTC AAT GAT GCC ATG GAC ATT CTG                4230
Gln His Tyr Glu Gln Ser Lys Met Phe Asn Asp Ala Met Asp Ile Leu
1225                1230                1235                1240

AAC ATG GTC TTC ACC GGG GTG TTC ACC GTC GAG ATG GTT TTG AAA GTC                4278
Asn Met Val Phe Thr Gly Val Phe Thr Val Glu Met Val Leu Lys Val
                1245                1250                1255

ATC GCA TTT AAG CCT AAG GGG TAT TTT AGT GAC GCC TGG AAC ACG TTT                4326
Ile Ala Phe Lys Pro Lys Gly Tyr Phe Ser Asp Ala Trp Asn Thr Phe
            1260                1265                1270

GAC TCC CTC ATC GTA ATC GGC AGC ATT ATA GAC GTG GCC CTC AGC GAA                4374
Asp Ser Leu Ile Val Ile Gly Ser Ile Ile Asp Val Ala Leu Ser Glu
        1275                1280                1285

GCA GAC CCA ACT GAA AGT GAA AAT GTC CCT GTC CCA ACT GCT ACA CCT                4422
Ala Asp Pro Thr Glu Ser Glu Asn Val Pro Val Pro Thr Ala Thr Pro
    1290                1295                1300

GGG AAC TCT GAA GAG AGC AAT AGA ATC TCC ATC ACC TTT TTC CGT CTT                4470
Gly Asn Ser Glu Glu Ser Asn Arg Ile Ser Ile Thr Phe Phe Arg Leu
1305                1310                1315                1320

TTC CGA GTG ATG CGA TTG GTG AAG CTT CTC AGC AGG GGG GAA GGC ATC                4518
Phe Arg Val Met Arg Leu Val Lys Leu Leu Ser Arg Gly Glu Gly Ile
                1325                1330                1335

CGG ACA TTG CTG TGG ACT TTT ATT AAG TTC TTT CAG GCG CTC CCG TAT                4566
Arg Thr Leu Leu Trp Thr Phe Ile Lys Phe Phe Gln Ala Leu Pro Tyr
            1340                1345                1350

GTG GCC CTC CTC ATA GCC ATG CTG TTC TTC ATC TAT GCG GTC ATT GGC                4614
Val Ala Leu Leu Ile Ala Met Leu Phe Phe Ile Tyr Ala Val Ile Gly
        1355                1360                1365

ATG CAG ATG TTT GGG AAA GTT GCC ATG AGA GAT AAC AAC CAG ATC AAT                4662
Met Gln Met Phe Gly Lys Val Ala Met Arg Asp Asn Asn Gln Ile Asn
    1370                1375                1380

AGG AAC AAT AAC TTC CAG ACG TTT CCC CAG GCG GTG CTG CTC CTC TTC                4710
Arg Asn Asn Asn Phe Gln Thr Phe Pro Gln Ala Val Leu Leu Leu Phe
1385                1390                1395                1400
```

| | |
|---|---|
| AGG TGT GCA ACA GGT GAG GCC TGG CAG GAG ATC ATG CTG GCC TGT CTC<br>Arg Cys Ala Thr Gly Glu Ala Trp Gln Glu Ile Met Leu Ala Cys Leu<br>                1405                      1410                     1415 | 4758 |
| CCA GGG AAG CTC TGT GAC CCT GAG TCA GAT TAC AAC CCC GGG GAG GAG<br>Pro Gly Lys Leu Cys Asp Pro Glu Ser Asp Tyr Asn Pro Gly Glu Glu<br>                1420                      1425                     1430 | 4806 |
| CAT ACA TGT GGG AGC AAC TTT GCC ATT GTC TAT TTC ATC AGT TTT TAC<br>His Thr Cys Gly Ser Asn Phe Ala Ile Val Tyr Phe Ile Ser Phe Tyr<br>                1435                      1440                     1445 | 4854 |
| ATG CTC TGT GCA TTT CTG ATC ATC AAT CTG TTT GTG GCT GTC ATC ATG<br>Met Leu Cys Ala Phe Leu Ile Ile Asn Leu Phe Val Ala Val Ile Met<br>                1450                      1455                     1460 | 4902 |
| GAT AAT TTC GAC TAT CTG ACC CGG GAC TGG TCT ATT TTG GGG CCT CAC<br>Asp Asn Phe Asp Tyr Leu Thr Arg Asp Trp Ser Ile Leu Gly Pro His<br>1465                     1470                     1475                     1480 | 4950 |
| CAT TTA GAT GAA TTC AAA AGA ATA TGG TCA GAA TAT GAC CCT GAG GCA<br>His Leu Asp Glu Phe Lys Arg Ile Trp Ser Glu Tyr Asp Pro Glu Ala<br>                1485                      1490                     1495 | 4998 |
| AAG GGA AGG ATA AAA CAC CTT GAT GTG GTC ACT CTG CTT CGA CGC ATC<br>Lys Gly Arg Ile Lys His Leu Asp Val Val Thr Leu Leu Arg Arg Ile<br>                1500                      1505                     1510 | 5046 |
| CAG CCT CCC CTG GGG TTT GGG AAG TTA TGT CCA CAC AGG GTA GCG TGC<br>Gln Pro Pro Leu Gly Phe Gly Lys Leu Cys Pro His Arg Val Ala Cys<br>                1515                      1520                     1525 | 5094 |
| AAG AGA TTA GTT GCC ATG AAC ATG CCT CTC AAC AGT GAC GGG ACA GTC<br>Lys Arg Leu Val Ala Met Asn Met Pro Leu Asn Ser Asp Gly Thr Val<br>                1530                      1535                     1540 | 5142 |
| ATG TTT AAT GCA ACC CTG TTT GCT TTG GTT CGA ACG GCT CTT AAG ATC<br>Met Phe Asn Ala Thr Leu Phe Ala Leu Val Arg Thr Ala Leu Lys Ile<br>1545                     1550                     1555                     1560 | 5190 |
| AAG ACC GAA GGG AAC CTG GAG CAA GCT AAT GAA GAA CTT CGG GCT GTG<br>Lys Thr Glu Gly Asn Leu Glu Gln Ala Asn Glu Glu Leu Arg Ala Val<br>                1565                      1570                     1575 | 5238 |
| ATA AAG AAA ATT TGG AAG AAA ACC AGC ATG AAA TTA CTT GAC CAA GTT<br>Ile Lys Lys Ile Trp Lys Lys Thr Ser Met Lys Leu Leu Asp Gln Val<br>                1580                      1585                     1590 | 5286 |
| GTC CCT CCA GCT GGT GAT GAT GAG GTA ACC GTG GGG AAG TTC TAT GCC<br>Val Pro Pro Ala Gly Asp Asp Glu Val Thr Val Gly Lys Phe Tyr Ala<br>                1595                      1600                     1605 | 5334 |
| ACT TTC CTG ATA CAG GAC TAC TTT AGG AAA TTC AAG AAA CGG AAA GAA<br>Thr Phe Leu Ile Gln Asp Tyr Phe Arg Lys Phe Lys Lys Arg Lys Glu<br>                1610                      1615                     1620 | 5382 |
| CAA GGA CTG GTG GGA AAG TAC CCT GCG AAG AAC ACC ACA ATT GCC CTA<br>Gln Gly Leu Val Gly Lys Tyr Pro Ala Lys Asn Thr Thr Ile Ala Leu<br>1625                     1630                     1635                     1640 | 5430 |
| CAG GCG GGA TTA AGG ACA CTG CAT GAC ATT GGG CCA GAA ATC CGG CGT<br>Gln Ala Gly Leu Arg Thr Leu His Asp Ile Gly Pro Glu Ile Arg Arg<br>                1645                      1650                     1655 | 5478 |
| GCT ATA TCG TGT GAT TTG CAA GAT GAC GAG CCT GAG GAA ACA AAA CGA<br>Ala Ile Ser Cys Asp Leu Gln Asp Asp Glu Pro Glu Glu Thr Lys Arg<br>                1660                      1665                     1670 | 5526 |
| GAA GAA GAA GAT GAT GTG TTC AAA AGA AAT GGT GCC CTG CTT GGA AAC<br>Glu Glu Glu Asp Asp Val Phe Lys Arg Asn Gly Ala Leu Leu Gly Asn<br>                1675                      1680                     1685 | 5574 |
| CAT GTC AAT CAT GTT AAT AGT GAT AGG AGA GAT TCC CTT CAG CAG ACC<br>His Val Asn His Val Asn Ser Asp Arg Arg Asp Ser Leu Gln Gln Thr<br>                1690                      1695                     1700 | 5622 |
| AAT ACC ACC CAC CGT CCC CTG CAT GTC CAA AGG CCT TCA ATT CCA CCT<br>Asn Thr Thr His Arg Pro Leu His Val Gln Arg Pro Ser Ile Pro Pro<br>1705                     1710                     1715                     1720 | 5670 |

| | |
|---|---|
| GCA AGT GAT ACT GAG AAA CCG CTG TTT CCT CCA GCA GGA AAT TCG GTG<br>Ala Ser Asp Thr Glu Lys Pro Leu Phe Pro Pro Ala Gly Asn Ser Val<br>                 1725                              1730                          1735 | 5718 |
| TGT CAT AAC CAT CAT AAC CAT AAT TCC ATA GGA AAG CAA GTT CCC ACC<br>Cys His Asn His His Asn His Asn Ser Ile Gly Lys Gln Val Pro Thr<br>                 1740                              1745                          1750 | 5766 |
| TCA ACA AAT GCC AAT CTC AAT AAT GCC AAT ATG TCC AAA GCT GCC CAT<br>Ser Thr Asn Ala Asn Leu Asn Asn Ala Asn Met Ser Lys Ala Ala His<br>                 1755                              1760                          1765 | 5814 |
| GGA AAG CGG CCC AGC ATT GGG AAC CTT GAG CAT GTG TCT GAA AAT GGG<br>Gly Lys Arg Pro Ser Ile Gly Asn Leu Glu His Val Ser Glu Asn Gly<br>                 1770                              1775                          1780 | 5862 |
| CAT CAT TCT TCC CAC AAG CAT GAC CGG GAG CCT CAG AGA AGG TCC AGT<br>His His Ser Ser His Lys His Asp Arg Glu Pro Gln Arg Arg Ser Ser<br>1785                         1790                              1795                          1800 | 5910 |
| GTG AAA AGA ACC CGC TAT TAT GAA ACT TAC ATT AGG TCC GAC TCA GGA<br>Val Lys Arg Thr Arg Tyr Tyr Glu Thr Tyr Ile Arg Ser Asp Ser Gly<br>                 1805                              1810                          1815 | 5958 |
| GAT GAA CAG CTC CCA ACT ATT TGC CGG GAA GAC CCA GAG ATA CAT GGC<br>Asp Glu Gln Leu Pro Thr Ile Cys Arg Glu Asp Pro Glu Ile His Gly<br>                 1820                              1825                          1830 | 6006 |
| TAT TTC AGG GAC CCC CAC TGC TTG GGG GAG CAG GAG TAT TTC AGT AGT<br>Tyr Phe Arg Asp Pro His Cys Leu Gly Glu Gln Glu Tyr Phe Ser Ser<br>                 1835                              1840                          1845 | 6054 |
| GAG GAA TGC TAC GAG GAT GAC AGC TCG CCC ACC TGG AGC AGG CAA AAC<br>Glu Glu Cys Tyr Glu Asp Asp Ser Ser Pro Thr Trp Ser Arg Gln Asn<br>                 1850                              1855                          1860 | 6102 |
| TAT GGC TAC TAC AGC AGA TAC CCA GGC AGA AAC ATC GAC TCT GAG AGG<br>Tyr Gly Tyr Tyr Ser Arg Tyr Pro Gly Arg Asn Ile Asp Ser Glu Arg<br>1865                         1870                              1875                          1880 | 6150 |
| CCC CGA GGC TAC CAT CAT CCC CAA GGA TTC TTG GAG GAC GAT GAC TCG<br>Pro Arg Gly Tyr His His Pro Gln Gly Phe Leu Glu Asp Asp Asp Ser<br>                 1885                              1890                          1895 | 6198 |
| CCC GTT TGC TAT GAT TCA CGG AGA TCT CCA AGG AGA CGC CTA CTA CCT<br>Pro Val Cys Tyr Asp Ser Arg Arg Ser Pro Arg Arg Arg Leu Leu Pro<br>                 1900                              1905                          1910 | 6246 |
| CCC ACC CCA GCA TCC CAC CGG AGA TCC TCC TTC AAC TTT GAG TGC CTG<br>Pro Thr Pro Ala Ser His Arg Arg Ser Ser Phe Asn Phe Glu Cys Leu<br>                 1915                              1920                          1925 | 6294 |
| CGC CGG CAG AGC AGC CAG GAA GAG GTC CCG TCG TCT CCC ATC TTC CCC<br>Arg Arg Gln Ser Ser Gln Glu Glu Val Pro Ser Ser Pro Ile Phe Pro<br>                 1930                              1935                          1940 | 6342 |
| CAT CGC ACG GCC CTG CCT CTG CAT CTA ATG CAG CAA CAG ATC ATG GCA<br>His Arg Thr Ala Leu Pro Leu His Leu Met Gln Gln Gln Ile Met Ala<br>1945                         1950                              1955                          1960 | 6390 |
| GTT GCC GGC CTA GAT TCA AGT AAA GCC CAG AAG TAC TCA CCG AGT CAC<br>Val Ala Gly Leu Asp Ser Ser Lys Ala Gln Lys Tyr Ser Pro Ser His<br>                 1965                              1970                          1975 | 6438 |
| TCG ACC CGG TCG TGG GCC ACC CCT CCA GCA ACC CCT CCC TAC CGG GAC<br>Ser Thr Arg Ser Trp Ala Thr Pro Pro Ala Thr Pro Pro Tyr Arg Asp<br>                 1980                              1985                          1990 | 6486 |
| TGG ACA CCG TGC TAC ACC CCC CTG ATC CAA GTG GAG CAG TCA GAG GCC<br>Trp Thr Pro Cys Tyr Thr Pro Leu Ile Gln Val Glu Gln Ser Glu Ala<br>                 1995                              2000                          2005 | 6534 |
| CTG GAC CAG GTG AAC GGC AGC CTG CCG TCC CTG CAC CGC AGC TCC TGG<br>Leu Asp Gln Val Asn Gly Ser Leu Pro Ser Leu His Arg Ser Ser Trp<br>                 2010                              2015                          2020 | 6582 |
| TAC ACA GAC GAG CCC GAC ATC TCC TAC CGG ACT TTC ACA CCA GCC AGC<br>Tyr Thr Asp Glu Pro Asp Ile Ser Tyr Arg Thr Phe Thr Pro Ala Ser<br>2025                         2030                              2035                          2040 | 6630 |

```
CTG ACT GTC CCC AGC AGC TTC CGG AAC AAA AAC AGC GAC AAG CAG AGG            6678
Leu Thr Val Pro Ser Ser Phe Arg Asn Lys Asn Ser Asp Lys Gln Arg
            2045                    2050                2055

AGT GCG GAC AGC TTG GTG GAG GCA GTC CTG ATA TCC GAA GGC TTG GGA            6726
Ser Ala Asp Ser Leu Val Glu Ala Val Leu Ile Ser Glu Gly Leu Gly
            2060                    2065                2070

CGC TAT GCA AGG GAC CCA AAA TTT GTG TCA GCA ACA AAA CAC GAA ATC            6774
Arg Tyr Ala Arg Asp Pro Lys Phe Val Ser Ala Thr Lys His Glu Ile
            2075                    2080                2085

GCT GAT GCC TGT GAC CTC ACC ATC GAC GAG ATG GAG AGT GCA GCC AGC            6822
Ala Asp Ala Cys Asp Leu Thr Ile Asp Glu Met Glu Ser Ala Ala Ser
            2090                    2095                2100

ACC CTG CTT AAT GGG AAC GTG CGT CCC CGA GCC AAC GGG GAT GTG GGC            6870
Thr Leu Leu Asn Gly Asn Val Arg Pro Arg Ala Asn Gly Asp Val Gly
2105                    2110                2115                2120

CCC CTC TCA CAC CGG CAG GAC TAT GAG CTA CAG GAC TTT GGT CCT GGC            6918
Pro Leu Ser His Arg Gln Asp Tyr Glu Leu Gln Asp Phe Gly Pro Gly
            2125                    2130                2135

TAC AGC GAC GAA GAG CCA GAC CCT GGG AGG GAT GAG GAG GAC CTG GCG            6966
Tyr Ser Asp Glu Glu Pro Asp Pro Gly Arg Asp Glu Glu Asp Leu Ala
            2140                    2145                2150

GAT GAA ATG ATA TGC ATC ACC ACC TTG TAGCCCCCAG CGAGGGGCAG                  7013
Asp Glu Met Ile Cys Ile Thr Thr Leu
            2155                    2160

ACTGGCTCTG GCCTCAGGTG GGGCGCAGGA GAGCCAGGGG AAAAGTGCCT CATAGTTAGG          7073

AAAGTTTAGG CACTAGTTGG GAGTAATATT CAATTAATTA GACTTTTGTA TAAGAGATGT          7133

CATGCCTCAA GAAAGCCATA AACCTGGTAG GAACAGGTCC CAAGCGGTTG AGCCTGGCAG          7193

AGTACCATGC GCTCGGCCCC AGCTGCAGGA AACAGCAGGC CCCGCCCTCT CACAGAGGAT          7253

GGGTGAGGAG GCCAGACCTG CCCTGCCCCA TTGTCCAGAT GGGCACTGCT GTGGAGTCTG          7313

CTTCTCCCAT GTACCAGGGC ACCAGGCCCA CCCAACTGAA GGCATGGCGG CGGGGTGCAG          7373

GGGAAAGTTA AAGGTGATGA CGATCATCAC ACCTGTGTCG TTACCTCAGC CATCGGTCTA          7433

GCATATCAGT CACTGGGCCC AACATATCCA TTTTTAAACC CTTTCCCCCA AATACACTGC          7493

GTCCTGGTTC CTGTTTAGCT GTTCTGAAAT ACGGTGTGTA AGTAAGTCAG AACCCAGCTA          7553

CCAGTGATTA TTGCGAGGGC AATGGGACCT CATAAATAAG GTTTTCTGTG ATGTGACGCC          7613

AGTTTACATA AGAGAATATC AC                                                   7635
```